US008338605B2

(12) United States Patent
Rockway et al.

(10) Patent No.: US 8,338,605 B2
(45) Date of Patent: Dec. 25, 2012

(54) ANTI-VIRAL COMPOUNDS

(75) Inventors: Todd W. Rockway, Grayslake, IL (US);
David A. Betebenner, Libertyville, IL
(US); Allan C. Krueger, Gurnee, IL
(US); Nobuhiko Iwasaki, Buffalo
Grove, IL (US); Curt S. Cooper, Vernon
Hills, IL (US); David D. Anderson,
Kenosh, WI (US); Dale J. Kempf,
Libertyville, IL (US); **Darold L.
Madigan**, Elk Grove Village, IL (US);
Christopher E. Motter, Oak Creek, WI
(US); Jason P. Shanley, Chicago, IL
(US); Michael D. Tufano, Chicago, IL
(US); Rolf Wagner, Antioch, IL (US);
Rong Zhang, Niskayuna, NY (US);
Akteruzzaman Molla, Gurnee, IL (US);
Hongmei Mo, Foster City, CA (US);
Tami J. Pilot-Matias, Green Oaks, IL
(US); Sherie V. L. Masse, Kenosha, WI
(US); Robert J. Carrick, Pleasant
Prairie, WI (US); Wenping He,
Libertyville, IL (US); Liangjun Lu,
Kildeer, IL (US)

(73) Assignee: Abbott Laboratories, Abbott Park, IL
(US)

( * ) Notice: Subject to any disclaimer, the term of this
patent is extended or adjusted under 35
U.S.C. 154(b) by 0 days.

(21) Appl. No.: 12/817,808

(22) Filed: Jun. 17, 2010

(65) Prior Publication Data
US 2010/0256139 A1    Oct. 7, 2010

Related U.S. Application Data

(62) Division of application No. 11/613,836, filed on Dec. 20, 2006, now Pat. No. 7,763,731.

(60) Provisional application No. 60/752,473, filed on Dec. 21, 2005.

(51) Int. Cl.
*C07D 471/02*         (2006.01)
(52) U.S. Cl. ..................................................... 546/122
(58) Field of Classification Search .................... 546/122
See application file for complete search history.

(56) References Cited

U.S. PATENT DOCUMENTS

| 5,350,749 | A | 9/1994 | Hackler et al. |
| 5,464,781 | A | 11/1995 | Armitage et al. |
| 5,654,307 | A | 8/1997 | Bridges et al. |
| 5,925,644 | A | 7/1999 | Jakobi et al. |
| 6,130,217 | A | 10/2000 | Arnold et al. |
| 6,169,091 | B1 | 1/2001 | Cockerill et al. |
| 6,174,889 | B1 | 1/2001 | Cockerill et al. |
| 6,184,226 | B1 | 2/2001 | Chakravarty et al. |
| 6,277,989 | B1 | 8/2001 | Chakravarty et al. |
| 6,284,764 | B1 | 9/2001 | Kath et al. |
| 6,323,180 | B1 | 11/2001 | Llinas-Brunet et al. |
| 6,348,587 | B1 | 2/2002 | Schinazi et al. |
| 6,413,971 | B1 | 7/2002 | Arnold et al. |
| 6,476,031 | B1 | 11/2002 | Chakravarty et al. |
| 6,541,481 | B2 | 4/2003 | Bhattacharya et al. |
| 6,703,403 | B2 | 3/2004 | Norbeck et al. |
| 6,723,726 | B1 | 4/2004 | Cockerill et al. |
| 6,809,097 | B1 | 10/2004 | Thomas et al. |
| 6,903,096 | B2 | 6/2005 | Chakravarty et al. |
| 7,037,913 | B2 | 5/2006 | Wang et al. |
| 7,183,302 | B2 | 2/2007 | Romine et al. |
| 2003/0125343 | A1 | 7/2003 | Gambacorti-Passerini et al. |
| 2004/0242604 | A1 | 12/2004 | Bhattacharya et al. |
| 2004/0265792 | A1 | 12/2004 | Glenn et al. |
| 2005/0075331 | A1 | 4/2005 | Pratt et al. |
| 2005/0090522 | A1 | 4/2005 | Wang et al. |
| 2005/0107364 | A1 | 5/2005 | Hutchinson et al. |
| 2006/0035965 | A1 | 2/2006 | Dalton et al. |
| 2007/0197558 | A1 | 8/2007 | Betebenner et al. |
| 2007/0232645 | A1 | 10/2007 | Rockway et al. |

FOREIGN PATENT DOCUMENTS

| EP | 414386 A1 | 2/1991 |
| EP | 912570 A1 | 5/1999 |
| EP | 1162196 A1 | 12/2001 |
| WO | WO-9313097 A1 | 7/1993 |
| WO | WO-9500511 A1 | 1/1995 |
| WO | WO-9519774 A1 | 7/1995 |
| WO | WO-9609294 A1 | 3/1996 |
| WO | WO-9640142 A1 | 12/1996 |
| WO | WO-9713771 A1 | 4/1997 |
| WO | WO-9802428 A1 | 1/1998 |
| WO | WO-9802437 A1 | 1/1998 |
| WO | WO-9802438 A1 | 1/1998 |
| WO | WO-9805661 A1 | 2/1998 |
| WO | WO-9808846 A1 | 3/1998 |
| WO | WO-9813350 A1 | 4/1998 |

(Continued)

OTHER PUBLICATIONS

Venkatesh et al. Role of the Development Scientist in Compound Lead Selection and Optimization by Venkatesh et al., J. Pharm. Sci. 89, 145-54 (2000).*
Dorwald F. A. (Side Reactions in Organic Synthesis, 2005, Wiley: VCH, Weinheim p. IX of Preface p. 1-15).*
Barlin et al., "Potential Antimalarials. I 1,8-Naphthyridines, STN Accession No. 1984:530611, Document No. 101:130611 ," Abstract of Australian Journal of Chemistry, vol. 37 (5), pp. 1065-1173, 1984.
Blight K.J. et al., "Efficient Initiation of HCV RNA Replication in Cell Culture," Science, vol. 290, pp. 1972-1974 , 2000.

(Continued)

*Primary Examiner* — Nizal Chandrakumar
(74) *Attorney, Agent, or Firm* — Bradley E. Davis

(57) ABSTRACT

Compounds effective in inhibiting replication of Hepatitis C virus ("HCV") or other viruses are disclosed. This invention is also directed to compositions comprising such compounds, co-formulation or co-administration of such compounds with other anti-viral or therapeutic agents, processes and intermediates for the syntheses of such compounds, and methods of using such compounds for the treatment of HCV or other viral infections.

13 Claims, No Drawings

FOREIGN PATENT DOCUMENTS

| | | |
|---|---|---|
| WO | WO-9822444 A1 | 5/1998 |
| WO | WO-9823613 A1 | 6/1998 |
| WO | WO-9959587 A1 | 11/1999 |
| WO | WO-0012497 A2 | 3/2000 |
| WO | WO-0044728 A1 | 8/2000 |
| WO | WO-0056738 A1 | 9/2000 |
| WO | WO-0132153 A2 | 5/2001 |
| WO | WO-0132632 A2 | 5/2001 |
| WO | WO-0157040 A1 | 8/2001 |
| WO | WO-0160315 A2 | 8/2001 |
| WO | WO-0190121 A2 | 11/2001 |
| WO | WO-0204425 A2 | 1/2002 |
| WO | WO-2004014313 A2 | 2/2004 |
| WO | WO-2004014852 A2 | 2/2004 |
| WO | WO-2004024693 A1 | 3/2004 |
| WO | WO-2004047818 A2 | 6/2004 |
| WO | WO-2004055004 A1 | 7/2004 |
| WO | WO-2004065392 A1 | 8/2004 |
| WO | WO-2004087056 A2 | 10/2004 |
| WO | WO-2005007652 A2 | 1/2005 |
| WO | WO-2005047288 A1 | 5/2005 |
| WO | WO-2005105761 A1 | 11/2005 |
| WO | WO-2006012333 A1 | 2/2006 |
| WO | WO-2006035061 A1 | 4/2006 |
| WO | WO-2006038039 A1 | 4/2006 |
| WO | WO-2006120251 A1 | 11/2006 |
| WO | WO-2006120252 A2 | 11/2006 |
| WO | WO-2007035010 A2 | 3/2007 |

OTHER PUBLICATIONS

Bundgaard H., "Design of prodrugs," pp. 7-9 & 21-24, 1985.
Cortese et al., "A Synthesis of Conjugatred Bile Acids. I. Glycocholic Acid," JAGS, vol. 57, pp. 1393-1395, 1935.
Cross L.C. et al. , "Rules for the Nomenclature of Organic Chemistry—Section E: Stereochemistry," Pure Appl. Chem., vol. 45, pp. 11-30, 1976.
Das S. et al., "A Small yeast RNA Blocks Hepatitis C Virus Internal Ribosome Entry Site (HCV IRES)-Mediated Translation and Inhibits Replication of a Chimeric Poliovirus under Translational control of the HCV IRES Element," J of Virology, vol. 72 (7), pp. 5638-5647, 1998.
Deeb A. et al., "Pyridazine Derivatives and Related Comp9unds Part 5. Pyrazolo[3,4-c]Pyridazine: Synthesis and Some Reactoins," Heterocycles, vol. 32 (5), pp. 895-900, 1991.
Gomtsyan A.et al., "Design, Synthesis, and Structure-Activity Relationship of 6-Alkynylpyrimidines as Potent Adenosine Kinase Inhibitors," J. Med. Chem, vol. 45, pp. 3639-3648, 2002.
Hoover J.E, Remington's Pharmaceutical Sciences, Tbl of Cont, 1975.
Ikeda M. et al., "Selectable Subgenomic and Genome-Length Dicistronic RNAs Derived from an Infectious Molecular Clone of the HCV-N Strain of Hepatitis C Virus Replicate Efficiently in Clutured Huh? Cells," J of Virology, vol. 76 (6), pp. 2997-3006, 2002.
International Search Report for application No. PCT/US06/048685, Mailed on Oct. 30, 2007, 5 pages.
International Search Report for application No. PCT/US06/049079, Mailed on Aug. 17, 2007, 3 pages.
International Search Report for application No. PCT/US06/049080, Mailed on Aug. 23, 2007, 3 pages.
International Search Report for application No. PCT/US07/088027, Mailed on Oct. 24, 2008, 1 page.
Jacques et al., "Enantiomers, Racemates, and Resolutions," J. Wiley & Sons, Chapter 3, pp. 197-213, 1981.
Janout V., et al., "Design and Synthesis of Molecular Umbrellas," I Am. Chem. Soc, vol. 119, pp. 640-647, 1997.
Lieberman H.A. et al., "Compression-Coated and Layer tablets (Tbl of Cont)," Pharmaceutical dosage forms, vol. 1, 1980.
Livi et al. , "Farmaco, STN Document No. 86:89704; Abstract of Edizione Scientifica ," vol. 31 (11), pp. 797-808, 1976.
Martini C. et al., "Specific Inhibition of Benzodiazepine Receptor Binding by Some 1,2,3-Triazole Derivatives,STN Accession No. 1989:50722 Document No. 110:50722," Abstract of Journal of Pharmaceutical Sciences, vol. 77 (11), pp. 977-980, 1988.
McKenzie A. & Clough G.W, "XLVIII.—Experiments on the Ealden Inversion. Part VIII. a-Amino-a-phenylpropionic Acids," J. Chem. Soc, vol. (101) , pp. 390-397, 1912.
Miranda E.I et al., , "Thiols, Unsymmetrical Sulfides and Thioacetals From the New Reagent: Trisopropysilanethiol," Tetrahedron Ltrs, vol. 35 (20) , pp. 3221-3224 , 1994.
Nakamura S., "Studies on Growth Inhibition of hiochi-bacteria, Specific Saprophytes of Sake," Agr. Biol. Chem, vol. 25 (8), pp. 665-670, 1961.
U.S. Appl. No. 11/960,298, filed Dec. 19, 2007.
Prakash, G.K.Su. et al., "Facile preparation of di- and monofluoromethyl ketones form trifluoromethyl ketones via fluorinated enol silyl ethers," J. of Fluorine Chem, vol. 112, pp. 357-362, 2001.
Refai M et al., "New Synthesis of some 1,8- Naphthyridines of Possible Antimicrobial Activity," Egyptian Journal of Harmaceutical Sciences, National Information and Documentation Centre, vol. 37 (1-6), pp. 241-249, 1996.
Shuman R.T. et al., "Structure-Activity Study of Tripeptide Thrombin Inhibitors Using a-Alkyl Amino Lacids and Other Conformationally Constrained Amino Acid Substitutions," I Med. Chem, vol. 38, pp. 4446-4453, 1995.
Yi M. et al., "Subjenomic Hepatitis C Virus Replicaons Inducting Expression of a Secreted Enzymatic Reporter Protein,"Virology, vol. 304, pp. 197-210, 2002.

\* cited by examiner

ANTI-VIRAL COMPOUNDS

This application is a divisional application of U.S. patent application Ser. No. 11/613,836, filed Dec. 20, 2006, which claims the benefit and incorporates herein by references the entire content of U.S. Provisional Application No. 60/752,473, filed Dec. 21, 2005.

FIELD

The present invention relates to compounds effective in inhibiting replication of Hepatitis C virus ("HCV"). The present invention also relates to methods of making such compounds, compositions comprising such compounds, intermediates for the syntheses of such compounds, and methods of using such compounds/compositions for the treatment of HCV infection or conditions/symptoms associated therewith. In addition, the present invention relates to use of such compounds for the manufacture of medicaments for the treatment of HCV infection.

BACKGROUND

HCV, a human pathogen, is an RNA virus belonging to the Hepacivirus genus in the Flaviviridae family. As is characteristic with all other members of the Flaviviridae family, HCV has enveloped virions that contain a positive stranded RNA genome encoding all known virus-specific proteins in one single, uninterrupted, open reading frame. The open reading frame comprises approximately 9500 nucleotides encoding a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B. A cellular protease cleaves the viral protein at the NS2-NS3 junction allowing a viral protease (NS3 protease) to mediate subsequent cleavages. The NS3 protein also exhibits nucleoside triphosphatase and RNA helicase activities. NS2 and NS4A may, too, be involved in proteolytic activity. NS5A is a phosphoprotein involved in replication. NS5B is a RNA-dependent RNA polymerase. U.S. Patent Pub. No. 2004/0265792, published 30 Dec. 2004, mentions that inhibition of the aforementioned non-structural proteins may inhibit HCV replication.

HCV infection is associated with progressive liver pathology, including cirrhosis and hepatocellular carcinoma. HCV-associated end-stage liver disease is the most frequent indication for liver transplantation among adults. Chronic hepatitis C may be treated with a once-weekly injection of peginterferon-alpha in combination with daily ribavarin. Peginterferon-alpha is interferon-alpha attached to polyethylene glycol to slow elimination of the drug from the body. This results in enhanced compliance and clinically superior anti-viral activity when compared to treatments of interferon-alpha daily injections. Substantial limitations to efficacy and tolerability remain as many users suffer from side effects and viral elimination from the body is often inadequate.

Attempts have been made to design drugs that specifically inhibit functions of the hepatitis C virus. Boehringer Ingelheim U.S. Pat. No. 6,323,180 mentions tri-peptide compounds as HCV serine protease inhibitors proposed for treatment of HCV infection.

Another approach is ISIS-14803 (Isis Pharmaceuticals), an antisense inhibitor complementary to a conserved sequence of the hepatitis C virus RNA. This molecule binds to the viral RNA and inhibits the expression of proteins required for replication.

Inhibition of HCV translation, by a yeast RNA that binds to cellular polypeptides and prevents their interaction with the viral internal ribosome entry site (IRES), is described in Das et al, J. VIROLOGY, 72(7):5638-5647 (1998).

Fused-bicyclic heterocyclic compounds have been proposed for diverse life-science-related uses. Examples of such heterocyclic compounds include naphthyridine, pyridopyrimidine, pyrimidopyrimidine, pyrazolopyrimidine and thiazolo/thienopyrimidine compounds.

Naphthyridine-type fused-bicyclic compounds have been investigated for disease-treatment uses. For example, Boots WO 93/13097, published 8 Jul. 1993, mentions [1,8]naphthyridine compounds, such as ethyl 4-(4-methoxyanilino)-6-ethoxy-7-methyl-1,8-naphthyridine-3-carboxylate hydrochloride, proposed for use as anti-rheumatic agents. Boots WO 95/00511, published 5 Jan. 1995, mentions substituted ring-fused 4-aminopyridines, such as 3-ethoxy-5-(2-ethoxy-5-pyridylamino)-2-methyl-1,8-naphthyridine, proposed for use as anti-rheumatic agents. Zeneca WO 98/13350, published 2 Apr. 1998, mentions [1,8]naphthyridine compounds, such as 2-acetamido-5-(2-fluoro-5-hydroxy-4-methylanilino)-1,8-naphthyridine hydrochloride, proposed as anti-angiogenic agents. Neurogen WO 2004/055004, published 1 Jul. 2004, mentions naphthyridine compounds as capsaicin-receptor modulators, specific compounds being 5-(4-trifluoromethyl-phenylamino)-2-(3-trifluoromethyl-pyridin-2-yl)-[1,6]naphthyridine-7-carboxylic acid, and 2-methoxymethyl-4-(4-trifluoromethyl-phenylamino)-7-(3-trifluoromethyl-pyridin-2-yl)-[1,8]naphthyridine-3-carboxylic acid.

Pyridopyrimidine-type fused-bicyclic compounds have been investigated for various disease-treatment uses. For example, Pfizer WO 98/05661, published 12 Feb. 1998, mentions substituted pyridopyrimidine compounds, such as [8-(1-ethyl-propyl)-2-methyl-5,6,7,8-tetrahydro-pyrido(2,3-d)pyrimidin-4-yl]-(2,4,6-trimethyl-phenyl)-amine, as corticotrophin releasing factor (hormone) CRF (CRH) antagonists proposed for treatment of Alzheimer's Disease and obesity. Pfizer WO 98/23613, published 4 Jun. 1998, mentions fused-bicyclic pyrimidine compounds, including pyridopyrimidinyl-aminophenyl compounds, such as (3-ethynyl-phenyl)-pyrido[3,4-d]pyrimidin-4-yl-amine, proposed for treatment of hyperproliferative diseases such as cancer. Glaxo Wellcome U.S. Pat. No. 6,169,091, issued 2 Jan. 2001, mentions bicyclic heteroaromatic compounds, such as 4-(4-benzyloxyanilino)pyrido[2,3-d]-pyrimidine, as tyrosine kinase inhibitors proposed for treatment of fibrosis, inflammation, nervous system diseases and cancer. Eli Lilly WO 01/32632, published 10 May 2001, mentions 4-substituted pyrimidine compounds, including 2-trifluoromethyl-4-[2-(2-(2-chlorophenyl)ethylamino]pyrido-[2,3-d]pyrimidine hydrochloride, as mGluR1 antagonists proposed for treatment of neurological disorders associated with glutamate dysfunction such as convulsions, migraine, psychosis, anxiety and pain. Abbott Laboratories WO 01/57040 published 9 Aug. 2001, mentions 6,7-disubstituted-4-aminopyrido[2,3-d]pyrimidine compounds, such as 4-amino-6-(4-methylphenyl)-7-(4-bromophenyl)pyrido[2,3-d]pyrimidine, as adenosine kinase inhibitors proposed for treatment of pain and inflammation. Neurogen WO 2004/055004, published 1 Jul. 2004, mentions pyridopyrmidinyl-aminophenyl compounds, such as 2-methyl-2-{4-[2-methyl-7-(3-methyl-pyridin-2-yl)-pyrido[2,3-d]pyrimidin-4-ylamino]-phenyl}-propionic acid, as capsaicin-receptor modulators. Pfizer U.S. Pat. No. 6,395,733, issued 28 May 2002, mentions heterocyclic ring-fused pyrimidine compounds, such as 3-chloro-phenyl-pyrido[2,3- d]pyrimidin-4-yl-amine, proposed for treatment of hyperproliferative disease, such as cancer.

Pyrimidopyrimidine-type fused bicyclic compounds have been investigated for both pest-control and disease-treatment uses. For example, Dow Elanco U.S. Pat. No. 5,350,749, issued 27 Sep. 1994, mentions 4-substituted-pyrimido[2,3-d]pyrimidine compounds proposed for use as fungicides, insecticides and miticides. Warner-Lambert WO 95/19774, published 27 Jul. 1995, mentions pyrimidopyrimidine compounds, such as 4-benzylamino-7-methylaminopyrimido[4,5-d]pyrimidine, as tyrosine kinase inhibitors proposed for treatment of cancer, vascular restenosis and psoriasis.

Thienopyrimidine-type fused-bicyclic compounds have been investigated for various disease-treatment uses. For example, Warner-Lambert WO 95/19774, published 27 Jul. 1995, mentions fused heterocyclic pyrimidine compounds, including 4-(3-bromoanilino)thieno[2,3-d]pyrimidine, as tyrosine kinase inhibitors proposed for treatment of cancer, vascular restenosis and psoriasis. Glaxo Wellcome U.S. Pat. No. 6,169,091, issued 2 Jan. 2001, mentions bicyclic heteroaromatic compounds, such as 5-methyl-4-(4-phenoxyanilino)thieno[2,3-d]pyrimidine hydrochloride as tyrosine kinase inhibitors, proposed for treatment of fibrosis, inflammation, nervous system diseases and cancer. Eli Lilly WO 01/32632, published 10 May 2001, mentions 4-substituted-pyrimidine compounds, such as 6-methyl-4-[2,6-dichlorobenzylthio)ethylamino]thieno[2,3-d]pyrimidine hydrochloride, as mGluR1 antagonists proposed for treatment of neurological disorders associated with glutamate dysfunction such as convulsions, migraine, psychosis, anxiety and pain.

Bristol-Myers Squibb WO 2004/014852, published 19 Feb. 2004, mentions iminothiazolidinones, including fused-bicyclic derivatives of 2-(4-aminophenyl)-5H-thiazolo[2,3-6]quinazolin-3-one, as NS5A-protein-inhibitors proposed to prevent HCV replication.

Bristol-Myers Squibb WO 2004/014313, published 19 Feb. 2004, mentions combination therapies for treatment of viral diseases, including iminothiazolidinone NS5A-protein-inhibiting anti-HCV compounds in combination with other agents capable of interfering with HCV function.

SUMMARY

The present invention features compounds having Formulae I(a), I(b), II(a) or II(b), tautomers of these compounds, and pharmaceutically acceptable salts of these compounds or tautomers. These compounds, tautomers or salts can be used, either individually or in combination with other drugs or agents, to inhibit the replication of HCV or other viruses. These compounds, tautomers or salts can also be used, either individually or in combination with other drugs or agents, to disrupt functions of HCV or other viruses.

The present invention also features compositions that comprise the compounds, tautomers or salts of the present invention. A composition of the present invention can include one or more compounds, tautomers or salts of the present invention. A composition of the present invention can also include one or more other antiviral or therapeutic agents.

In addition, the present invention features methods of using the compounds, tautomers or salts of the present invention, or compositions comprising the same, to inhibit the replication of HCV or other viruses. These methods comprise contacting HCV or another virus, or cells infected with HCV or said another virus, with an effective amount of a compound, tautomer or salt of the present invention, thereby inhibiting the replication of HCV or said another virus.

The present invention further features methods of using the compounds, tautomers or salts of the present invention, or compositions comprising the same, to inhibit the proliferation or transmission of HCV or other viruses. These methods comprise contacting HCV or another virus, or contacting cells infected with HCV or another virus, with an effective amount of a compound, tautomer or salt of the present invention, thereby inhibiting the proliferation or transmission of HCV or said another virus.

Moreover, the present invention features methods of using the compounds, tautomers or salts of the present invention, or compositions comprising the same, to treat HCV or other viral infections. These methods comprise administering to a patient in need of such treatment an effective amount of a compound, tautomer or salt of the present invention, thereby reducing the blood or tissue level of HCV or other viruses in the patient.

The present invention also features use of the compounds, tautomers or salts of the present invention for the manufacture of medicaments for the treatment of HCV or other viral infections.

Furthermore, the present invention features processes of making the compounds, tautomers or salts of the present invention, and intermediates employed in these processes.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The following description is exemplary in nature and is not intended to limit the present disclosure, application, or uses.

Compounds

The present invention features compounds having Formulae I(a) or I(b), tautomers thereof, and pharmaceutically acceptable salts of the compounds or tautomers,

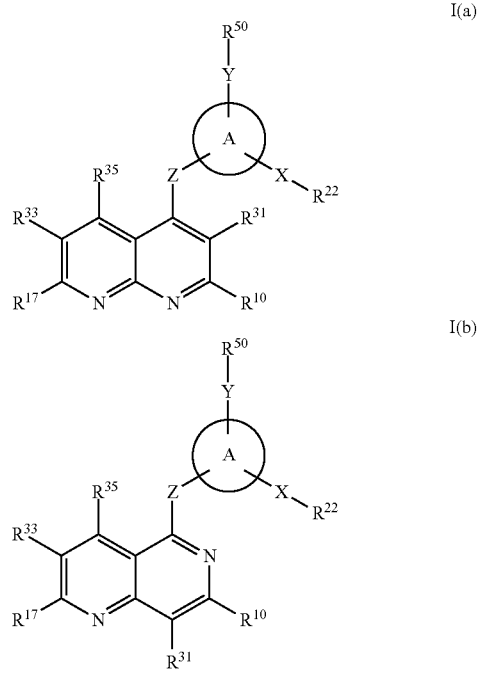

wherein:

Z is —$NR^{41}$—;

A is carbocyclyl or heterocyclyl, and is optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=$NR_S$)$R_{S''}$, -$L_S$-S(O)$R_S$, -$L_S$-SO$_2R_S$, -$L_S$-C(O)N($R_S R_{S'}$), -$L_S$-N($R_S$)C(O)$R_{S''}$, -$L_S$-C(=$NR_S$)N($R_S R_{S''}$), -$L_S$-N($R_{S'}$)C(=$NR_S$)$R_{S''}$, -$L_S$-N($R_S$)C(O)N($R_S R_{S''}$), -$L_S$-N($R_S$)SO$_2R_{S''}$, -$L_S$-SO$_2$N($R_S R_{S'}$), and -$L_S$-N($R_S$)SO$_2$N($R_S R_S''$);

$R^{10}$, $R^{17}$, $R^{31}$, $R^{33}$, $R^{35}$ and $R^{41}$ are each independently selected at each occurrence from the group consisting of hydrogen, halogen, oxo, thioxo, hydroxy, mercapto, nitro, cyano, amino, carboxy, formyl, phosphate, azido, alkyl, alkenyl, alkynyl, carbocyclyl, heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=$NR_S$)$R_{S''}$, -$L_S$-S(O)$R_S$, -$L_S$-SO$_2R_S$, -$L_S$-C(O)N($R_S R_{S'}$), -$L_S$-N($R_S$)C(O)$R_{S''}$, -$L_S$-C(=$NR_S$)N($R_S R_{S''}$), -$L_S$-N($R_{S'}$)C(=$NR_S$)$R_{S''}$, -$L_S$-N($R_S$)C(O)N($R_S R_{S''}$), -$L_S$-N($R_S$)SO$_2R_{S''}$, -$L_S$-SO$_2$N($R_S R_{S'}$), -$L_S$-N($R_S$)SO$_2$N($R_S R_{S''}$), -$L_E$-Q-$L_{E'}$-(C$_3$-C$_{18}$carbocyclyl) and -$L_E$-Q-$L_{E'}$-(M$_3$-M$_{18}$heterocyclyl);

X is selected from the group consisting of a bond, -$L_S$-O—, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N($R_S$)—, -$L_S$-N($R_S$)C(O)N($R_{S'}$)—, -$L_S$-C(=$NR_S$)N($R_{S'}$)—, -$L_S$-N($R_{S'}$)C(=$NR_S$)—, -$L_S$-S(O)—, -$L_S$-SO$_2$—, -$L_S$-C(O)O— and -$L_S$-OC(O)—;

$R^{22}$ is carbocyclyl, heterocyclyl, carbocyclylalkyl or heterocyclylalkyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=$NR_S$)$R_{S''}$, -$L_S$-S(O)$R_S$, -$L_S$-SO$_2R_S$, -$L_S$-OS(O)$R_S$, -$L_S$-OSO$_2R_S$, -$L_S$-C(O)N($R_S R_{S'}$), -$L_S$-N($R_S$)C(O)$R_{S''}$, -$L_S$-C(=$NR_S$)N($R_S R_{S''}$), -$L_S$-N($R_{S'}$)C(=$NR_S$)$R_{S''}$, -$L_S$-N($R_S$)C(O)N($R_S R_{S''}$), -$L_S$-N=C($NR_S R_{S'}$)(N$R_S R_{S'}$), -$L_S$-N($R_S$)SO$_2R_{S''}$, -$L_S$-SO$_2$N($R_S R_{S'}$), -$L_S$-N($R_S$)SO$_2$N($R_S R_{S''}$), -$L_E$-Q-$L_{E'}$-(C$_3$-C$_{18}$carbocyclyl) and -$L_E$-Q-$L_{E'}$-(M$_3$-M$_{18}$heterocyclyl); or $R^{22}$ is alkyl, alkenyl or alkynyl, and is optionally substituted with one or more $R^{26}$; or $R^{22}$ is hydrogen;

Y is selected from the group consisting of a bond, -$L_S$-O—, -$L_S$-C(O)—, -$L_S$-S(O)$_2$—, -$L_S$-S(O)—, -$L_S$-OS(O)$_2$—, -$L_S$-OS(O)—, -$L_S$-C(O)O—, -$L_S$-OC(O)—, -$L_S$-OC(O)O—, -$L_S$-C(O)N($R^{15}$)—, -$L_S$-N($R^{15}$)C(O)—, -$L_S$-C(O)N($R^{15}$)O—, -$L_S$-N($R^{15}$)C(O)O—, -$L_S$-C(O)N($R^{15}$)N($R^{15'}$)—, -$L_S$-S—, -$L_S$-C(S)—, -$L_S$-C(S)O—, -$L_S$-OC(S)—, -$L_S$-C(S)N($R^{15}$)—, -$L_S$-N($R^{15}$)—, -$L_S$-N($R^{15}$)C(S)—, -$L_S$-N($R^{15}$)S(O)—, -$L_S$-N($R^{15}$)S(O)$_2$—, -$L_S$-S(O)$_2$N($R^{15}$)—, -$L_S$-S(O)N($R^{15}$)—, -$L_S$-C(S)N($R^{15}$)O—, and -$L_S$-C(S)N($R^{15}$)N($R^{15'}$)—, wherein $R^{15}$ and $R^{15'}$ are each independently selected at each occurrence from the group consisting of hydrogen, alkyl, alkenyl and alkynyl;

$R^{50}$ is -$L^1$-$A^1$, wherein $A^1$ is selected from the group consisting of carbocyclyl, heterocyclyl, alkyl, alkenyl and alkynyl, and $L^1$ is selected from the group consisting of a bond, alkylene, alkenylene and alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=$NR_S$)$R_{S''}$, -$L_S$-S(O)$R_S$, -$L_S$-SO$_2R_S$, -$L_S$-C(O)N($R_S R_{S'}$), -$L_S$-N($R_S$)C(O)$R_{S''}$, -$L_S$-C(=$NR_S$)N($R_S R_{S''}$), -$L_S$-N($R_{S'}$)C(=$NR_S$)$R_{S''}$, -$L_S$-N($R_S$)C(O)N($R_S R_{S''}$), -$L_S$-N($R_S$)SO$_2R_{S''}$, -$L_S$-SO$_2$N($R_S R_{S'}$), -$L_S$-N($R_S$)SO$_2$N($R_S R_{S''}$), -$L_E$-Q-$L_{E'}$-(C$_3$-C$_{18}$carbocyclyl) and -$L_E$-Q-$L_{E'}$-(M$_3$-M$_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, alkoxy, thioalkoxy, alkylcarbonyl, alkoxycarbonyl, alkylcarbonyloxy, alkylamino, alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=$NR_S$)$R_{S''}$, -$L_S$-S(O)$R_S$, -$L_S$-SO$_2R_S$, -$L_S$-C(O)N($R_S R_{S'}$), -$L_S$-N($R_S$)C(O)$R_{S''}$, -$L_S$-C(=$NR_S$)N($R_S R_{S''}$), -$L_S$-N($R_{S'}$)C(=$NR_S$)$R_{S''}$, -$L_S$-N($R_S$)C(O)N($R_S R_{S''}$), -$L_S$-N($R_S$)SO$_2R_{S''}$, -$L_S$-SO$_2$N($R_S R_{S'}$), -$L_S$-N($R_S$)SO$_2$N($R_S R_{S''}$), carbocyclyl, heterocyclyl, carbocyclylalkyl, heterocyclylalkyl, -$L_E$-Q-$L_{E'}$-(C$_3$-C$_{18}$carbocyclyl) and -$L_E$-Q-$L_{E'}$-(M$_3$-M$_{18}$heterocyclyl);

$L_S$ is independently selected at each occurrence from the group consisting of a bond, alkylene, alkenylene and alkynylene;

$R_S$, $R_{S'}$ and $R_{S''}$ are each independently selected at each occurrence from the group consisting of hydrogen, alkyl, alkenyl, alkynyl, alkoxy, thioalkoxy, alkoxyalkyl, alkoxyalkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl;

$L_E$ and $L_{E'}$ are each independently selected at each occurrence from the group consisting of a bond, alkylene, alkenylene, alkynylene, -alkylene-O-alkylene-, -alkylene-S-alkylene-, -alkylene-NC(O)-alkylene-, and -alkylene-C(O)N-alkylene-;

Q is independently selected at each occurrence from the group consisting of a bond, alkylene, alkenylene, alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, C(=$NR_S$)N($R_{S'}$)—, —N($R_{S'}$)C(=$NR_S$)—, —S(O)—, —SO$_2$—, —O—SO$_2$—, —SO$_2$—O—, —O—S(O)—, —S(O)—O—, —C(O)O— and —OC(O)—;

$R^{10}$, $R^{15}$, $R^{15'}$, $R^{17}$, $R^{18}$, $R^{26}$, $R^{30}$, $R^{31}$, $R^{33}$, $R^{35}$, $R^{38}$ and $R^{41}$ are each independently optionally substituted at each occurrence with at least one substituent selected from the group consisting of halogen, oxo, thioxo, hydroxy, mercapto, nitro, cyano, amino, carboxy, formyl, phosphate, alkoxy, alkylamino, alkoxycarbonyl, and azido; and each C$_3$-C$_{18}$carbocyclyl and M$_3$-M$_{18}$heterocyclyl moiety in -$L_E$-Q-$L_{E'}$-(C$_3$-C$_{18}$carbocyclyl) and -$L_E$-Q-$L_{E'}$-(M$_3$-M$_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, alkyl, alkenyl, alkynyl, alkoxy, thioalkoxy, alkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, carbocyclyloxy, heterocyclyloxy, carbocycloalkoxy, heterocycloalkoxy, carbocycloalkoxycarbonyl, heterocycloalkoxycarbonyl, and alkoxycarbonylaminoalkyl.

In one embodiment, the present invention features compounds having Formulae I(a) or I(b), tautomers thereof, and pharmaceutically acceptable salts of the compounds or tautomers, wherein:

Z is $-NR^{41}-$;

A is carbocyclyl or heterocyclyl, and is optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), and -$L_S$-N($R_S$)SO$_2$N($R_{S'} R_{S''}$);

$R^{10}$, $R^{17}$, $R^{31}$, $R^{33}$, $R^{35}$ and $R^{41}$ are each independently selected at each occurrence from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_3$-$C_6$-carbocyclyl, $M_3$-$M_6$heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl);

X is selected from the group consisting of a bond, -$L_S$-O—, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N($R_S$)—, -$L_S$-N($R_S$)C(O)N($R_{S'}$)—, -$L_S$-C(=N$R_S$)N($R_{S'}$)—, -$L_S$-N($R_{S'}$)C(=N$R_S$)—, -$L_S$-S(O)—, -$L_S$-SO$_2$—, -$L_S$-C(O)O— and -$L_S$-OC(O)—;

$R^{22}$ is carbocyclyl, heterocyclyl, carbocyclyl$C_1$-$C_6$alkyl or heterocyclyl$C_1$-$C_6$alkyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-OS(O)$R_S$, -$L_S$-OSO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N=C(N$R_S R_{S'}$)(N$R_{S''} R_{S'''}$), -$L_S$-N($R_S$)SO$_2 R_{S'}$, -$L_S$-SO$_2$N($R_S R_{S'}$), -$L_S$-N($R_S$)SO$_2$N($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl); or $R^{22}$ is $C_1$-$C_6$alkyl, $C_2$-$C_6$alkenyl or $C_2$-$C_6$alkynyl, and is optionally substituted with one or more $R^{26}$; or $R^{22}$ is hydrogen;

Y is selected from the group consisting of a bond, -$L_S$-O—, -$L_S$-C(O)—, -$L_S$-S(O)$_2$—, -$L_S$-S(O)—, -$L_S$-OS(O)$_2$—, -$L_S$-OS(O)—, -$L_S$-C(O)O—, -$L_S$-OC(O)—, -$L_S$-OC(O)O—, -$L_S$-C(O)N($R^{15}$)—, -$L_S$-N($R^{15}$)C(O)—, -$L_S$-C(O)N($R^{15}$)N($R^{15'}$)O—, -$L_S$-N($R^{15}$)C(O)O—, -$L_S$-OC(O)N($R^{15}$)N($R^{15'}$)—, -$L_S$-S—, -$L_S$-C(S)—, -$L_S$-C(S)O—, -$L_S$-OC(S)—, -$L_S$-C(S)N($R^{15}$)—, -$L_S$-N($R^{15}$)—, -$L_S$-N($R^{15}$)C(S)—, -$L_S$-N($R^{15}$)S(O)—, -$L_S$-N($R^{15}$)S(O)$_2$—, -$L_S$-S(O)$_2$N($R^{15}$)—, -$L_S$-S(O)N($R^{15}$)—, -$L_S$-C(S)N($R^{15}$)O—, and -$L_S$-C(S)N($R^{15}$)N($R^{15'}$)—, wherein $R^{15}$ and $R^{15'}$ are each independently selected at each occurrence from the group consisting of hydrogen$C_1$-$C_6$alkyl, $C_2$-$C_6$alkenyl and $C_2$-$C_6$alkynyl;

$R^{50}$ is -$L^1$-$A^1$, wherein $A^1$ is selected from the group consisting of carbocyclyl, heterocyclyl, $C_1$-$C_6$alkyl, $C_2$-$C_6$alkenyl and $C_2$-$C_6$alkynyl, and $L^1$ is selected from the group consisting of a bond, $C_1$-$C_6$alkylene, $C_2$-$C_6$alkenylene and $C_2$-$C_6$alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N($R_{S'} R_{S''}$), carbocyclyl, heterocyclyl, carbocyclyl$C_1$-$C_6$alkyl, heterocyclyl$C_1$-$C_6$alkyl, -$L_E$-Q-$L_{E'}$-($C_3$-$C_{18}$carbocyclyl) and -$L_E$-Q-$L_{E'}$-($M_3$-$M_{18}$heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkylene, $C_2$-$C_6$alkenylene and $C_2$-$C_6$alkynylene, $C_1$-$C_6$alkylene-O—$C_1$-$C_6$alkylene-, —$C_1$-$C_6$alkylene-S—$C_1$-$C_6$alkylene-, —$C_1$-$C_6$alkylene-NC(O)—$C_1$-$C_6$alkylene-, and —$C_1$-$C_6$alkylene-C(O)N—$C_1$-$C_6$alkylene-;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N $(R_S)$—, —N($R_S$)C(O)O—, —C(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—;

$R^{10}$, $R^{15}$, $R^{15'}$, $R^{17}$, $R^{18}$, $R^{26}$, $R^{30}$, $R^{31}$, $R^{33}$, $R^{35}$, $R^{38}$ and $R^{41}$ are each independently optionally substituted at each occurrence with at least one substituent selected from the group consisting of halogen, oxo, thioxo, hydroxy, mercapto, nitro, cyano, amino, carboxy, formyl, phosphate, $C_1$-$C_6$alkoxy, $C_1$-$C_6$alkylamino, $C_1$-$C_6$alkoxycarbonyl, and azido; and each $C_3$-$C_{18}$carbocyclyl and $M_3$-$M_{18}$heterocyclyl moiety in -$L_E$-Q-$L_{E'}$-($C_3$-$C_{18}$carbocyclyl) and -$L_E$-Q-$L_{E'}$-($M_3$-$M_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, $C_3$-$C_7$carbocyclyloxy, $M_3$-$M_7$heterocyclyloxy, $C_3$-$C_7$carbocyclo$C_1$-$C_6$alkoxy, $M_3$-$M_7$heterocyclo$C_1$-$C_6$alkoxy, $C_3$-$C_7$carbocyclo$C_1$-$C_6$alkoxycarbonyl, $M_3$-$M_7$heterocyclo$C_1$-$C_6$alkoxycarbonyl, and $C_1$-$C_6$alkoxycarbonylamino$C_1$-$C_6$alkyl.

In one example of this embodiment, A is a $C_5$-$C_6$carbocyclyl optionally substituted with one or more $R^{18}$.

In another example of this embodiment, A is a $M_5$-$M_6$heterocyclyl optionally substituted with one or more $R^{18}$.

In yet another example of this embodiment, Y is -$L_S$-O—, -$L_S$-S—, -$L_S$-C(O)N($R^{15}$)— or -$L_S$-N($R^{15}$)C(O)—, $R^{15}$ is hydrogen, $C_1$-$C_6$alkyl, $C_2$-$C_6$alkenyl or $C_2$-$C_6$alkynyl, and $L^1$ is $C_1$-$C_6$alkylene optionally substituted with one or more $R^{38}$, wherein $A^1$ is a $C_4$-$C_6$carbocyclyl or $M_4$-$M_6$heterocyclyl and is optionally substituted with one or more $R^{30}$.

In still yet another example of this embodiment, Y is -$L_S$-O—, -$L_S$-S—, -$L_S$-C(O)N($R^{15}$)— or -$L_S$-N($R^{15}$)C(O)—, $R^{15}$ is hydrogen, $C_1$-$C_6$alkyl, $C_2$-$C_6$alkenyl or $C_2$-$C_6$alkynyl, and $L^1$ is a bond (i.e., $R^{50}$ is -$A^1$), wherein $A^1$ is a $C_4$-$C_6$carbocyclyl or $M_4$-$M_6$heterocyclyl and is optionally substituted with one or more $R^{30}$.

In a further example of this embodiment, Y is -$L_S$-O—, -$L_S$-S—, -$L_S$-C(O)N($R^{15}$)— or -$L_S$-N($R^{15}$)C(O)—, $R^{15}$ is hydrogen, $C_1$-$C_6$alkyl, $C_2$-$C_6$alkenyl or $C_2$-$C_6$alkynyl, and $L^1$ is a bond (i.e., $R^{50}$ is -$A^1$) or $C_1$-$C_6$alkylene optionally substituted with one or more $R^{38}$, wherein $A^1$ is a bicyclic ring (e.g., a fused bicyclic ring or a bridged bicyclic ring) which has from 6 to 14 ring atoms and is optionally substituted with one or more $R^{30}$.

In another example of this embodiment, X is —O— or —S—, and $R^{22}$ is $C_5$-$C_6$carbocyclyl or $M_5$-$M_6$heterocyclyl and is optionally substituted with one or more $R^{26}$.

In still another example of this embodiment, X is —S— or —O—, and $R^{22}$ is

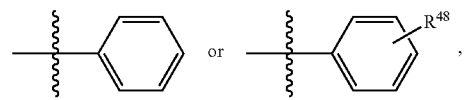

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy, and $R^{22}$ (e.g., $R^{48}$ or the phenyl ring in $R^{22}$) is optionally substituted with one or more $R^{26}$.

In another example of this embodiment, A is $C_5$-$C_6$carbocyclyl or $M_5$-$M_6$heterocyclyl and is optionally substituted with one or more $R^{18}$, wherein:

X is —O— or —S—;

$R^{22}$ is

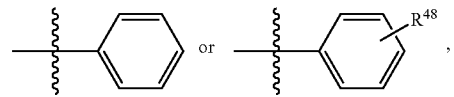

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy, and $R^{22}$ (e.g., $R^{48}$ or the phenyl ring in $R^{22}$) is optionally substituted with one or more $R^{26}$;

Y is -$L_S$-O—, -$L_S$-S—, -$L_S$-C(O)N($R^{15}$)— or -$L_S$-N($R^{15}$)C(O)—, wherein $R^{15}$ is hydrogen, $C_1$-$C_6$alkyl, $C_2$-$C_6$alkenyl or $C_2$-$C_6$alkynyl;

$R^{50}$ is -$L^1$-$A^1$, wherein:

$L^1$ is $C_1$-$C_6$alkylene optionally substituted with one or more $R^{38}$, and $A^1$ is $C_4$-$C_6$carbocyclyl or $M_4$-$M_6$heterocyclyl and is optionally substituted with one or more $R^{30}$; or $L^1$ is a bond (i.e., $R^{50}$ is -$A^1$), wherein $A^1$ is a $C_4$-$C_6$carbocyclyl or $M_4$-$M_6$heterocyclyl and is optionally substituted with one or more $R^{30}$; or $L^1$ is a bond (i.e., $R^{50}$ is -$A^1$) or $C_1$-$C_6$alkylene optionally substituted with one or more $R^{38}$, wherein $A^1$ is a bicyclic ring (e.g., a fused bicyclic ring or a bridged bicyclic ring) which has from 6 to 14 ring atoms and is optionally substituted with one or more $R^{30}$.

The ring atom(s) in the moiety

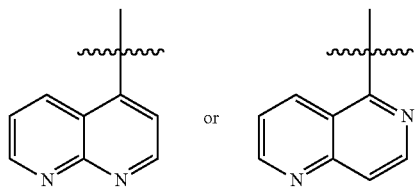

may be further substituted with S or other heteroatoms.

In another embodiment, the present invention features compounds having Formulae II(a) or II(b), tautomers of these compounds, and pharmaceutically acceptable salts of these compounds or tautomers,

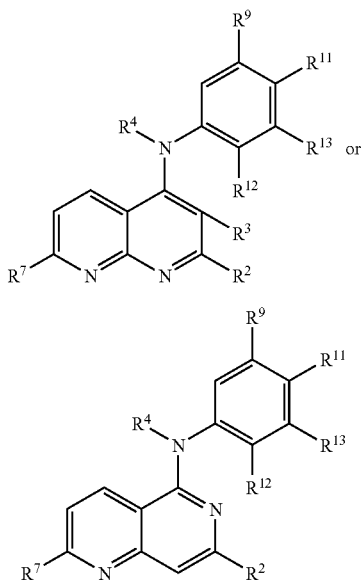

II(a)

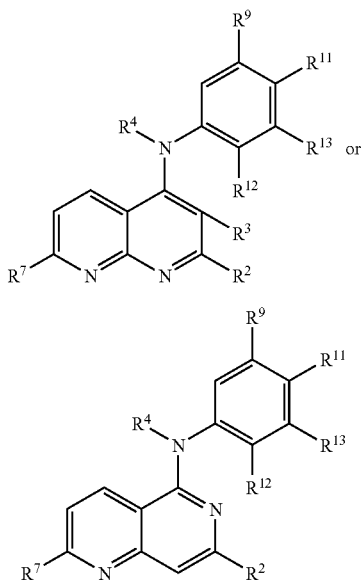

II(b)

wherein:

$R^2$ and $R^3$ are independently selected from the group consisting of hydrogen, alkyl, alkoxycarbonyl, and alkoxyalkylaminocarbonyl;

$R^4$ is selected from the group consisting of hydrogen, alkoxycarbonyl, and alkoxycarbonylalkyl;

$R^7$ is selected from the group consisting of hydrogen, alkyl, haloalkyl, alkoxy, cycloalkyl, alkoxycarbonylalkyl, alkoxycarbonylalkylamino, cyanoalkoxycarbonylalkyl, cyanoalkyl, hydroxyalkyl, morpholino, hydrazino, alkylaminoalkoxy, alkoxyalkylamino, and aryl;

$R^9$ is selected from the group consisting of hydrogen, alkyl, alkoxy, haloalkyl, arylalkylamino, hydroxy, alkoxycarbonylaminoalkyl, alkylcarbonyl, amino, halogen, N-[alkylarylamino(arylsulfanyl)arylalkyl]-N-[(alkoxycarbonyl)alkyl] amino, alkoxyarylalkoxy, haloarylalkoxy, nitroarylalkoxy, cyanoarylalkoxy, aryloxyalkyl, haloaryloxyalkyl, cyanoalkoxy, arylalkoxy, alkylarylalkoxy, haloalkylarylaminocarbonyl, alkylaminoarylaminocarbonyl, arylalkoxy, alkylallyloxy, and alkoxycarbonyl;

$R^{11}$ is selected from the group consisting of hydrogen, hydroxy, haloaryloxy, and alkyl;

$R^{12}$ is selected from the group consisting of hydrogen, arylsulfanyl, arylsulfinyl, aryloxy, mercapto, arylaminocarbonyl, aryl, alkoxyaryl, arylalkoxy, and alkylcarbonylaminoaryl; wherein $R^{12}$ is optionally substituted with one or more substituents independently selected from $R^{16}$;

$R^{16}$ is selected from the group consisting of hydrogen, halogen, alkyl, alkoxy, hydroxy, aminocarbonyl, alkylaminocarbonyl, amino, alkylcarbonylamino, alkylheteroarylcarbonylamino, heteroarylcarbonylamino, hydroxyheteroarylcarbonylamino, hydroxyalkylheteroarylcarbonylamino, heteroarylcarbonylaminoalkylcarbonylamino, heteroarylalkylcarbonylamino, aryloxyarylalkylcarbonylamino, allylaminocarbonyl, alkoxycarbonyl, hydroxyalkyl, arylaminocarbonyl, hydroxyarylaminocarbonyl, alkoxyalkyl, alkoxyarylaminocarbonyl, azidoalkyl, alkylaminoarylsulfonyloxy, alkylsulfonyloxy, arylalkylsulfonyloxy, alkoxycarbonylalkoxy, hydroxycarbonylalkoxy, cycloalkylcarbonylamino, arylalkoxycarbonylheterocyclecarbonylamino, aryloxy, iminoalkyl, alkylthione, arylalkylcarbonylamino, alkylaryloxyalkylcarbonylamino, arylalkoxyalkylcarbonylamino, heteroarylcarbonylaminoalkylcarbonylamino, heteroarylalkylcarbonylamino, alkylcarbonylheterocyclecarbonylamino, amino, aminocarbonyl, alkylaminocarbonyl, hydroxyalkyl, aminoalkyl, alkoxyalkylaminocarbonyl, hydroxyiminoalkyl, heteroaryl substituted with alkyl, and heteroaryl;

$R^{13}$ is selected from the group consisting of hydrogen, halogen, alkyl, alkylcarbonylaminoarylsulfonyl, aminoarylsulfanyl, arylalkoxy, haloarylalkoxy, alkylcarbonylaminoaryloxy, alkylaminoaryloxy, hydroxyaryloxy, alkylaminocarbonylarylalkoxy, and alkylcarbonylaminoarylalkoxy.

In a subset family of this embodiment within Formulae II(a) or II(b), $R^{12}$ is selected from the group consisting of

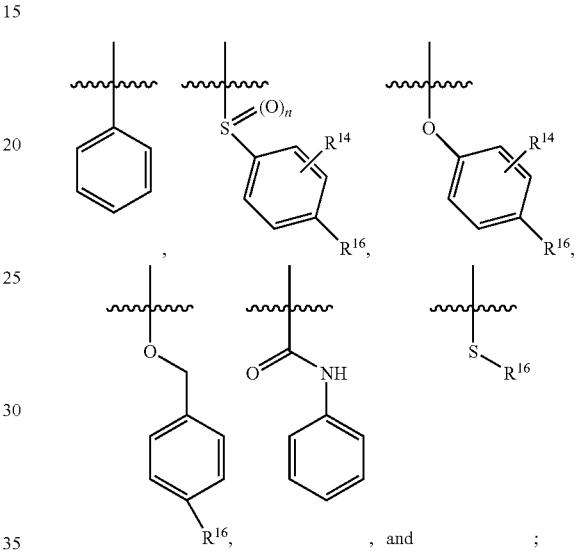

, and ;

n is an integer selected from the group consisting of zero and one;

$R^{14}$ is selected from the group consisting of hydrogen, halogen, alkyl, alkoxy, hydroxy, aminocarbonyl, alkylaminocarbonyl, amino, alkylcarbonylamino, alkylheteroarylcarbonylamino, heteroarylcarbonylamino, hydroxyheteroarylcarbonylamino, hydroxyalkylheteroarylcarbonylamino, heteroarylcarbonylaminoalkylcarbonylamino, heteroarylalkylcarbonylamino, aryloxyarylalkylcarbonylamino, allylaminocarbonyl, alkoxycarbonyl, hydroxyalkyl, arylaminocarbonyl, hydroxyarylaminocarbonyl, alkoxyalkyl, alkoxyarylaminocarbonyl, and azidoalkyl;

$R^{16}$ is selected from the group consisting of hydrogen, halogen, alkyl, alkoxy, hydroxy, aminocarbonyl, alkylaminocarbonyl, amino, alkylcarbonylamino, alkylheteroarylcarbonylamino, heteroarylcarbonylamino, hydroxyheteroarylcarbonylamino, hydroxyalkylheteroarylcarbonylamino, heteroarylcarbonylaminoalkylcarbonylamino, heteroarylalkylcarbonylamino, aryloxyarylalkylcarbonylamino, allylaminocarbonyl, alkoxycarbonyl, hydroxyalkyl, arylaminocarbonyl, hydroxyarylaminocarbonyl, alkoxyalkyl, alkoxyarylaminocarbonyl, azidoalkyl, alkylaminoarylsulfonyloxy, alkylsulfonyloxy, arylalkylsulfonyloxy, alkoxycarbonylalkoxy, hydroxycarbonylalkoxy, cycloalkylcarbonylamino, arylalkoxycarbonylheterocyclecarbonylamino, aryloxy, iminoalkyl, alkylthione, arylalkylcarbonylamino, alkylaryloxyalkylcarbonylamino, arylalkoxyalkylcarbonylamino, heteroarylcarbonylaminoalkylcarbonylamino, heteroarylalkylcarbonylamino, alkylcarbonylheterocyclecarbonylamino, amino, aminocarbonyl, alkylaminocarbonyl, hydroxyalkyl, aminoalkyl, alkoxyalkylaminocarbonyl, hydroxyiminoalkyl, heteroaryl substituted with alkyl, and heteroaryl.

In a further subset of this first embodiment within Formulae II(a) or II(b), $R^2$ and $R^3$ are independently selected from the group consisting of hydrogen, ethoxycarbonyl, 3-N-methoxy-N-methylaminocarbonyl, and methyl;

$R^4$ is selected from the group consisting of hydrogen, t-butoxycarbonyl, and ethoxycarbonylmethyl;

$R^7$ is selected from the group consisting of hydrogen, methyl, ethyl, propyl, butyl, isopropyl, isobutyl, sec-butyl, trifluoromethyl, methoxy, ethoxy, cyclopentyl, hydroxyethyl, butyl, 1,1-bis-(ethoxycarbonyl)methyl, ethoxycarbonylmethylamino, 1,1-bis-(t-butoxycarbonyl), cyano-1-ethyoxy-carbonylmethyl, cyano-1-t-butoxy-carbonylmethyl, cyanomethyl, morpholinyl, ethoxycarbonylethyl, hydrazino, N,N-dimethylaminoethoxy, methoxyethylamino, and cyano-1-ethoxy-carbonylmethyl;

$R^9$ is selected from the group consisting of hydrogen, methyl, methoxy, phenyl, trifluoromethyl, phenylmethylamino, hydroxy, t-butoxy-carbonylaminomethyl, carbonylamino, methylcarbonyl, amino, bromo, chloro, fluoro, methyl[1,8]naphthyridin-4-ylamino-(2-phenylsulfanylphen-5-ylmethyl)amino-(N-t-butoxy-carbonyl-N-methyl), methoxyphenylmethoxy, bromophenylmethoxy, nitrophenylmethoxy, cyanophenylmethoxy, trifluoromethyl, phenoxymethyl, bromophenoxymethyl, cyanomethoxy, phenylmethoxy, methylallyloxy, propoxy, methylphenylmethoxy, methylphenylmethoxy, fluoro-3-methylphenylaminocarbonyl, trifluoromethylphenylaminocarbonyl, trifluoromethylphenylaminocarbonyl, N,N-dimethylaminophenylaminocarbonyl, fluorophenylmethoxy, and chlorophenylmethoxy;

$R^{11}$ is selected from the group consisting of hydrogen, hydroxy, chlorophenoxy, and methyl;

$R^{12}$ is as described above in relation to Formulae II(a) and II(b);

$R^{13}$ is selected from the group consisting of hydrogen, chloro, methyl, methylcarbonylaminophenylsulfanyl, aminophenylsulfanyl, phenylmethoxy, bromophenylmethoxy, methylcarbonylaminophenoxy, N,N-dimethylaminophenoxy, hydroxyphenoxy, and methylaminocarbonylphenoxy;

$R^{14}$ is selected from the group consisting of hydrogen, fluoro, methyl, methoxy, hydroxy, aminocarbonyl, N-methylaminocarbonyl, N,N-dimethylaminocarbonyl, amino, t-butylcarbonylamino, 2,6-dimethylfuranyl)carbonylamino, thienylcarbonylamino, hydroxypyridinyylcarbonylamino, (2-hydroxy-6-methylpyridinyl)carbonylamino, (3-pyrazinyl)carbonylamino, furanylcarbonylaminomethylcarbonylamino, (3-thienyl)propylcarbonylamino, (3-phenoxy)phenylmethylcarbonylamino, N-allylaminocarbonyl, ethoxycarbonyl, 1-hydroxyethyl, aminocarbonyl, ethylaminocarbonyl, phenylaminocarbonyl, hydroxyphenylaminocarbonyl, propylaminocarbonyl, hydroxymethyl, hydroxyethyl, azidoethyl, and N,N-dimethylaminocarbonyl;

$R^{16}$ is selected from the group consisting of hydrogen, hydroxy, methylcarbonylamino, methyl, isopropyl, fluoro, methoxy, ethoxy, propoxy, isopropoxy, N,N-dimethylaminonaphth-1-ylsulfonyloxy, ethylsulfonyloxy, isopropylsulfonyloxy, methylsulfonyloxy, benzylsulfonyloxy, ethoxycarbonylmethoxy, hydroxycarbonylmethoxy, t-butylcarbonylamino, cyclopropylcarbonylamino, benzyloxycarbonylpyrrolidinylcarbonylamino, phenoxy, methylcarbonylamino, iminoethyl, thionoethyl, (S)-1-phenylpropylcarbonylamino, methylphenoxymethylcarbonylamino, (R)-1-phenyl-1-methoxymethylcarbonylamino, (S)-1-phenyl-1-methoxymethylcarbonylamino, furanylcarbonylaminomethylcarbonylamino, thienylpropylcarbonylamino, methylcarbonylpiperidinylcarbonylamino, amino, aminocarbonyl, N-methylaminocarbonyl, ethoxycarbonylmethoxy, isopropylsulfonyloxy, methylsulfonyloxy, ethylsulfonyloxy, phenylmethylsulfonyloxy, methylcarbonylamino, N-methylaminocarbonyl, hydroxymethyl, aminoethyl, methoxyethylaminocarbonyl, propylaminocarbonyl, N-methoxy-N-methylaminocarbonyl, N,N-diethylaminocarbonyl, N-(2-methoxyethyl)aminocarbonyl, N-ethyl-N-methylaminocarbonyl, N-hydroxy-1-iminoethyl, hydroxyethyl, aminomethyl, N,N-dimethylamino-carbonyl, 2,6-dimethylfuranyl, 1H-[1,2,4]triazolyl, and pyridinyl.

Salts of the Compounds of this Invention

The compounds of the present invention, or tautomers thereof, can be used in the form of salts. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient, the salt preferably is pharmaceutically acceptable. Pharmaceutically acceptable salts include, but are not limited to, salts commonly used to form alkali metal salts and/or to form addition salts of free acids or free bases. In general, these salts typically may be prepared by conventional means with a compound of this invention by reacting, for example, the appropriate acid or base with the compound.

Pharmaceutically acceptable acid addition salts of the compounds of this invention may be prepared from an inorganic or organic acid. Examples of suitable inorganic acids include hydrochloric, hydrobromic acid, hydroionic, nitric, carbonic, sulfuric, and phosphoric acid. Suitable organic acids generally include, for example, aliphatic, cycloaliphatic, aromatic, araliphatic, heterocyclyl, carboxyic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically acceptable base addition salts of the compounds of this invention include, for example, metallic salts and organic salts. Preferred metallic salts include, but are not limited to, alkali metal (group Ia) salts, alkaline earth metal (group IIa) salts, and other physiological acceptable metal salts. Such salts may be made from aluminum, calcium, lithium, magnesium, potassium, sodium, and zinc. Non-limiting examples of preferred organic salts can be made from tertiary amines and quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), aralkyl halides (e.g., benzyl and phenethyl bromides), and others.

Solvates, Prodrugs, and Isomers

The compounds of the present invention, tautomers thereof, and their salts, may also exist in the form of solvates with water, for example hydrates, or with organic solvents such as methanol, ethanol or acetonitrile to form, respectively, a methanolate, ethanolate or acetonitrilate. The compounds of the present invention may exist in each form of solvate or mixtures thereof.

In one aspect, the compounds, tautomers or salts of the present invention may be in the form of prodrugs. Some are aliphatic or aromatic esters derived from acidic groups on compounds of this invention. Others are aliphatic or aromatic esters of hydroxyl or amino groups on compounds of this invention. The present invention also features phosphate prodrugs of hydroxyl groups on the compounds of this invention.

The compounds of the invention may comprise asymmetrically substituted carbon atoms known as chiral centers. These chiral centers are designated as "R" or "S" depending on the configuration of substituents around the chiral carbon atom. The terms "R" and "S" used herein are configurations as defined in Nomenclature of Organic Chemistry, Section E: Stereochemistry, Recommendations 1974, PURE APPL. CHEM., 45:11-30 (1976). The compounds of this invention may exist, without limitation, as single stereoisomers (e.g., single enantiomers or single diastereomer), mixtures of stereoisomers (e.g. any mixture of enantiomers or diastereomers), or racemic mixtures. All such single stereoisomers, mixtures and racemates are encompassed within the scope of the invention. Compounds identified herein as single stereoisomers are meant to describe compounds that are present in a form that is substantially free from other stereoisomers (e.g., other enantiomers or diastereomers). By "substantially free," it means that at least 80% of the compound in a composition is the desired stereoisomer; preferably, at least 90% of the compound in a composition is the desired stereoisomer; and more preferably, at least 95%, 96%, 97%, 98% or 99% of the compound in a composition is the desired stereoisomer. Where the stereochemistry of the chiral carbon(s) present in a chemical structure is not specified, the chemical structure is intended to encompass compounds containing either stereoisomer of each chiral center present in the chemical structure.

Individual stereoisomers of the compounds of this invention can be prepared using many methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished on chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

A compound of this invention may possess one or more unsaturated carbon-carbon double bonds. All double bond isomers, such as the cis (Z) and trans (E) isomers, and mixtures thereof are intended to be encompassed within the scope of a recited compound unless otherwise specified. In addition, where a compound exists in various tautomeric forms, a recited compound is not limited to any one specific tautomer, but rather is intended to encompass all tautomeric forms.

Certain compounds of the invention may exist in different stable conformational forms which may be separable. Torsional asymmetry due to restricted rotations about an asymmetric single bond, for example because of steric hindrance or ring strain, may permit separation of different conformers. The compounds of the invention includes each conformational isomer of these compounds and mixtures thereof.

Certain compounds of the invention may also exist in zwitterionic form and the invention includes each zwitterionic form of these compounds and mixtures thereof.

DEFINITIONS

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms. Certain compounds are described herein using general formulas that include variables (e.g., $R^{17}$, $A^1$, $L^1$, X, Y, or Z). Unless otherwise specified, each variable within such a formula is defined independently of any other variable, and any variable that occurs more than one time in a formula is defined independently at each occurrence. If substituents are described as being "independently selected" from a group, each substituent is selected independently from the other. Each substituent therefore can be identical to or different from the other substituent(s).

The number of carbon atoms in a hydrocarbyl substituent can be indicated by the prefix "$C_x$-$C_y$," where x is the minimum and y is the maximum number of carbon atoms in the substituent. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms. A prefix attached to a multiple-component substituent only applies to the first component that immediately follows the prefix. To illustrate, the term "alkylaryl" contains two components: alkyl and aryl. Thus, for example, $C_1$-$C_6$alkylaryl refers to a $C_1$-$C_6$alkyl appended to the parent molecular moiety through an aryl group. Likewise, alkyl$C_6$-$C_{10}$aryl refers to an alkyl group appended to the parent molecular moiety through a $C_6$-$C_{10}$aryl group. Similarly, the prefix "halo" on haloalkoxyalkyl indicates that the alkoxy component is substituted with one or more halogen radicals, while the prefix "halo" on alkoxyhaloalkyl indicates that the alkyl component is substituted with one or more halogen radicals.

When words are used to describe a linking element between two other elements of a depicted chemical structure, the leftmost-described component of the linking element is the component that is bound to the left element in the depicted structure. To illustrate, if the chemical structure is X-L-Y and L is described as methylarylethyl, then the chemical would be X-methyl-aryl-ethyl-Y.

If a linking element in a depicted structure is a bond, then the left element in the depicted structure is bound directly to the right element in the depicted structure. For example, if a chemical structure is depicted as X-L-Y and L is selected as a bond, then the chemical structure would be X—Y. For another example, if a chemical moiety is depicted as -L-X and L is selected as a bond, then the chemical moiety would be —X. For yet another example, if a chemical structure is depicted as X-$L_1$-$L_2$-Y, X-$L_1$-$L_2$-$L_3$-Y or X-$L_1$-$L_2$-....-$L_N$-Y, and $L_1$, $L_2$, $L_3$, ... $L_N$ are selected as bonds, then the chemical structure would be X—Y.

When a chemical formula is used to describe a substituent, the dash on the right (or left) side of the formula indicates the portion of the substituent that has the free valence(s).

If a substituent is described as being "substituted," a non-hydrogen radical is in the place of one or more hydrogen radials on a carbon, nitrogen or oxygen of the substituent. Thus, for example, a substituted alkyl substituent is an alkyl substituent wherein at least one non-hydrogen radical is in the place of a hydrogen radical(s) on the alkyl substituent. To illustrate, monofluoroalkyl is alkyl substituted with one fluoro radical, and difluoroalkyl is alkyl substituted with two fluoro radicals. It should be recognized that if there are two or more substitutions on a substituent, each of the non-hydrogen radicals may be identical or different unless otherwise stated.

A substituent is "substitutable" if it comprises at least one carbon, nitrogen or oxygen atom that is bonded to one or more hydrogen atoms.

If a substituent is described as being "optionally substituted", the substituent may be either substituted or not substituted. If a substituent is described as being optionally substituted with up to a particular number of non-hydrogen radicals, that substituent may be either not substituted, or substituted by up to that particular number of non-hydrogen radicals or by up to the maximum number of substitutable positions on the substituent, whichever is less. Thus, for example, if a substituent is described as a heteroaryl optionally substituted with up to three non-hydrogen radicals, then any heteroaryl with less than three substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

The term "alkenyl" (alone or in combination with another term(s)) means a straight- or branched-chain hydrocarbyl substituent containing one or more double bonds and typically from 2 to 20 carbon atoms, more typically from 2 to 8 carbon atoms, and even more typically from 2 to 6 carbon atoms. Each carbon-carbon double bond may have either cis or trans geometry within the alkenyl moiety, relative to groups substituted on the double bond carbons. Non-limiting examples of such substituents include ethenyl (vinyl), 2-propenyl, 3-propenyl, 1,4-pentadienyl, 1,4-butadienyl, 1-butenyl, 2-butenyl, and 3-butenyl.

The term "alkenylene" (alone or in combination with another term(s)) refers to a divalent unsaturated hydrocarbyl group which may be linear or branched and which has at least one carbon-carbon double bond. An alkenylene group typically contains 2 to 20 carbon atoms, more typically from 2 to 8 carbon atoms, and even more typically from 2 to 6 carbon atoms. Non-limiting examples of alkenylene groups include —C(H)=C(H)—, —C(H)=C(H)—CH$_2$—, —C(H)=C(H)—CH$_2$—CH$_2$—, —CH$_2$—C(H)=C(H)—CH$_2$—, —C(H)=C(H)—CH(CH$_3$)—, and —CH$_2$—C(H)=C(H)—CH(CH$_2$CH$_3$)—.

The term "alkoxy" (alone or in combination with another term(s)) refers to an alkyl group appended to the parent molecular moiety through an oxy moiety (i.e., —O-alkyl). Non-limiting examples of such a substituent include methoxy (—O—CH$_3$), ethoxy, n-propoxy, isopropoxy, n-butoxy, isobutoxy, sec-butoxy, and tert-butoxy.

The term "alkoxyalkyl" (alone or in combination with another term(s)) refers to an alkoxy group appended to the parent molecular moiety through an alkylene group. Non-limiting examples of alkoxyalkyl include tert-butoxymethyl, 2-ethoxyethyl, 2-methoxyethyl, and methoxymethyl.

The term "alkoxycarbonyl" (alone or in combination with another term(s)) refers to an alkoxy group appended to the parent molecular moiety through a carbonyl group (i.e., —C(O)—O-alkyl). Representative examples of alkoxycarbonyl include, but are not limited to, methoxycarbonyl, ethoxycarbonyl

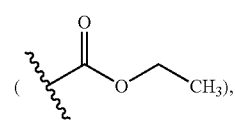

and tert-butoxycarbonyl.

The term "alkoxycarbonylamino" (alone or in combination with another term(s)) refers to N(R$_A$R$_B$)—, where R$_A$ is alkyl-O—C(O)—, and R$_B$ is alkyl-O—C(O)— or hydrogen. R$_A$ and R$_B$ may be identical or different.

The term "alkoxycarbonylaminoalkyl" (alone or in combination with another term(s)) refers to N(R$_A$R$_B$)-alkylene-, where R$_A$ is alkyl-O—C(O)—, and R$_B$ is alkyl-O—C(O)— or hydrogen. R$_A$ and R$_B$ may be identical or different.

The term "alkoxycarbonylalkyl" (alone or in combination with another term(s)) refers to an alkoxycarbonyl group appended to the parent molecular moiety through an alkylene group. Representative examples of alkoxycarbonylalkyl include, but are not limited to, 2-methoxy-2-oxoethyl, 2-ethoxy-2-oxoethyl, 3-methoxy-3-oxopropyl, 3-ethoxy-3-oxopropyl, 4-ethoxy-2-(ethoxycarbonyl)-4-oxobutyl, 5-methoxy-5-oxopentyl, and 6-methoxy-6-oxohexyl.

The term "alkyl" (alone or in combination with another term(s)) means a straight- or branched-chain saturated hydrocarbyl substituent typically containing from 1 to 20 carbon atoms, more typically from 1 to 8 carbon atoms, and even more typically from 1 to 6 carbon atoms. Non-limiting examples of such substituents include methyl, ethyl, n-propyl, isopropyl, n-butyl, isobutyl, sec-butyl, t-butyl, pentyl, iso-amyl, hexyl, and octyl.

The term "alkylamino" (alone or in combination with another term(s)) refers to —NR$_A$R$_B$, wherein R$_A$ is alkyl, and R$_B$ is hydrogen or alkyl. R$_A$ and R$_B$ may be identical or different. For instance, C$_1$-C$_6$alkylamino refers to —NR$_A$R$_B$, wherein R$_A$ is C$_1$-C$_6$alkyl, and R$_B$ is hydrogen or C$_1$-C$_6$alkyl.

The term "alkylaminoalkyl" (alone or in combination with another term(s)) refers to N(R$_A$R$_B$)-alkylene-, wherein R$_A$ is alkyl, and R$_B$ is hydrogen or alkyl. R$_A$ and R$_B$ may be identical or different. Thus, C$_1$-C$_6$alkylaminoC$_1$-C$_6$alky refers to N(R$_A$R$_B$)—C$_1$-C$_6$alkylene-, wherein R$_A$ is C$_1$-C$_6$alkyl, and R$_B$ is hydrogen or C$_1$-C$_6$alkyl.

The term "alkylcarbonyl" (alone or in combination with another term(s)) refers to an alkyl group appended to the parent molecular moiety through a carbonyl group (i.e., —C(O)-alkyl). Representative examples of alkylcarbonyl include, but are not limited to, acetyl, ethylcarbonyl

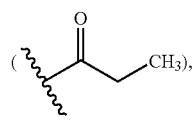

1-oxopropyl, 2,2-dimethyl-1-oxopropyl, 1-oxobutyl, and 1-oxopentyl.

The term "alkylcarbonylalkyl" (alone or in combination with another term(s)) refers to an alkylcarbonyl group appended to the parent molecular moiety through an alkylene group. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" (alone or in combination with another term(s)) refers to an alkylcarbonyl group appended to the parent molecular moiety through an oxy moiety. Representative examples of alkylcarbonyloxy include, but are not limited to, acetyloxy, ethylcarbonyloxy, and tert-butylcarbonyloxy.

The term "alkylcarbonyloxyalkyl" (alone or in combination with another term(s)) refers to an alkylcarbonyloxy group appended to the parent molecular moiety through an alkylene moiety. Representative examples of alkylcarbonyloxyalkyl include, but are not limited to, 2-(acetyloxy)ethyl, 3-(acetyloxy)propyl, and 3-(propionyloxy)propyl.

The terms "alkylene" or "alkylenyl" (alone or in combination with another term(s)) denote a divalent group derived from a straight or branched saturated hydrocarbyl chain typically containing from 1 to 20 carbon atoms, more typically from 1 to 8 carbon atoms, and even more typically from 1 to 6 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" (alone or in combination with another term(s)) means a straight- or branched-chain hydrocarbyl substituent containing one or more triple bonds and typically from 2 to 20 carbon atoms, more typically from 2 to 8 carbon atoms, and even more typically from 2 to 6 carbon atoms. Non-limiting examples of such substituents include ethynyl, 1-propynyl, 2-propynyl, 3-propynyl, decynyl, 1-butynyl, 2-butynyl, and 3-butynyl.

The terms "alkynylene" (alone or in combination with another term(s)) refers to a divalent unsaturated hydrocarbon group which may be linear or branched and which has at least one carbon-carbon triple bonds. Representative alkynylene groups include, by way of example, —C≡C—, —C≡C—CH$_2$—, —C≡C—CH$_2$—CH$_2$—, —CH$_2$—C≡C—CH$_2$—, —C≡C—CH(CH$_3$)—, and —CH$_2$—C≡C—CH(CH$_2$CH$_3$)—.

The term "amino" (alone or in combination with another term(s)) means —NH$_2$. The term "monosubstituted amino" (alone or in combination with another term(s)) means an amino substituent wherein one of the hydrogen radicals is replaced by a non-hydrogen substituent. The term "disubstituted amino" (alone or in combination with another term(s)) means an amino substituent wherein both of the hydrogen atoms are replaced by non-hydrogen substituents, which may be identical or different.

The term "aminocarbonyl" (alone or in combination with another term(s)) means —C(O)—NH$_2$, which also may be depicted as:

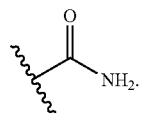

The term "aminoalkyl" (alone or in combination with another term(s)) means -alkylene-NH$_2$.

The term "aminoalkylcarbonyl" (alone or in combination with another term(s)) means —C(O)-alkylene-NH$_2$. For example, "aminomethylcarbonyl" may be depicted as:

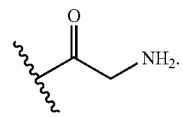

The term "aminosulfonyl" (alone or in combination with another term(s)) means —S(O)$_2$—NH$_2$, which also may be depicted as:

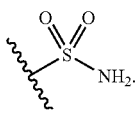

The term "aryl" (alone or in combination with another term(s)) refers to an aromatic carbocyclyl containing from 6 to 14 carbon ring atoms. Non-limiting examples of aryls include phenyl, naphthalenyl, anthracenyl, and indenyl. An aryl group can be connected to the parent molecular moiety through any substitutable carbon atom of the group.

The term "arylalkyl" (alone or in combination with another term(s)) refers to an aryl group appended to the parent molecular moiety through an alkylene group. Representative examples of substituted/unsubstituted arylalkyl include, but are not limited to, benzyl, 4-(benzyloxy)benzyl, 4-methoxybenzyl, 4-hydroxybenzyl, 3-(1,3-benzodioxol-5-yl)-2-methylpropyl, 3-(phenoxy)benzyl, 3-(1,3-benzodioxol-5-yl)propyl, 2-phenylethyl, 3-phenylpropyl, 2-naphthylmethyl, 3,5-ditert-butyl-2-hydroxybenzyl, 3-methoxybenzyl, 3,4-dimethoxybenzyl, 4-(dimethylamino)benzyl, 4-[3-(dimethylamino)propoxy]benzyl, (6-methoxy-2-naphthyl)methyl, and 2-naphth-2-ylethyl.

The term "arylalkylcarbonyl" (alone or in combination with another term(s)) refers to an arylalkyl group appended to the parent molecular moiety through a carbonyl group (i.e., arylalkyl-C(O)—). Representative examples of arylalkylcarbonyl include, but are not limited to, 2-naphthylacetyl and phenylacetyl.

The term "arylalkoxy" (alone or in combination with another term(s)) refers to an arylalkyl group appended to the parent molecular moiety through an oxy moiety (i.e., arylalkyl-O—). Representative examples of arylalkoxy include, but are not limited to, 2-phenylethoxy, 3-naphth-2-ylpropoxy, and 5-phenylpentyloxy.

The term "arylalkoxyalkyl" (alone or in combination with another term(s)) refers to an arylalkoxy group appended to the parent molecular moiety through an alkylene group. Representative examples of arylalkoxyalkyl include, but are not limited to, benzyloxymethyl, 2-(benzyloxy)ethyl, and (2-phenylethoxy)methyl.

The term "arylalkoxycarbonyl" (alone or in combination with another term(s)) refers to an arylalkoxy group appended to the parent molecular moiety through a carbonyl group. Representative examples of arylalkoxycarbonyl include, but are not limited to, benzyloxycarbonyl, and naphth-2-ylmethoxycarbonyl.

The term "arylcarbonyl" (alone or in combination with another term(s)) refers to an aryl group appended to the parent molecular moiety through a carbonyl group. Representative examples of arylcarbonyl include, but are not limited to, benzoyl and naphthoyl.

The term "aryloxy" (alone or in combination with another term(s)) refers to an aryl group appended to the parent molecular moiety through an oxy moiety. Representative examples of substituted/unsubstituted aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" (alone or in combination with another term(s)) refers to an aryloxy group appended to the parent molecular moiety through an alkylene group. Representative examples of aryloxyalkyl include, but are not limited to, 2-phenoxyethyl, 3-naphth-2-yloxypropyl, and phenoxymethyl.

The term "aryloxycarbonyl" (alone or in combination with another term(s)) refers to an aryloxy group appended to the parent molecular moiety through a carbonyl group.

The term "arylthio" (alone or in combination with another term(s)) refers to an aryl group appended to the parent molecular moiety through a sulfur atom (i.e., aryl-S—). Representative examples of arylthio include, but are not limited to, phenylthio, naphthalen-1-ylthio, and naphthalen-2-ylthio.

The term "arylthioalkyl" (alone or in combination with another term(s)) refers to aryl-S-alkylene-. Representative examples of arylthioalkyl include, but are not limited to, (phenylthio)methyl, 2-(phenylthio)ethyl, and 3-(phenylthio)propyl.

The term "arylthioalkoxy" (alone or in combination with another term(s)) refers to an arylthioalkyl group appended to the parent molecular moiety through an oxy group.

The term "arylthioalkoxyalkyl" (alone or in combination with another term(s)) refers to an arylthioalkoxy group appended to the parent molecular moiety through an alkylene group.

The terms "carbocycle" or "carbocyclic" or "carbocyclyl" (alone or in combination with another term(s)) refer to a saturated (e.g., "cycloalkyl"), partially saturated (e.g., "cycloalkenyl" or "cycloalkynyl") or completely unsaturated (e.g., "aryl") ring system containing zero heteroatom ring atom and typically from 3 to 18 carbon ring atoms. "Ring atoms" or "ring members" are the atoms bound together to form the ring or rings of a cyclic substituent. A carbocyclyl may be, without limitation, a single ring, or two or more fused rings, or bridged or spiro rings. A carbocyclyl may contain from 3 to 14 ring members (i.e., $C_3$-$C_{14}$carbocyclyl, such as $C_3$-$C_{14}$cycloalkyl), from 3 to 10 ring members (i.e., $C_3$-$C_{10}$carbocyclyl, such as $C_3$-$C_{10}$cycloalkyl), from 3 to 8 ring members (i.e., $C_3$-$C_8$carbocyclyl, such as $C_3$-$C_8$cycloalkyl), from 3 to 6 ring members (i.e., $C_3$-$C_6$carbocyclyl, such as $C_3$-$C_6$cycloalkyl), from 4 to 10 ring members (i.e., $C_4$-$C_{10}$carbocyclyl, such as $C_4$-$C_{10}$cycloalkyl and $C_4$-$C_{10}$cycloalkenyl), from 4 to 8 ring members (i.e., $C_4$-$C_8$carbocyclyl, such as $C_4$-$C_8$cycloalkyl and $C_4$-$C_8$cycloalkenyl), or from 5 to 7 ring members (i.e., $C_5$-$C_7$carbocyclyl, such as $C_5$-$C_7$cycloalkyl, $C_5$-$C_7$cycloalkenyl and phenyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydroindenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl. A carbocyclyl group can be attached to the parent molecular moiety through any substitutable carbon atom of the group.

The term "carbocyclylalkyl" (alone or in combination with another term(s)) refers to a carbocyclyl group appended to the parent molecular moiety through an alkylene group. For instance, $C_3$-$C_{10}$carbocyclyl$C_1$-$C_6$alkyl refers to a $C_3$-$C_{10}$carbocyclyl group appended to the parent molecular moiety through $C_1$-$C_6$alkylene. Likewise, $C_5$-$C_7$carbocyclyl$C_1$-$C_6$alkyl refers to a $C_5$-$C_7$carbocyclyl group appended to the parent molecular moiety through $C_1$-$C_6$alkylene.

The term "carbocyclylalkoxy" (alone or in combination with another term(s)) refers to a carbocyclylalkyl group appended to the parent molecular moiety through an oxy group (i.e., carbocyclyl-alkylene-O—). For instance, $C_3$-$C_{10}$carbocyclyl$C_1$-$C_6$alkoxy refers to a $C_3$-$C_{10}$carbocyclyl$C_1$-$C_6$alkyl group appended to the parent molecular moiety through an oxy group. Likewise, a $C_5$-$C_7$carbocyclyl$C_1$-$C_6$alkoxy group refers to a $C_5$-$C_7$carbocyclyl$C_1$-$C_6$alkyl group appended to the parent molecular moiety through an oxy group.

The term "carbocyclylalkoxyalkyl" (alone or in combination with another term(s)) refers to a carbocyclylalkoxy group appended to the parent molecular moiety through an alkylene group (i.e., carbocyclyl-alkylene-O-alkylene-). For instance, $C_3$-$C_{10}$carbocyclyl$C_1$-$C_6$alkoxy$C_1$-$C_6$alkyl refers to $C_3$-$C_{10}$carbocyclyl$C_1$-$C_6$alkoxy group appended to the parent molecular moiety through a $C_1$-$C_6$alkylene group.

The term "carbocyclylalkoxycarbonyl" (alone or in combination with another term(s)) refers to a carbocyclylalkoxy group appended to the parent molecular moiety through a carbonyl group (i.e., —C(O)—O-alkylene-carbocyclyl). For instance, $C_3$-$C_{10}$carbocyclyl$C_1$-$C_6$alkoxycarbonyl refers to a $C_3$-$C_{10}$carbocyclyl$C_1$-$C_6$alkoxy group appended to the parent molecular moiety through a carbonyl group. As a non-limiting example, "phenylethoxycarbonyl" may be depicted as:

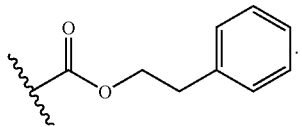

The term "carbocyclylalkylcarbonyl" (alone or in combination with another term(s)) refers to a carbocyclylalkyl group appended to the parent molecular moiety through a carbonyl group (i.e., —C(O)-alkylene-carbocyclyl). For example, "phenylethylcarbonyl" may be depicted as:

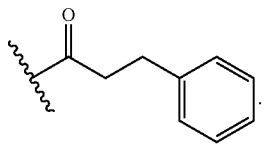

The term "carbocyclylcarbonyl" (alone or in combination with another term(s)) refers to a carbocyclyl group appended to the parent molecular moiety through a carbonyl group (i.e., carbocyclyl-C(O)—). For example, "phenylcarbonyl" may be depicted as:

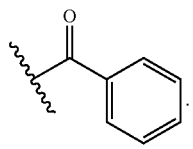

The term "carbocyclyloxy" (alone or in combination with another term(s)) refers to a carbocyclyl group appended to the parent molecular moiety through an oxy moiety (i.e., carbocyclyl-O—).

The term "carbocyclyloxyalkyl" (alone or in combination with another term(s)) refers to a carbocyclyloxy group appended to the parent molecular moiety through an alkylene group (i.e., carbocyclyl-O-alkylene-).

The term "carbocyclyloxycarbonyl" (alone or in combination with another term(s)) refers to a carbocyclyloxy group appended to the parent molecular moiety through a carbonyl group (i.e., —C(O)—O-carbocyclyl). For example, "phenyloxycarbonyl" may be depicted as:

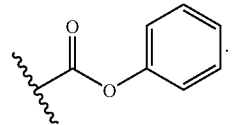

The term "carbocyclylthio" (alone or in combination with another term(s)) refers to a carbocyclyl group appended to the parent molecular moiety through a sulfur atom (i.e., carbocyclyl-S—).

The term "carbocyclylthioalkoxy" (alone or in combination with another term(s)) refers to carbocyclyl-alkylene-S—.

The term "carbocyclylthioalkoxyalkyl" (alone or in combination with another term(s)) refers to carbocyclyl-alkylene-S-alkylene-.

The term "carbocyclylthioalkyl" (alone or in combination with another term(s)) refers to a carbocyclylthio group appended to the parent molecular moiety through an alkylene group (i.e., carbocyclyl-S-alkylene-).

The term "carbocyclylcarbocyclyl" (alone or in combination with another term(s)) refers to a carbocyclyl group appended to the parent molecular moiety through another carbocyclyl group (i.e., carbocyclyl-carbocyclyl-). For instance, $C_3$-$C_{10}$carbocyclyl$C_5$-$C_7$carbocyclyl refers to a $C_3$-$C_{10}$carbocyclyl group appended to the parent molecular moiety through a $C_5$-$C_7$carbocyclyl group (i.e., $C_3$-$C_{10}$carbocyclyl-$C_5$-$C_7$carbocyclyl-).

The term "carbocyclylcarbocyclylalkyl" (alone or in combination with another term(s)) refers to a carbocyclylcarbocyclyl group appended to the parent molecular moiety through an alkylene group.

The term "carbocyclylalkoxycarbocyclylalkyl" (alone or in combination with another term(s)) refers to carbocyclyl-alkylene-O-carbocyclyl-alkylene-. For instance, $C_3$-$C_{10}$carbocyclyl$C_1$-$C_6$alkoxy$C_5$-$C_7$carbocyclyl$C_3$-$C_4$alkyl refers to $C_3$-$C_{10}$carbocyclyl-$C_1$-$C_6$alkylene-O—$C_5$-$C_7$carbocyclyl-$C_3$-$C_4$alkylene-.

The term "(carbocyclylalkyl)carbocyclylalkyl" (alone or in combination with another term(s)) refers to carbocyclyl-alkylene-carbocyclyl-alkylene-. For instance, $C_3$-$C_{10}$carbocyclyl$C_1$-$C_6$alkyl$C_5$-$C_7$carbocyclyl$C_3$-$C_4$alkyl refers to $C_3$-$C_{10}$carbocyclyl-$C_1$-$C_6$alkylene-$C_5$-$C_7$carbocyclyl-$C_3$-$C_4$alkylene-.

The term "carbocyclylalkoxyheterocycloalkyl" (alone or in combination with another term(s)) refers to carbocyclyl-alkylene-O-heterocyclyl-alkylene-.

The term "carbocyclylcarbonylheterocycloalkyl" (alone or in combination with another term(s)) refers to carbocyclyl-C(O)-heterocyclyl-alkylene-.

The term "carbocyclylheterocycloalkyl" (alone or in combination with another term(s)) refers to carbocyclyl-heterocyclyl-alkylene-.

The term "carbocyclylcarbonylcarbocyclylalkyl" (alone or in combination with another term(s)) refers to carbocyclyl-C(O)-carbocyclyl-alkylene-. For instance, $C_3$-$C_{10}$carbocyclylcarbonyl$C_4$-$C_8$carbocyclyl$C_1$-$C_6$alkyl refers to $C_3$-$C_{10}$carbocyclyl-C(O)—$C_4$-$C_8$carbocyclyl-$C_1$-$C_6$alkylene-.

The term "(carbocyclylalkyl)heterocycloalkyl" (alone or in combination with another term(s)) refers to carbocyclyl-alkylene-heterocyclyl-alkylene.

The term "carbonyl" (alone or in combination with another term(s)) refers to —C(O)—, which also may be depicted as:

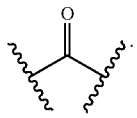

The term "carboxy" (alone or in combination with another term(s)) means —C(O)—OH, which also may be depicted as:

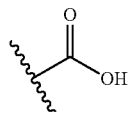

The term "carboxyalkyl" (alone or in combination with another term(s)) refers to a carboxy group appended to the parent molecular moiety through an alkylene group. Representative examples of carboxyalkyl include, but are not limited to, carboxymethyl, 2-carboxyethyl, and 3-carboxypropyl.

The term "cyclic amino" (alone or in combination with another term(s)) means a heterocyclyl moiety comprising at least one nitrogen ring atom, with the remaining ring atoms being carbon and optionally nitrogen or sulfur. Non-limiting examples of such moieties include piperidinyl, piperazinyl, and thiazine groups.

The term "cycloalkenyl" (alone or in combination with another term(s)) refers to a non-aromatic, partially unsaturated carbocyclyl substituent having zero heteroatom ring member and typically from 4 to 18 carbon ring members. Representative examples of cycloalkenyl groups include, but are not limited to, cyclobutenyl, cyclopentenyl, cyclohexenyl, and octahydronaphthalenyl.

The term "cycloalkyl" (alone or in combination with another term(s)) refers to a saturated carbocyclyl group containing zero heteroatom ring member and typically from 3 to 18 carbon ring members. Non-limiting examples of cycloalkyls include cyclopropyl, cyclobutyl, cyclopentyl, cyclohexyl, cycloheptyl, cyclooctyl, decalinyl and norpinanyl.

The term "cycloalkylcarbonyl" (alone or in combination with another term(s)) refers to a cycloalkyl group appended to the parent molecular moiety through a carbonyl group.

The term "cyano" (alone or in combination with another term(s)) means —CN, which also may be depicted as

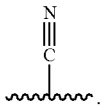

The term "dialkylamino" (alone or in combination with another term(s)) refers to —$NR_A R_B$, wherein $R_A$ and $R_B$ are independently selected from alkyl groups.

The term "dialkylaminocarbonyl" (alone or in combination with another term(s)) refers to a dialkylamino group appended to the parent molecular moiety through a carbonyl group (i.e., $N(R_A R_B)$—C(O)—, wherein $R_A$ and $R_B$ are independently selected from alkyl groups).

The term "formyl" (alone or in combination with another term(s)) refers to a —C(O)H group.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

The prefix "halo" indicates that the substituent to which the prefix is attached is substituted with one or more independently selected halogen radicals. For example, "haloalkyl" (alone or in combination with another term(s)) means an alkyl substituent wherein at least one hydrogen radical is replaced with a halogen radical. Non-limiting examples of haloalkyls include chloromethyl, 1-bromoethyl, fluoromethyl, difluoromethyl, trifluoromethyl, and 1,1,1-trifluoroethyl. Illustrating further, "haloalkoxy" (alone or in combination with another term(s)) means an alkoxy substituent wherein at least one hydrogen radical is replaced by a halogen radical. Non-limiting examples of haloalkoxy substituents include chloromethoxy, 1-bromoethoxy, fluoromethoxy, difluoromethoxy, trifluoromethoxy (also known as "perfluoromethyloxy"), and 1,1,1-trifluoroethoxy. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical. Non-limiting examples of perfluoroalkyl substituents include trifluoromethyl (—$CF_3$), perfluoroisopropyl, perfluorobutyl, perfluorodecyl, and perfluorododecyl. To illustrate further, the term "perfluoroalkoxy" means an alkoxy substituent wherein each hydrogen radical is replaced with a fluorine radical. Non-limiting examples of perfluoroalkoxy substituents include trifluoromethoxy (—O—$CF_3$), perfluoroisopropoxy, perfluorobutoxy, perfluorodecoxy, and perfluorododecoxy.

The terms "heterocycle" or "heterocyclo" or "heterocyclyl" (alone or in combination with another term(s)) refer to a saturated (e.g., "heterocycloalkyl"), partially unsaturated (e.g., "heterocycloalkenyl" or "heterocycloalkynyl") or completely unsaturated (e.g., "heteroaryl") ring system typically containing from 3 to 18 ring atoms, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results.

A heterocyclyl may be, without limitation, a single ring, which typically contains from 3 to 14 ring atoms (i.e., $M_3$-$M_{14}$heterocyclyl), from 3 to 8 ring atoms (i.e., $M_3$-$M_8$heterocyclyl), from 3 to 6 ring atoms (i.e., $M_3$-$M_6$heterocyclyl), or from 5 to 6 ring atoms (i.e., $M_5$-$M_6$heterocyclyl). Non-limiting examples of single-ring heterocyclyls include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl, oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5,2-oxadiazinyl), morpholinyl, azepinyl, oxepinyl, thiepinyl, and diazepinyl.

A heterocyclyl may also include, without limitation, two or more rings fused together, such as, for example, naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocyclyls include benzo-fused heterocyclyls, such as indolyl, isoindolyl, indoleninyl (also known as "pseudoindolyl"), isoindazolyl (also known as "benzpyrazolyl"), benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzisoxazinyl (including 1,2-benzisoxazinyl and 1,4-benzisoxazinyl), tetrahydroisoquinolinyl, carbazolyl, xanthenyl, and acridinyl.

The term "two-fused-ring" heterocyclyl (alone or in combination with another term(s)) means a saturated, partially saturated, or aromatic heterocyclyl containing two fused rings. Non-limiting examples of two-fused-ring heterocyclyls include naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzoimidazolyl, benzotriazolyl, benzoxazinyl, benzoisoxazinyl, and tetrahydroisoquinolinyl.

A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

As used herein, the number of ring atoms in a heterocyclyl moiety can be identified by the prefix "$M_x$-$M_y$," where x is the minimum and y is the maximum number of ring atoms in the heterocyclyl moiety.

The term "heterocycloalkoxy" (alone or in combination with another term(s)) refers to a heterocycloalkyl group appended to the parent molecular moiety through an oxy group.

The term "heterocycloalkoxyalkyl" (alone or in combination with another term(s)) refers to a heterocycloalkoxy group appended to the parent molecular moiety through an alkylene group (i.e., heterocyclyl-alkylene-O-alkylene-).

The term "heterocycloalkoxycarbonyl" (alone or in combination with another term(s)) refers to a heterocycloalkoxy group appended to the parent molecular moiety through a carbonyl group (i.e., heterocyclyl-alkylene-O—C(O)—).

The term "heterocycloalkyl" (alone or in combination with another term(s)) refers to a heterocyclyl appended to the parent molecular moiety through an alkylene group (e.g., heterocyclo$C_1$-$C_6$alkyl).

The term "heterocycloalkylcarbonyl" (alone or in combination with another term(s)) refers to a heterocycloalkyl group appended to the parent molecular moiety through a carbonyl group (i.e., —C(O)-alkylene-heterocyclyl).

The term "heterocyclocarbonyl" (alone or in combination with another term(s)) refers to a heterocyclyl appended to the parent molecular moiety through a carbonyl group (i.e., —C(O)-heterocyclyl).

The terms "heterocyclyloxy" or "(heterocyclo)oxy" (alone or in combination with another term(s)) refers to a heterocyclyl group appended to the parent molecular moiety through an oxy moiety.

The term "(heterocyclyo)oxyalkyl" (alone or in combination with another term(s)) refers to a heterocyclyloxy group appended to the parent molecular moiety through an alkylene group (i.e., heterocyclyl-O-alkylene-).

The term "(heterocyclo)oxycarbonyl" (alone or in combination with another term(s)) refers to a (heterocyclo)oxy group appended to the parent molecular moiety through a carbonyl group (i.e., heterocyclyl-O—C(O)—).

The term "heterocyclothio" (alone or in combination with another term(s)) refers to a heterocyclyl appended to the parent molecular moiety through —S—.

The term "heterocyclothioalkoxy" (alone or in combination with another term(s)) refers to heterocyclyl-alkylene —S—.

The term "heterocyclothioalkoxyalkyl" (alone or in combination with another term(s)) refers to heterocyclyl-alkylene-S-alkylene-.

The term "heterocyclothioalkyl" (alone or in combination with another term(s)) refers to a heterocyclothio group appended to the parent molecular moiety through an alkylene group (i.e., heterocyclyl-S-alkylene-).

The term "heterocyclocarbocyclyl" (alone or in combination with another term(s)) refers to a heterocyclyl appended to the parent molecular moiety through a carbocyclyl group (i.e., heterocyclo-carbocyclyl-).

The term "heterocyclocarbocyclylalkyl" (alone or in combination with another term(s)) refers to a heterocyclocarbocyclyl group appended to the parent molecular moiety through an alkylene group (i.e., heterocyclyl-carbocyclyl-alkylene-).

The term "(heterocyclo)alkoxycarbocyclylalkyl" (alone or in combination with another term(s)) refers to heterocyclo-alkylene-O-carbocyclyl-alkylene-.

The term "(heterocyclo)carbonylcarbocyclylalkyl" (alone or in combination with another term(s)) refers to heterocyclo-C(O)-carbocyclyl-alkylene-.

The term "(heterocyclo)heterocycloalkyl" (alone or in combination with another term(s)) refers to heterocyclo-heterocyclo-alkylene-.

The term "(heterocyclo)alkoxyheterocycloalkyl" (alone or in combination with another term(s)) refers to heterocyclo-alkylene-O-heterocyclo-alkylene-.

The term "(heterocyclo)carbonylheterocycloalkyl" (alone or in combination with another term(s)) refers to heterocyclo-C(O)-heterocyclo-alkylene-.

The term "(heterocycloalkyl)carbocyclylalkyl" (alone or in combination with another term(s)) refers to heterocyclo-alkylene-carbocyclyl-alkylene-.

The term "(heterocycloalkyl)heterocycloalkyl" (alone or in combination with another term(s)) refers to heterocyclo-alkylene-heterocyclo-alkylene-. Thus, for example, $(M_3-M_{10}heterocycloC_1-C_6alkyl)M_5-M_6heterocycloC_1-C_3alkyl$ means $M_3-M_{10}heterocyclo-C_1-C_6alkylene-M_5-M_6heterocyclo-C_1-C_3alkylene-$.

The term "heteroaryl" (alone or in combination with another term(s)) means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3, 4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heteroarylalkoxy" (alone or in combination with another term(s)) refers to a heteroarylalkyl appended to the parent molecular moiety through an oxy group (i.e., heteroaryl-alkylene-O—). Representative examples of heteroarylalkoxy include, but are not limited to, 2-pyridin-3-ylethoxy, 1,3-thiazol-5-ylmethoxy, 3-quinolin-3-ylpropoxy, and 5-pyridin-4-ylpentyloxy.

The term "heteroarylalkoxyalkyl" (alone or in combination with another term(s)) refers to a heteroarylalkoxy group appended to the parent molecular moiety through an alkylene group (i.e., heteroaryl-alkylene-O-alkylene-). Representative examples of heteroarylalkoxyalkyl include, but are not limited to, (2-pyridin-3-ylethoxy)methyl, (3-quinolin-3-ylpropoxy)methyl, (1,3-thiazol-5-ylmethoxy)methyl, and 2-(5-pyridin-4-ylpentyloxy)ethyl.

The term "heteroarylalkoxycarbonyl" (alone or in combination with another term(s)) refers to a heteroarylalkoxy group appended to the parent molecular moiety through a carbonyl group (i.e., heteroaryl-alkylene-O—C(O)—). Representative examples of heteroarylalkoxycarbonyl include, but are not limited to, (2-pyridin-3-ylethoxy)carbonyl, (3-quinolin-3-ylpropoxy)carbonyl, 2-(1,3-thiazol-5-ylmethoxy)carbonyl, and (5-pyridin-4-ylpentyloxy)carbonyl.

The term "heteroarylalkyl" (alone or in combination with another term(s)) refers to a heteroaryl group appended to the parent molecular moiety through an alkylene group. Representative examples of heteroarylalkyl include, but are not limited to, 3-quinolinylmethyl, 3-pyridinylmethyl, 4-pyridinylmethyl, 1H-imidazol-4-ylmethyl, 1H-pyrrol-2-ylmethyl, pyridin-3-ylmethyl, and 2-pyrimidin-2-ylpropyl.

The term "heteroarylalkylcarbonyl" (alone or in combination with another term(s)) refers to a heteroarylalkyl group appended to the parent molecular moiety through a carbonyl group (i.e., heteroaryl-alkylene-C(O)—).

The term "heteroarylcarbonyl" (alone or in combination with another term(s)) refers to a heteroaryl group appended to the parent molecular moiety through a carbonyl group. Representative examples of heteroarylcarbonyl include, but are not limited to, pyridin-3-ylcarbonyl, (1,3-thiazol-5-yl)carbonyl, and quinolin-3-ylcarbonyl.

The term "heteroaryloxy" (alone or in combination with another term(s)) refers to a heteroaryl group appended to the parent molecular moiety through an oxy moiety. Representative examples of heteroaryloxy include, but are not limited to, pyridin-3-yloxy, and quinolin-3-yloxy.

The term "heteroaryloxyalkyl" (alone or in combination with another term(s)) refers to a heteroaryloxy group appended to the parent molecular moiety through an alkylene group (i.e., heteroaryl-O-alkylene-).

The term "heteroaryloxycarbonyl" (alone or in combination with another term(s)) refers to a heteroaryloxy group appended to the parent molecular moiety through a carbonyl group (i.e., heteroaryl-O—C(O)—).

The term "heteroarylthio" (alone or in combination with another term(s)) refers to a heteroaryl group appended to the parent molecular moiety through —S—.

The term "heteroarylthioalkoxy" (alone or in combination with another term(s)) refers to heteroaryl-alkylene-S—.

The term "heteroarylthioalkoxyalkyl" (alone or in combination with another term(s)) refers to heteroaryl-alkylene-S-alkylene-.

The term "heteroarylthioalkyl" (alone or in combination with another term(s)) refers to a heteroarylthio group appended to the parent molecular moiety through an alkylene group (i.e., heteroaryl-S-alkylene-).

The term "hydrogen" (alone or in combination with another term(s)) refers to a hydrogen radical, and may be depicted as —H.

The term "hydroxy" (alone or in combination with another term(s)) refers to —OH.

The term "hydroxyalkyl" (alone or in combination with another term(s)) refers to an alkyl substituent wherein one or more hydrogen radicals are replaced with —OH. Representative examples of hydroxyalkyl include, but are not limited to, hydroxymethyl, 2-hydroxyethyl, 3-hydroxypropyl, and 2-ethyl-4-hydroxyheptyl.

The term "keto" (alone or in combination with another term(s)) means an oxo radical, and may be depicted as =O.

The term "iminoalkyl" (alone or in combination with another term(s)) refers to a radical of the formula

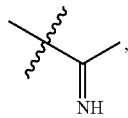

wherein the H may be optionally substituted with alkyl or hydroxy, in which case the substituent would be alkyliminoalkyl or hydroxyiminoalkyl respectively.

The term "nitro" (alone or in combination with another term(s)) means —NO$_2$.

The term "oxo" (alone or in combination with another term(s)) refers to a =O moiety (i.e., 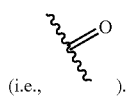).

The term "oxy" (alone or in combination with another term(s)) means —O—.

The term "propargyl" (alone or in combination with another term(s)) means the monovalent radical depicted as: —CH$_2$—CH≡CH.

The term "sulfonyl" (alone or in combination with another term(s)) means —S(O)$_2$—, which also may be depicted as:

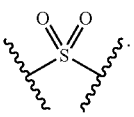

The term "sulfinyl" (alone or in combination with another term(s)) means —S(O)—, which also may be depicted as:

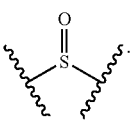

The term "thio" or "thia" (alone or in combination with another term(s)) means —S—.

The term "thiol," "mercapto" or "sulfhydryl" (alone or in combination with another term(s)) means a sulfhydryl substituent, (i.e., —SH). Thus, for example, thioalkyl means an alkyl substituent wherein one or more hydrogen radicals are replaced with —SH, while alkylthio means alkyl-S—.

The term "thioalkoxy" (alone or in combination with another term(s)) refers to an alkyl group appended to the parent molecular moiety through —S—. Representative examples of thioalkoxy include, but are not limited to, methylthio, ethylthio, and butylthio.

The term "thioalkoxyalkyl" (alone or in combination with another term(s)) refers to a thioalkoxy group appended to the parent molecular moiety through an alkylene group (i.e., alkyl-S-alkylene-).

The term "thiocarbonyl" (alone or in combination with another term(s)) means a carbonyl wherein the oxygen atom has been replaced with a sulfur. Such a substituent may be depicted as —C(S)—, and also may be depicted as:

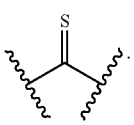

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g. a reduction in viral load.

The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy or carboxy group). The prodrug derivative form often offers advantages of solubility, tissue compatibility, or delayed release in a mammalian organism (see, Bungard, H., DESIGN OF PRODRUGS, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to the physical association of a compound of this invention with one or more solvent molecules, whether organic or inorganic. This physical association often includes hydrogen bonding. In certain instances the solvate will be capable of isolation, for example when one or more solvent molecules are incorporated in the crystal lattice of the crystalline solid.

"Solvate" encompasses both solution-phase and isolable solvates. Exemplary solvates include, but are not limited to, hydrates, ethanolates, and methanolates.

The term "chiral" refers to molecules that do not have a plane of symmetry and are therefore not superimposable on their mirror image. A chiral molecule may exists in two forms, one right-handed and one left-handed.

The term "stereoisomer" refers to isomers that have their atoms connected in the same order but have different three-dimensional arrangements. The term stereoisomer includes, for example, enantiomers and diastereomers.

The term "cis-trans isomer" refers to stereoisomers that differ in their stereochemistry about a double bond or ring. Cis-trans isomers are also called geometric isomers.

The term "enantiomer" refers to stereoisomers of a chiral substance that have a mirror-image relationship.

The term "diastereomer" refers to stereoisomers that are not enantiomers, or mirror images of each other.

The term "racemic mixture" refers to a mixture consisting of equal parts (+) and (−) enantiomers of a chiral substance. Even though the individual molecules are chiral, racemic mixtures are optically inactive.

The term "tautomer" refers to isomers that are interconvertable. For example, enols and ketones are tautomers because they are interconverted by treatment with either acid or base.

The term "position isomer" refers to any of two or more constitutional isomers that differ in the position of a particular substituent or group. Functional groups can be attached at structurally nonequivalent positions on a carbon skeleton. For example, [1,3]imidazole, depicted as

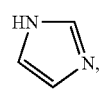

and [1,4]imidazole, depicted as

are position isomers.

The term "N-protecting group" or "N-protected" refers to those groups capable of protecting an amino group against undesirable reactions. Commonly used N-protecting groups are described in Greene and Wuts, PROTECTING GROUPS IN CHEMICAL SYNTHESIS (3$^{rd}$ ed., John Wiley & Sons, NY (1999), which is incorporate herein by reference in its entirety. Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The following abbreviations are used in the General Synthetic Methods and Examples described below:

| | |
|---|---|
| AcOH = | acetic acid |
| atm = | atmospheres |
| Boc = | N-t-butoxycarbonyl (protecting group) |
| CDI = | 1,1'-carbonyldiimidazole |
| CH$_2$Cl$_2$ = | methylene chloride (dichloromethane) |
| CuI = | cuprous iodide [copper (I) iodide] |
| DCE = | 1,2-dichloroethane |
| DEAD = | diethyl azodicarboxylate |
| DMA = | N-N-dimethylacetamide |
| DMAP = | 4-dimethylaminopyridine |
| DMF = | N,N-dimethylformamide |
| DMSO = | dimethylsulfoxide |
| EDCI = | (N-ethyl-N'-(3-dimethylaminopropyl)-carbodiimide hydrochloride |
| EMME = | 2-ethoxymethylene-malonic acid diethyl ester |
| Et$_3$N = | triethylamine |
| Ether = | diethyl ether |
| EtI = | ethyl iodide |
| EtOAc = | ethyl acetate |
| EtOH = | ethanol |
| Fe = | iron |

| | |
|---|---|
| Fe(AcAc)3 = | Iron(III)-acetylacetonate |
| Fmoc chloride = | 9-fluorenylmethyl chloroformate |
| HOBt = | N-Hydroxybenzotriazole |
| Hunig's base = | N,N-diisopropylethylamine |
| IPA = | isopropyl alcohol |
| K$_2$CO$_3$ = | potassium carbonate |
| KOH = | potassium hydroxide |
| LDA = | lithium diisopropylamine |
| MeOH = | methanol |
| MsCl = | methanesulfonyl chloride |
| NaH = | sodium hydride |
| NH$_2$OH•HCl = | hydroxylamine hydrochloride |
| NMP = | 1-methyl-2-pyrrolidinone |
| Mg$_2$SO$_4$ = | magnesium sulfate |
| Na$_2$SO$_4$ = | sodium sulfate |
| NH$_3$ = | ammonia |
| NH$_4$Cl = | ammonium chloride |
| NH$_4$OH = | ammonium hydroxide |
| PG = | protecting group such as Boc- or Troc- |
| POCl$_3$ = | phosphorous oxy chloride |
| R-MgCl = | Grignard reagent |
| R-I = | alkyl iodide or substituted alkyl iodide |
| SnCl2 = | Stannous chloride (Tin (II) chloride) |
| TFA = | trifluoroacetic acid |
| THF = | tetrahydrofuran |
| TLC = | thin layer chromatography |
| Triflic Anhydride = | trifluoromethanesulfonic anhydride |
| Troc = | 2,2,2-trichloroethoxycarbonyl-(protecting group) |

General Synthetic Methods and Examples

The following synthetic methods and schemes illustrate the general methods by which the compounds of the present invention can be prepared. Starting materials can be obtained from commercial sources or prepared using methods well known to those of ordinary skill in the art. By way of example, synthetic routes similar to those shown hereinbelow may be used, together with synthetic methods known in the art of synthetic organic chemistry, or variations thereon, as appreciated by those skilled in the art.

The present invention is intended to encompass compounds prepared by either synthetic processes or metabolic processes. Metabolic processes include those occurring in the human or animal body (in vivo), or those occurring in vitro.

If a substituent described herein is not compatible with the synthetic methods of this invention, the substituent may be protected with a suitable protecting group that is stable to the reaction conditions used in these methods. The protecting group may be removed at a suitable point in the reaction sequence to provide a desired intermediate or target compound. Suitable protecting groups and methods for protecting or deprotecting substituents are well know in the art, examples of which can be found in Greene and Wuts, supra.

Preparation of
7-Substituted-4-Substituted-[1,8]Naphthyridine
Compounds

Compounds of Formulae I(a) or I(b) can be synthesized by reacting

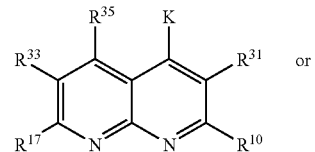

or

-continued

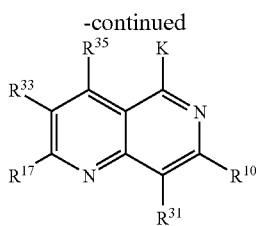

with

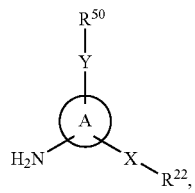

wherein A, X, Y, $R^{10}$, $R^{17}$, $R^{22}$, $R^{31}$, $R^{33}$, $R^{35}$, and $R^{50}$ have the meanings as set forth in the above embodiments or examples, and K is Cl or another halogen. Likewise, the synthesis of compounds of Formulae II(a) or II(b) generally involve reaction of

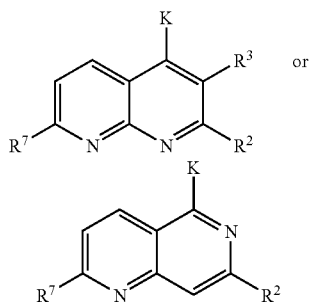

with

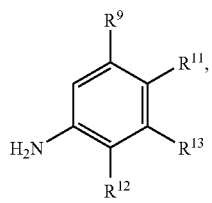

wherein $R^2$, $R^3$, $R^7$, $R^9$, $R^{11}$, $R^{12}$, and $R^{13}$ have the meanings as set forth in the above embodiments or examples, and K is Cl or another halogen. Shown in Schemes 1, 2, 3 and 4 below is a representative method for the preparation of these [1,8] naphthyridine-type compounds.

The 7-substituted-4-substituted-[1,8]naphthyridine compounds are generally synthesized (Scheme 4) by coupling a 7-substituted-4-chloro-[1,8]naphthyridine compound 8 with a coupling compound such as 10, 11 and 12 (Scheme 3). Other 4-substituted [1,8]naphthyridines can be prepared in a similar manner utilizing the appropriate coupling compounds.

Preparation of 6-Substituted-2-aminopyridines

In a typical preparation described in Scheme 1, a solution of 2,6-dichloropyridine is treated with ammonium hydroxide in a sealed metal reactor at about 180° C. for about 40 hours. After cooling to room temperature the product is filtered giving 6-chloro-2-aminopyridine. A solution of this product and hexane-2,5-dione in benzene is treated with acetic acid, heated under reflux conditions with azeotropic removal of water for about 20 hours. This reaction mixture is cooled to room temperature, diluted with diethyl ether, washed with dilute hydrochloric acid and water. The organic layer is dried over magnesium sulfate, filtered and concentrated under vacuum to give 6-chloro-2-(2,5-dimethyl-pyrrol-1-yl-pyridine 1. Compound 1 is treated with a Grignard reagent (R—MgX) in dry tetrahydrofuran (THF) and 1-methyl-2-pyrrolidinone (NMP) at room temperature under a nitrogen atmosphere and iron (III) acetylacetonate [Fe(AcAc)$_3$] is added and the mixture is stirred at room temperature for about 18 hours. During the reaction two addition charges of the Grignard reagent and iron catalyst are added. The reaction is quenched by pouring unto 5% acetic acid and extracting with ether. The ether layer is dried over sodium sulfate, filtered and concentrated under vacuum to give 6-substituted-2-(2,5-dimethyl-pyrrol-1-yl)-pyridine 2. Compound 2 can be directly converted to a 6-substituted-2-aminopyridine 4 or it can be further functionalized by reacting it with an alkyl iodide or a substituted alkyl iodide in the presence of lithium diisopropylamide (LDA). In this case, a solution of compound 2 in dry tetrahydrofuran is added dropwise over about 30 minutes to a stirred solution of lithium diisopropylamide in dry tetrahydrofuran at −30° C. An alkyl iodide or a substituted alky iodide (R—I) in tetrahydrofuran is then added dropwise over about 30 minutes then warmed to room temperature. After two hours the reaction mixture is quenched by pouring into saturated sodium chloride solution and extracted with ether. The ether solution is dried over magnesium sulfate, filtered and concentrated under vacuum giving the 6-substituted-2-(2,5-dimethyl-pyrrol-1-yl)pyridine 3. A solution of either compound 2 or 3 and hydroxylamine hydrochloride in ethanol and water is heated at about 100° C. for about 16 hours, cooled to room temperature and extracted with methylene chloride, dried over magnesium sulfate, filtered and concentrated under vacuum giving the 6-substituted-aminopyridine 4 used in Scheme 2. The 6-substituent in Scheme 1 is $R^7$ which is described before.

Scheme 1

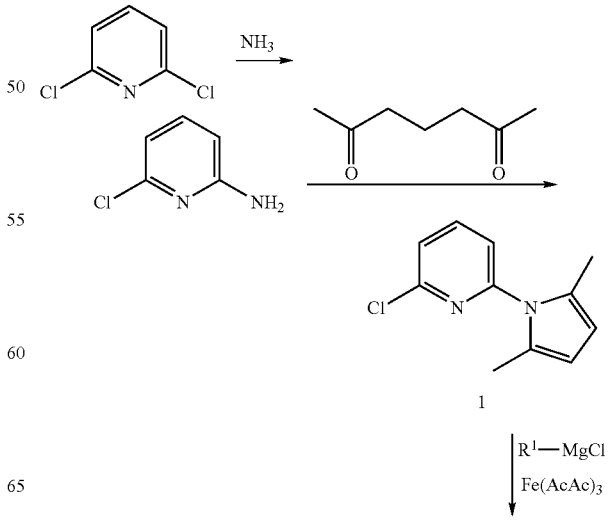

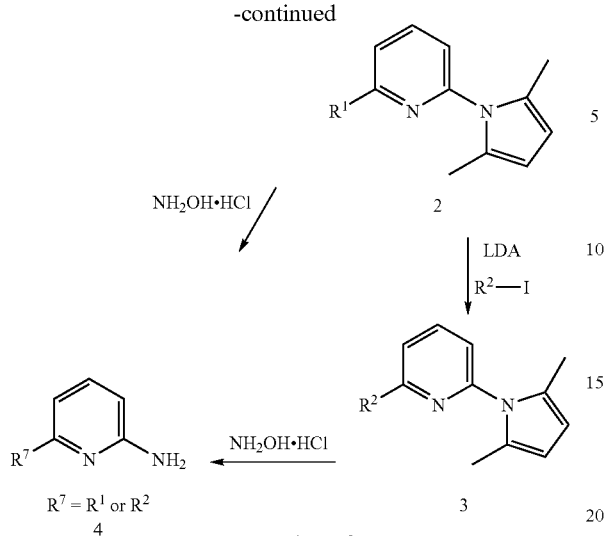

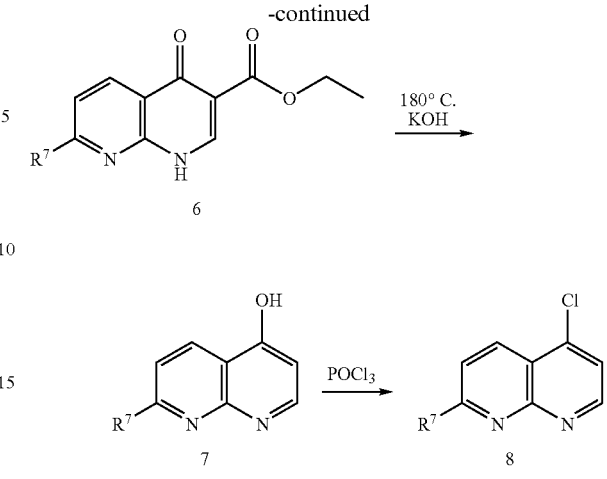

Preparation of 7-Substituted-4-Chloro-[1,8]Naphthyridines

A typical preparation described in Scheme 2 consists of mixing a 6-substituted 2-aminopyridine 4 and 2-ethoxymethylene-malonic acid diethyl ester (EMME) and heating to about 100° C. with stirring for about 2.5 hours. The reaction mixture is cooled to room temperature and diluted with hexane, the resulting solid is filtered and dried under vacuum to give the aminomethylene malonic acid ester 5. Compound 5 is then dissolved in diphenylether and the resulting solution heated to 250° C. for about 30 minutes. After cooling to room temperature, diluting with hexane the resulting solid is filtered and dried under vacuum giving the substituted 7-substituted-4-oxo-1,4-dihydro-[1,8]naphthyridine-3-carboxylic acid ethyl ester "E". A solution of compound 6 and potassium hydroxide (KOH) is heated in a sealed metal reactor at 180° C. for about 16 hours, cooled to room temperature and adjusted to pH 6 with 1N hydrochloric acid. The resulting precipitate is filtered and dried giving the 7-substituted [1,8] napthyridin-4-ol 7. A mixture of compound 7 is mixed with phosphorous oxychloride (POCl$_3$) and heated to about 50° C. with stirring for 6 hours, cooled quenched by pouring unto ice. It is cooled then adjusted to pH 10 with concentrated ammonium hydroxide and extracted with methylene chloride, dried over anhydrous sodium sulfate, filtered and concentrated under vacuum giving the 7-substituted-4-chloro-[1,8]naphthyridine 8. The substituents for compound 8 are shown in Scheme 2 as R$^7$ which has been described before.

Scheme 2

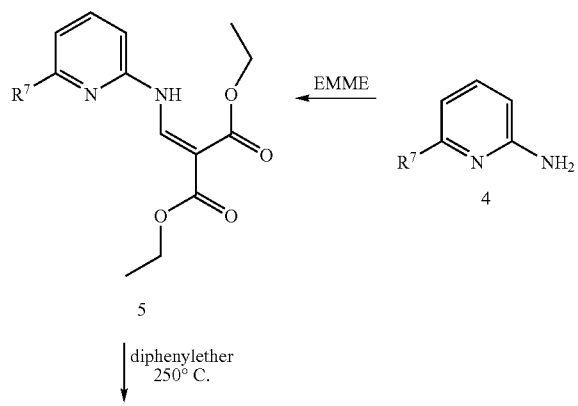

Preparation of Aminophenyl Coupling Agents (10, 11 and 12)

A wide variety of aminophenyl coupling agents are possible. The agents in Scheme 3 are exemplary of this variety.

In a typical preparation, a substituted 2-chloro-nitrobenzene compound in dimethylformamide (DMF) is treated with a sodium thiophenolate at about 50° C. for about 2 hours, is cooled and diluted with methylene chloride, washed with water, dried over sodium sulfate, filtered and concentrated under vacuum to give the substituted-2-phenylsulfanyl-nitrobenzene compound. This nitrobenzene compound is then reduced with stannous chloride (SnCl$_2$) or iron (Fe) in ethanol. The reaction mixture is adjusted to pH 12 with 1 N sodium hydroxide, extracted with ethyl acetate, dried over sodium sulfate, filtered and concentrated under vacuum giving the substituted-2-phenylsulfanyl-aminobenzene compound 10.

Similarly, the corresponding substituted-2-hydroxy-nitrobenzene compound is dissolved in dimethylformamide reacted with a sodium phenoxide solution, stirred and heated to 100° C. for about 5 days. The reaction mixture is cooled and diluted with methylene chloride, washed with water, dried over sodium sulfate, filtered and concentrated under vacuum to give the substituted-2-phenoxy-nitrobenzene compound. This nitrobenzene compound is then reduced with stannous chloride (SnCl$_2$) and iron (Fe) in ethanol. The reaction mixture is adjusted to pH 12 with 1 N sodium hydroxide, extracted with ethyl acetate, dried over sodium sulfate, filtered and concentrated under vacuum giving the substituted-2-phenoxy-aminobenzene compound 12.

Similarly, either compound 10 where R$^9$ is hydroxy- or protected hydroxyl- can be further modified by alkylating the hydroxy-group using a substituted benzyl bromide to give the corresponding 5-substituted-phenoxy-2-substituted-phenylsulfanyl-aminobenzene compound 11.

Scheme 3
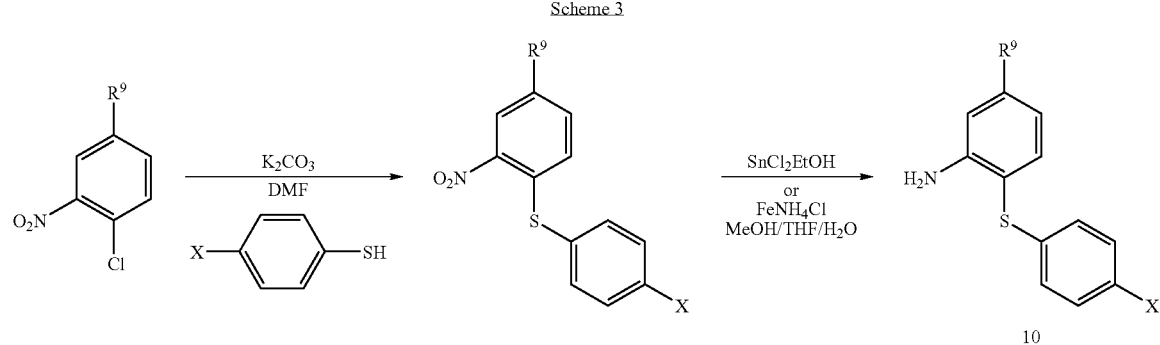
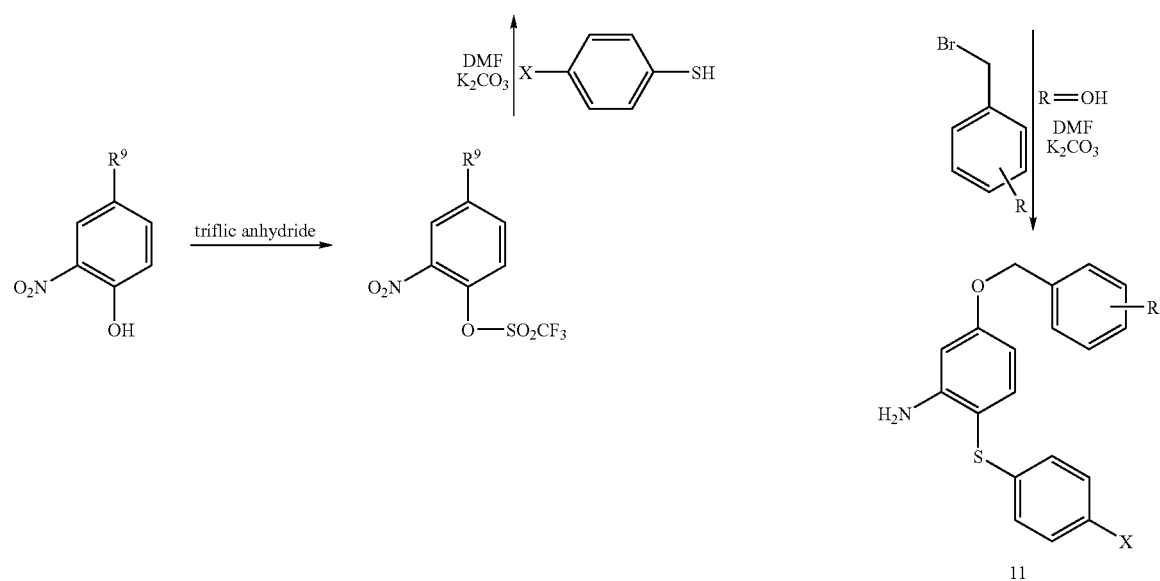
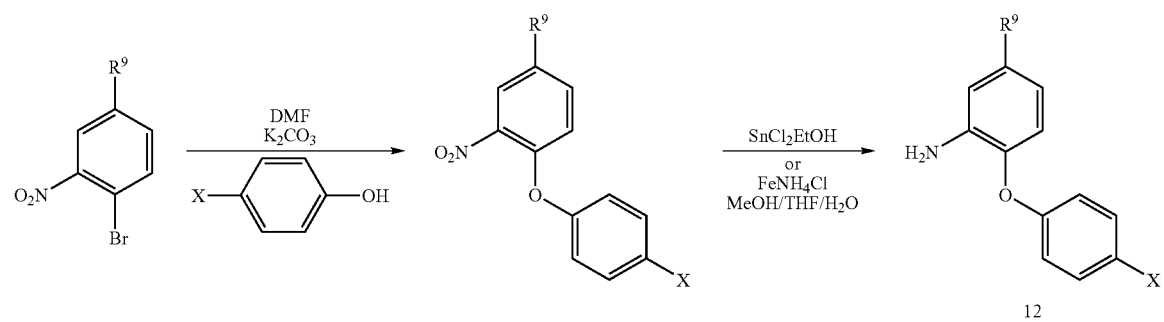
$R^9$ is defined above;
X is OH, NH2, NHR, halo, alkyl, or alkoxy
R is alkylm alkoxy, bromo, fluoro, chloro, or cyano

Preparation of 7-Substituted-4-aminophenyl-[1,8]naphthyridines

As shown in Scheme 4, the coupling agent (compound 10, 11, 12 or the like) appropriate for the synthesis of the desired 7-substituted-4-aminophenyl-[1,8]naphthyridine is dissolved in ethanol and reacted with compound 8 in ethanol at 80° C. for about 7 hours. The reaction mixture is concentrated under vacuum and recrystallized from tetrahydrofuran with a few drops of methanol. Filtration gives the desired 7-substituted-4-aminophenyl-[1,8]naphthyridine 13, 14 or 15.

Scheme 4

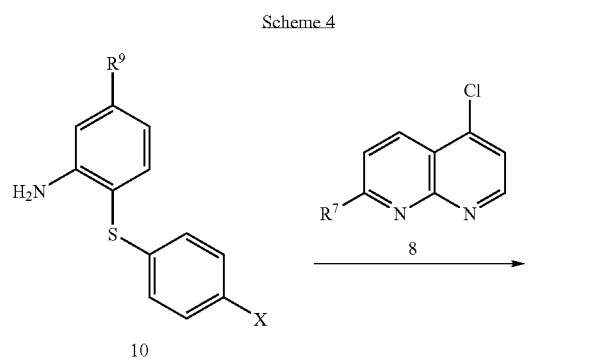

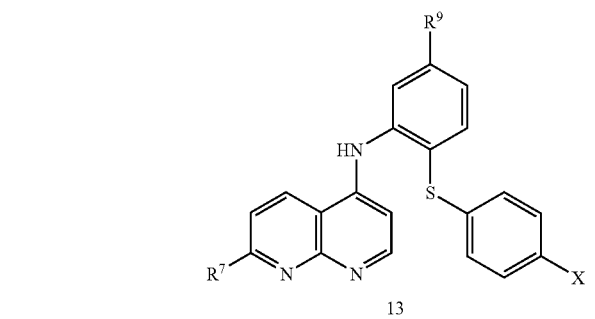

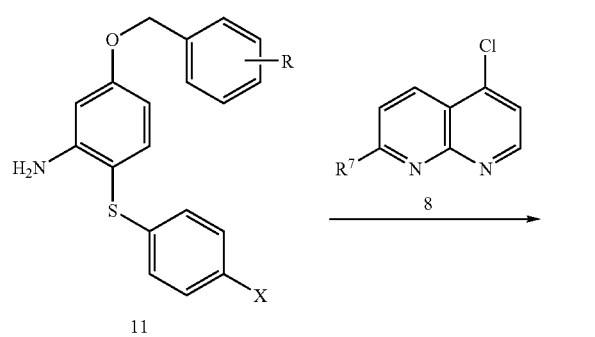

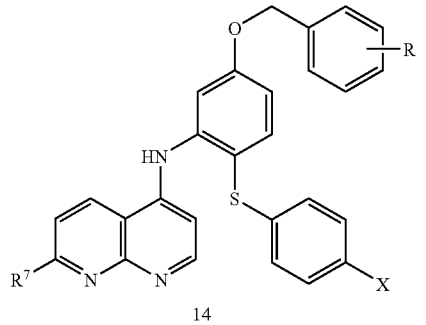

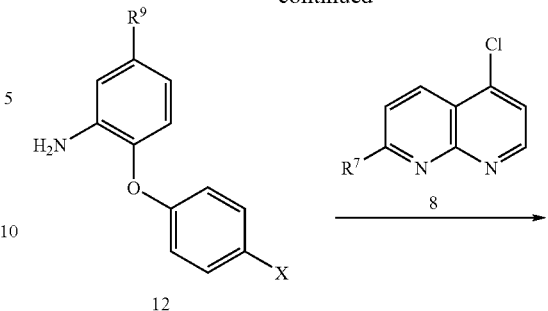

$R^9$ is defined above;
X is defined above;
R is defined above

Preparation of Amide Coupling Agents

As described in Scheme 3, a wide variety of aminophenyl coupling agents are possible. These aminophenyl coupling agents can be used to prepare desired 7-substituted-4-aminophenyl-[1,8]naphthyridine according to the procedures depicted in Scheme 4.

In Scheme 5, aminophenyl compounds with amide substitution in the 3-phenyl position are described.

A substituted aniline in methylene chloride is treated with 4-chloro-3-nitrobenzoyl chloride and N,N-diisopropylamine and stirred at room temperature for about 17 hours. The solvent is removed under vacuum, the residue dissolved in ethyl acetate, washed with water and brine, dried over sodium sulfate, filtered and concentrated under vacuum to give the N-substituted phenyl-4-chloro-3-nitrobenzamide 16.

Compound 16 can be further modified by displacement of the 4-chloro group to produce the 3-amino-4-substituted phenoxybenzamides 17 and the 3-amino-4-substituted phenylsulfanylbenzamides 18.

Compounds 17 can typically be prepared by reacting the benzamide 16 in anhydrous N,N-dimethylformamide with 4-(N-t-butoxycarbonyl)aminophenol (N-Boc-4-hydroxyaniline) and potassium carbonate at room temperature, then heated to about 80° C. for about 5 hours. The reaction is cooled to room temperature, the solvent removed under vacuum, the residue taken up in ethyl acetate, washed with water and brine. The organic layer is dried over sodium sulfate, filtered and concentrated under vacuum to produce the 4-N-t-butoxycarbonylamino substituted compound 17. The Boc protecting group can be removed under a variety of methods to produce compounds of structure 17.

In a similar manner, compound 16 can be reacted with 4-aminothiophenol and anhydrous sodium acetate in anhydrous ethanol heating under reflux four about 19 hours. Upon cooling to room temperature the ethanol is removed under vacuum, the residue taken up in water and extracted with ethyl acetate. The organic extracts are washed with brine, dried over sodium sulfate, filtered and concentrated under vacuum. Trituration of the solid with ethylacetate-methylene chloride afforded compound 18.

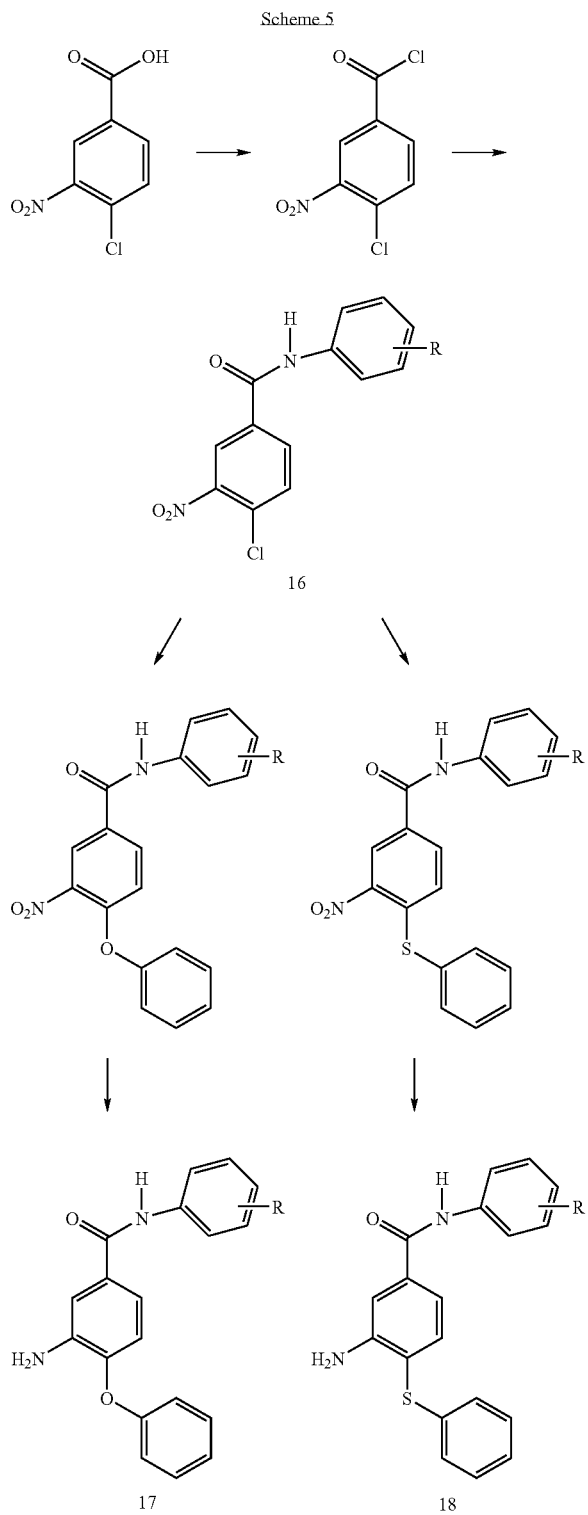

Scheme 5

The amide phenyl ring, the phenyoxy ring and the phenylsuflanyl ring can be substituted as described above. Some examples will require the use of protecting groups followed by removal of the protecting group at the appropriate time.
R is as defined above.

Preparation of Reverse Amide Coupling Agents

The preparation of reverse amide agents for coupling is shown in Scheme 6. In a typical preparation 4-fluoro-3-nitroaniline is reacted with a substituted benzoyl chloride, Hunig's base (N,N-diisopropylethylamine) in tetrahydrofuran with stirring at room temperature for about 1 hour. Water is added to the solution and the resulting solid (compound 19) is collected by filtration and dried in a vacuum oven.

A solution of compound 19, 4-hydroxythiophenol and potassium carbonate in N,N-dimethylformamide is heated to about 80° C. for about 2 hours. After cooling to room temperature, the mixture is poured unto ice water, extracted with ethyl acetate, the extracts dried over magnesium sulfate, filtered and concentrated under vacuum to give the 4-hydroxyphenylsulfanyl intermediate. A solution of this intermediate, iron powder and ammonium chloride in tetrahydrofuran and water is heated to reflux for about 3 hours. The resulting mixture is cooled and diluted with methanol and filtered. The filtrate is diluted with water and extracted with methylene chloride. The methylene chloride extracts are dried over magnesium sulfate, filtered and concentrated under vacuum to give the 4-hydroxy analog of compound 23.

Similarly a compound 19 can be reacted with 4-aminothiophenol and cesium carbonate in N,N-dimethylformamide at about 90° C. for about 4 hours. After cooling to room temperature the mixture is poured into ice water and acidified to pH 5 with 1 N hydrochloric acid. The solution is extracted with ethyl acetate, the extracts dried over sodium sulfate, filtered and concentrated under vacuum to give the corresponding 4-aminophenylsulfanyl-3-nitroanilide. A methylene chloride solution of this anilide is then reacted with 2,2,2-trichloroethyl chloroformate and pyridine for about 16 hours. The solution is then washed with water, then brine and then the extracts are dried over sodium sulfate, filtered and concentrated under vacuum. The residue is triturated with hexane and ethyl acetate to give the corresponding Troc-amino-protected compound 22. This Troc-protected amino compound is then dissolved in ethanol and tetrahydrofuran and reacted with iron powder and ammonium chloride at reflux for about 6 hours. The resultant mixture is cooled diluted with ethanol and filtered. The filtrates are concentrated under vacuum to give the Troc-amino protected compound 23.

Similarly a solution of compound 19 in anhydrous N,N-dimethylformamide can also be reacted with the 4-t-butoxycarbonylaminophenol (N-Boc-4-hydroxyaniline) and potassium carbonate at room temperature, and then heated to about 80° C. for about 5 hours. The reaction is cooled to room temperature, the solvent removed under vacuum and the residue taken up in ethyl acetate, washed with water and brine dried over sodium sulfate, filtered and concentrated under vacuum to give the N-Boc protected compound 20. Compound 20 is then dissolved in ethanol, tetrahydrofuran and water and reacted with iron powder and ammonium chloride heating the mixture at about 90° C. for about 2 hours. After cooling to room temperature the mixture is diluted with ethyl acetate, filtered and the filtrate washed with water and brine. The organic phase is dried over sodium sulfate, filtered and concentrated under vacuum to give the coupling agent compound 22.

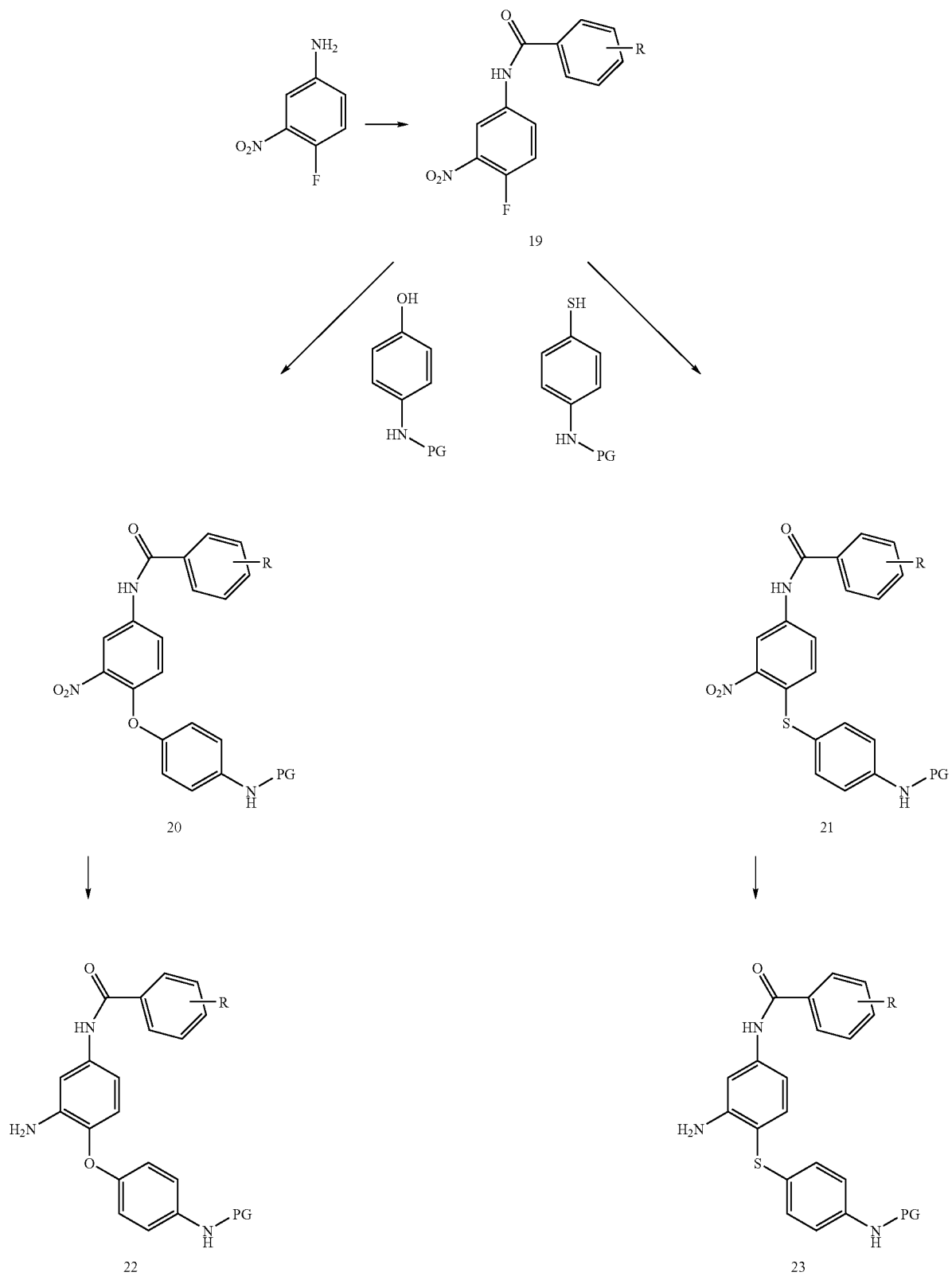
PG = Protecting Group
such as Boc-, Troc- and the like.
R is as defined above Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Reactions may be worked up in the convention manner, e.g. by eliminating the solvent from the residue and further purified according to methodologies generally known in the art such as, but not limited to, crystallization, distillation, extraction, trituration and chromatography.

It should be understood that the above-described embodiments and schemes and the following examples are given by way of illustration, not limitation. Various changes and modifications within the scope of the present invention will become apparent to those skilled in the art from the present description.

Example 1

(7-Methyl-[1,8]naphthyridin-4-yl)-(5-methyl-2-phenylsulfanyl-phenyl)-amine

Example 1a

2-[(6-Methyl-pyridin-2-ylamino)-methylene]-malonic acid diethyl ester

A mixture of 2-methyl-5-aminopyridine (12.48 g, 115 mmol) and 2-ethoxymethylene-malonic acid diethyl ester (7.46 mL, 89.2 mmol) was heated at 100° C. with stirring for 2.5 h. Cooled to room temperature and diluted with hexane. Filtered and dried under vacuum giving the title compound (21.05 g, 85%).

Example 1b

7-Methyl-4-oxo-1,4-dihydro-[1,8]naphthyridine-3-carboxylic acid ethyl ester

A solution of diphenyl ether was heated to 250° C. and the product of Example 1a (2.50 g, 9.0 mmol) was added in several small portions over a period of about 5 min then heated at 250° C. for 30 min. After cooling to room temperature diluted with hexane. The resulting solid was filtered and was dried under vacuum giving the title compound as a tan solid (1.47 g, 71%).

Example 1c

7-Methyl-[1,8]naphthyridin-4-ol

A solution of the product from Example 1b (1.30 g, 5.59 mmol) and NaOH (233 mg, 5.82 mmol) in 20 mL of water was heated in a sealed metal reactor at 180° C. for 16 h. Cooled to room temperature and adjusted to pH 6 with 1N HCl. The resulting precipitates was filtered and dried under vacuum giving the title compound as a black solid (743 mg, 82%).

Example 1d

5-Chloro-2-methyl-[1,8]naphthyridine

A mixture of the product from Example 1c (320 mg, 2.0 mmol) in 6 mL of $POCl_3$ was heated at 50° C. with stirring for 6 h. Cooled to room temperature and quenched by pouring into ice. Adjusted to pH 10 with $NH_4OH$ and extracted with $CH_2Cl_2$. Dried over $Na_2SO_4$, filtered and concentrated under vacuum giving the title compound as a tan solid (322 mg, 90%).

Example 1e

4-Methyl-2-nitro-1-phenylsulfanyl-benzene

A solution of sodium thiophenolate (3.96 g, 30 mmol) in 60 mL of DMF was heated at 50° C. with 4-chloro-3-nitrotoluene (2.65 mL, 20 mmol) with stirring for 2 days. Cooled to room temperature and diluted with $CH_2Cl_2$. Washed with water and dried the organic layer over $Na_2SO_4$. Filtered and concentrated under vacuum giving the title compound (4.29 g, 87%) $^1H$ NMR (300 MHz, $CDCl_3$) δ ppm: 2.36 (s, 3H) 6.76 (d, J=8.09 Hz, 1H) 7.16 (d, J=8.46 Hz, 1H) 7.45 (m, 3H) 7.58 (m, 2H) 8.03 (s, 1H).

Example 1f

5-Methyl-2-phenylsulfanyl-phenylamine

A solution of the product from Example 1e (1.17 g, 7.0 mmol) in 25 mL of absolute EtOH and $SnCl_2$ (3.58 g, 29.8 mmol) was stirred at room temperature for 16 h. Adjusted to pH 12 with 1N NaOH and extracted with EtOAc. Dried over $Na_2SO_4$, filtered and concentrated under vacuum giving the title compound (835 mg, 82%) $^1H$ NMR (300 MHz, $CDCl_3$) δ ppm: 2.30 (2, 3H) 6.62 (d, J=8.83 Hz, 1H) 6.69 (s, 1H) 7.10 (m, 3H) 7.21 (m, 2H) 7.54 (d, J=7.72 Hz, 2H).

Example 1g (7-Methyl-[1,8]naphthyridin-4-yl)-(5-methyl-2-phenylsulfanyl-phenyl)-amine A stirred solution of the product from Example 1d (65 mg, 0.36 mmol) and the product from Example 1f (77 mg, 0.36 mmol) in 3 mL of EtOH was heated at 80° C. for 7 h. Concentrated under vacuum. Recrystallized from THF with a few drops of MeOH. Filtration gave the title compound as the hydrochloride salt as a white solid (62 mg, 43%) $^1H$ NMR (300 MHz, $CDCl_3$) δ ppm: 1.62 (brs, 1H) 2.43 (s, 3H) 2.52 (s, 3H) 6.02 (d, J=7.0 Hz, 1H) 7.05-7.35 (m, 8H) 7.70 (brs, 1H) 8.00 (d, J=7.0 Hz, 1H) 8.85 (d, J=8.5 Hz, 1H) 10.80 (brs, 1H); MS (ESI+) m/z 358 (M–Cl)+; (ESI–) m/z 356 (M–HCl)–.

Example 2

(5-Methyl-2-phenylsulfanyl-phenyl)-(7-propyl-[1,8]naphthyridin-4-yl)-amine

Example 2a 2-(2,5-Dimethyl-pyrrol-1-yl)-6-methyl-pyridine

A solution of 2-methyl-5-aminopyridine (5.0 g, 46 mmol) and hexane-2,5-dione (5.4 mL, 46 mmol) in 60 mL benzene was treated with HOAc (0.5 mL, 7.9 mmol). The solution was heated under reflux with the azeotropic removal of water for 20 h. Cooled to room temperature and diluted with ether. Washed with dilute HCl and water. The organic layer was dried over $MgSO_4$, filtered and concentrated under vacuum giving the title compound (4.7 g, 55%).

Example 2b 2-(2,5-Dimethyl-pyrrol-1-yl)-6-propyl-pyridine

A solution of the product from Example 2a (7.53 g, 40.0 mmol) in 30 mL of dry THF was added dropwise with stirring to a solution of LDA (42.4 mmol) in 30 mL of dry THF at −30° C. Stirred at −30° C. for 30 min. Added EtI (3.42 mL, 42.0 mmol) in 20 mL of dry THF dropwise with stirring for 30 min then warmed to room temperature. After 2 h quenched by pouring into saturated NaCl solution and extracted with ether. Dried over MgSO$_4$, filtered and concentrated under vacuum giving the title compound. The product was purified by silica gel column chromatography eluting with EtOAc/hexane to give the title compound (5.21 g, 60%).

Example 2c

6-Propyl-pyridin-2-ylamine

A solution of the product from Example 2b (348 mg, 1.52 mmol) and NH$_2$OH HCl (530 mg, 7.62 mmol) in 4 mL of EtOH/1.5 mL water. Heated at 100° C. for 16 h, cooled to room temperature and extracted with CH$_2$Cl$_2$. Dried over MgSO$_4$ filtered and concentrated under vacuum giving the title compound as an amber oil (223 mg, 100%).

Example 2d

2-[(6-Propyl-pyridin-2-ylamino)-methylene]-malonic acid diethyl ester

The product from Example 2c (223 mg, 1.52 mmol) was reacted with 2-ethoxymethylene-malonic acid diethyl ester 0.350 mL, 1.75 mmol) following the procedure in Example 1a to give the title compound after silica gel column chromatography eluting with EtOAc/hexane (386 mg, 80%).

Example 2e

4-Oxo-7-propyl-1,4-dihydro-[1,8]naphthyridine-3-carboxylic acid ethyl ester

The product of Example 2d (6.87 g, 22.4 mmol) was heated in diphenyl ether following the procedure in Example 1b giving the title compound as a tan solid (4.73 g, 81%).

Example 2f

7-Propyl-[1,8]naphthyridin-4-ol

The product from Example 2e (4.73 g, 18.1 mmol) was reacted with NaOH (756 mg, 18.9 mmol) following the procedure from Example 1c giving the title compound as a solid (3.42 g, 100%).

Example 2g

5-Chloro-2-propyl-[1,8]naphthyridine

The product from Example 2f (145 mg, 0.76 mmol) was reacted with POCl$_3$ 4 mL following the procedure from Example 1d giving the title compound as a solid (135 mg, 86%).

Example 2h (5-Methyl-2-phenylsulfanyl-phenyl)-(7-propyl-[1,8]naphthyridin-4-yl)-amine The product from Example 2g (65 mg, 0.3 µmol) was reacted with the product from Example 1f (68 mg, 0.31 mmol) for 24 h following the procedure from Example 1g giving the title compound as a hydrochloride salt as a solid which was triturated with ether giving (10 mg, 84%). $^1$H NMR (300 MHz, DMSO-d$_6$) δ ppm: 0.97 (t, J=7.35 Hz, 3H) 2.38 (qnt, J=7.35 Hz, 2H) 2.99 (dd, J=7.35 Hz, J=7.72 Hz, 2H) 6.31 (d, J=7.35 Hz, 1H) 7.23 (s, 5H) 7.35 (m, 4H) 7.79 (d, J=8.46 Hz, 1H) 8.38 (d, J=6.98 Hz, 1H) 9.01 (d, J=8.46 Hz, 1H) 11.10 (s, 1H) 14.35 (br s , 1H); MS (ESI+) m/z 386 (M−Cl)+; (ESI−) m/z 384 (M−HCl)−.

Example 3

(7-Ethyl-[1,8]naphthyridin-4-yl)-(5-methyl-2-phenylsulfanyl-phenyl)-amine

Example 3a 2-(2,5-Dimethyl-pyrrol-1-yl)-6-ethyl-pyridine

To a solution of the product from Example 2a (6.82 g, 36.6 mmol) in 75 mL of dry THF cooled to 40° C. under a N$_2$ atmosphere was added dropwise n-BuLi as a 2.5M solution in hexanes (16 mL, 40 mmol). The resulting solution was stirred at low temperature for thirty minutes then treated with CH$_3$I (2.4 mL, 38.6 mmol). On completion of the addition the mixture was allowed to warm to −30° C. and after 20 min to room temperature. The reaction was subsequently quenched by pouring into brine solution, the product isolated by extraction with EtOAc. Dried over MgSO$_4$, filtered and concentration under vacuum. Purified by silica gel column chromatography eluting with EtOAc/hexane gave the title compound (4.42 g, 60%).

Example 3b

6-Ethyl-pyridin-2-ylamine

The product from Example 1a (4.93 g, 0.025 mol) was dissolved in a mixture of EtOH (80 mL) and water (30 mL). To this was added hydroxylamine hydrochloride (8.6 g, 0.123 mol) and the resulting mixture heated to 100° C. for 8 h. The reaction mixture was poured into dilute sodium hydroxide solution and the crude product isolated by extraction with CH$_2$Cl$_2$ and dried over MgSO$_4$ filtered and concentrated under vacuum giving the title compound. The material was used as isolated.

Example 3c

2-[(6-Ethyl-pyridin-2-ylamino)-methylene]-malonic acid diethyl ester

The crude product from Example 3b was combined with 2-ethoxymethylene-malonic acid diethyl ester (6.6 mL, 0.032 mol) and the mixture heated under a N$_2$ atmosphere in an oil bath at 100° C. for 2 h. Purified by flash chromatography on silica gel eluting with EtOAc/hexane giving the title compound (7.16 g, 98%).

Example 3d

7-Ethyl-4-oxo-1,4-dihydro-[1,8]naphthyridine-3-carboxylic acid ethyl ester

The product of Example 3c (7.16 g, 0.024 mol) was heated in diphenyl ether following the procedure in Example 1b giving the title compound (4.73 g, 79%) as a tan solid.

Example 3e

7-Ethyl-[1,8]naphthyridin-4-ol

The product from Example 3d (4.70 g, 19.1 mmol) was reacted with NaOH (0.808 g, 20.2 mmol) following the procedure of Example 1c giving the title compound as a light green solid (2.43 g, 73%).

Example 3f

5-Chloro-2-ethyl-[1,8]naphthyridine

The product from Example 3e (200 mg, 1.14 mmol) was treated with $POCl_3$ following the procedure from Example 1d giving the title compound as a brown solid (183 mg, 83%).

Example 3g (7-Ethyl-[1,8]naphthyridin-4-yl)-(5-methyl-2-phenylsulfanyl-phenyl)-amine The product from Example 3f (88 mg, 0.46 mmol) was reacted with the product from Example 1f (100 mg, 0.46 mmol) for 24 h following the procedure from Example 1f giving the title compound as a hydrochloride salt which was triturated with ether giving (134 mg, 70%). $^1$H NMR (300 MHz, DMSO-$d_6$) δ ppm: 1.34 (t, J=7.35 Hz, 3H) 3.02 (q, J=7.35 Hz, 2H) 6.69 (d, J=6.99 Hz, 1H) 6.97 (d, J=8.82 Hz, 2H) 7.10 (dd, J=7.35 Hz, 1H) 7.15 (d, J=8.82 Hz, 2H) 7.30 (dd, J=8.09 Hz, J=7.72 Hz, 2H) 7.56 (dd, J=2.94 Hz, J=9.19 Hz, 1H) 7.71 (d, J=2.57 Hz, 1H) 7.88 (d, J=8.82 Hz, 1H) 8.52 (d, J=6.99 Hz, 1H) 9.02 (d, J=8.45 Hz, 1H) 11.16 (br s, 1H) 14.56 (br s, 1H); MS (ESI+) m/z 376 (M−Cl)+; (ESI−) m/z 374 (M−HCl)−.

Example 4

4-[2-(7-Ethyl-[1,8]naphthyridin-4-ylamino)-4-methyl-phenylsulfanyl]-phenol

Example 4a

Trifluoro-methanesulfonic acid 4-methyl-2-nitro-phenyl ester

A solution of the 4-methyl-2-nitro phenol (6.0 g, 39.1 mmol) and $Et_3N$ (16.38 mL, 117.5 mmol) in 100 mL of $CH_2Cl_2$ under a $N_2$ atmosphere was treated with trifluoromethanesulfonic anhydride (7.25 mL, 43.1 mmol) at 0° C. for 30 min. Quenched by addition of MeOH. Washed sequentially with 10% citric acid, 0.5 m KOH and water. Dried over $MgSO_4$, filtered and concentrated under vacuum giving the title compound which was purified by silica gel column chromatography eluting with $CH_2Cl_2$ giving an amber oil (11.22 g, 100%).

Example 4b 4-(4-Methyl-2-nitro-phenylsulfanyl)-phenol

The product from Example 4a (11.22 g, 39.3 mmol) and 4-mercaptophenol (4.96 g, 39.3 mmol) in 100 mL of EtOH was treated with $Na_2CO_3$ and heated overnight under efflux. Cooled to room temperature and quenched with water. Extracted with EtOAc. Dried over $MgSO_4$, filtered and concentrated under vacuum giving the title compound, which was purified by silica gel column chromatography eluting with 25% EtOAc/hexane giving a red oil (8.65 g, 85%).

Example 4c 4-(2-Amino-4-methyl-phenylsulfanyl)-phenol

The product from Example 4b (8.65 g, 31.3 mmol) was reduced with $SnCl_2$ following the procedure from Example 1f giving the title compound as a white solid (8.51 g, 100%).

Example 4d

4-[2-(7-Ethyl-[1,8]naphthyridin-4-ylamino)-4-methyl-phenylsulfanyl]-phenol

The product from Example 4c (131 mg, 0.530 mmol) was reacted with the product from Example 3f (97 mg, 0.503 mmol) for 21 h following the procedure from Example 1g giving the title compound as a hydrochloride salt which was triturated with 5:1 ether/THF giving (210 mg, 98%). $^1$H NMR (300 MHz, DMSO-$d_6$) δ ppm: 1.37 (t, J=7.35 Hz, 3H) 2.33 (s, 3H) 3.05 (q, J=7.35 Hz, 2H) 6.29 (d, J=6.99 Hz, 1H) 6.74 (d, J=8.46 Hz, 2H) 7.00 (m, 1H) 7.17-7.29 (m, 4H) 7.84 (d, J=8.83 Hz, 1H) 8.43 (d, J=6.98 Hz, 1H) 9.09 (d, J=8.83 Hz, 1H) 9.90 (s, 1H) 11.12 (br s, 1H) 14.38 (br s, 1H); MS (ESI+) m/z 388 (M−Cl)+; (ESI−) m/z 386 (M−HCl)−.

Example 5

4-[4-Methyl-2-(7-methyl-[1,8]naphthyridin-4-ylamino)-phenylsulfanyl]-phenol

The product from Example 1d (277 mg, 0.156 mmol) was reacted with the product from Example 4c (361 mg, 0.156 mmol) for 5 h by the procedure in Example 1g giving the title compound after purification of the crude product by HPLC with TFA as the trifluoroacetic acid salt (231 mg, 30%). $^1$H NMR (300 MHz, DMSO-$d_6$) δ ppm: 2.33 (s, 3H) 2.77 (s, 3H) 6.29 (d, J=6.99 Hz, 1H) 6.73 (d, J=8.82 Hz, 2H) 7.01 (d, J=7.72 Hz, 1H) 7.19 (d, J=8.46 Hz, 2H) 7.24 (s, 1H) 7.27 (s, 1H) 7.81 (d, J=8.82 Hz, 1H) 8.44 (d, J=6.99 Hz, 1H) 9.01 (d, J=8.82 Hz, 1H) 9.91 (s, 1H) 11.03 (s, 1H) 14.38 (br. s, 1H); MS (ESI+) m/z 374 (M+H)+.

Example 6

4-[4-Methyl-2-(7-propyl-[1,8]naphthyridin-4-ylamino)-phenylsulfanyl]-phenol

The product from Example 2g (275 mg, 0.133 mmol) was reacted with the product from Example 4c (231 mg, 0.133 mol) for 5 h following the procedure from Example 1g giving the title compound after purification of the crude product by HPLC with TFA as the trifluoroacetic acid salt (288 mg, 42%). $^1$H NMR (300 MHz, DMSO-$d_6$) δ ppm: 0.98 (t, J=7.35 Hz, 2H) 1.85 (m, 2H) 2.33 (s, 3H) 3.00 (t, J=7.35 Hz 2H) 6.29

(d, J=6.99 Hz, 1H) 6.73 (d, J=8.46 Hz, 2H) 7.00 (m, 2H) 7.19 (d, J=8.46 Hz, 2H) 7.27 (s, 1H) 7.83 (d, J=8.82 Hz, 1H) 8.43 (d, J=7.35 Hz, 1H) 9.04 (d, J=8.46 Hz, 1H) 9.90 (s, 1H) 11.04 (s, 1H) 14.40 (br. s, 1H); MS (ESI+) m/z 402 (M+H)+.

Example 7

(5-Methyl-2-phenylsulfanyl-phenyl)-(7-trifluoromethyl-[1,8]naphthyridin-4-yl)-amine Example 7a 2,6-Dibromo-nicotinic acid A sample of 2,6-dichloro-nicotinic acid (2.50 g, 13.0 mmol) was reacted with 25 mL of 30% HBr/HOAc in a sealed metal reactor at 110° C. for 2 h at 177 psi. Cooled to room temperature and extracted with EtOAc and washed with water. Dried over $MgSO_4$, filtered and concentrated under vacuum giving the title compound giving the tile compound as a solid (3.22 g, 88%).

Example 7b

7-Bromo-1-tert-butyl-4-oxo-1,4-dihydro-[1,8]naphthyridine-3-carboxylic acid ethyl ester The product from Example 7a was subjected to the reaction sequence in the U.S. Pat. No. 6,818,654 to give the title compound.

Example 7c 1-tert-Butyl-4-oxo-7-trifluoromethyl-1,4-dihydro-[1,8]naphthyridine-3-carboxylic acid ethyl ester The product from Example 7b (101 mg, 0.28 mmol) was reacted with difluoro-fluorosulfonyl-acetic acid methyl ester (0.132 mL, 1.43 mmol) in 2 mL of DMF with CuI (71 mg, 0.37 mmol) at 75° C. for 15 h under an atmosphere of $N_2$ giving the title compound as a solid (57 mg, 59%).

Example 7d

5-Chloro-2-trifluoromethyl-[1,8]naphthyridine

The product from Example 7c was deprotected with trifluoroacetic acid following the procedure from Example 16b and then treated sequentially using the procedures from Examples 1b-1d to give the title compound as a solid (142 mg, 87%). Yield is for the last step of the sequence.

Example 7e (5-Methyl-2-phenylsulfanyl-phenyl)-(7-trifluoromethyl-[1,8]naphthyridin-4-yl)-amine The product from Example 7d (65 mg, 0.28 mmol) and the product from Example 1f (61.5 mg, 0.28 mmol) was reacted 28 h following the procedure from Example 1g giving the title compound as a hydrochloride salt after trituration with ether giving (131 mg, 99%). $^1$H NMR (300 MHz, DMSO-$d_6$) δ ppm: 6.43 (d, J=6.99 Hz, 1H) 7.23 (m, 4H) 7.35 (m, 4H) 8.39 (d, J=8.82 Hz, 1H) 8.55 (d, J=6.99 Hz, 1H) 9.48 (d, J=8.46 Hz, 1H) 11.55 (brs, 1H); MS (ESI+) m/z 412 (M−Cl)+; (ESI−) m/z 410 (M−HCl)−.

Example 8

(7-Isopropyl-[1,8]naphthyridin-4-yl)-(5-methyl-2-phenylsulfanyl-phenyl)-amine

Examples 8a 2-(2,5-Dimethyl-pyrrol-1-yl)-6-isopropyl-pyridine

The product from Example 12b (1.5 g, 7.26 mmol) was reacted with isopropylmagnesium bromide (4.35 mL, 8.7 mmol) following the procedure from Example 12c, after 1 h a second charge of both the Grignard reagent and the iron catalyst were given giving the title compound. The product was purified by silica gel column chromatography eluting with 2% EtOAc/hexane giving (880 mg, 56%).

Example 8b

5-Chloro-2-isopropyl-[1,8]naphthyridine

The product from Example 8a was treated sequentially using the procedures from Examples 2c-2g to give the title compound.

Example 8c (7-Isopropyl-[1,8]naphthyridin-4-yl)-(5-methyl-2-phenylsulfanyl-phenyl)-amine The product from Example 8b (0.098 g, 0.475 mmol) was reacted with the product from Example 1f (0.102 g, 0.475 mmol) for 18 h following the procedure from Example 1g to give the title compound, which was purified by HPLC with TFA. Converted to the hydrochloride salt by treatment with 4N HCl in dioxane at room temperature gave the hydrochloride salt (0.076 g, 38%). $^1$H NMR (300 MHz, DMSO-$d_6$) δ ppm 1.37 (d, J=6.99 Hz, 6H) 2.38 (s, 3H) 3.30 (m, 1H) 6.32 (d, J=6.99 Hz, 1H) 7.24 (s, 5H) 7.34 (m, 3H) 7.86 (d, J=8.82 Hz, 1H) 8.39 (d, J=7.35 Hz, 1H) 9.08 (d, J=8.46 Hz, 1H) 11.16 (s, 1H) 14.36 (m, 1H); MS (ESI+) m/z 386.0 (M+H)+.

Example 9

(5-Methoxy-2-phenylsulfanyl-phenyl)-(7-methyl-[1,8]naphthyridin-4-yl)-amine

Example 9a

4-Methoxy-2-nitro-1-phenylsulfanyl-benzene

A solution of 1-Chloro-4-methoxy-2-nitro-benzene (3.75 g, 20.0 mmol) was reacted with sodium thiophenolate (3.96 g, 30.0 mmol) at 70° C. for 48 h following the procedure in Example 1e giving the title compound as a yellow oil after silica gel column chromatography eluting with 25% EtOAc/hexane (2.70 g, 54%).

Example 9b

5-Methoxy-2-phenylsulfanyl-phenylamine

The product from Example 9a (2.70 g, 10.2 mmol) was reacted with $SnCl_2$ (9.40 g, 50.0 mmol) for 22 h following the procedure from Example 1f giving the title compound as a white solid (2.28 g, 96%).

Example 9c (5-Methoxy-2-phenylsulfanyl-phenyl)-(7-methyl-[1,8]naphthyridin-4-yl)-amine The product from Example 9b (69 mg, 0.30 mmol) was reacted with the product from Example 1d (53 mg, 0.30 mmol) following the procedure from Example 1g giving the title compound as a hydrochloride salt after trituration with solid (119 mg, 96%). $^1$H NMR (300 MHz, DMSO-$d_6$) δ ppm: 2.75 (s, 3H) 3.83 (s, 3H) 6.34 (d, J=6.99 Hz, 1H) 7.07 (m, 7H) 7.57 (d, J=8.46 Hz, 1H) 7.76 (d, J=8.46 Hz, 1H) 8.85 (d, J=6.99 Hz, 1H) 8.99 (d, J=8.46 Hz, 1H) 11.16 (br s, 1H) 14.43 (brs, 1H); MS (ESI+) m/z 374 (M−Cl)+; (ESI−) m/z 372 (M−HCl)−.

Example 10

7-Methyl-4-(5-methyl-2-phenylsulfanyl-phenylamino)-[1,8]naphthyridine-3-carboxylic acid ethyl ester

Example 10a

4-Chloro-7-methyl-[1,8]naphthyridine-3-carboxylic acid ethyl ester

The product from Example 1b (1.0 g, 4.30 mmol) was reacted with 12 mL of POCl$_3$ for 4 h following the procedure from Example 1d giving the title compound as a brownish-pink solid (619 mg, 57%).

Example 10b

7-Methyl-4-(5-methyl-2-phenylsulfanyl-phenylamino)-[1,8]naphthyridine-3-carboxylic acid ethyl ester The product from Example 10a (438 mg, 2.03 mmol) was reacted with the product from Example 1f (510 mg, 2.03 mmol) for 10 min following the procedure from Example 1g giving the title compound which was purified by silica gel column chromatography eluting with 4% MeOH/CH$_2$Cl$_2$ as a solid (114 mg, 57%). $^1$H NMR (300 MHz, DMSO-$d_6$) δ ppm: 1.33 (t, J=6.99 Hz, 3H) 2.16 (s, 3H) 2.62 (s, 3H) 4.29 (q, J=7.11 Hz, 2H) 6.86 (s, 1H) 7.04 (d, J=8.09 Hz, 1H) 7.15-7.34 (m, 6H) 7.39 (d, J=7.72 Hz, 1H) 7.69 (d, J=8.82 Hz, 1H) 9.17 (s, 1H) 10.13 (s, 1H); MS (ESI+) m/z 430 (M+H)+, (ESI−) m/z 428 (M−H)−.

Example 11

7-Methyl-4-(5-methyl-2-phenylsulfanyl-phenylamino)-[1,8]naphthyridine-3-carboxylic acid methoxy-methyl-amide

Example 11a

7-Methyl-4-(5-methyl-2-phenylsulfanyl-phenylamino)-[1,8]naphthyridine-3-carboxylic acid The product from Example 10 (250 mg, 0.58 mmol) was reacted with 2 mL of 1N NaOH in 4 mL of dioxane at 65° C. for 30 min. Cooled to room temperature and diluted with water, adjusted to pH 3 with 1N HCl and isolated the resulting solid by vacuum filtration to give the title compound (215 mg, 92%).

Example 11b

7-Methyl-4-(5-methyl-2-phenylsulfanyl-phenylamino)-[1,8]naphthyridine-3-carboxylic acid methoxy-methyl-amide The product from Example 11a (50.5 mg, 0.125 mmol) was reacted with 1,1'-carbonyldiimidazole (40.8 mg, 0.215 mmol) in 2 mL of DMF under an atmosphere of N$_2$ for 30 min. Added N,O-dimethylhydroxylamine hydrochloride (25 mg, 0.215 mmol) and stirred ate room temperature for 24 h. The solvent was concentrated under vacuum giving the title compound. After purification of the crude product by HPLC with AA the product was isolated as the free base (12 mg, 21%). $^1$H NMR (300 MHz, DMSO-D6) δ ppm: 2.23 (s, 3H) 2.67 (s, 3H) 2.89 (s, 3H) 3.39 (s, 3H) 6.86 (s, 1H) 6.91-7.04 (m, 1H) 7.15-7.35 (m, 7H) 7.44 (d, J=8.46 Hz, 1H) 8.34 (d, J=8.09 Hz, 1H) 8.67 (s, 1H); MS (ESI+) m/z 445 (M+H)$^+$, 467 (M+Na)$^+$, MS (ESI−) m/z 443 (M−H)$^−$.

Example 12

4-[2-(7-Isobutyl-[1,8]naphthyridin-4-ylamino)-4-methyl-phenylsulfanyl]-phenol

Example 12a

6-Chloro-pyridin-2-ylamine

A solution of 2,6-dichloropyridine (500 g, 3.37 mol) was treated with NH4OH in a sealed metal reactor at 180° C. for 40 h. After cooling to room temperature the product was isolated by suction filtration giving the title compound as a solid (400 g, 92%).

Example 12b

2-Chloro-6-(2,5-dimethyl-pyrrol-1-yl)-pyridine

The product from Example 12a (20 g, 156 mmol) was treated with hexane-2,5-dione (18.3 mL, 156 mmol) for 2 h following the procedure from Example 2a giving the title compound (17.7 g 55%).

Example 12c 2-(2,5-Dimethyl-pyrrol-1-yl)-6-isobutyl-pyridine

The product from Example 12b (1.0 g, 4.84 mmol) was treated with 2.0 M isobutylmagnesium chloride (2.90 mL, 5.81 mmol) in 30 mL THF and 3 mL NMP at room temperature under a N$_2$ atmosphere. Added Fe(acac)$_3$ (85 mg, 0.242 mmol) and stirred at room temperature for 18 h. During the course of the reaction two additional charges of Grignard reagent and catalyst were added. The reaction was quenched by pouring into 5% acetic acid and extracting with ether. Dried over Na$_2$SO$_4$, filtered and concentrated under vacuum giving the title compound that was purified by silica gel column chromatography eluting with 10% EtOAc/hexane to give (620 mg, 56%).

Example 12d

5-Chloro-2-isobutyl-[1,8]naphthyridine

The product from Example 12c was treated sequentially using the procedures from Examples 2c-2g to give the title compound.

Example 12e

4-[2-(7-Isobutyl-[1,8]naphthyridin-4-ylamino)-4-methyl-phenylsulfanyl]-phenol The product from Example 12d (100 mg, 45.3 mmol) was reacted with the product from Example 4c (105 mg, 45.3 mmol) for 18 h following the procedure from Example 1g giving the title compound after purification of the crude product by HPLC with TFA as the trifluoroacetic acid salt (90 mg, 47%). $^1$H NMR (300 MHz, DMSO-d$_6$) δ ppm 0.97 (d, J=6.62 Hz, 6H), 2.13-2.30 (m, 1H), 2.33 (s, 3H), 2.89 (d, J=6.99 Hz, 2H), 6.29 (d, J=6.99 Hz, 1H), 6.73 (d, J=8.46 Hz, 2H), 7.00 (d, J=8.09 Hz, 1H), 7.13-7.34 (m, 4H), 7.81 (d, J=8.46 Hz, 1H), 8.43 (d, J=6.99 Hz, 1H), 9.03 (d, J=8.46 Hz, 1H), 10.99 (br. s., 1H), 14.36 (br. s., 1H); MS (ESI+) m/z 416 (M+H)+; (ESI−) m/z 414 (M−H)−.

Example 13

4-[2-(7-Ethoxy-[1,8]naphthyridin-4-ylamino)-4-methyl-phenylsulfanyl]-phenol

Example 13a

1-tert-Butyl-7-chloro-4-oxo-1,4-dihydro-[1,8]naphthyridine-3-carboxylic acid ethyl ester This compound was prepared from 2,6-dichloro-nicotinic acid as described in the U.S. Pat. No. 6,818,654 to give the title compound.

Example 13b

7-Chloro-4-oxo-1,4-dihydro-[1,8]naphthyridine-3-carboxylic acid ethyl ester The product from Example 13a (0.282 gm, 0.91 mmol) was combined at room temperature with 2 mL of TFA containing 2 drops of sulfuric acid. The resulting mixture was heated at 70° C. for 16.5 h. The volatiles were removed under vacuum and the residue suspended in water. The product was collected by vacuum filtration, water washed and dried under vacuum to give the title compound as a cream colored solid (0.214 gm, 93%).

Example 13c

[1,8]Naphthyridine-2,5-diol

The product from Example 13b (0.208 gm, 0.82 mmol) was reacted as described in Example 1c to give the title compound as a dark brown solid (0.196 gm, 97%).

Example 13d

2,5-Dichloro-[1,8]naphthyridine

The product from Example 13c (0.111 gm, 0.68 mmol) was reacted as described in Example 1d to give the title compound as a pale yellow solid (0.124 gm, 91%).

Example 13e

4-[2-(7-Chloro-[1,8]naphthyridin-4-ylamino)-4-methyl-phenylsulfanyl]-phenol The product from Example 13d (0.67 g, 3.36 mmol) and the product from Example 4c (0.78 g, 3.36 mmol) in 10 mL ethanol were heated under reflux for 5.5 hr. The reaction mixture was cooled to room temperature and the solvent was removed concentrated under vacuum leaving yellow solid that was used without further purification (1.43 g, 100%).

Example 13f

4-[2-(7-Ethoxy-[1,8]naphthyridin-4-ylamino)-4-methyl-phenylsulfanyl]-phenol The product from Example 13e (0.025 g, 0.063 mmol) was treated with 2 mL 21% by weight NaOEt in EtOH. The resulting mixture was heated at reflux 4 h. The solvent was concentrated under vacuum leaving a brown oily residue. The crude oil was purified by HPLC with TFA. The title compound was isolated as a trifluoroacetic acid salt giving a light brown powder (20 mg, 78%). $^1$H NMR (300 MHz, DMSO-d$_6$) δ ppm: 1.44 (t, J=6.99 Hz, 3H) 2.32 (s, 3H) 4.56 (q, J=6.99 Hz, 2H) 6.24 (d, J=6.99 Hz, 1H) 6.68-6.81 (m, 2H) 6.98 (d, J=8.09 Hz, 1H) 7.05-7.34 (m, 3H) 7.34 (d, J=9.19 Hz, 1H) 8.30 (d, J=6.99 Hz, 1H) 8.92 (d, J=9.19 Hz, 1H) 10.81 (s, 1H) 14.17 (s, 1H); MS (ESI+) m/z 404 (M+H)+; (ESI−) m/z 402 (M+H)−.

Example 14

4-[2-(2,7-Dimethyl-[1,8]naphthyridin-4-ylamino)-4-methyl-phenylsulfanyl]-phenol

Example 14a

2,7-Dimethyl-1H-[1,8]naphthyridin-4-one

A flask containing 2-methyl-5-aminopyridine (5.0 g, 46.2 mmol) and ethyl acetoacetate (6.54 mL, 552.3 mmol) and 5 mL of polyphosphoric acid was heated at 120° C. for 2 h. Cooled to room temperature and poured into water, neutralized with 1N NaOH. Extracted with CH$_2$Cl$_2$ dried over MgSO$_4$, filtered and concentrated under vacuum giving a yellow oil that was heated in diphenyl ether at 250° C. for 1 h. Cooled to room temperature, diluted with hexane and the product was isolated by suction filtration giving the title compound which was used without purification.

Example 14b

4-Chloro-2,7-dimethyl-[1,8]naphthyridine

The product from Example 14a (500 mg, 2.87 mmol) was reacted with 10 mL of POCl$_3$ for 2 h following the procedure from Example 1d giving the title compound, which was used without purification.

Example 14c

4-[2-(2,7-Dimethyl-[1,8]naphthyridin-4-ylamino)-4-methyl-phenylsulfanyl]-phenol The product from Example 14b (60 mg, 0.31 mmol) was reacted with the product from Example 4c (72 mg, 0.31 mmol) for 12 h following the procedure from Example 1g giving the title compound as a crude solid which was purified by HPLC with TFA giving the product as a trifluoroacetic acid salt (45 mg, 37%). $^1$H NMR (300 MHz, DMSO-d$_6$) δ ppm: 2.23 (s, 3H) 2.75 (s, 3H) 3.43 (s, 3H) 6.10 (s, 1H) 6.68 (d, J=8.82 Hz, 2H) 6.99-7.20 (m, 3H) 7.20-7.38 (m, 2H) 7.75 (d, J=8.82 Hz, 1H) 8.96 (d, J=8.82 Hz, 1H) 9.86 (s, 1H) 10.78 (s, 1H) 14.21 (s, 1H); MS (APCI) m/z 386 (M−H)−.

Example 15

4-[2-(7-Methoxy-[1,8]naphthyridin-4-ylamino)-4-methyl-phenylsulfanyl]-phenol

Example 15a

4-[2-(7-Chloro-[1,8]naphthyridin-4-ylamino)-4-methyl-phenylsulfanyl]-phenol

The product from Example 13e (670 mg, 3.36 mmol) was reacted with the product from Example 4c (780 mg. 3.36 mmol) for 5.5 h following the procedure from Example 1g giving the title compound as the hydrochloride salt (1.43 g, 100%).

Example 15b

4-[2-(7-Methoxy-[1,8]naphthyridin-4-ylamino)-4-methyl-phenylsulfanyl]-phenol

The product from Example 15a (0.100 g, 0.254 mmol) was treated with 5 mL Methanol and powdered NaOMe (95%, 0.27 g, 5 mmol). The resulting mixture was heated at reflux 18 h. The solvent was concentrated under vacuum leaving an orange oily residue. The crude oil was purified by HPLC (gradient 0 to 95% CH$_3$CN/0.1% TFA) giving the title compound as a trifluoroacetic acid salt that was isolated as a yellow powder (75 mg, 76%). $^1$H NMR (300 MHz, DMSO-d$_6$) δ ppm: 2.32 (s, 3H) 4.10 (s, 3H) 6.25 (d, J=7.35 Hz, 1H) 6.65-6.81 (m, 3H) 6.99 (d, J=8.09 Hz, 1H) 7.13-7.29 (m, 3H) 7.38 (d, J=9.19 Hz, 1H) 8.30 (d, J=7.35 Hz, 1H) 8.94 (d, J=9.19 Hz, 1H) 9.89 (s, 1H) 10.81 (s, 1H) 14.21 (s, 1H); MS (ESI+) m/z 390 (M+H)+; (ESI−) m/z 388 (M+H)−.

Example 16

4-[4-Methyl-2-([1,8]naphthyridin-4-ylamino)-phenylsulfanyl]-phenol

Example 16a 1-tert-Butyl-4-oxo-1,4-dihydro-[1,8]naphthyridine-3-carboxylic acid ethyl ester A sample of 2-chloro-nicotinic acid was subjected to the reaction sequence in the U.S. Pat. No. 6,818,654 to give the title compound.

Example 16b

4-Hydroxy-[1,8]naphthyridine-3-carboxylic acid ethyl ester

The product from Example 16a (6.36 g, 23.1 mmol) was reacted with 50 mL of trifluoroacetic acid and 1 mL of H$_2$SO$_4$ for 1 h at room temperature. The solvent was concentrated under vacuum giving the title compound as a solid (5.05 g, 99%).

Example 16c

4-Chloro-[1,8]naphthyridine

The product from Example 16b was subjected to the reactions following the procedures from Example 1c and Example 1d giving the title compound as a solid (106 mg, 96%).

Example 16d

4-[4-Methyl-2-([1,8]naphthyridin-4-ylamino)-phenylsulfanyl]-phenol

The product from Example 16c as a 0.9M solution in methanol (0.080 mL, 0.07 mmol) was reacted with the product from Example 4c as a 0.7M solution in ethanol (0.100 mL, 0.07 mmol) for 18 h following the procedure from Example 1g to give the crude product which was purified by HPLC with TFA to give the title compound as the trifluoroacetic acid salt (0.017 g, 51%). $^1$H NMR (300 MHz, DMSO-d$_6$) δ ppm: 2.33 (s, 3H) 6.33 (d, J=6.99 Hz, 1H) 6.69-6.78 (m, 2H) 7.02 (d, J=8.09 Hz, 1H) 7.16-7.20 (m, 2H) 7.23-7.29 (m, 2H) 7.92 (dd, J=8.46, 4.41 Hz, 1H) 8.51 (d, J=6.99 Hz, 1H) 9.10-9.23 (m, 2H) 11.14 (s, 1H); MS (ESI+) m/z 360.0 (M+H)+, (ESI−) m/z 358.1 (M−H)−.

Example 17

4-[2-(7-Isopropyl-[1,8]naphthyridin-4-ylamino)-4-methyl-phenylsulfanyl]-phenol

The product from Example 8b (100 mg, 0.435 mmol) was reacted with the product from Example 4c (105 mg, 0.435 mmol) for 18 h following the procedure from Example 1g producing the crude title compound that was purified by HPLC with TFA giving the trifluoroacetic acid salt (90 mg, 47%). $^1$H NMR (300 MHz, DMSO-d$_6$) δ ppm: 0.97 (d, J=6.62 Hz, 6H), 2.13-2.30 (m, 1H), 2.33 (s, 3H), 2.89 (d, J=6.99 Hz, 2H), 6.29 (d, J=6.99 Hz, 1H), 6.73 (d, J=8.46 Hz, 2H), 7.00 (d, J=8.09 Hz, 1H), 7.13-7.34 (m, 4H), 7.81 (d, J=8.46 Hz, 1H), 8.43 (d, J=6.99 Hz, 1H), 9.03 (d, J=8.46 Hz, 1H), 10.99 (br. s., 1H), 14.36 (br. s., 1H); MS ESI+ m/z 416 (M+H)+; ESI− m/z 414 (M−H)−.

Example 18

N-{4-[4-Methyl-2-(7-methyl-[1,8]naphthyridin-4-ylamino)-phenylsulfanyl]-phenyl}-acetamide

Example 18a

N-[4-(4-Methyl-2-nitro-phenylsulfanyl)-phenyl]-acetamide

The product from Example 4a (1 g, 3.51 mmol) was reacted with N-(4-mercapto-phenyl)-acetamide (0.65 g, 351 mmol)

for 18 h following the procedure from Example 4b giving the title compound (1.04 g, 98%).

Example 18b

N-[4-(2-Amino-4-methyl-phenylsulfanyl)-phenyl]-acetamide

The product from Example 18a (0.30 gm, 1 mmol) was reacted with $SnCl_2$ as described in Example 1f to give the title compound (0.27 gm, 100%) as an amber oil which was used without further purification.

Example 18c

N-{4-[4-Methyl-2-(7-methyl-[1,8]naphthyridin-4-ylamino)-phenylsulfanyl]-phenyl}-acetamide The product from Example 18c (0.27 gm, 1 mmol) was combined with the product from Example 1d (0.178 gm, 1 mmole) and reacted according to the procedure described in Example 1g to give the crude product as a brown solid that purified by HPLC with TFA providing the trifluoroacetic acid salt which was converted to the hydrochloride salt by treatment with 4N HCl in dioxane at room temperature to give the title compound (40.0 mg, 7.5%). $^1$H NMR (300 MHz, DMSO-$d_6$) δ ppm: 2.04 (s, 3H) 2.35 (s, 3H) 2.76 (s, 3H) 6.29 (d, J=6.99 Hz, 1H) 7.24 (m, 5H) 7.50 (d, J=8.82 Hz, 2H) 7.78 (d, J=8.82 Hz, 1H) 8.40 (d, J=6.99 Hz, 1H) 9.02 (m, 1H) 10.08 (s, 1H) 11.09 (s, 1H) 14.37 (s, 1H); MS (ESI+) m/z 415.1 (M+H)+, (ESI−) m/z 413.1 (M−H)−.

Example 19

N-{4-[2-(7-Ethyl-[1,8]naphthyridin-4-ylamino)-4-methyl-phenylsulfanyl]-phenyl}-acetamide The product from Example 3f (92 mg, 0.47 mmol) was reacted with the product from Example 18b (130 mg, 0.47 mmol) for 22 h following the procedure from Example 1g giving the title compound as a solid after purification of the crude product by HPLC with TFA as a trifluoroacetic acid salt (68 mg, 26%). $^1$H NMR (300 MHz, DMSO-$d_6$) δ ppm: 1.37 (t, J=7.72 Hz, 1H) 2.04 (s, 3H) 2.35 (s, 3H) 3.05 (q, J=7.72 Hz, 2H) 6.31 (d, J=6.98 Hz, 1H) 7.15 (d, J=8.83 Hz, 1H) 7.20-7.35 (m, 3H) 7.49 (d, J=8.83 Hz, 2H) 7.82 (d, J=8.82 Hz, 1H) 8.41 (d, J=6.99 Hz, 1H) 8.99 (d, J=8.82 Hz, 1H) 10.04 (s, 1H) 11.01 (br s, 1H) 14.39 (br s, 1H). MS (ESI+) m/z 429 (M+H−Cl)+; (ESI−) m/z 427 (M−H−Cl)−.

Example 20

N-{4-[4-Methyl-2-(7-propyl-[1,8]naphthyridin-4-ylamino)-phenylsulfanyl]-phenyl}-acetamide The product from Example 2g (93 mg, 0.44 mmol) was reacted with the product from Example 18b (123 mg, 0.44 mmol) for 23 h following the procedure from Example 1g giving the title compound after purification of the crude product by HPLC with TFA as a trifluoroacetic acid salt solid (72 mg, 29%). $^1$H NMR (300 MHz, DMSO-$d_6$) δ ppm: 0.98 (t, J=7.35 Hz, 3H), 1.84 (dq, J=14.75, 7.46 Hz, 2H), 2.04 (s, 3H), 2.35 (s, 3H), 2.99 (t, J=7.35 Hz, 2H), 6.31 (d, J=6.99 Hz, 1H), 7.15 (d, J=8.09 Hz, 1H), 7.20-7.33 (m, 4H), 7.50 (d, J=8.46 Hz, 2H), 7.81 (d, J=8.46 Hz, 1H), 8.41 (d, J=6.99 Hz, 1H), 9.00 (d, J=8.46 Hz, 1H), 10.05 (s, 1H), 11.02 (s, 1H); MS (ESI+) m/z 443 (M+H)+; (ESI−) m/z 441 (M−H)−.

Example 21

N-{4-[4-Methyl-2-(7-trifluoromethyl-[1,8]naphthyridin-4-ylamino)-phenylsulfanyl]-phenyl}-acetamide A solution of the product of Example 7d (50.0 mg, 0.215 mmol), and the product of Example 18b (59.0 mg, 0.215 mmol) in ethanol (2 mL) was stirred in an oil bath preheated to 80° C. for 16 hours. The mixture was then cooled to room temperature, the ethanol removed under vacuum, and the resultant crude residue purified by HPLC with TFA to provide the title compound as a trifluoroacetic acid salt (22.0 mg, 22%). $^1$H NMR (300 MHz, DMSO-$d_6$) δ ppm: 2.03 (s, 3H), 2.32 (s, 3H), 6.33 (d, J=5.52 Hz, 1H), 7.01 (d, J=8.09 Hz, 1H), 7.15 (d, J=8.46 Hz, 1H), 7.21-7.27 (m, 3H), 7.54 (d, J=8.82 Hz, 2H), 8.01 (d, J=8.46 Hz, 1H), 8.65 (d, J=5.51 Hz, 1H), 9.17 (d, J=8.46 Hz, 1H), 9.42 (s, 1H), 10.04 (s, 1H); MS (ESI+) m/z 469 (M+H−TFA)+, (ESI−) m/z 467 (M−H−TFA)−.

Example 22

N-{4-[2-(7-sec-Butyl-[1,8]naphthyridin-4-ylamino)-4-methyl-phenylsulfanyl]-phenyl}-acetamide

Example 22a 2-sec-Butyl-5-chloro-[1,8]naphthyridine

Example 22b

N-{4-[2-(7-sec-Butyl-[1,8]naphthyridin-4-ylamino)-4-methyl-phenylsulfanyl]-phenyl}-acetamide The product from Example 22a (50 mg, 0.226 mmol) was reacted with the product from Example 18b (62 mg, 0.226 mmol) for 16 h following the procedure from Example 1g giving the crude title compound which was purified by HPLC in TFA providing the product as a trifluoroacetic acid salt (33 mg, 32%). $^1$H NMR (300 MHz, DMSO-$d_6$) δ ppm: 0.85 (t, J=7.35 Hz, 3H), 1.35 (d, J=6.99 Hz, 3H), 1.73 (dd, J=13.60, 6.99 Hz, 1H), 1.79-1.90 (m, 1H), 2.03 (s, 3H), 2.35 (s, 3H), 3.01-3.13 (m, 1H), 6.32 (d, J=7.35 Hz, 1H), 7.14 (d, J=7.72 Hz, 1H), 7.22-7.32 (m, 4H), 7.51 (d, J=8.82 Hz, 2H), 7.84 (d, J=8.46 Hz, 1H), 8.41 (d, J=6.99 Hz, 1H), 9.02 (d, J=8.46 Hz, 1H), 10.05 (s, 1H), 11.02 (s, 1H); MS (ESI+) m/z 457 (M+H)+, (ESI−) m/z 455 (M−H)−.

Example 23

N-{4-[2-(7-Cyclopentyl-[1,8]naphthyridin-4-ylamino)-4-methyl-phenylsulfanyl]-phenyl}-acetamide

Example 23a

5-Chloro-2-cyclopentyl-[1,8]naphthyridine

Example 23b

N-{4-[2-(7-Cyclopentyl-[1,8]naphthyridin-4-ylamino)-4-methyl-phenylsulfanyl]-phenyl}-acetamide The product from Example 23a (50 mg, 0.215 mmol) was reacted with the product from Example 18b (58 mg, 0.215 mmol) for 16 h following the procedure from Example 1g giving the crude title compound which was purified by HPLC with TFA providing the product as a trifluoroacetic acid salt (29 mg, 29%). $^1$H NMR (300 MHz, DMSO-$d_6$) δ ppm: 1.71-1.76 (m, 3H), 1.79-1.93 (m, 4H), 2.04 (s, 3H), 2.14 (d, J=7.72 Hz, 2H), 2.35 (s, 3H), 6.31 (d, J=6.99 Hz, 1H), 7.14 (d, J=8.09 Hz, 1H), 7.21-7.32 (m, 4H), 7.51 (d, J=8.82 Hz, 2H), 7.84 (d, J=8.82 Hz, 1H), 8.40 (d, J=6.99 Hz, 1H), 8.99 (d, J=8.46 Hz, 1H), 10.05 (s, 1H), 11.00 (s, 1H); MS (ESI+) m/z 469 (M+H)+, (ESI−) m/z 467 (M−H)−.

Example 24

N-(4-{2-[7-(2-Hydroxy-ethyl)-[1,8]naphthyridin-4-ylamino]-4-methyl-phenylsulfanyl}-phenyl)-acetamide Example 24a N-{4-[2-(7-Chloro-[1,8]naphthyridin-4-ylamino)-4-methyl-phenylsulfanyl]-phenyl}-acetamide The product from Example 13d (200 mg, 1.0 mmol) and the product from Example 18b (215 mg, 1.0 mmol) were reacted following the procedure from Example 1g giving a crude solid that was purified by HPLC with TFA to give the title compound 200 mg, 48%).

Example 24b

2-{5-[2-(4-Acetylamino-phenylsulfanyl)-5-methyl-phenylamino]-[1,8]naphthyridin-2-yl}-malonic acid diethyl ester To a slurry of sodium hydride (95%, 0.045 g, 1.8 mmol) in 10 mL anhydrous THF at 0° C. under an atmosphere of $N_2$ was added diethyl malonate (0.32 g, 2.0 mmol) dropwise. The mixture was stirred for 30 minutes at ambient temperature, treated with the product from Example 24a (0.141 g, 0.3 mmol), heated at 110° C. for two hours, cooled and partitioned between EtOAc and water. The ethyl acetate layer washed with saturated brine, dried over sodium sulfate, filtered and concentrated giving the title compound as a yellow glass, (0.14 g, 84% yield).

Example 24c

N-(4-{2-[7-(2-Hydroxy-ethyl)-[1,8]naphthyridin-4-ylamino]-4-methyl-phenylsulfanyl}-phenyl)-acetamide The product from Example 24b (56 mg, 0.10 mmol) was reacted with $NaBH_4$ (40 mg, 1.00 mmol) in 5 mL EtOH for 24 h. Quenched with aqueous $NH_4Cl$ and adjusted to pH 7 with dilute HCl. Extracted with EtOAc and dried over $Na_2SO_4$, filtered and concentrated under vacuum giving the crude title compound which was purified by HPLC with TFA giving the trifluoroacetic acid salt (15 mg, 25%). $^1$H NMR (300 MHz, DMSO-$d_6$) δ ppm: 2.04 (s, 3H) 2.35 (s, 3H) 3.16 (t, J=6.43 Hz, 2H) 3.91 (t, J=6.25 Hz, 2H) 6.31 (d, J=6.99 Hz, 1H) 7.14 (d, J=8.09 Hz, 1H) 7.22-7.33 (m, 4H) 7.51 (d, J=8.82 Hz, 1H) 7.83 (d, J=8.82 Hz, 1H) 8.42 (d, J=6.99 Hz, 1H) 8.94-9.05 (m, 1H) 10.04 (s, 1H) 11.03 (s, 1H) 14.40 (s, 1H); MS (ESI+) m/z 445 (M+H−TFA)+.

Example 25

N-{4-[2-(7-Butyl-[1,8]naphthyridin-4-ylamino)-4-methyl-phenylsulfanyl]-phenyl}-acetamide Example 25a 2-Butyl-6-(2,5-dimethyl-pyrrol-1-yl)-pyridine The product from Example 2a 1.0 g, 5.37 mmol) was reacted with propyl iodide 0.55 mL, 5.64 mmol) in place of ethyl iodide following the procedure from Example 2b to give the title compound (790 mg, 64%).

Example 25b

2-Butyl-5-chloro-[1,8]naphthyridine

The product from Example 2a was subjected to the synthetic sequence in Examples 2b-2g to give the title compound.

Example 25c

N-{4-[2-(7-Butyl-[1,8]naphthyridin-4-ylamino)-4-methyl-phenylsulfanyl]-phenyl}-acetamide The product from Example 25b (170 mg, 0.77 mmol) was reacted with the product from Example 18b (209 mg, 0.77 mmol) for 19 h following the procedure from Example 1g giving the title compound after purification of the crude product by HPLC with TFA as a trifluoroacetic acid salt as a solid (130 mg, 30%). $^1$H NMR (300 MHz, DMSO-$d_6$) δ ppm: 0.95 (t, J=7.72 Hz, 3H) 1.39 (sext, 2H), J=7.72 Hz) 1.80 (qnt, J=7.72 Hz, 2H) 2.04 (s, 3H) 2.35 (s, 3H) 3.01 (dd, J=7.36 Hz, 2H) 6.81 (d, J=6.99 Hz, 1H) 7.15 (d, J=8.09 Hz, 1H) 7.22-7.32 (m, 4H) 7.50 (d, J=8.82 Hz, 2H) 7.82 (d, J=8.46 Hz, 1H) 8.41 (d, J=6.99 Hz, 1H) 9.00 (d, J=8.82 Hz, 1H) 10.06 (br s, 1H) 11.02 (br s, 1H) 14.41 (br s, 1H); MS (ESI+) m/z 457 (M+H); (ESI−) m/z 455 (M−H)−.

Example 26

N-{4-[4-Methyl-2-([1,8]naphthyridin-4-ylamino)-phenylsulfanyl]-phenyl}-acetamide The product from Example 16c (50 mg, 0.304 mmol) was reacted with the product from Example 18b (83 mg, 0.304 mmol) for 16 h following the procedure from Example 1g giving the crude title compound which was purified by HPLC with TFA providing the trifluoroacetic acid salt (29 mg, 24%). $^1$H NMR (300 MHz, DMSO-$d_6$) δ ppm: 2.04 (s, 3H), 2.35 (s, 3H), 6.34 (d, J=6.99 Hz, 1H), 7.17 (d, J=7.72 Hz, 1H), 7.23 (d, J=8.46 Hz, 2H), 7.28-7.34 (m, 2H), 7.49 (d, J=8.82 Hz, 2H), 7.90 (dd, J=8.46, 4.41 Hz, 1H), 8.48 (d, J=6.99 Hz, 1H), 9.11 (dd, J=8.46, 1.47 Hz, 1H), 9.17 (dd, J=4.41, 1.47 Hz, 1H), 10.04 (s, 1H), 11.12 (s, 1H); MS (ESI+) m/z 401 (M+H)+, (ESI−) m/z 399 (M−H)−.

Example 27

2-{5-[2-(4-Acetylamino-phenylsulfanyl)-5-methyl-phenylamino]-[1,8]naphthyridin-2-yl}-malonic acid diethyl ester The crude product from Example 24b was purified by silica gel column chromatography eluting with 3% MeOH/$CH_2Cl_2$ followed by HPLC with TFA giving the tile compound as a trifluoroacetic acid salt (70 mg, 42%). $^1$H NMR (300 MHz, DMSO-d$_6$) δ ppm: 1.22 (t, J=7.17 Hz, 6H) 2.04 (s, 3H) 2.35 (s, 3H) 4.24 (q, J=6.99 Hz, 4H) 5.55 (s, 1H) 6.36 (d, J=6.99 Hz, 1H) 7.12 (d, J=8.09 Hz, 1H) 7.22-7.33 (m, 4H) 7.54 (d, J=8.82 Hz, 2H) 7.96 (d, J=8.46 Hz, 1H) 8.46 (d, J=6.99 Hz, 1H) 9.16 (d, J=8.46 Hz, 1H) 10.06 (s, 1H) 11.20 (s, 1H) 14.53 (s, 1H); MS (ESI+) m/z 559 (M+H=TFA)+.

Example 28

{5-[2-(4-Acetylamino-phenylsulfanyl)-5-methyl-phenylamino]-[1,8]naphthyridin-2-ylamino}-acetic acid ethyl ester The product from Example 24a (47 mg, 0.10 mmol) was reacted with the glycine ethyl ester hydrochloride (84 mg, 0.10 mmol) in 2 mL of EtOH in a sealed tube at 150° C. for 1 h. Cooled to room temperature and concentrated. Adjusted to pH 7 with 1M HCl and extracted with EtOAc, dried over Na$_2$SO$_4$, filtered and concentrated under vacuum giving the crude title compound which was purified by HPLC with TFA providing the product as a trifluoroacetic acid solid (12 mg, 19%). $^1$H NMR (300 MHz, DMSO-d$_6$) δ ppm: 1.22 (t, J=6.99 Hz, 3H) 2.04 (s, 3H) 2.33 (s, 3H) 4.15 (q, J=7.23 Hz, 2H) 4.27 (d, J=6.25 Hz, 2H) 6.08 (d, J=6.99 Hz, 1H) 7.04 (d, J=5.52 Hz, 1H) 7.07 (d, J=6.62 Hz, 1H) 7.19-7.30 (m, 4H) 7.57 (d, J=8.46 Hz, 2H) 8.04 (t, J=6.62 Hz, 1H) 8.53 (d, J=9.19 Hz, 1H) 8.72 (t, J=5.88 Hz, 1H) 10.08 (s, 1H) 10.43 (s, 1H) 13.43 (d, J=5.88 Hz, 1H); MS (ESI+) m/z 502 (M+H−TFA)+.

Example 29

2-{5-[2-(4-Acetylamino-phenylsulfanyl)-5-methyl-phenylamino]-[1,8]naphthyridin-2-yl}-malonic acid tert-butyl ester ethyl ester To a slurry of sodium hydride (95%, 0.025 g, 1.0 mmol) in 5 mL anhydrous THF at 0° C. under an atmosphere of N$_2$ was added tert-butyl ethyl malonate (0.188 g, 1.0 mmol) dropwise. The mixture was stirred for 30 minutes at ambient temperature, treated with the product from Example 46a (0.47 g, 0.1 mmol), heated at 110° C. for 2 h. The solution was cooled and added into water, acidified by 1M HCl to pH 4 and extracted with EtOAc and washed with saturated brine. Dried over Na$_2$SO$_4$, filtered and concentrated under vacuum giving the crude title compound which was purified by chromatography on silica eluting with 1% MeOH in CH$_2$Cl$_2$ to give the title compound as a hydrochloride salt (0.040 g, 64% yield). $^1$H NMR (300 MHz, DMSO-d$_6$) δ ppm: 1.26 (t, J=7.11 Hz, 3H) 1.49 (s, 9H) 2.04 (s, 3H) 2.30 (s, 3H) 4.16 (q, J=7.11 Hz, 2H) 5.76 (s, 1H) 6.07 (d, J=5.88 Hz, 1H) 6.98 (d, J=7.72 Hz, 1H) 7.11 (d, J=8.09 Hz, 1H) 7.26 (m, 4H) 7.56 (d, J=8.82 Hz, 2H) 8.03 (d, J=5.88 Hz, 1H) 8.25 (d, J=9.93 Hz, 1H) 9.07 (s, 1H) 10.05 (s, 1H) 13.18 (s, 1H); MS (ESI+) m/z 587 (M+H)+.

Example 30

{5-[2-(4-Acetylamino-phenylsulfanyl)-5-methyl-phenylamino]-[1,8]naphthyridin-2-yl}-cyano-acetic acid ethyl ester The title compound was prepared according to the procedure of Example 27 substituting ethyl cyanoacetate (0.240 mg, 2.1 mmol) for diethyl malonate. The crude product was purified by chromatography on silica eluting with 2% methanol in dichloromethane to give to give a yellow powder (0.092 g, 55% yield). $^1$H NMR (300 MHz, DMSO-d$_6$) δ ppm: 1.28 (t, J=6.99 Hz, 3H) 03 (s, 3H) 2.31 (s, 3H) 4.24 (q, J=6.99 Hz, 2H) 6.15 (d, J=5.88 Hz, 1H) 7.01 (d, J=8.09 Hz, 1H) 7.12 (d, J=1.47 Hz, 1H) 7.17 (d, J=9.56 Hz, 2H) 7.23 (d, J=8.46 Hz, 2H) 7.53 (d, J=8.82 Hz, 2H) 8.13 (d, J=5.88 Hz, 1H) 8.60 (d, J=9.56 Hz, 1H) 9.37 (s, 1H) 10.03 (s, 1H) 13.09 (s, 1H); MS (ESI+) m/z 512 (M+H)+.

Example 31

{5-[2-(4-Acetylamino-phenylsulfanyl)-5-methyl-phenylamino]-[1,8]naphthyridin-2-yl}-cyano-acetic acid tert-butyl ester The title compound was prepared according to the procedure of Example 27 substituting tert-butyl cyanoacetate (0.282 mg, 2.0 mmol) for diethyl malonate. The crude product was purified by chromatography on silica eluting with 2% methanol in dichloromethane to give to give a yellow powder (0.067 g, 37% yield). $^1$H NMR (300 MHz, DMSO-d$_6$) δ ppm: 1.52 (s, 9H) 2.03 (s, 3H) 2.30 (s, 3H) 6.14 (d, J=5.88 Hz, 1H) 6.98-7.27 (m, 6H) 7.53 (d, J=8.82 Hz, 2H) 8.11 (d, J=5.88 Hz, 1H) 8.55 (d, J=9.56 Hz, 1H) 9.33 (s, 1H) 10.03 (s, 1H) 13.12 (s, 1H); MS (ESI+) m/z 540 (M+H)+.

Example 32

N-{4-[2-(7-Cyanomethyl-[1,8]naphthyridin-4-ylamino)-4-methyl-phenylsulfanyl]-phenyl}-acetamide The product from Example 31 (0.101 g, 0.19 mmol) was added into 5 mL trifluoroacetic acid and 5 mL of CH$_2$Cl$_2$. The mixture was stirred at ambient temperature for 2 h and concentrated under vacuum giving the crude title compound. The residue was purified by HPLC with TFA to give the title compound as the trifluoroacetic acid salt (0.083 g, 80%). $^1$H NMR (300 MHz, DMSO-d$_6$) δ ppm: 2.04 (s, 3H) 2.35 (s, 3H) 4.64 (s, 2H) 6.35 (d, J=6.99 Hz, 1H) 7.18 (d, J=8.46 Hz, 1H) 7.23 (d, J=8.82 Hz, 2H) 7.30 (m, 2H) 7.48 (d, J=8.46 Hz, 2H) 7.85 (d, J=8.82 Hz, 1H) 8.44 (d, J=6.99 Hz, 1H) 9.09 (d, J=8.82 Hz, 1H) 10.04 (s, 1H) 11.14 (s, 1H) 14.58 (s, 1H); MS (ESI+) m/z 440 (M+H)+.

Example 33

N-{4-[3-(7-Methyl-[1,8]naphthyridin-4-ylamino)-biphenyl-4-ylsulfanyl]-phenyl}-acetamide The product from Example 106c (53 mg, 0.11 mmol) in a mixture of saturated sodium bicarbonate solution (0.5 mL) and toluene (1 mL) is treated with phenyl boronic acid (14 mg, 0.11 mmol) and tetrakistriphenylphospinopalladium (8 mg, 0.0074 mmol) and the mixture heated at reflux 4 hr. The reaction mixture was cooled and partitioned between ethyl acetate and water. The layers were separated and the organic layer washed with brine, dried over sodium sulfate and filtered. The organic layer was concentrated under vacuum leaving the crude title compound as an orange oil which was purified by HPLC with TFA providing the product as a trifluoroacetic acid salt (15 mg, 30%). $^1$H NMR (300 MHz, DMSO-d$_6$) δ ppm: 2.06 (s, 3H), 2.77 (s, 3H), 6.44 (d, J=6.99 Hz, 1H), 7.21 (d, J=8.09 Hz, 1H), 7.36 (d, J=8.46 Hz, 2H) 7.41-7.52 (m, 3H), 7.58 (d, J=8.82 Hz, 2H), 7.71 (d, J=7.35 Hz, 2H), 7.75-7.87 (m, 3H), 8.44 (d, J=6.62 Hz, 1H), 9.02 (d, J=8.82 Hz, 1H), 10.0 (s, 1H) 11.12 (s, 1H), 14.41 (s, 1H); MS (ESI+) m/z 477 (M+H)+.

Example 34

N-{4-[5-Hydroxy-4-methyl-2-(7-methyl-[1,8]naphthyridin-4-ylamino)-phenylsulfanyl]-phenyl}-acetamide

Example 34a

N-[4-(5-Hydroxy-4-methyl-2-nitro-phenylsulfanyl)-phenyl]-acetamide

A mixture of 2-Methyl-4-nitro-5-chloro phenol (1.5 g, 8.0 mmol), 4-Acetamido thiophenol (1.6 g, 8.8 mmol) and cesium carbonate (5.74 g, 17.6 mmol) in DMF (10 mL) was heated 2.5 h at 100° C. The mixture was cooled, diluted with ethyl acetate (100 mL) and the organic layer washed with water and aqueous 10% sodium chloride solution, then, dried over anhydrous sodium sulfate. The drying agent was filtered and the solvent removed under vacuum leaving the title compound as a solid (2.5 g, 81%).

Example 34b

N-[4-(2-Amino-5-hydroxy-4-methyl-phenylsulfanyl)-phenyl]-acetamide

A solution of the product of Example 34a (2.5 g, 6.45 mmol), iron powder (1.79 g, 32 mmol) and ammonium chloride (0.514 g, 9.6 mmol) in a methanol (10 mL), tetrahydrofuran (10 mL), and water (5 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (1.7 g, 91%).

Example 34c

N-{4-[5-Hydroxy-4-methyl-2-(7-methyl-[1,8]naphthyridin-4-ylamino)-phenylsulfanyl]-phenyl}-acetamide The product from Example 1d (102 mg, 0.570 mmol) was reacted in ethanol (2 mL) with the product from Example 34b (161 mg, 0.560 mmol) for 18 h following the procedure from Example 1g giving the crude title compound which was purified by HPLC with TFA providing the product as a trifluoroacetic acid salt (50 mg, 21%). $^1$H NMR (300 MHz, DMSO-$d_6$) δ ppm: 2.05 (s, 3H) 2.12 (s, 3H) 2.75 (s, 3H) 6.31 (d, J=6.99 Hz, 1H) 6.61 (s, 1H) 7.15 (s, 1H) 7.29 (d, J=8.46 Hz, 2H) 7.56 (d, J=8.82 Hz, 2H) 7.77 (d, J=8.82 Hz, 1H) 8.39 (d, J=5.52 Hz, 1H) 8.96 (d, J=8.82 Hz, 1H) 9.90 (s, 1H) 10.08 (s, 1H) 10.84 (s, 1H) 14.24 (br s, 1H); MS (ESI+) m/z 431 (M+H)+.

Example 35

N-{4-[2-(7-Propyl-[1,8]naphthyridin-4-ylamino)-4-trifluoromethyl-phenylsulfanyl]-phenyl}-acetamide

Example 35a

N-[4-(2-Amino-4-trifluoromethyl-phenylsulfanyl)-phenyl]-acetamide

A solution of 2-chloro-5-trifluoromethyl-phenylamine (250 mg, 1.11 mmol) in DMF was reacted with N-(4-mercapto-phenyl)-acetamide (185 mg, 1.11 mmol) following the procedure from Example 1e for 16 h to give the product 350 mg, 88%) which was reduced with $SnCl_2$ following the procedure in Example 1f to give the title compound as a solid (260 mg, 80%).

Example 35b

N-{4-[2-(7-Propyl-[1,8]naphthyridin-4-ylamino)-4-trifluoromethyl-phenylsulfanyl]-phenyl}-acetamide The product from Example 2g (50 mg, 0.242 mmol) was reacted with the product from Example 35a (79.0 mg, 0.242 mmol) for 16 h following the procedure from Example 1g giving the crude title compound which was purified by HPLC with TFA providing the ditrifluoroacetic acid salt (10.5 mg, 10%). $^1$H NMR (300 MHz, DMSO-$d_6$) δ ppm: 0.98 (t, J=7.35 Hz, 3H), 1.81-1.92 (m, J=7.35 Hz, 2H), 2.07 (s, 3H), 3.01 (t, J=7.54 Hz, 2H), 6.44 (d, J=6.99 Hz, 1H), 7.11 (d, J=8.46 Hz, 1H), 7.42-7.49 (m, J=8.46 Hz, 2H), 7.69 (d, J=8.82 Hz, 2H), 7.78 (dd, J=8.82, 1.47 Hz, 1H), 7.87 (d, J=8.82 Hz, 1H), 7.91 (d, J=1.10 Hz, 1H), 8.52 (d, J=6.99 Hz, 1H), 9.03 (d, J=8.46 Hz, 1H), 11.14 (s, 1H); MS (ESI+) m/z 497 (M+H)+, ESI− m/z 495 (M−H)−.

Example 36

N-{4-[2-(7-Methyl-[1,8]naphthyridin-4-ylamino)-4-trifluoromethyl-phenylsulfanyl]-phenyl}-acetamide The product from Example 1d (50 mg, 0.280 mmol) was reacted with the product from Example 35a (91 mg, 0.280 mmol) for 16 h following the procedure from Example 1g giving the crude title compound which was purified by HPLC with TFA providing the trifluoroacetic acid salt (21.5 mg, 20%). $^1$H NMR (300 MHz, DMSO-$d_6$) δ ppm: 2.07 (s, 3H), 2.78 (s, 3H), 6.43 (d, J=6.99 Hz, 1H), 7.09-7.15 (m, 1H), 7.44 (d, J=8.46 Hz, 2H), 7.68 (d, J=8.46 Hz, 2H), 7.78 (dd, J=8.64, 1.65 Hz, 1H), 7.84 (d, J=8.82 Hz, 1H), 7.92 (d, J=1.84 Hz, 1H), 8.52 (d, J=7.35 Hz, 1H), 9.00 (d, J=8.46 Hz, 1H), 10.19 (s, 1H), 11.12 (s, 1H); MS (ESI+) m/z 469 (M+H−TFA)+, (ESI−) m/z 467 (M−H−TFA)−.

Example 37

[2-(4-Acetylamino-phenylsulfanyl)-5-methyl-phenyl]-[7-(2-hydroxy-ethyl)-[1,8]naphthyridin-4-yl]-carbamic acid tert-butyl ester The product from Example 24 (22 mg, 0.05 mmol) was reacted with the di-tert-butyl dicarbonate (16 mg, 0.07 mmol) in 2 mL of dry THF. Added Et3N (8.0 mg, 0.08 mmol) and a catalytic amount of N,N-4-dimethylaminopyridine and stirred for 2 h. Poured into water and neutralized with 1M HCl. Extracted with EtOAc, dried over $Na_2SO_4$ and filtered and concentrated under vacuum giving the crude title compound which was purified by silica gel column chromatography eluting with 1% MeOH/$CH_2Cl_2$ providing the product as a free base solid (7.0 mg, 26%). $^1$H NMR (300 MHz, DMSO-$d_6$) δ ppm: 1.59 (s, 9H) 2.03 (s, 3H) 2.25 (s, 3H) 2.96 (t, J=6.62 Hz, 2H) 3.81 (m, 2H) 4.74 (t, J=5.33 Hz, 1H) 5.76 (d, J=6.90 Hz, 1H) 6.63 (s, 1H) 6.85 (m, 2H) 7.22 (d, J=8.82 Hz, 2H) 7.36 (d, J=8.09 Hz, 1H) 7.52 (d, J=8.82 Hz, 2H) 7.70 (d, J=8.46 Hz, 1H) 8.50 (d, J=8.09 Hz, 1H) 10.00 (s, 1H); MS (ESI−) m/z 545 (M+H)+.

Example 38

N-{4-[2-(7-Butyl-[1,8]naphthyridin-4-ylamino)-4-methyl-benzenesulfinyl]-phenyl}-acetamide The product of Example 20 (100 mg, 0.226 mmol) was dissolved in HOAc (1 mL) and cooled to 0° C. To this was added Magnesium bis(monoperoxyphtalate) hexahydrate (56 mg, 0.113 mmol) and the reaction mixture was allowed to warm to room temperature. The crude title compound was purified by HPLC with TFA providing the product as a trifluoroacetic acid (34 mg, 32%). $^1$H NMR (500 MHz, DMSO-$d_6$) δ ppm: 1.07 (t, J=7.32 Hz, 3H), 1.91-1.98 (m, 4H), 2.11 (s, 3H), 2.49 (s, 3H), 3.05-3.10 (m, 2H), 6.03 (d, J=6.84 Hz, 1H), 7.31 (d, J=8.79 Hz, 2H), 7.35 (s, 1H), 7.48 (d, J=8.79 Hz, 2H), 7.67 (d, J=7.81 Hz, 1H), 7.83 (d, J=8.79 Hz, 1H), 8.10 (d, J=7.81 Hz, 1H), 8.19 (d, J=6.84 Hz, 1H), 9.05 (d, J=8.79 Hz, 1H); MS (ESI+) m/z 459 (M+H–TFA)+; (ESI–) m/z 457 (M–H–TFA)–.

Example 39

N-{3-Fluoro-4-[4-methyl-2-(7-propyl-[1,8]naphthyridin-4-ylamino)-phenylsulfanyl]-phenyl}-acetamide

Example 39a

2-Fluoro-1-methylsulfanyl-4-nitro-benzene

To a solution of 1,2-difluoro-4-nitrobenzene (1.50 g, 9.3 mmol) in MeOH (15 mL) was added 15% NaSMe aqueous solution (4.44 mL, 10.3 mmol) dropwise at 5° C., and then the mixture was stirred at room temperature for 1 hour and evaporated. The obtained solid was dissolved in 150 mL of EtOAc, washed with $H_2O$ (twice) and brine, dried over $MgSO_4$ and evaporated to give the crude product, which was purified by washing with cold n-hexane to give the desired product as yellow crystals (1.58 g, 90%).

Example 39b

3-Fluoro-4-methylsulfanyl-phenylamine

The product form Example 39a (1.57 g, 8.4 mmol) and Fe powder (1.41 g, 25.2 mmol) in a mixture of EtOH (7.5 mL) and HOAc (7.5 mL) was gradually heated to 80° C. and heated at the same temperature for 1 hour. The reaction mixture was evaporated. The residue was portioned between $CHCl_3$ and 10% $NaHCO_3$, and then filtered through celite. The organic layer washed with $H_2O$, dried over $MgSO_4$, and evaporated to give the crude product, which was purified by washing with n-hexane to give the desired product as pale brown crystals (1.08 g, 82%).

Example 39c

N-(3-Fluoro-4-methylsulfanyl-phenyl)-acetamide

The product from Example 39c (1.08 g, 6.9 mmol) and $Ac_2O$ (0.97 mL, 10.3 mmol) in pyridine (10 mL) was heated at 50° C. for 2 hours, and then evaporated. The residue was diluted with $H_2O$, acidified to pH 3 with 10% HCl, and then extracted with EtOAc. The organic layer washed with $H_2O$ and brine, dried over $MgSO_4$ and evaporated to give the crude product, which was purified by washing with n-hexane to give the title compound as colorless crystals (1.26 g, 92%).

Example 39d

N-[3-Fluoro-4-(4-methyl-2-nitro-phenylsulfanyl)-phenyl]-acetamide

The product from Example 39c (1.00 g, 5.0 mmol) and t-BuSNa (1.88 g, 15.1 mmol) in anhydrous DMF (10 mL) was heated at 160° C. for 4 hours under $N_2$ flow, and then cooled to room temperature. To the reaction mixture was added 1-chloro-4-methyl-2-nitrobenzene (2.36 mL, 17.6 mmol) at room temperature and then the mixture was heated at 80° C. for 4 hours under $N_2$ flow. The mixture was diluted with $H_2O$ and then extracted with EtOAc. The extract washed with $H_2O$ and brine, dried over $MgSO_4$, and evaporated. The residue was purified by silica gel column chromatography eluting with 2:1 EtOAc/hexane to give the title compound as yellow crystals (1.04 g, 65%).

Example 39e

N-[4-(2-Amino-4-methyl-phenylsulfanyl)-3-fluoro-phenyl]-acetamide

The product from Example 39d was reduced with Fe and $NH_4Cl$ following the procedure from Example 237E to give the title compound.

Example 39f

N-{3-Fluoro-4-[4-methyl-2-(7-propyl-[1,8]naphthyridin-4-ylamino)-phenylsulfanyl]-phenyl}-acetamide The product from Example 2g (100 mg, 0.48 mmol) was reacted with the product from Example 39e (140 mg, 0.48 mmol) for 22 h at 120° C. following the procedure from Example 1g giving the title compound as a solid (120 mg, 54%). $^1$H NMR (300 MHz, DMSO-$d_6$) δ ppm: 0.99 (t, J=7.3 Hz, 3H), 1.86 (sextet, J=7.3 Hz, 2H), 2.06 (s, 3H), 2.36 (s, 3H), 3.01 (t, J=7.3 Hz, 2H), 6.28 (d, J=6.9 Hz, 1H), 7.12-7.35 (m, 5H), 7.55 (dd, J=12.1, 2.2 Hz, 1H), 7.82 (d, J=8.8 Hz, 1H), 8.42 (d, J=6.9 Hz, 1H), 9.04 (d, J=8.8 Hz, 1H); MS (ESI+) m/z 461 (M+H)+, ESI– m/z 459 (M–H)–.

Example 40

N-{3,5-Difluoro-4-[4-methyl-2-(7-propyl-[1,8]naphthyridin-4-ylamino)-phenylsulfanyl]-phenyl}-acetamide

Example 40a

N-[3,5-Difluoro-4-(4-methyl-2-nitro-phenylsulfanyl)-phenyl]-acetamide

The title compound was prepared using the procedure from Example 39a using 1,2,3-trifluoro-5-nitrobenzene in place of 1,2-difluoro-4-nitrobenzene. The product 2,6-difluoro-1-methylsulfanyl-4-nitrobenzene was then subjected to the procedures from Examples 39b, 39c and 39d to give the title compound.

Example 40b

N-[4-(2-Amino-4-methyl-phenylsulfanyl)-3,5-difluoro-phenyl]-acetamide

The product from Example 40a was reduced with Fe and $NH_4Cl$ following the procedure from Example 237E to give the title compound.

Example 40c

N-{3,5-Difluoro-4-[4-methyl-2-(7-propyl-[1,8]naphthyridin-4-ylamino)-phenylsulfanyl]-phenyl}-acetamide The product from Example 40c (100 mg, 0.48 mmol) was reacted with the product from Example 2g (140 mg, 0.48 mmol) for 16 h at 120° C. following the procedure from Example 1g giving the title compound as a salt (120 mg, 52%). $^1$H NMR (300 MHz, DMSO-$d_6$) δ ppm: 0.99 (t, J=7.3 Hz, 3H), 1.86 (sextet, J=7.3 Hz, 2H), 2.06 (s, 3H), 2.36 (s, 3H), 3.01 (t, J=7.3 Hz, 2H), 6.28 (d, J=6.9 Hz, 1H), 7.12-7.35 (m, 5H), 7.55 (dd, J=12.1, 2.2 Hz, 1H), 7.82 (d, J=8.8 Hz, 1H), 8.42 (d, J=6.9 Hz, 1H), 9.04 (d, J=8.8 Hz, 1H); MS (ESI+) m/z 461 (M+H)+, (ESI−) m/z 459 (M−H)−.

Example 41

(7-Methyl-[1,8]naphthyridin-4-yl)-(5-methyl-2-phenoxy-phenyl)-amine

Example 41a

4-Methyl-2-nitro-1-phenoxy-benzene

A solution of sodium phenoxide trihydrate (5.0 g, 30 mmol) and 4-chloro-3-nitrotoluene (2.65 mL, 30 mmol) was heated in 60 mL of DMF at 100° C. for 5 days with stirring following the procedure from Example 1c. The product was purified by silica gel column chromatography eluting with $CH_2Cl_2$ giving the title compound as an orange solid (1.36 g, 30%).

Example 41b

5-Methyl-2-phenoxy-phenylamine

The product from Example 41a (884 mg, 3.86 mmol) was treated with $SnCl_2$ (3.5 g, 19.0 mmol) for 24 h following the procedure from Example 1f giving the title compound as a yellow oil (710 mg, 93%).

Example 41c (7-Methyl-[1,8]naphthyridin-4-yl)-(5-methyl-2-phenoxy-phenyl)-amine The product from Example 41b (65 mg, 0.36 mmol) was reacted with the product from Example 1d following the procedure from Example 1g giving the tile compound that was triturated with ether giving the product as a hydrochloride salt (12 mg, 8.8%). $^1$H NMR (300 MHz, DMSO-$d_6$) δ ppm: 0.95 (t, J=7.73 Hz, 3H) 1.82 (q, J=7.72 Hz, 2H) 2.97 (dd, J=7.73 Hz, 2H) 6.68 (d, J=6.99 Hz, 1H) 6.99 (d, J=7.72 Hz, 2H) 7.12 (dd, J=8.82 Hz, 2H) 7.30 (dd, J=8.09 Hz, 2H) 7.66 (dd, J=8.82 Hz, J=2.58 Hz, 1H) 7.71 (d, J=2.2 Hz, 1H) 7.77 (d, J=8.82 Hz, 1H) 8.52 (d, J=6.98 Hz, 1H) 9.07 (d, J=8.82 Hz, 1H) 11.26 (br s, 1H) 14.45 (brs, 1H); MS (ESI+) m/z 390 (M−Cl)+; (ESI−) m/z 388 (M−HCl)−.

Example 42

(5-Chloro-2-phenoxy-phenyl)-(7-ethyl-[1,8]naphthyridin-4-yl)-amine

Example 42a

4-Chloro-2-nitro-1-phenoxy-benzene

To a solution of DMF (50 mL) was added 1-bromo-2-nitro-4-chloro-benzene (5.0 g, 21.1 mmol), phenol (1.9 g, 21.1 mmol), and $Na_2CO_3$ (2.3 g, 21.1 mmol). The solution was heated to 85° C. and stirred overnight. The reaction was poured into water and extracted with EtOAc. Washed with water and dried over $Na_2SO_4$, filtered and concentrated under vacuum giving a yellow oil that was purified by silica gel column chromatography eluting with Hexanes:Ethyl Acetate (90:10) to give the title compound (3.8 g, 74%).

Example 42b

5-Chloro-2-phenoxy-phenylamine

The product from Example 42a (13 g, 52.1 mmol) was reacted with $SnCl_2$ (49.3 g, 260 mmol) following the procedure from Example 1f giving the title compound as a white solid 9.0 g, 79%).

Example 42c (5-Chloro-2-phenoxy-phenyl)-(7-ethyl-[1,8]naphthyridin-4-yl)-amine The product from Example 42b (100 mg, 0.46 mmol) was reacted with the product from Example 3f (88 mg, 0.46 mmol) following the procedure from Example 1g giving the title compound which was triturated with 2:1 ether/THF giving the product as a hydrochloride salt (134 mg, 70%). $^1$H NMR (300 MHz, DMSO-$d_6$) δ ppm: 1.34 (t, J=7.35 Hz, 3H) 3.02 (q, J=7.35 Hz, 2H) 6.69 (d, J=6.99 Hz, 1H) 6.97 (d, J=8.82 Hz, 2H) 7.10 (dd, J=7.35 Hz, 1H) 7.15 (d, J=8.82 Hz, 2H) 7.30 (dd, J=8.09 Hz, J=7.72 Hz, 2H) 7.56 (dd, J=2.94 Hz, J=9.19 Hz, 1H) 7.71 (d, J=2.57 Hz, 1H) 7.88 (d, J=8.82 Hz, 1H) 8.52 (d, J=6.99 Hz, 1H) 9.02 (d, J=8.45 Hz, 1H) 11.16 (br s, 1H) 14.56 (br s, 1H); MS (ESI+) m/z 376 (M−Cl)+; (ESI−) m/z 374 (M−HCl)−.

Example 43

(5-Chloro-2-phenoxy-phenyl)-(7-trifluoromethyl-[1,8]naphthyridin-4-yl)-amine

The product from Example 42b (60 mg, 0.27 mmol) was reacted with the product from Example 7d (63 mg, 0.27 mmol) for 24 h following the procedure from Example 1g giving the crude title compound as a solid which was triturated with 4:1 ether/THF giving the product as a hydrochloride salt (112 mg, 91%). $^1$H NMR (300 MHz, DMSO-$d_6$) δ ppm: 6.82 (d, J=6.99 Hz, 1H) 6.98 (d, J=7.72 Hz, 2H) 7.13 (m, 2H) 7.32 (dd, J=7.73 Hz, J=8.82 Hz, 2H) 7.57 (dd, J=2.57 Hz, J=8.82 Hz, 1H) 7.71 (d, J=2.57 Hz, 1H) 8.36 (d, J=8.82 Hz, 1H) 8.69 (d, J=6.99 Hz, 1H) 9.42 (d, J=8.82 Hz, 1H) 11.47 (br s, 1H) 14.40 (br s, 1H); MS (ESI+) m/z 416 (M−Cl)+; (ESI−) m/z 414 (M−HCl)−.

Example 44

4-[4-Benzylamino-2-(7-propyl-[1,8]naphthyridin-4-ylamino)-phenylsulfanyl]-phenol

Example 44a 4-(4-Amino-2-nitro-phenylsulfanyl)-phenol

A solution of 4-chloro-3-nitro aniline (1.0 g, 5.79 mmol), 4-hydroxythiophenol (0.75 g, 6.00 mmol), cesium carbonate (3.9 g, 12 mmol) in DMSO (10 mL) was heated at 100° C. for 16 hours. Afterwards ice water (50 mL) was added to the solution and the resultant slurry was treated with ethyl acetate (100 mL). The layers were separated and the organic layer washed with 10% sodium bicarbonate and 10% sodium chloride, then dried over anhydrous sodium sulfate. The drying agent was filtered and concentrated under vacuum giving the title compound as a red solid (1.45 g, 92%).

Example 44b 4-(4-Benzylamino-2-nitro-phenylsulfanyl)-phenol

A solution of the product of Example a (0.63 g, 2.4 mmol), benzaldehyde (0.24 g, 2.3 mmol) and sodium cyanoborohydride (0.15 g, 2.4 mmol) in methanol (10 mL) containing 1% acetic acid was stirred at room temperature for 16 hours. The reaction mixture was quenched with water (20 mL) and the resultant solution was concentrated in vacuo to a yellow solid. The solid was dissolved in ethyl acetate (50 mL), and washed with water, 10% sodium bicarbonate and 10% sodium chloride. The organic layer was dried over anhydrous sodium sulfate, filtered and solvent removed in vacuo leaving a light yellow oil. The oil was applied to a silica gel column and was eluted with $CH_2Cl_2$ then 1% methanol in $CH_2Cl_2$. The fractions which contained product were combined and evaporated to dryness giving the title compound as a yellow solid (0.63 g, 77%).

Example 44c 4-(2-Amino-4-benzylamino-phenylsulfanyl)-phenol

The product form Example 44b was reduced with Fe and $NH_4Cl$ following the procedure from Example 237E to give the title compound.

Example 44d

4-[4-Benzylamino-2-(7-propyl-[1,8]naphthyridin-4-ylamino)-phenylsulfanyl]-phenol The product from Example 2g (105 mg, 0.50 mmol) was reacted with the product from Example 44c (161 mg, 0.50 mmol) for 18 h following the procedure from Example 1g giving the crude title compound which was purified by HPLC with TFA providing the trifluoroacetic acid salt (68 mg, 22%). $^1H$ NMR (300 MHz, DMSO-$d_6$) δ ppm: 0.97 (t, J=7.35 Hz, 3H) 1.83 (sext, J=7.35 Hz, 2H) 2.97 (dd, J=7.35 Hz, 2H) 4.29 (m, 2H) 6.15 (d, J=6.99 Hz, 1H) 6.51 (d, J=8.46 Hz, 2H) 6.93 (d, J=8.46 Hz, 2H) 7.22-7.38 (m, 8H) 7.78 (d, J=8.83 Hz, 1H) 8.95 (d, J=8.46 Hz, 1H) 9.66 (s, 1H) 10.90 (br s, 1H) 14.21 (br s, 1H); MS (ESI+) m/z 493 (M+H–TFA)+.

Example 45

4-[4-Benzylamino-2-(7-methyl-[1,8]naphthyridin-4-ylamino)-phenylsulfanyl]-phenol The product from Example 1d (57 mg, 0.319 mmol) was reacted with the product from Example 44c (102 mg, 0.319 mmol) for 72 h following the procedure from Example 1g giving the crude title compound which was purified by HPLC with TFA providing the trifluoroacetic acid salt (169 mg, 91%). $^1H$ NMR (300 MHz, DMSO-$d_6$) δ ppm: 2.74 (s, 3H) 4.30 (s, 2H) 6.15 (d, J=6.99 Hz, 1H) 6.52 (d, J=8.46 Hz, 1H) 6.56-7.39 (m, 11H) 7.75 (d, J=8.46 Hz, 1H) 8.28 (d, J=7.36 Hz, 1H) 9.50 (br s, 1H) 10.85 (br s, 1H) 14.25 (br s, 1H); MS (ESI+) m/z 465 (M+H–TFA)+; (ESI–) m/z 463 (M–H–TFA)–.

Example 46

N-{4-[4-Methyl-2-(7-morpholin-4-yl-[1,8]naphthyridin-4-ylamino)-phenylsulfanyl]-phenyl}-acetamide

Example 46a

N-{4-[2-(7-Chloro-[1,8]naphthyridin-4-ylamino)-4-methyl-phenylsulfanyl]-phenyl}-acetamide The product from Example 13d (200 mg, 1.0 mmol) was reacted with the product from Example 18b (215 mg, 1.0 mmol) for 24 h following the procedure from Example 1g giving the crude title compound which was purified by HPLC with TFA providing the trifluoroacetic acid salt (200 mg, 45%).

Example 46b

N-{4-[4-Methyl-2-(7-morpholin-4-yl-[1,8]naphthyridin-4-ylamino)-phenylsulfanyl]-phenyl}-acetamide The product from Example 46a (0.047 g, 0.1 mmol) and morpholine (0.087 g, 1.0 mmol) in ethanol (0.5 mL) were heated in a sealed tube at 110° C. for 1 h, cooled and concentrated. The crude residue was purified by HPLC with TFA to give the title compound as a trifluoroacetic acid salt (0.030 g, 50%). $^1H$ NMR (300 MHz, DMSO-$d_6$) δ ppm: 2.04 (s, 3H), 2.33 (s, 3H), 3.56-3.93 (m, 8H), 6.07 (d, J=6.99 Hz, 1H), 7.09 (d, J=8.09 Hz, 1H), 7.20-7.32 (m, 4H), 7.54 (d, J=8.82 Hz, 2H), 8.07 (t, J=6.80 Hz, 1H), 8.64 (d, J=9.56 Hz, 1H), 10.06 (s, 1H), 10.45 (s, 1H), 13.42 (d, J=5.88 Hz, 1H); MS (ESI+) m/z 486 (M+H)+.

Example 47

(7-Methyl-[1,8]naphthyridin-4-yl)-(5-methyl-2-p-tolylsulfanyl-phenyl)-amine

Example 47a

4-Methyl-2-nitro-1-p-tolylsulfanyl-benzene

The product from Example 4a (5.00 g, 17.53 mmol) was reacted with 4-methylthiophenol (2.17 g, 17.53 mmol) in place of thiophenol following the procedure from Example 1e for 18 h giving the crude title compound which was purified by silica gel column chromatography eluting with 5% EtOAc /hexane providing a solid (3.53 g, 78%).

Example 47b

5-Methyl-2-p-tolylsulfanyl-phenylamine

The product from Example 47a was reduced with $SnCl_2$ following the procedure from Example 1f giving the title compound.

Example 47c (7-Methyl-[1,8]naphthyridin-4-yl)-(5-methyl-2-p-tolylsulfanyl-phenyl)-amine The product from Example 1d (267 mg, 1.56 mmol) was reacted with the product from Example 47b (358 mg, 1.56 mmol) for 48 h following the procedure from Example 1g giving the crude title compound which was purified by HPLC with TFA providing the trifluoroacetic acid salt (347 mg, 46%). $^1$H NMR (300 MHz, DMSO-d$_6$) δ ppm: 2.22 (s, 3H) 2.37 (s, 3H) 2.77 (s, 3H) 6.27 (d, J=7.35 Hz, 1H) 7.04 (d, J=7.72 Hz, 2H) 7.14 (m, 2H) 7.29 (m, 3H) 7.79 (d, J=8.82 Hz, 1H) 8.39 (d, J=6.99 Hz, 1H) 8.95 (d, J=8.46 Hz, 1H) 11.25 (br. s., 1H) 14.39 (br. s., 1H); MS (ESI+) m/z 372 (M+H)+.

Example 48

(7-Methyl-[1,8]naphthyridin-4-yl)-(5-methyl-2-m-tolylsulfanyl-phenyl)-amine

Example 48a

4-Methyl-2-nitro-1-m-tolylsulfanyl-benzene

The product from Example 4a (9.46 g, 33.17 mmol) was reacted with 3-methylthiophenol (4.12 g, 33.17 mmol) in place of thiophenol following the procedure from Example 1e for 18 h giving the crude title compound which was purified by silica gel column chromatography eluting with 5% EtOAc hexane providing a solid (7.50 g, 87%).

Example 48b

5-Methyl-2-m-tolylsulfanyl-phenylamine

The product from Example 48a was reduced with SnCl$_2$ following the procedure from Example 1f giving the title compound.

Example 48c (7-Methyl-[1,8]naphthyridin-4-yl)-(5-methyl-2-m-tolylsulfanyl-phenyl)-amine The product from Example 1d (267 mg, 1.56 mmol) was reacted with the product from Example 48b (358 mg, 1.56 mmol) for 48 h following the procedure from Example 1g giving the crude title compound which was purified by HPLC with TFA providing the trifluoroacetic acid salt (116 mg, 15%). $^1$H NMR (300 MHz, DMSO-d$_6$) δ ppm: 2.10 (s, 3H) 2.38 (s, 3H) 2.76 (s, 3H) 6.27 (d, J=7.35 Hz, 1H) 7.00 (m, 3H) 7.40 (m, 3H) 7.78 (d, J=8.82 Hz, 1H) 8.37 (d, J=6.99 Hz, 1H) 8.92 (d, J=8.82 Hz, 1H) 11.08 (br. s., 1H) 14.45 (br. s., 1H); MS (ESI+) m/z 372 (M+H)+.

Example 49

[2-(4-Fluoro-phenylsulfanyl)-5-methyl-phenyl]-(7-methyl-[1,8]naphthyridin-4-yl)-amine Example 49a 1-(4-Fluoro-phenylsulfanyl)-4-methyl-2-nitro-benzene The product from Example 4a (5.00 g, 17.53 mmol) was reacted with 4-fluorothiophenol (2.24 g, 17.53 mmol) in place of thiophenol following the procedure from Example 1e for 18 h giving the crude title compound which was purified by silica gel column chromatography eluting with 5% EtOAc hexane providing a solid (3.39 g, 74%).

Example 49b 2-(4-Fluoro-phenylsulfanyl)-5-methyl-phenylamine

The product from Example 49a was reduced with SnCl$_2$ following the procedure from Example 1f giving the title compound.

Example 49c

[2-(4-Fluoro-phenylsulfanyl)-5-methyl-phenyl]-(7-methyl-[1,8]naphthyridin-4-yl)-amine The product from Example 1d (167 mg, 0.94 mmol) was reacted with the product from Example 49b (218 mg, 0.94 mmol) for 48 h following the procedure from Example 1g giving the crude title compound which was purified by HPLC with TFA providing the trifluoroacetic acid salt (224 mg, 49%). $^1$H NMR (300 MHz, DMSO-d$_6$) δ ppm: 2.37 (m, 3H) 2.77 (m, 3H) 6.29 (d, J=6.99 Hz, 1H) 7.10 (m, 2H) 7.32 (m, 5H) 7.80 (d, J=8.46 Hz, 1H) 8.41 (d, J=6.99 Hz, 1H) 8.95 (d, J=8.46 Hz, 1H) 11.04 (br. s., 1H) 14.43 (br. s., 1H); MS (ESI+) m/z 376 (M+H)+.

Example 50

[2-(4-Methoxy-phenylsulfanyl)-5-methyl-phenyl]-(7-methyl-[1,8]naphthyridin-4-yl)-amine Example 50a 1-(4-Methoxy-phenylsulfanyl)-4-methyl-2-nitro-benzene The product from Example 4a (5.0 g, 175 mmol) was reacted with 4-methoxy-benzenethiol (2.45 g, 175 mmol) for 18 h following the procedure from Example 4b giving the product as a solid (3.76 g, 78%).

Example 50b 2-(4-Methoxy-phenylsulfanyl)-5-methyl-phenylamine

The product from Example 50a was reduced with SnCl$_2$ following the procedure from Example 1f giving the title compound.

Example 50c

[2-(4-Methoxy-phenylsulfanyl)-5-methyl-phenyl]-(7-methyl-[1,8]naphthyridin-4-yl)-amine The product from Example 1d (167 mg, 0.94 mmol) was reacted with the product from Example 50b (245 mg, 0.94 mmol) for 48 h following the procedure from Example 1g giving the crude title compound which was purified by HPLC with TFA providing the trifluoroacetic acid salt (325 mg, 70%). $^1$H NMR (300 MHz, DMSO-d$_6$) δ ppm: 2.35 (s, 3H) 2.77 (s, 3H) 3.73 (s, 3H) 6.26 (d, J=6.99 Hz, 1H) 6.85 (d, J=8.82 Hz, 2H) 7.11 (d, J=7.72 Hz, 1H) 7.26 (d, J=8.82 Hz, 2H) 7.31 (s, 1H) 7.80 (d, J=8.46 Hz, 1H) 8.41 (d, J=6.99 Hz, 1H) 8.99 (d, J=8.82 Hz, 1H) 11.04 (br. s., 1H) 14.32 (br. s., 1H); MS ESI+ m/z 388 (M+H)+.

Example 51

[2-(3,4-Dimethoxy-phenylsulfanyl)-5-methyl-phenyl]-(7-methyl-[1,8]naphthyridin-4-yl)-amine

Example 51a 2-(3,4-Dimethoxy-phenylsulfanyl)-5-methyl-phenylamine

The product from Example 4a (11.25 g, 39.5 mmol) was reacted with 3,4-dimethoxy-benzenethiol (6.71 g, 39.5 mmol) for 18 h following the procedure from Example 4b giving the product as a solid (7.75 g, 64%).

Example 51b 2-(3,4-Dimethoxy-phenylsulfanyl)-5-methyl-phenylamine

The product from Example 51a was reduced with $SnCl_2$ following the procedure from Example 1f giving the title compound.

Example 51c

[2-(3,4-Dimethoxy-phenylsulfanyl)-5-methyl-phenyl]-(7-methyl-[1,8]naphthyridin-4-yl)-amine The product from Example 1d (277 mg, 1.56 mmol) was reacted with the product from Example 51b (430 mg, 1.56 mmol) for 5 h following the procedure from Example 1g giving the crude title compound which was purified by HPLC with TFA providing the trifluoroacetic acid salt (628 mg, 79%). $^1$H NMR (300 MHz, DMSO-$d_6$) δ ppm: 2.35 (s, 3H) 2.76 (s, 3H) 3.56 (s, 3H) 3.68 (s, 3H) 6.24 (d, J=6.99 Hz, 1H) 6.82 (m, 3H) 7.29 (m, 3H) 7.79 (d, J=8.46 Hz, 1H) 8.38 (d, J=6.99 Hz, 1H) 8.97 (d, J=8.46 Hz, 1H) 10.97 (s, 1H) 14.35 (s, 1H); MS (ESI+) m/z 418 (M+H)+.

Example 52

3-[4-Methyl-2-(7-methyl-[1,8]naphthyridin-4-ylamino)-phenylsulfanyl]-phenol

Example 52a 3-(4-Methyl-2-nitro-phenylsulfanyl)-phenol

The product from Example 4a (10.14 g, 35.6 mmol) was reacted with 3-(4-Methyl-2-nitro-phenylsulfanyl)-phenol (4.48 g, 35.6 mmol) for 18 h following the procedure from Example 4b giving the product as a solid (7.88 g, 85%).

Example 52b 3-(2-Amino-4-methyl-phenylsulfanyl)-phenol

The product from Example 52a was reduced with $SnCl_2$ following the procedure from Example 1f giving the title compound.

Example 52c

3-[4-Methyl-2-(7-methyl-[1,8]naphthyridin-4-ylamino)-phenylsulfanyl]-phenol

The product from Example 1d (277 mg, 1.56 mmol) was reacted with the product from Example 52b (245 mg, 1.56 mmol) for 5 h following the procedure from Example 1g giving the crude title compound which was purified by HPLC with TFA providing the trifluoroacetic acid salt (399 mg, 52%). $^1$H NMR (300 MHz, DMSO-$d_6$) δ ppm: 2.38 (s, 3H) 2.75 (s, 3H) 6.30 (d, J=6.99 Hz, 1H) 6.53-6.58 (m, 2H) 6.61 (d, J=8.09 Hz, 1H) 6.90-7.08 (m, 1H) 7.27-7.47 (m, 3H) 7.77 (d, J=8.46 Hz, 1H) 8.39 (d, J=6.99 Hz, 1H) 8.94 (d, J=8.82 Hz, 1H) 9.58 (s, 1H) 10.96 (s, 1H) 14.34 (s, 1H); MS (ESI+) m/z 374 (M+H)+.

Example 53

[3-(7-Methyl-[1,8]naphthyridin-4-ylamino)-4-phenylsulfanyl-phenyl]-methanol

Example 53a

4-Hydroxy-3-nitro-benzoic acid ethyl ester

A solution of 4-hydroxy-3-nitro-benzoic acid ethyl ester (15.0 g, 76.1 mmol) was reacted with trifluoromethanesulfonic anhydride (14.0 mL, 83.7 mmol) for 15 min following the procedure from Example 4a to give the title compound as an amber oil (22.26 g, 89%).

Example 53b

3-Nitro-4-phenylsulfanyl-benzoic acid ethyl ester

The product from Example 53a (22.6 g, 67.6 mmol) was reacted with sodium thiophenolate (7.54 g, 67.6 mmol) for 24 h following the procedure from Example 1e giving the title compound as a solid (13.2 g, 67%).

Example 53c

3-Amino-4-phenylsulfanyl-benzoic acid ethyl ester

The product from Example 53b was reacted with the $SnCl_2$ following the procedure from Example 1f giving the title compound as a solid.

Example 53c 3-(7-Methyl-[1,8]naphthyridin-4-ylamino)-4-phenylsulfanyl-benzoic acid ethyl ester The product from Example 1d (2.06 g, 1.16 mmol) was reacted with the Product from Example 53b (3.18 g, 1.16 mmol) for 5 h following the procedure from Example 1g giving the crude title compound which was purified by HPLC with TFA providing the trifluoroacetic acid salt (3.61 g, 59%).

Example 53d

[3-(7-Methyl-[1,8]naphthyridin-4-ylamino)-4-phenylsulfanyl-phenyl]-methanol

The product from Example 53c (2.30 g, 5.54 mmol) in 60 mL of THF was reacted with the $LiAlH_4$ (420 mg, 11.0 mmol)

for 18 h followed quenching with dilute HCl. Adjusted to pH 10 with NH$_4$OH. Extracted with CH$_2$Cl$_2$, dried over MgSO$_4$ filtered and concentrated under vacuum giving the crude title compound which was purified by HPLC with TFA providing the trifluoroacetic acid salt (325 mg, 70%). $^1$H NMR (300 MHz, DMSO-d$_6$) δ ppm: 2.76 (s, 3H) 3.99 (br. s, 1H) 4.58 (s, 2H) 6.31 (d, J=7.35 Hz, 1H) 7.25 (s, 5H) 7.40 (m, 2H) 7.46 (s, 1H) 7.78 (d, J=8.82 Hz, 1H) 8.42 (d, J=6.99 Hz, 1H) 8.95 (d, J=8.46 Hz, 1H) 11.06 (br. s., 1H) 14.44 (br. s., 1H); MS (ESI+) m/z 374 (M+H)+.

Example 54

[2-(4-Ethoxy-phenylsulfanyl)-5-methyl-phenyl]-(7-methyl-[1,8]naphthyridin-4-yl)-amine

Example 54a 1-(4-Ethoxy-phenylsulfanyl)-4-methyl-2-nitro-benzene

The product from Example 4b (500 mg, 1.91 mmol) was reacted with NaH (0.048 g, 2.01 mmol) in 10 mL THF at 0° C. for 2 h. Warmed to room temperature and added EtI (0.232 mL, 2.87 mmol) slowly then stirred at room temperature for 4 days. Quenched with water separated layers and Dried over MgSO$_4$, filtered and concentrated under vacuum giving the product as a solid (510 mg, 92%). Reduced with SnCl$_2$ following the procedure from Example 1f giving the title compound.

Example 54b

[2-(4-Ethoxy-phenylsulfanyl)-5-methyl-phenyl]-(7-methyl-[1,8]naphthyridin-4-yl)-amine The product from Example 1d (250 mg, 1.56 mmol) was reacted with the product from Example 54a (259 mg, 1.56 mmol) for 5 h following the procedure from Example 1g giving the crude title compound which was purified by HPLC with TFA providing the trifluoroacetic acid salt (241 mg, 30%). $^1$H NMR (300 MHz, DMSO-d$_6$) δ ppm: 1.31 (t, J=6.99 Hz, 3H) 2.34 (s, 3H) 2.76 (s, 3H) 3.97 (q, J=6.99 Hz, 2H) 6.26 (d, J=7.35 Hz, 1H) 6.83 (d, J=8.82 Hz, 2H) 7.11 (d, J=7.72 Hz, 1H) 7.24 (d, J=8.82 Hz, 2H) 7.27 (s, 1H) 7.30 (s, 1H) 7.80 (d, J=8.82 Hz, 1H) 8.41 (d, J=6.99 Hz, 1H) 8.99 (d, J=8.82 Hz, 1H) 11.01 (s, 1H) 14.38 (s, 1H); MS (ESI+) m/z 402 (M+H)+.

Example 55

(7-Methyl-[1,8]naphthyridin-4-yl)-[5-methyl-2-(4-propoxy-phenylsulfanyl)-phenyl]-amine

Example 55a

4-Methyl-2-nitro-1-(4-propoxy-phenylsulfanyl)-benzene

The product from Example 4b (600 mg, 2.30 mmol) was reacted with NaH (0.83 g, 2.30 mmol) in 10 mL THF at 0° C. for 2 h. Warmed to room temperature and added EtI (0.232 mL, 2.87 mmol) slowly then stirred at 50° C. for 7 days. Quenched with water separated layers and Dried over MgSO$_4$, filtered and concentrated under vacuum giving the product as a solid (700 mg, 100%). Reduced with SnCl$_2$ following the procedure from Example 1f giving the title compound.

Example 55b (7-Methyl-[1,8]naphthyridin-4-yl)-[5-methyl-2-(4-propoxy-phenylsulfanyl)-phenyl]-amine The product from Example 1d (250 mg, 1.56 mmol) was reacted with the product from Example 55a (273 mg, 1.56 mmol) for 5 h following the procedure from Example 1g giving the crude title compound which was purified by HPLC with TFA providing the trifluoroacetic acid salt (187 mg, 23%). $^1$H NMR (300 MHz, DMSO-d$_6$) δ ppm: 0.97 (t, J=7.35 Hz, 3H) 1.62-1.79 (m, 2H) 2.34 (s, 3H) 2.76 (s, 3H) 3.86 (t, J=6.43 Hz, 2H) 6.27 (d, J=6.99 Hz, 1H) 6.84 (d, J=8.82 Hz, 2H) 7.11 (d, J=7.72 Hz, 1H) 7.24 (d, J=8.46 Hz, 2H) 7.29 (s, 1H) 7.80 (d, J=8.46 Hz, 1H) 8.42 (d, J=6.99 Hz, 1H) 8.99 (d, J=8.46 Hz, 1H) 11.01 (s, 1H) 14.39 (s, 1H); MS (ESI+) m/z 416 (M+H)+.

Example 56

[2-(4-Isopropoxy-phenylsulfanyl)-5-methyl-phenyl]-(7-methyl-[1,8]naphthyridin-4-yl)-amine

Example 56a 2-(4-Isopropoxy-phenylsulfanyl)-5-methyl-phenylamine

The product from Example 4b (600 mg, 2.30 mmol) was reacted with NaH (0.83 g, 2.44 mmol) in 10 mL THF at 0° C. for 2 h. Warmed to room temperature and added i-Pr—I (0.574 mL, 5.74 mmol) slowly then stirred at 50° C. for 10 days. Quenched with water separated layers and Dried over MgSO$_4$, filtered and concentrated under vacuum giving the product as a solid (730 mg, 100%). Reduced with SnCl$_2$ following the procedure from Example 1f giving the title compound.

Example 56b

[2-(4-Isopropoxy-phenylsulfanyl)-5-methyl-phenyl]-(7-methyl-[1,8]naphthyridin-4-yl)-amine The product from Example 1d (250 mg, 1.56 mmol) was reacted with the product from Example 56a (427 mg, 1.56 mmol) for 5 h following the procedure from Example 1g giving the crude title compound which was purified by HPLC with TFA providing the trifluoroacetic acid salt (185 mg, 23%). $^1$H NMR (300 MHz, DMSO-d$_6$) δ ppm: 1.23 (d, J=6.25 Hz, 6H) 2.34 (s, 3H) 2.76 (s, 3H) 4.48-4.58 (m, 1H) 6.27 (d, J=6.99 Hz, 1H) 6.81 (d, J=8.82 Hz, 2H) 7.14 (d, J=8.09 Hz, 1H) 7.22 (d, J=8.82 Hz, 2H) 7.27 (s, 1H) 7.30 (s, 1H) 7.79 (d, J=8.82 Hz, 1H) 8.41 (d, J=6.99 Hz, 1H) 8.99 (d, J=8.46 Hz, 1H) 10.99 (s, 1H) 14.36 (s, 1H); MS (ESI+) m/z 416 (M+H)+.

Example 57

N-(4-Bromo-phenyl)-4-(4-hydroxy-phenylsulfanyl)-3-(7-propyl-[1,8]naphthyridin-4-ylamino)-benzamide

Example 57a

N-(4-Bromo-phenyl)-4-chloro-3-nitro-benzamide

A mixture of 4-bromoaniline (2.58 g 14.99 mmol) in dry CH$_2$Cl$_2$ (100 mL) was treated with 4-chloro-3-nitrobenzoyl chloride (3.60 g, 17.99 mmol) and N,N-diisopropyl-ethylamine (3.14 mL, 17.99 mmol), and the resulting mixture stirred at room temperature for 17 hours. The solvent was concentrated under vacuum giving the title compound and the residue taken up in ethyl acetate (100 mL) and washed with water and brine. The organic extract was dried over $Na_2SO_4$, filtered and concentrated under vacuum giving the title compound as a tan solid (5.132 g, 14.45 mmol, 96%).

Example 57b

N-(4-Bromo-phenyl)-4-(4-hydroxy-phenylsulfanyl)-3-nitro-benzamide

A solution of the product of Example 57a (553 mg, 1.557 mmol) in anhydrous DMF (15 mL) was treated with 4-mercaptophenol (196 mg, 1.557 mmol) and cesium carbonate (1.015 g, 3.114 mmol) at room temperature, then heated at 100° under a nitrogen atmosphere for 3 hours. The reaction was cooled to room temperature and the solvent concentrated under vacuum giving the title compound. The residue was taken up in $H_2O$ (30 mL) and the pH adjusted to 3 with 1N aqueous HCl. The aqueous was then extracted with ethyl acetate, and the combined organic extracts washed with brine (25 mL). The organic layer was dried over $Na_2SO_4$, filtered and concentrated under vacuum giving the title compound. The residue was triturated with methylene chloride and purified by silica gel flash chromatography with a gradient of 6% to 30% ethyl acetate/methylene chloride to afford the title product as a dark yellow solid (517 mg, 1.16 mmol, 75%).

Example 57c

3-Amino-N-(4-bromo-phenyl)-4-(4-hydroxy-phenyl-sulfanyl)-benzamide

The product from Example 57b was reduced with Fe and $NH_4Cl$ following the procedure form Example 237E to give the title compound.

Example 57d

N-(4-Bromo-phenyl)-4-(4-hydroxy-phenylsulfanyl)-3-(7-propyl-[1,8]naphthyridin-4-ylamino)-benzamide The product from Example 2g (138 mg, 0.154 mmol) was reacted with the product form Example 57C (64 mg, 0.154 mmol) for 40 h following the procedure from Example 1g giving the crude title compound which was purified by HPLC with TFA providing the trifluoroacetic acid salt (30 mg, 20%). $^1$H NMR (300 MHz, DMSO-$d_6$) δ ppm: 0.99 (t, J=7.35 Hz, 3H) 1.69-1.96 (m, 2H) 3.02 (t, J=7.35 Hz, 2H) 6.42 (d, J=6.99 Hz, 1H) 6.87 (d, J=8.46 Hz, 2H) 7.02 (d, J=8.46 Hz, 1H) 7.33 (d, J=8.46 Hz, 2H) 7.54 (d, J=9.19 Hz, 2H) 7.72 (d, J=8.82 Hz, 2H) 7.87 (d, J=8.82 Hz, 1H) 7.98 (dd, J=8.46, 1.84 Hz, 1H) 8.02 (d, J=1.84 Hz, 1H) 8.52 (d, J=6.62 Hz, 1H) 9.09 (d, J=8.46 Hz, 1H) 10.09 (s, 1H) 10.37 (s, 1H) 11.14 (s, 1H) 14.54 (s, 1H); MS (ESI+) m/z 585/587 (M+H)+.

Example 58

5-Dimethylamino-naphthalene-1-sulfonic acid 4-[4-methyl-2-(7-methyl-[1,8]naphthyridin-4-ylamino)-phenylsulfanyl]-phenyl ester The product from Example 5 (167 mg, 0.94 mmol) was reacted with 5-Dimethylamino-naphthalene-1-sulfonyl chloride (245 mg, 0.94 mmol) in 10 mL of $CH_2Cl_2$ with N,N-diisopropylethylamine (0.530 mL, 410 mmol) for 22 h. Washed with water and dried over $Na_2SO_4$, filtered and concentrated under vacuum giving the crude title compound which was purified by HPLC with TFA providing the trifluoroacetic acid salt (35 mg, 40%). $^1$H NMR (300 MHz, DMSO-$d_6$) δ ppm: 2.75 (s, 3H) 2.86 (s, 6H) 6.65 (d, J=6.99 Hz, 1H) 6.76 (d, J=9.19 Hz, 2H) 6.87 (d, 2H) 7.16 (d, J=8.82 Hz, 1H) 7.34 (d, J=7.72 Hz, 1H) 7.53-7.62 (m, 2H) 7.69-7.79 (m, 3H) 7.97 (d, J=7.35 Hz, 1H) 8.22 (d, J=8.82 Hz, 1H) 8.50 (d, J=6.99 Hz, 1H) 8.60 (d, J=8.46 Hz, 1H) 8.82 (d, J=8.82 Hz, 1H); MS 1H) 8.50 (d, J=6.99 Hz, 1H) 8.60 (d, J=8.46 Hz, 1H) 8.82 (d, J=8.82 Hz, 1H); MS (DCI NH3+) m/z 611 (M+H)+.

Example 59

Ethanesulfonic acid 4-[4-methyl-2-(7-methyl-[1,8]naphthyridin-4-ylamino)-phenylsulfanyl]-phenyl ester The product from Example 5 (100 mg, 0.24 mmol) was reacted with ethanesulfonyl chloride (31.0 mg, 0.24 mmol) for 18 h following the procedure from Example 58 giving the crude title compound which was purified by HPLC with TFA providing the trifluoroacetic acid salt (20 mg, 14%). $^1$H NMR (300 MHz, DMSO-$d_6$) δ ppm: 10.98 (s, 1H) 8.89 (d, J=8.46 Hz, 1H) 8.39 (d, J=6.99 Hz, 1H) 7.76 (d, J=8.82 Hz, 1H) 7.45-7.50 (m, 1H) 7.36-7.42 (m, 2H) 7.25 (d, 2H) 7.17 (d, 2H) 6.33 (d, J=6.99 Hz, 1H) 3.47 (q, J=7.35 Hz, 2H) 2.75 (s, 3H) 2.40 (s, 3H) 1.34 (t, J=7.35 Hz, 3H); MS (DCI NH3+) m/z 466 (M+H)+.

Example 60

Propane-2-sulfonic acid 4-[4-methyl-2-(7-methyl-[1,8]naphthyridin-4-ylamino)-phenylsulfanyl]-phenyl ester The product from Example 5 (80.0 mg, 0.195 mmol) was reacted with the propane-2-sulfonyl chloride (27.8 mg, 0.195 mmol) for 18 h following the procedure from Example 58 giving the crude title compound which was purified by HPLC with TFA providing the trifluoroacetic acid salt (20 mg, 21%). $^1$H NMR (300 MHz, DMSO-$d_6$) δ ppm: 8.90 (d, J=8.46 Hz, 1H) 8.39 (d, J=6.99 Hz, 1H) 7.76 (d, J=8.82 Hz, 1H) 7.43-7.49 (m, 1H) 7.35-7.42 (m, 2H) 7.24-7.29 (m, 2H) 7.12-7.19 (m, 2H) 6.33 (d, J=6.99 Hz, 1H) 2.75 (s, 3H) 3.66 (m, 1) 2.39 (s, 3H) 1.40 (d, J=6.99 Hz, 6H); MS (DCI NH3+) m/z 480 (M+H)+.

Example 61

Methanesulfonic acid 4-[4-methyl-2-(7-methyl-[1,8]naphthyridin-4-ylamino)-phenylsulfanyl]-phenyl ester The product from Example 5 (80 mg, 0.195 mmol) was reacted with the methanesulfonyl chloride (22.3 mg, 0.195 mmol) for 18 h following the procedure from Example 58 giving the crude title compound which was purified by HPLC with TFA providing the trifluoroacetic acid salt (36 mg, 32%). $^1$H NMR (300 MHz, DMSO-$d_6$) δ ppm: 8.88 (d, J=8.46 Hz, 1H) 8.39 (d, J=6.99 Hz, 1H) 7.76 (d, J=8.46 Hz, 1H) 7.45-7.51 (m, 1H) 7.35-7.42 (m, 2H) 7.26 (d, 2H) 7.19 (d, 2H) 6.33 (d, J=6.99 Hz, 1H) 3.34 (s, 3H) 2.75 (s, 3H) 2.40 (s, 3H); MS (DCI NH3+) m/z 452 (M+H)+.

Example 62

Ethanesulfonic acid 4-[2-(7-ethyl-[1,8]naphthyridin-4-ylamino)-4-methyl-phenylsulfanyl]-phenyl ester The product from Example 4 (20 mg, 0.47 mmol) was reacted with ethanesulfonyl chloride (72 mg, 0.56 mmol) for 22 h following the procedure from Example 58 giving the crude title compound which was purified by HPLC with TFA providing the trifluoroacetic acid salt (70 mg, 25%). $^1$H NMR (300 MHz, DMSO-$d_6$) δ ppm: 8.31 (d, 1H) 7.73 (d, 1H) 7.11 (d, 1H) 6.85 (d, 1H) 6.74 (s, 2H) 6.64 (d, 2H) 6.53 (d, 2H) 5.75 (d, 1H) 2.81 (q, 2H) 2.42 (q, 2H) 1.78 (s, 3H) 0.76 (m, 6H); MS (ESI+) m/z 484 (M+H)+.

Example 63

Phenyl-methanesulfonic acid 4-[4-methyl-2-(7-methyl-[1,8]naphthyridin-4-ylamino)-phenylsulfanyl]-phenyl ester The product from Example 5 (120 mg, 0.294 mmol) was reacted with phenyl-methanesulfonyl chloride (55 mg, 0.294 mmol) for 22 h following the procedure from Example 58 giving the crude title compound which was purified by HPLC with TFA providing the trifluoroacetic acid salt (15 mg, 9%). $^1$H NMR (300 MHz, DMSO-$d_6$) δ ppm: 8.31 (d, 1H) 7.73 (d, 1H) 7.11 (d, 1H) 6.85 (d, 1H) 6.74 (s, 2H) 6.64 (d, 2H) 6.53 (d, 2H) 5.75 (d, 1H) 2.81 (q, 2H) 2.42 (q, 2H) 1.78 (s, 3H) 0.76 (m, 6H); MS (ESI+) m/z 484 (M+H)$^+$.

Example 64

{4-[4-Methyl-2-(7-methyl-[1,8]naphthyridin-4-ylamino)-phenylsulfanyl]-phenoxy}-acetic acid ethyl ester Material from Example 5 (0.200 g, 0.536 mmol) was suspended in acetone to which $K_2CO_3$ was added. This was treated with bromo-ethyl-acetate (0.089 g, 0.536 mmol) at which time the reaction mixture was heated to reflux for 4 hrs. Reaction mixture cooled to room temperature, solid filtered and concentrated under vacuum giving the crude title compound which was purified by HPLC with TFA providing the product as a trifluoroacetic acid salt (24 mg, 10%). $^1$H NMR (300 MHz, DMSO-$d_6$) δ ppm: 1.22 (t, J=6.99 Hz, 3H), 2.34 (s, 3H), 2.74 (s, 3H), 4.20 (q, J=6.99 Hz, 2H), 5.47 (s, 2H), 6.49 (d, J=7.72 Hz, 1H), 6.75 (d, J=8.82 Hz, 2H), 7.00 (d, J=8.09 Hz, 1H), 7.20 (d, J=8.46 Hz, 2H), 7.25-7.40 (m, 2H), 7.87 (d, J=8.82 Hz, 1H), 8.63 (d, J=7.72 Hz, 1H), 9.06 (d, J=8.46 Hz, 1H), 9.89 (s, 1H); MS(ESI) m/z 460 (M+H)+, (ESI−) m/z 458 (M−H)−.

Example 65

{4-[4-Methyl-2-(7-methyl-[1,8]naphthyridin-4-ylamino)-phenylsulfanyl]-phenoxy}-acetic acid The product from Example 64 (0.246 g 0.535 mmol) was dissolved in 10 mL of 5% NaOH and 10 mL of EtOH and heated to 100° C. for 2 hrs and then stirred at room temperature for 110 hrs. At this time all the solvent was removed under vacuum and the brown oil was redissolved in water, to which 2 mL of HCl was added and a yellow precipitate formed. Precipitate collected by filtration and solid dried in under vacuum overnight (150 mg, 64%) $^1$H NMR (300 MHz, DMSO-$d_6$) δ ppm: 2.33 (s, 3H), 2.75 (s, 3H), 5.42 (s, 2H), 6.46 (d, J=7.35 Hz, 1H), 6.52 (s, 1H), 6.75 (d, J=8.46 Hz, 2H), 6.99 (d, J=8.46 Hz, 1H), 7.15-7.40 (m, J=8.46 Hz, 4H), 7.85 (s, 1H), 8.62 (s, 1H), 9.08 (d, J=8.09 Hz, 1H), 9.90 (s, 1H); MS (ESI) m/z 432 (M+H)+, (ESI−) m/z 430 (M−H)−.

Example 66

2,2-Dimethyl-N-{4-[4-methyl-2-(7-methyl-[1,8]naphthyridin-4-ylamino)-phenylsulfanyl]-phenyl}-propionamide The product from Example 83 (0.50 g, 0.134 mmol) was dissolved in DMF and treated with 2,2-dimethyl-propionyl chloride (0.016 g, 0.134 mmol) and stirred at room temperature for 1 h. DMF removed under a stream of $N_2$, and the crude residue purified by HPLC with TFA providing the title compound as a trifluoroacetic acid salt (40.0 mg, 65%). $^1$H NMR (300 MHz, DMSO-$d_6$) δ ppm: 1.22 (s, 9H), 2.35 (s, 3H), 2.76 (s, 3H), 6.33 (d, J=6.99 Hz, 1H), 7.15 (s, 1H), 7.24 (d, J=8.46 Hz, 3H), 7.31 (s, 1H), 7.61 (d, J=8.82 Hz, 2H), 7.80 (s, 1H), 8.42 (s, 1H), 8.96 (s, 1H), 9.27 (s, 1H), 10.99 (s, 1H) MS (ESI+) m/z 457 (M+H)+, (ESI−) m/z 455 (M−H)−.

Example 67

N-{4-[4-Methyl-2-(7-methyl-[1,8]naphthyridin-4-ylamino)-phenylsulfanyl]-phenyl}-butyramide The product from Example 83 (0.50 g, 0.134 mmol) was dissolved in DMF and treated with butyryl chloride (0.016 g, 0.134 mmol) and stirred at room temperature for 1 h. DMF removed under a stream of $N_2$, and the crude residue purified by HPLC with TFA providing the title compound as a trifluoroacetic acid salt (41.0 mg, 65%). $^1$H NMR (300 MHz, DMSO-$d_6$) δ ppm: 0.91 (t, J=7.35 Hz, 3H), 1.54-1.65 (m, 2H), 2.27 (t, J=7.35 Hz, 2H), 2.35 (s, 3H), 2.76 (s, 3H), 6.31 (d, J=6.99 Hz, 1H), 7.15 (d, J=8.09 Hz, 1H), 7.21-7.32 (m, 4H), 7.53 (d, J=8.82 Hz, 2H), 7.78 (d, J=8.82 Hz, 1H), 8.41 (d, J=6.99 Hz, 1H), 8.96 (d, J=8.46 Hz, 1H), 9.98 (s, 1H), 11.00 (s, 1H); MS (ESI+) m/z 443 (M+H)+, (ESI−) m/z 441 (M−H)−.

Example 68

Cyclopropanecarboxylic acid {4-[4-methyl-2-(7-methyl-[1,8]naphthyridin-4-ylamino)-phenylsulfanyl]-phenyl}-amide The product from Example 83 (0.50 g, 0.134 mmol) was dissolved in DMF and treated with cyclopropanecarbonyl chloride (0.016 g, 0.134 mmol) and stirred at room temperature for 1 hr. DMF removed under a stream of $N_2$, and the crude residue purified by HPLC with TFA giving the title compound as a trifluoroacetic acid salt (25. mg, 40%). $^1$H NMR (300 MHz, DMSO-$d_6$) δ ppm: 0.80 (d, J=6.25 Hz, 4H), 1.71-1.79 (m, 1H), 2.35 (s, 3H), 2.76 (s, 3H), 6.31 (d, J=7.35 Hz, 1H), 7.16 (d, J=7.72 Hz, 1H), 7.21-7.32 (m, 4H), 7.51 (d, J=8.82 Hz, 2H), 7.78 (d, J=8.82 Hz, 1H), 8.41 (d, J=7.35 Hz, 1H), 8.96 (d, J=8.82 Hz, 1H), 10.29 (s, 1H), 10.99 (s, 1H); MS (ESI+) m/z 441 (M+H)+, (ESI−) m/z 439 (M−H)−.

Example 69

2-{4-[4-Methyl-2-(7-methyl-[1,8]naphthyridin-4-ylamino)-phenylsulfanyl]-phenylcarbamoyl}-pyrrolidine-1-carboxylic acid benzyl ester Carbobenzyloxy-proline (0.110 g, 0.443 mmol) was dissolved in THF to which was added N-methyl morpholine (0.133 g, 0.443 mmol). Neat isopropenyl chlorofromate (0.053 g, 0.443 mmol) was then added and the reaction mixture was stirred at room temperature for 30 min. At this time the product from Example 83 (0.150 g, 0.402 mmol) was added as a solution in THF, stirred at room temperature for 1 h. The reaction mixture was diluted with water and extracted with $CH_2Cl_2$, dried over $Na_2SO_4$, filtered and concentrated under vacuum giving the crude title compound which was purified by HPLC with TFA providing the title compound as a trifluoroacetic acid salt (118 mg, 48%). $^1$H NMR (300 MHz, DMSO-$d_6$) δ ppm: 1.82-1.98 (m, 3H), 2.22 (s, 2H), 2.35 (s, 3H), 2.75 (s, 3H), 4.27-4.40 (m, 1H), 4.89-4.98 (m, 1H), 5.00-5.13 (m, 2H), 6.35 (t, J=6.80 Hz, 1H), 7.06-7.22 (m, 3H), 7.24-7.39 (m, 6H), 7.55 (d, J=8.46 Hz, 2H), 7.78 (d, J=8.82 Hz, 1H), 8.44 (d, J=6.99 Hz, 1H), 8.96 (dd, J=11.95, 8.64 Hz, 1H), 10.20 (s, 1H), 11.04 (s, 1H), 14.39 (s, 1H); MS (ESI+) m/z 604 (M+H)+, (ESI−) m/z 602 (M−H)−.

Example 70

(7-Methyl-[1,8]naphthyridin-4-yl)-[5-methyl-2-(4-phenoxy-phenylsulfanyl)-phenyl]-amine Example 70a 5-Methyl-2-(4-phenoxy-phenylsulfanyl)-phenylamine The product from Example 4c (0.500 g, 1.91 mmol) was dissolved in $CH_2Cl_2$ along with phenyl boronic acid (0.701 g, 5.74 mmol), copper(II) acetate (0.659 g, 3.83 mmol), and triethylamine (0.387 g, 3.83 mmol). Stirred at room temperature for 48 h, at which time 2 more equivalents of each reagent was added. Stirred at room temperature for another 16 h at which time another 2 eq of each reagent was added. Stirred at room temperature for another 16 h. The reaction was diluted with water and extracted with ethyl acetate Dried over $Na_2SO_4$, filtered and concentrated under vacuum giving the crude product which was purified silica gel column chromatography eluting with 20% EtOAc/hexane (0.100 g, 15%). The product was reduced with $SnCl_2$ following the procedure from Example 1f to give the title compound (90 mg, 98%).

Example 70b (7-Methyl-[1,8]naphthyridin-4-yl)-[5-methyl-2-(4-phenoxy-phenylsulfanyl)-phenyl]-amine The product from Example 1d (50 mg, 0.28 mmol) was reacted with the product from Example 70a (86 mg, 0.28 mmol) for 24 h following the procedure from Example 1g giving the crude title compound which was purified by HPLC with TFA providing the product as a trifluoroacetic acid salt (64 mg, 50%). $^1$H NMR (300 MHz, DMSO-$d_6$) δ ppm: 2.37 (s, 3H), 2.73-2.79 (m, 3H), 6.30 (d, J=6.99 Hz, 1H), 6.78-6.87 (m, 2H), 6.97 (d, J=7.72 Hz, 2H), 7.17-7.24 (m, 1H), 7.24-7.28 (m, 2H), 7.32-7.36 (m, 3H), 7.37-7.46 (m, 2H), 7.79 (d, J=8.82 Hz, 1H), 8.42 (d, J=7.35 Hz, 1H), 8.96 (d, J=8.46 Hz, 1H), 11.00 (s, 1H); MS (ESI+) m/z 450 (M+H)+, (ESI−) m/z 448 (M−H)−.

Example 71

N-{3-[4-Methyl-2-(7-methyl-[1,8]naphthyridin-4-ylamino)-phenylsulfanyl]-phenyl}-acetamide Example 71a 3-(4-Methyl-2-nitro-phenylsulfanyl)-phenylamine The product from Example 4a (1.00 g, 3.51 mmol) and 3-Amino-benzenethiol (658 mg, 5.26 mmol) were dissolved in DMF to which was added $K_2CO_3$ (848 mg, 6.14 mmol). The reaction mixture was then heated to 10° C. for 16 hrs. Reaction mixture was then cooled to room temperature, diluted with water and extracted with ethyl acetate providing the title compound (650 mg, 71%).

Example 71b

N-[3-(4-Methyl-2-nitro-phenylsulfanyl)-phenyl]-acetamide

The product from Example 71a (650 mg, 2.50 mmol) was dissolved in DCM and acetyl chloride (196 mg, 2.50 mmol) was added. Allowed to stir at room temperature for 1 h, at which time a solid was collected by filtration providing the title compound (690 mg, 61%)

Example 71c

N-[3-(2-Amino-4-methyl-phenylsulfanyl)-phenyl]-acetamide

The product from Example 71b was reduced with $SnCl_2$ following the procedure from Example 1f providing the title compound (120 mg, 20%).

Example 71d

N-{3-[4-Methyl-2-(7-methyl-[1,8]naphthyridin-4-ylamino)-phenylsulfanyl]-phenyl}-acetamide The product from Example 1d (100 mg, 0.559 mmol) was reacted with the product from Example 71c (152 mg, 0.559 mmol) for 18 h following the procedure from Example 1g giving the crude title compound which was purified by HPLC with TFA providing the product as a trifluoroacetic acid (45 mg, 18%). $^1$H NMR (300 MHz, DMSO-$d_6$) δ ppm: 1.97 (s, 3H), 2.38 (s, 3H), 2.74 (s, 3H), 6.26 (d, J=6.99 Hz, 1H), 6.84 (d, J=8.46 Hz, 1H), 7.06 (t, J=8.09 Hz, 1H), 7.25 (d, J=8.09 Hz, 1H), 7.33-7.41 (m, 2H), 7.41-7.54 (m, 2H), 7.74 (d, J=8.82 Hz, 1H), 8.33 (d, J=6.99 Hz, 1H), 8.89 (d, J=8.82 Hz, 1H), 9.81 (s, 1H), 10.91 (s, 1H); MS (ESI+) m/z 415 (M+H)+, (ESI−) m/z 413 (M−H)−.

Example 72

{2-[4-(1-Imino-ethyl)-phenylsulfanyl]-5-methyl-phenyl}-(7-methyl-[1,8]naphthyridin-4-yl)-amine Example 72a Thioacetimidic acid naphthalen-2-ylmethyl ester; HBr salt 2-Bromomethyl-naphthalene (2.00 g, 9.05 mmol) and thioacetimide (680 mg, 9.05 mmol) were dissolved in $CH_3Cl$ and stirred at room temperature for 1 hr. Product collected by filtration providing the title compound (1.500 g, 77%).

Example 72b

{2-[4-(1-Imino-ethyl)-phenylsulfanyl]-5-methyl-phenyl}-(7-methyl-[1,8]naphthyridin-4-yl)-amine The product from Example 72a (239 mg, 0.805 mmol) and the product from Example 83 (150 mg, 0.403 mmol) were dissolved in EtOH and stirred at room temperature for 1 h.

Solvent was concentrated under vacuum giving the crude title compound which was purified by HPLC with TFA providing the title compound as a trifluoroacetic acid salt (118 mg, 70%). $^1$H NMR (300 MHz, DMSO-d$_6$) δ ppm: 2.32 (s, 3H), 2.36-2.43 (m, 3H), 2.76 (s, 3H), 6.38 (d, J=6.99 Hz, 1H), 7.19-7.27 (m, 2H), 7.32-7.45 (m, 5H), 7.79 (d, J=8.82 Hz, 1H), 8.44 (d, J=6.99 Hz, 1H), 8.57 (s, 1H), 8.89-9.00 (m, 1H), 9.55 (s, 1H), 11.10 (s, 1H); MS (ESI+) m/z 414 (M+H)+, (ESI−) m/z 412 (M−H)−.

Example 73

1-{4-[4-Methyl-2-(7-methyl-[1,8]naphthyridin-4-ylamino)-phenylsulfanyl]-phenyl}-ethanethione The product from Example 18 (265 mg, 0.639 mmol) and Lawesson reagent (517 mg, 1.28 mmol) were dissolved in 3 mL of toluene and heated to 80° C. for 16 h. Reaction mixture cooled to room temperature, washed with water and extracted with EtOAc. Dried over Na$_2$SO$_4$, filtered and concentrated under vacuum giving the crude title compound which was purified by HPLC with TFA providing the trifluoroacetic acid salt (14 mg, 5%). $^1$H NMR (300 MHz, DMSO-d$_6$) δ ppm: 2.33 (s, 3H), 2.59 (s, 3H), 2.63 (s, 3H), 3.75 (s, 1H), 6.17 (s, 1H), 6.88 (d, J=10.30 Hz, 1H), 7.06-7.21 (m, 3H), 7.21-7.27 (m, 2H), 7.39 (d, J=8.46 Hz, 1H), 7.78 (d, J=8.46 Hz, 2H), 8.63 (d, J=8.82 Hz, 1H), 11.59 (s, 1H); MS (ESI+) m/z 431 (M+H)+, (ESI−) m/z 429 (M−H)−.

Example 74

N-{4-[4-Methyl-2-(7-methyl-[1,8]naphthyridin-4-ylamino)-phenylsulfanyl]-phenyl}-2-phenyl-butyramide To a flask containing 3 equivalents of PS-DCC resin (polymer-bound 'N,N,'-dicylcohexylcarbodiimide) was added 2-Phenyl-butyric acid (27 mg, 0.16 mmol) dissolved in 3 mL of DMA, followed by HOBt (22 mg, 0.16 mmol), the product from Example 83 (50 mg, 0.134 mmol) and diethylisopropylamine (52 mg, 0.402 mmol). The reaction was heated to 55° C. overnight, filtered and transferred to a vial containing 3 eqivalents of MP-Carbonate (macroporous carbonate) resin. The reaction vessel and PS-DCC resin were washed with MeOH and the combined filtrates were shaken over the MP-carbonate resin for 2 hours at room temperature. The MP-Carbonate resin was removed via filtration and the reactions were concentrated to dryness. Purified by HPLC with TFA providing the product as a trifluoroacetic acid (2 mg, 4%). $^1$H NMR (500 MHz, DMSO-D$_2$O) δ ppm: 0.83-0.89 (m, 3H), 1.66-1.74 (m, J=7.17, 6.90, 6.90, 6.90, 6.90 Hz, 1H), 2.00-2.08 (m, 1H), 2.32-2.38 (m, 3H), 2.72-2.75 (m, 3H), 3.53-3.57 (m, 1H), 6.37 (d, J=7.02 Hz, 1H), 7.14-7.19 (m, 1H), 7.21 (d, J=8.85 Hz, 2H), 7.24-7.31 (m, 3H), 7.32-7.39 (m, 4H), 7.50 (dd, J=8.85, 1.53 Hz, 2H), 7.69 (d, J=8.85 Hz, 1H), 8.39 (d, J=7.02 Hz, 1H), 8.84-8.88 (m, 1H), 10.28 (s, 1H); MS (ESI+) m/z 519; (ESI−) m/z 517, 631 (M+TFA−H)−.

Example 75

N-{4-[4-Methyl-2-(7-methyl-[1,8]naphthyridin-4-ylamino)-phenylsulfanyl]-phenyl}-4-phenyl-butyramide The title compound was prepared using 4-phenyl-butyric acid (27 mg, 0.16 mmol) as the acid following the procedure for Example 74. (1 mg, 2%). $^1$H NMR (300 MHz, DMSO-d$_6$) δ ppm: 1.85-1.92 (m, J=7.55, 7.55, 7.55, 7.55 Hz, 2H), 2.32 (t, J=7.32 Hz, 2H), 2.36 (s, 3H), 2.59-2.64 (m, J=7.63 Hz, 2H), 2.74 (s, 3H), 6.34 (d, J=7.02 Hz, 1H), 7.17-7.23 (m, 6H), 7.29-7.35 (m, 4H), 7.45 (d, J=8.85 Hz, 2H), 7.73 (d, J=8.54 Hz, 1H), 8.36 (d, J=7.32 Hz, 1H), 8.89 (d, J=8.54 Hz, 1H); MS (ESI+) m/z 519; (ESI−) m/z 517, 631 (M+TFA−H)−.

Example 76

N-{4-[4-Methyl-2-(7-methyl-[1,8]naphthyridin-4-ylamino)-phenylsulfanyl]-phenyl}-2-o-tolyloxy-acetamide The title compound was prepared using o-tolyloxy-acetic acid (26 mg, 0.16 mmol) as the acid following the procedure for Example 74 (3 mg, 5%). $^1$H NMR (300 MHz, DMSO-d$_6$) δ ppm: 2.25 (s, 3H), 2.36 (s, 3H), 2.75 (s, 3H), 4.70 (s, 2H), 6.34 (d, J=7.32 Hz, 1H), 6.86 (d, J=7.93 Hz, 1H), 6.90 (t, J=7.32 Hz, 1H), 7.14-7.20 (m, 2H), 7.21-7.26 (m, 3H), 7.30-7.33 (m, 2H), 7.48 (d, J=8.54 Hz, 2H), 7.73 (d, J=8.85 Hz, 1H), 8.36 (d, J=7.02 Hz, 1H), 8.88 (d, J=8.85 Hz, 1H); MS (ESI+) m/z 521; (ESI−) m/z 519, 633 (M+TFA−H)−.

Example 77

N-{4-[4-Methyl-2-(7-methyl-[1,8]naphthyridin-4-ylamino)-phenylsulfanyl]-phenyl}-2-p-tolyloxy-acetamide The title compound was prepared using p-tolyloxy-acetic acid (26 mg, 0.16 mmol) as the acid following the procedure for Example 74 (3 mg, 5%). $^1$H NMR (300 MHz, DMSO-d$_6$) δ ppm: 2.24 (s, 3H), 2.36 (s, 3H), 2.75 (s, 3H), 4.64 (s, 2H), 6.33 (d, J=7.32 Hz, 1H), 6.89 (d, J=8.54 Hz, 2H), 7.13 (d, J=8.24 Hz, 2H), 7.21 (d, J=8.85 Hz, 2H), 7.25-7.29 (m, 1H), 7.31-7.33 (m, 2H), 7.48 (d, J=8.54 Hz, 2H), 7.72 (d, J=8.54 Hz, 1H), 8.35 (d, J=7.02 Hz, 1H), 8.87 (d, J=8.85 Hz, 1H); MS (ESI+) m/z 521; (ESI−) m/z 519, 633 (M+TFA−H)−.

Example 78

2-Methoxy-N-{4-[4-methyl-2-(7-methyl-[1,8]naphthyridin-4-ylamino)-phenylsulfanyl]-phenyl}-2-phenyl-acetamide The title compound was prepared using R-methoxy-phenyl-acetic acid (26 mg, 0.16 mmol) as the acid following the procedure for Example 74 (3 mg, 5%). $^1$H NMR (300 MHz, DMSO-d$_6$) δ ppm: 2.35 (s, 3H), 2.73 (s, 3H), 3.36 (s, 3H), 4.82 (s, 1H), 6.36 (d, J=7.02 Hz, 1H), 7.21 (d, J=8.54 Hz, 3H), 7.28-7.33 (m, 2H), 7.37 (d, J=7.02 Hz, 1H), 7.41 (t, J=7.32 Hz, 2H), 7.47 (d, J=7.02 Hz, 2H), 7.53-7.58 (m, 2H), 7.69 (d, J=8.85 Hz, 1H), 8.38 (d, J=7.02 Hz, 1H), 8.86 (d, J=8.54 Hz, 1H); MS (ESI+) m/z 521; (ESI−) m/z 519, 633 (M+TFA−H)−.

Example 79

2-Methoxy-N-{4-[4-methyl-2-(7-methyl-[1,8]naphthyridin-4-ylamino)-phenylsulfanyl]-phenyl}-2-phenyl-acetamide The title compound was prepared using S-methoxy-phenyl-acetic acid (26 mg, 0.16 mmol) as the acid following the procedure for Example 74 (3 mg, 5%). $^1$H NMR (300 MHz, DMSO-d$_6$) δ ppm: 2.35 (s, 3H), 2.73 (s, 3H), 3.36 (s, 3H), 4.82 (s, 1H), 6.36 (d, J=7.32 Hz, 1H), 7.21 (d, J=8.54 Hz, 3H), 7.29-7.32 (m, 2H), 7.35-7.38 (m, 1H), 7.41 (t, J=7.17 Hz, 2H), 7.46-7.49 (m, 2H), 7.54-7.57 (m, 2H), 7.69 (d, J=8.54 Hz, 1H), 8.38 (d, J=7.02 Hz, 1H), 8.86 (d, J=8.54 Hz, 1H); MS (ESI+) m/z 521; (ESI−) m/z 519, 633 (M+TFA−H)−.

Example 80

Furan-3-carboxylic acid ({4-[4-methyl-2-(7-methyl-[1,8]naphthyridin-4-ylamino)-phenylsulfanyl]-phenylcarbamoyl}-methyl)-amide The title compound was prepared using [(furan-2-carbonyl)-amino]-acetic acid (27 mg, 0.16 mmol) as the acid following the procedure for Example 74 (1 mg, 2%). $^1$H NMR (300 MHz, DMSO-$d_6$) δ ppm: 2.36 (s, 3H), 2.75 (s, 3H), 4.02 (s, 2H), 6.34 (d, J=7.02 Hz, 1H), 6.67 (dd, J=3.66, 1.83 Hz, 2H), 7.16 (d, J=3.05 Hz, 1H), 7.22 (t, J=8.85 Hz, 3H), 7.29-7.33 (m, 2H), 7.46 (d, J=8.85 Hz, 2H), 7.74 (d, J=8.54 Hz, 1H), 7.85 (s, 1H), 8.37 (d, J=7.32 Hz, 1H), 8.87 (d, J=8.85 Hz, 1H); MS (ESI+) m/z 524; (ESI−) m/z 521.

Example 81

N-{4-[4-Methyl-2-(7-methyl-[1,8]naphthyridin-4-ylamino)-phenylsulfanyl]-phenyl}-4-thiophen-3-yl-butyramide The title compound was prepared using 4-thiophen-2-yl-butyric acid (27 mg, 0.16 mmol) as the acid following the procedure for Example 74 (0.7 mg, 1%). $^1$H NMR (300 MHz, DMSO-$d_6$) δ ppm: 1.89-1.96 (m, 2H), 2.34-2.39 (m, 5H), 2.75 (s, 3H), 2.85 (t, J=7.63 Hz, 2H), 6.34 (d, J=7.32 Hz, 1H), 6.88 (d, J=2.44 Hz, 1H), 6.96 (dd, J=5.19, 3.36 Hz, 1H), 7.18-7.25 (m, 3H), 7.29-7.33 (m, 3H), 7.45 (d, J=8.85 Hz, 2H), 7.73 (d, J=8.54 Hz, 1H), 8.36 (d, J=7.32 Hz, 1H), 8.89 (d, J=8.54 Hz, 1H); MS (ESI+) m/z 525; (ESI−) m/z 523, 637 (M+TFA−H)−.

Example 82

1-Acetyl-piperidine-4-carboxylic acid {4-[4-methyl-2-(7-methyl-[1,8]naphthyridin-4-ylamino)-phenylsulfanyl]-phenyl}-amide The title compound was prepared using 1-Acetyl-piperidine-4-carboxylic acid (27 mg, 0.16 mmol) as the acid following the procedure for Example 74 (0.7 mg, 1%). $^1$H NMR (300 MHz, DMSO-$d_6$) δ ppm: 1.77-1.84 (m, 2H), 2.03 (s, 3H), 2.36 (s, 4H), 2.56-2.64 (m, 2H), 2.75 (s, 3H), 3.05-3.12 (m, 1H), 3.83-3.91 (m, 1H), 4.37-4.43 (m, 1H), 6.30-6.36 (m, 1H), 7.18-7.25 (m, 4H), 7.29-7.34 (m, 2H), 7.41-7.48 (m, 2H), 7.72-7.77 (m, 1H), 8.34-8.38 (m, 1H), 8.87-8.91 (m, 1H); MS (ESI+) m/z 526; (ESI−) m/z 524, 638 (M+TFA−H)−.

Example 83

[2-(4-Amino-phenylsulfanyl)-5-methyl-phenyl]-(7-methyl-[1,8]naphthyridin-4-yl)-amine The product from Example 18 (200 mg, 0.48 mmol) was suspended in 6N HCl (10 mL) and heated in air to 100° C. for one hour. The solution was subsequently cooled in an ice bath and made basic with solid NaOH (2.64 gm). The crude product was isolated by extraction with dichloromethane and purified by HPLC with TFA providing the title compound as the trifluoroacetic acid salt (96.1 mg, 37%). $^1$H NMR (300 MHz, DMSO-$d_6$) δ ppm; 2.31 (s, 3H) 2.77 (s, 3H) 6.30 (d, J=6.99 Hz, 1H) 6.57 (d, J=8.46 Hz, 2H) 6.90 (d, J=7.72 Hz, 1H) 7.07 (d, J=8.46 Hz, 2H) 7.23 (m, J=7.72 Hz, 2H) 7.81 (d, J=8.82 Hz, 1H) 8.46 (d, J=7.35 Hz, 1H) 9.04 (d, J=8.46 Hz, 1H) 11.05 (s, 1H). MS (ESI+) m/z 373.1 (M+H)+; (ESI−) m/z 371.1 (M−H)−.

Example 84

4-[4-Methyl-2-(7-methyl-[1,8]naphthyridin-4-ylamino)-phenylsulfanyl]-benzamide

Example 84a 4-(4-Methyl-2-nitro-phenylsulfanyl)-benzoic acid

The product from Example 4a (0.94 g, 3.31 mmol) was reacted with 4-mercapto-benzoic acid (0.51 g, 3.31 mmol) in aqueous ethanol at 80° C. under nitrogen. The reaction mixture was poured into water and acidified with glacial acetic acid. The solid product was collected by filtration, water washed and dried in vacuo to give the title compound (0.877 g, 91%) sufficiently pure for use as isolated.

Example 84b 4-(4-Methyl-2-nitro-phenylsulfanyl)-benzamide

The product from Example 84a (0.3 g, 1.04 mmol) was dissolved in THF (15 mL) and treated with N-methylmorpholine (0.131 mL, 1.19 mmol) followed by cooling in an ice bath and addition of isobutylchloroforamte (0.148 mL, 1.14 mmol). The resulting mixture was allowed warm to room temperature with stirring for thirty minutes. Subsequent cooling in an ice bath was followed by addition of ammonia gas and warming to room temperature. The title compound was isolated by the addition of water and collection of the solid by vacuum filtration was used without further purification (0.289 g, 96%).

Example 84c

The product from Example 84c (0.289 g, 1.0 mmol) was reacted with stannous chloride (0.95 g, 5 mmol) as described in Example 1f to give the title compound as an off white solid (0.226 g, 88%).

Example 84d

4-[4-Methyl-2-(7-methyl-[1,8]naphthyridin-4-ylamino)-phenylsulfanyl]-benzamide

The product from Example 1d (0.156 g, 0.875 mmol) was reacted with the product from Example 84d (0.226 g, 0.875 mmol) for 24 hours following the procedure from Example 1g giving the crude title compound which was purified by HPLC with TFA providing the product as the trifluoroacetic acid salt (0.185 g, 38%). $^1$H NMR (300 MHz, DMSO-$d_6$) δ ppm: 2.37-2.46 (m, 3H) 2.74 (s, 3H) 6.36 (d, J=6.99 Hz, 1H) 7.19 (d, J=8.46 Hz, 2H) 7.31-7.46 (m, 3H) 7.47-7.57 (m, 1H) 7.68 (d, J=8.46 Hz, 2H) 7.75 (d, J=8.46 Hz, 1H) 7.90 (s, 1H) 8.39

(d, J=7.35 Hz, 1H) 8.90 (d, J=8.46 Hz, 1H) 11.02 (s, 1H); MS (ESI+) m/z 401.0 (M+H)+; (ESI−) m/z 399.0 (M−H−).

Example 85

N-Methyl-4-[4-methyl-2-(7-methyl-[1,8]naphthyridin-4-ylamino)-phenylsulfanyl]-benzamide

Example 85a

N-Methyl-4-(4-nitro-phenylsulafanyl)-benzamide

The product from Example 84b (0.32 g, 1.11 mmol) was reacted as described in Example 84c substituting N-methyl amine in methanol for ammonia to give the title compound (0.32 g, 94%).

Example 85b 4-(2-Amino-4-methyl-phenylsulfanyl)-N-methyl-benzamide

The product from Example 85a was reacted as described in Example 84d to give the title compound (0.28 g, 97%).

Example 85c

N-Methyl-4-[4-methyl-2-(7-methyl-[1,8]naphthyridin-4-ylamino)-phenylsulfanyl]-benzamide The product from Example 85b (0.277 g, 1.05 mmol) was reacted with the product from Example 1d (0.09 g, 0.504 mmol) for 41 h following the procedure from Example 1g giving the crude title compound which was purified by HPLC with TFA providing the product as the trifluoroacetic acid salt (0.078 g, 28%). $^1$H NMR (300 MHz, DMSO-$d_6$) δ ppm: 2.41 (s, 3H) 2.70-2.82 (m, 6H) 6.36 (d, J=6.99 Hz, 1H) 7.20 (d, J=8.46 Hz, 2H) 7.35-7.45 (m, 2H) 7.51 (d, 1H) 7.64 (d, J=8.46 Hz, 2H) 7.75 (d, J=8.82 Hz, 1H) 8.33-8.45 (m, 2H) 8.90 (d, J=8.82 Hz, 1H) 11.03 (s, 1H); MS (ESI+) m/z 415.0 (M+H)+; (ESI−) m/z 413.1 (M−H)−.

Example 86

3-[4-Methyl-2-(7-methyl-[1,8]naphthyridin-4-ylamino)-phenylsulfanyl]-benzamide

Example 86a 3-(4-Methyl-2-nitro-phenylsulfanyl)-benzoic acid

The product from Example 84a (0.94 g, 3.29 mmol) was reacted with 3-mercapto-benzoic acid (0.51 g, 3.31 mmol) as described in Example 84b to give the title compound (0.77 g, 80%).

Example 86b 3-(4-methyl-2-nitropnheylsulfanyl)-benzamide

The product from Example 86a (0.25 g, 0.86 mmol) was reacted as described in Example 84c to give the title compound (0.238 g, 95%).

Example 86c 3-(4-methyl-2-amino-phenylsulafanyl)-benzamide

The product from Example 86b was reacted as described in Example 84d to give the title compound (0.204 g, 96%).

Example 86d

3-[4-Methyl-2-(7-methyl-[1,8]naphthyridin-4-ylamino)-phenylsulfanyl]-benzamide

The product from Example 86c (0.204 g, 0.79 mmol) was reacted with the product from Example 1d (0.144 g, 0.79 mmol) for 24 h following the procedure from Example 1g giving the crude title compound which was purified by HPLC with TFA providing the product as the trifluoroacetic acid salt (0.159 gm, 38%). $^1$H NMR (300 MHz, DMSO-$d_6$) δ ppm 2.39 (s, 3H) 2.74 (s, 3H) 6.31 (d, J=6.99 Hz, 1H) 7.18-7.55 (m, 6H) 7.61-7.79 (m, 3H) 7.90 (s, 1H) 8.37 (d, J=6.99 Hz, 1H) 8.88 (d, J=8.82 Hz, 1H); MS (ESI+) m/z 401.0 (M+H)+; (ESI−) m/z 399.0 (M−H)−.

Example 87

N-Methyl-3-[4-methyl-2-(7-methyl-[1,8]naphthyridin-4-ylamino)-phenylsulfanyl]-benzamide

Example 87a

N-Methyl-3-(4-methyl-2-nitro-phenylsulfanyl)-benzamide

The product from Example 86a (0.25 g, 0.86 mmol) was reacted as described in Example 84c substituting N-methyl amine in methanol for ammonia to give the title compound (0.25 g, 96%).

Example 87b

N-Methyl-3-(4-methyl-2-amino-ohenylsulfanyl)-benzamide

The product from Example 87a was reacted as described in Example 84d to give the title compound (0.208 g, 92%).

Example 87c

N-Methyl-3-[4-methyl-2-(7-methyl-[1,8]naphthyridin-4-ylamino)-phenylsulfanyl]-benzamide The product from Example 87b (0.208 g, 0.76 mmol) was reacted with the product from Example 1d (0.136 g, 0.76 mmol) for 24 h following the procedure from Example 1g giving the crude title compound which was purified by HPLC with TFA providing the product as the trifluoroacetic acid salt (0.204, 49%). $^1$H NMR (300 MHz, DMSO-$d_6$) δ ppm: 2.39 (s, 3H) 2.65-2.81 (m, 6H) 6.27 (d, J=7.35 Hz, 1H) 7.20-7.82 (m, 8H) 8.35 (d, J=6.99 Hz, 2H) 8.87 (d, J=8.46 Hz, 1H) 10.97 (s, 1H); MS (ESI+) m/z 415.0 (M+H)+; (ESI−) m/z 413.0 (M−H)−.

Example 88

N,N-Dimethyl-3-[4-methyl-2-(7-methyl-[1,8]naphthyridin-4-ylamino)-phenylsulfanyl]-benzamide

Example 88a

N,N-Dimethyl-3-(4-methyl-2-nitro-phenylsulfanyl)-benzamide

The product from Example 86a (0.25 g, 0.86 mmol) was reacted as described in Example 84c substituting N,N-dimethylamine in methanol for ammonia to give the title compound (0.26 g, 100

Example 88b 3-(2-Amino-4-methyl-phenylsulfanyl)-N,N-dimethyl-benzamide

The product from Example 88a was reacted as described in Example 84d to give the title compound (0.175 g, 71%).

Example 88c

N,N-Dimethyl-3-[4-methyl-2-(7-methyl-[1,8]naphthyridin-4-ylamino)-phenylsulfanyl]-benzamide The product from Example 88b (0.175 g, 0.610 mmol) was reacted with the product from Example 1d (0.109 g, 0.61 mmol) for 24 h following the procedure from Example 1g giving the crude title compound which was purified by HPLC with TFA providing the product as a trifluoroacetic acid salt (0.1552 g, 45%). $^1$H NMR (300 MHz, DMSO-$d_6$) δ ppm: 2.40 (s, 3H) 2.75 (s, 6H) 2.92 (s, 3H) 6.34 (d, J=6.99 Hz, 1H) 7.11-7.53 (m, 7H) 7.76 (d, J=8.82 Hz, 1H) 8.39 (d, J=6.99 Hz, 1H) 8.94 (d, J=8.82 Hz, 1H); MS (ESI+) m/z 429.0 (M+H)+; (ESI−) m/z 427.0 (M−H)−

Example 89

[2-(2-Fluoro-phenylsulfanyl)-5-methyl-phenyl]-(7-methyl-[1,8]naphthyridin-4-yl)-amine

Example 89a 1-(2-Fluoro-phenylsulfanyl)-4-methyl-2-nitro-benzene

The product from Example 4a (1.50 g, 5.3 mmol) and 2-fluorobenzenethiol (0.56 mL, 5.3 mmol) in EtOH (15 mL) was added aqueous $Na_2CO_3$ solution (0.563 g, 5.3 mmol) dropwise at room temperature. The mixture was heated to reflux fluxed for 1 hour, and then evaporated. The residue was diluted with EtOAc, washed with $H_2O$, 5% KOH and brine, dried over $MgSO_4$, filtered and concentrated under vacuum giving the title compound as yellow crystal, which was purified by washing with cold n-hexane to give the title product as yellow crystal (1.15 g, 83%).

Example 89b 2-(2-Fluoro-phenylsulfanyl)-5-methyl-phenylamine

The product form Example 89a was reduced with Fe and $NH_4Cl$ following the procedure from Example 237E to give the title compound.

Example 89c

[2-(2-Fluoro-phenylsulfanyl)-5-methyl-phenyl]-(7-methyl-[1,8]naphthyridin-4-yl)-amine The product from Example 1d (200 mg, 1.12 mmol) was reacted with the product from Example 89b (260 mg, 1.12 mmol) for 72 h following the procedure from Example 1g giving the crude title compound which was purified by HPLC with TFA providing the product as a trifluoroacetic acid (180 mg, 43%). $^1$H NMR (300 MHz, DMSO-$d_6$) δ ppm: 2.32 (s, 3H), 2.62 (s, 3H), 6.11 (br-s, 1H), 6.95-7.45 (m, 8H), 8.26 (br-s, 1H), 8.55-8.70 (m, 1H), 9.08 (br-s, 1H); MS (ESI+) m/z 376 (M+H)+, (ESI−) m/z 374 (M−H)−.

Example 90

[3-(7-Methyl-[1,8]naphthyridin-4-ylamino)-4-phenylsulfanyl-benzyl]-carbamic acid tert-butyl ester

Example 90a 3-nitro-4-(phenylthio)benzonitrile

A solution of sodium thiophenolate (16.29 g, 123.3 mmol) in 150 mL of DMF was heated at 100° C. with 4-chloro-3-nitrobenzonitrile (15.0 g, 82.2 mmol) with stirring for 24 hours. Cooled to room temperature and diluted with EtOAc. Washed with water and dried the organic layer over $MgSO_4$. Filtered and concentrated under vacuum giving the title compound, which was purified by silica gel column chromatography eluting with 5% EtOAc/hexane giving a yellow solid (4.0 g, 19%).

Example 90b tert-butyl 3-amino-4-(phenylthio)benzylcarbamate

A solution of the product from Example 90a (4.0 g, 15.6 mmol) and di-tert-butyl-dicarbonate (1.70 g, 7.79 mmol) was catalytically reduced using Ra—Ni in MeOH at 60 psi under an atmosphere of $H_2$. Removal of the catalyst and concentration under vacuum gave the title compound which was purified by silica gel column chromatography eluting with 10% EtOAc/hexane giving a mixture of the two examples as a clear oil (2.41 g, 46%).

Example 90d tert-butyl (3-(7-methyl-1,8-naphthyridin-4-ylamino)-4-(phenylthio)phenyl)methylcarbamate The product from Example 1d (557 mg, 3.12 mmol) was reacted with the product from Example 90b (1.032 mg, 3.12 mmol) for 18 h following the procedure from Example 1g giving the crude title compound which was purified by HPLC with TFA providing the product as a trifluoroacetic acid (310 mg, 17%). $^1$H NMR (300 MHz, DMSO-$d_6$) δ ppm: 1.37 (s, 9H) 2.76 (s, 3H) 4.19 (d, J=6.25 Hz, 2H) 6.29 (d, J=6.99 Hz, 1H) 7.25 (s, 5H) 7.31 (s, 1H) 7.37 (d, J=3.31 Hz, 2H) 7.44-7.56 (m, 1H) 7.79 (d, J=8.82 Hz, 1H) 8.42 (d, J=6.99 Hz, 1H) 8.94 (d, J=8.46 Hz, 1H) 11.05 (s, 1H) 14.43 (s, 1H); MS (ESI+) m/z 473 (M+H)+.

Example 91

[2-(2,5-Dimethyl-furan-3-ylsulfanyl)-5-methyl-phenyl]-(7-methyl-[1,8]naphthyridin-4-yl)-amine

Example 91a 2,5-Dimethyl-3-(4-methyl-2-nitro-phenylsulfanyl)-furan

The title compound was prepared from 1-Chloro-4-methyl-2-nitro-benzene (2.00 g, 11.7 mmol), 2,5-Dimethyl-furan-3-thiol (1.50 g, 11.7 mmol), and $K_2CO_3$ (3.233 g, 23.4 mmol) heated in DMF at 100° C. for 4 hrs. Reaction mixture was then cooled to room temperature and diluted with water and extracted with ethyl acetate. Dried over $Na_2SO_4$, filtered and concentrated under vacuum giving the title compound (3.5 g, 85%).

Example 91b 2-(2,5-Dimethyl-furan-3-ylsulfanyl)-5-methyl-phenylamine

The product from Example 91a was reduced with $SnCl_2$ following the procedure from Example 1f to give the title compound.

Example 91c

[2-(2,5-Dimethyl-furan-3-ylsulfanyl)-5-methyl-phenyl]-(7-methyl-[1,8]naphthyridin-4-yl)-amine The product form Example 1d (50 mg, 0.217 mmol) was reacted with the product from Example 91b (51 mg, 0.217 mmol) for 18 h following the procedure from Example 1g giving the crude title compound which was purified by HPLC with TFA providing the product as a trifluoroacetic acid (2.6 mg, 3.2%). $^1$H NMR (300 MHz, DMSO-d6) δ ppm: 2.15 (d, J=15.08 Hz, 6H), 2.33 (s, 3H), 2.77 (s, 3H), 5.98 (s, 1H), 6.29 (d, J=6.99 Hz, 1H), 7.08 (d, J=8.09 Hz, 1H), 7.24-7.39 (m, 2H), 7.83 (d, J=8.46 Hz, 1H), 8.47 (d, J=6.62 Hz, 1H), 9.03 (d, J=8.46 Hz, 1H), 11.04 (s, 1H); MS (ESI+) m/z 378 (M+H−TFA)+; (ESI+) m/z 399 (M+Na−TFA)−; (ESI+) m/z 773 (2M+Na−TFA)−.

Example 92

(4-{2-[Ethoxycarbonylmethyl-(7-methyl-[1,8]naphthyridin-4-yl)-amino]-4-methyl-phenylsulfanyl}-phenoxy)-acetic acid ethyl ester The product from Example 5 (200 mg, 0.536 mmol) was suspended in acetone to which $K_2CO_3$ (81 mg, 0.589 mmol), and bromoethyl acetate (89 mg, 0.536 mmol) were added. The reaction mixture was then heated to reflux for 4 h reaction mixture was cooled to room temperature and solvent removed under vacuum. Purified by HPLC with TFA providing the product as a trifluoroacetic acid (15 mg, 6%). $^1$H NMR (300 MHz, DMSO-$d_6$) δ ppm: 1.21 (td, J=7.08, 2.39 Hz, 6H), 2.35 (s, 3H), 2.73 (s, 3H), 4.18 (ddd, J=14.16, 10.66, 7.17 Hz, 4H), 4.76 (s, 2H), 5.46 (s, 2H), 6.47 (d, J=7.35 Hz, 1H), 6.87 (d, J=8.82 Hz, 2H), 7.14 (d, J=8.09 Hz, 1H), 7.21-7.42 (m, 4H), 7.86 (d, J=8.46 Hz, 1H), 8.61 (d, J=7.72 Hz, 1H), 9.03 (d, J=8.46 Hz, 1H); MS (ESI+) m/z 546 (M+H−TFA)+.

Example 93

[3-Chloro-4-(4-chloro-phenoxy)-phenyl]-(7-methyl-[1,8]naphthyridin-4-yl)-amine

Example 93a

2-Chloro-1-(4-chloro-phenoxy)-4-nitro-benzene

A solution of 1,2-dichloro-4-nitro-benzene (9.2 g, 48 mmol), 4-chloro-phenol (6.2 g, 48 mmol) and potassium carbonate (19.9 g, 144 mmol) in DMF (80 mL) was heated to 90° C. for 16 hours. After cooling to room temperature the mixture was poured into water (600 mL) and extracted with ethyl acetate. The combined extracts were washed with brine, dried over magnesium sulfate, filtered and concentrated under vacuum to provide the title compound (13.5 g, 99%).

Example 93b

3-Chloro-4-(4-chloro-phenoxy)-phenylamine

A solution of the product of Example 93A (8.49 g, 30 mmol), iron powder (8.4 g, 150 mmol) and ammonium chloride (2.4 g, 45 mmol) in an ethanol (180 mL), THF (210 mL), and water (60 mL) solution was heated to reflux for 16 hours. The resultant mixture was cooled and filtered through a pad of celite. The filtrate was partitioned with water and ethyl acetate. The aqueous was extracted by ethyl acetate. The combined extracts were washed with brine, dried over sodium sulfate, filtered and concentrated. The residue was purified with silica gel eluting with hexane to hexane/ethyl acetate (8:2) to give the title compound (6.5 g, 86%).

Example 93c

[3-Chloro-4-(4-chloro-phenoxy)-phenyl]-(7-methyl-[1,8]naphthyridin-4-yl)-amine

Example 93B (254 mg, 1.0 mmol) and Example 1d (179 mg, 1.0 mmol) in ethanol (10 mL) were refluxed for 16 hours. The mixture was cooled to room temperature and filtered, the solid washed with ethyl acetate, dried to give the title compound as the hydrochloride salt (411 mg, 95%). $^1$H NMR (300 MHz, DMSO-D6) δ ppm 2.76 (s, 3H) 6.94 (d, J=7.35 Hz, 1H) 7.10 (m, 2H) 7.33 (d, J=8.46 Hz, 1H) 7.49 (m, 3H) 7.80 (m, 2H) 8.53 (d, J=6.99 Hz, 1H) 9.18 (d, J=8.82 Hz, 1H) 11.34 (s, 1H) 14.49 (s, 1H); (ESI−) m/z 394 (M−H)−.

Example 94

[2-(4-Methoxy-phenylsulfanyl)-5-methyl-phenyl]-(7-trifluoromethyl-[1,8]naphthyridin-4-yl)-amine The product form Example 7d (50 mg, 0.215 mmol) was reacted with the product from Example 50b (53 mg, 0.215 mmol) for 18 h following the procedure from Example 1g giving the crude title compound which was purified by HPLC with TFA providing the product as a trifluoroacetic acid (28 mg, 30%). $^1$H NMR (300 MHz, DMSO-$d_6$) δ ppm: 2.35 (s, 3H), 3.71 (s, 3H), 6.38 (d, J=6.99 Hz, 1H), 6.78-6.89 (m, 2H), 7.11-7.19 (m, 1H), 7.23-7.32 (m, 4H), 8.41 (d, J=8.46 Hz, 1H), 8.58 (d, J=6.99 Hz, 1H), 9.43 (d, J=8.46 Hz, 1H); MS (ESI+) m/z 442 (M+H−TFA)+; (ESI−) m/z 440 (M−H−TFA)−.

Example 95

4-Methyl-2-(7-methyl-[1,8]naphthyridin-4-ylamino)-N-phenyl-benzamide

Example 95a

4-Methyl-2-nitro-benzoic acid

A suspension of 4-methyl-2-nitrobenzonitrile (5.00 g, 30.8 mmol) and 50% $H_2SO_4$ (25 mL) in HOAc (25 mL) was heated to reflux for 22 h. The reaction mixture was poured into ice-water (150 g) under stirring and stirred at 5° C. for 30 minutes. The deposited crystals were collected by filtration, washed with $H_2O$ and n-hexane, and dried at 40° C. in vacuum to give the title compound as pale brown crystal (4.85 g, 87%).

Example 95b

4-Methyl-2-nitro-N-phenyl-benzamide

The product from Example 95a (1.00 g, 5.5 mmol) and $SOCl_2$ (4.03 mL, 55.0 mmol) were refluxed for 2 hours. Excess $SOCl_2$ was removed under reduced pressure to give the corresponding acid chloride as pale yellow oil. To a solution of the acid chloride obtained above in THF (15 mL) was added aniline (0.53 mL, 5.8 mmol) and $Et_3N$ (1.17 mL, 8.3 mmol) dropwise at 5° C. and the mixture was stirred at room temperature for 3.5 days. The reaction mixture was evaporated. The residue was diluted with $H_2O$, acidified to pH 3 with 10% HCl and then extracted with EtOAc. The extract washed with 10% $NaHCO_3$, dried over $MgSO_4$ filtered and concentrated under vacuum giving the title compound as a pale brown crystal, which was purified by washing with n-hexane to give the desired product as pale brown crystal (0.80 g, 57%).

Example 95c

2-Amino-4-methyl-N-phenyl-benzamide

The product from Example 95b was reduced with Fe and $NH_4Cl$ following the procedure from Example 237E to give the title compound.

Example 95d

4-Methyl-2-(7-methyl-[1,8]naphthyridin-4-ylamino)-N-phenyl-benzamide

The product from Example 1d (150 mg, 0.84 mmol) was reacted with the product from Example 95c (190 mg, 0.84 mmol) for 6 h following the procedure from Example 1g giving the crude title compound which was purified by silica gel column chromatography eluting with 50:1 $CH_2Cl_2$/MeOH providing the title compound (210 mg, 68%). $^1H$ NMR (300 MHz, DMSO-$d_6$) δ ppm: 2.40 (s, 3H), 2.68 (s, 3H), 6.62 (d, J=6.9 Hz, 1H), 6.98 (t, J=7.3 Hz, 1H), 7.19 (t, J=7.3 Hz, 2H), 7.36 (s, 1H), 7.38 (d, J=8.3 Hz, 1H), 7.52 (d, J=7.3 Hz, 2H), 7.67 (d, J=8.8 Hz, 1H), 7.78 (d, J=8.3 Hz, 1H), 8.40 (d, J=6.9 Hz, 1H), 8.94 (d, J=8.8 Hz, 1H); MS (ESI+) m/z 369 (M+H), ESI– m/z 367 (M–H).

Example 96

N-[3-(7-Methyl-[1,8]naphthyridin-4-ylamino)-4-phenylsulfanyl-phenyl]-acetamide

Example 96a

3-Nitro-4-phenylsulfanyl-phenylamine

A mixture of 2-Nitro-4-chloro aniline (1.0 g, 5.79 mmol), sodium thiophenol (0.84 g, 6.4 mmol) in DMF (10 mL) was heated 2.5 h at 100° C. The mixture was cooled, diluted with ethyl acetate (100 mL) and the organic layer washed with water, 20% aqueous potassium hydroxide solution and aqueous 10% sodium chloride solution, then, dried over anhydrous sodium sulfate. The drying agent was filtered and the solvent concentrated under vacuum leaving the title compound as a red solid (0.98 g, 69%).

Example 96b

N-(3-Nitro-4-phenylsulfanyl-phenyl)-acetamide

The product from Example 96a (0.98 g, 3.97 mmol) in pyridine (10 mL) was treated with acetic anhydride (0.38 g, 3.74 mmol) and heated at 80° C. 2 hr. the solvent was concentrated under vacuum leaving the title compound as a red oil which was used without further purification (0.96 g, 98%).

Example 96c

N-(3-Amino-4-phenylsulfanyl-phenyl)-acetamide

A solution of the product of Example 96b was reduced with Fe and $NH_4Cl$ following the procedure from Example 237E to give the title compound.

Example 96d

N-[3-(7-Methyl-[1,8]naphthyridin-4-ylamino)-4-phenylsulfanyl-phenyl]-acetamide The product form Example 1d (100 mg, 0.560 mmol) was reacted with the product from Example 96c (140 mg, 0.560 mmol) for 18 h following the procedure from Example 1g giving the crude title compound which was purified by HPLC with TFA providing the product as a trifluoroacetic acid (77 mg, 27%). $^1H$ NMR (300 MHz, DMSO-$d_6$) δ ppm: 2.08 (s, 3H) 2.75 (s, 3H) 6.33 (d, J=7.35 Hz, 1H) 7.06-7.26 (m, 4H) 7.43-7.61 (m, 2H) 7.77 (d, J=8.46 Hz, 1H) 7.97 (d, J=1.84 Hz, 1H) 8.39 (d, J=6.99 Hz, 1H) 8.89 (d, J=8.82 Hz, 1H) 10.36 (s, 1H) 11.02 (s, 1H) 14.36 (s, 1H); MS (ESI+) m/z 401 (M+H)+, (ESI–) m/z 399 (M+H)–.

Example 97

[2-(4-Methoxy-phenylsulfanyl)-5-methyl-phenyl]-(7-propyl-[1,8]naphthyridin-4-yl)-amine The product from Example 2g (275 mg, 1.33 mmol) was reacted with the product from Example 50b (326 mg, 1.33 mmol) for 18 h following the procedure from Example 1g giving the crude title compound which was purified by HPLC with TFA providing the product as a trifluoroacetic acid (392 mg, 56%). ¹H NMR (300 MHz, DMSO-d₆) δ ppm: 0.98 (t, J=7.35 Hz, 3H) 1.85 (m, 2H) 2.34 (s, 3H) 3.00 (t, J=7.54 Hz, 2H) 3.72 (s, 3H) 6.27 (d, J=6.99 Hz, 1H) 6.84 (d, J=8.82 Hz, 2H) 7.11 (d, J=7.72 Hz, 1H) 7.27 (m, 4H) 7.83 (d, J=8.82 Hz, 1H) 8.41 (d, J=6.99 Hz, 1H) 9.02 (d, J=8.46 Hz, 1H) 11.06 (br. s., 1H) 14.37 (br. s., 1H); MS (ESI+) m/z 416 (M+H)+.

Example 98

3-[4-Methyl-2-(7-propyl-[1,8]naphthyridin-4-ylamino)-phenylsulfanyl]-phenol

The product from Example 2g (275 mg, 1.33 mmol) was reacted with the product from Example 52b (307 mg, 1.33 mmol) for 18 h following the procedure from Example 1g giving the crude title compound which was purified by HPLC with TFA providing the product as a trifluoroacetic acid (305 mg, 45%). ¹H NMR (300 MHz, DMSO-d₆) δ ppm: 0.97 (t, J=7.35 Hz, 3H) 1.75-1.94 (m, 2H) 2.38 (s, 3H) 2.98 (t, J=7.35 Hz, 2H) 6.30 (d, J=6.99 Hz, 1H) 6.49-6.66 (m, 3H) 6.91-7.04 (m, 1H) 7.29-7.44 (m, 3H) 7.79 (d, J=8.82 Hz, 1H) 8.39 (d, J=7.35 Hz, 1H) 8.96 (d, J=8.46 Hz, 1H) 9.57 (s, 1H) 10.95 (s, 1H) 14.34 (s, 1H); MS (ESI+) m/z 402 (M+H−TFA)+.

Example 99

Propane-2-sulfonic acid 4-[4-methyl-2-(7-propyl-[1,8]naphthyridin-4-ylamino)-phenylsulfanyl]-phenyl ester The product from Example 6 (120 mg, 0.274 mmol) was reacted with isopropyl sulfonyl chloride (43 mg, 0.30 mmol), N,N-diisopropylethylamine (43 mg, 0.33 mmol), and catalytic DMAP in CH₂Cl₂ for 18 h giving the crude title compound which was purified by HPLC with TFA providing the product as the trifluoroacetic acid (40 mg, 23%). ¹H NMR (300 MHz, DMSO-d₆) δ ppm: 8.75 (d, J=8.54 Hz, 1H) 8.20 (d, J=6.71 Hz, 1H) 7.58 (d, J=8.54 Hz, 1H) 7.26 (d, J=7.93 Hz, 1H) 7.17-7.21 (m, 2H) 7.08 (d, J=9.16 Hz, 2H) 6.95 (d, J=8.54 Hz, 2H) 6.15 (d, J=6.71 Hz, 1H) 3.43-3.51 (m, J=13.43, 1H) 2.79 (t, J=7.63, 7.63 Hz, 2H) 2.20 (s, 3H) 1.61-1.67 (m, 2H) 1.21 (d, J=6.71 Hz, 6H) 0.78 (t, J=7.32 Hz, 3H); MS (ESI+) m/z 508 (M+H)+.

Example 100

Methanesulfonic acid 4-[4-methyl-2-(7-propyl-[1,8]naphthyridin-4-ylamino)-phenylsulfanyl]-phenyl ester The product from Example 6 (100 mg, 0.228 mmol) was reacted with methane sulfonyl chloride (28 mg, 0.251 mmol), N,N-diisopropylethylamine (88.4 mg, 0.684 mmol), and catalytic DMAP in CH₂Cl₂ for 18 h giving the crude title compound which was purified by HPLC with TFA providing the product as the trifluoroacetic acid (20 mg, 15%). ¹H NMR (300 MHz, DMSO-d₆) δ ppm: 0.97 (t, J=7.35 Hz, 3H) 1.77-1.90 (m, 2H) 2.40 (s, 3H) 2.98 (t, J=7.54 Hz, 2H) 3.43 (s, 3H) 6.34 (d, J=6.99 Hz, 1H) 7.19 (d, 2H) 7.27 (d, 2H) 7.36-7.40 (m, 2H) 7.48 (d, 1H) 7.78 (d, J=8.82 Hz, 1H) 8.39 (d, J=6.99 Hz, 1H) 8.91 (d, J=8.46 Hz, 1H); MS (DCI NH3+) 480 m/z (M+H)+.

Example 101

Ethanesulfonic acid 4-[4-methyl-2-(7-propyl-[1,8]naphthyridin-4-ylamino)-phenylsulfanyl]-phenyl ester The product from Example 6 (100 mg, 0.228 mmol) was reacted with ethane sulfonyl chloride (28 mg, 0.228 mmol), N,N-diisopropylethylamine (88.5 mg, 0.685 mmol), and catalytic DMAP in dichloroethane for 18 h giving the crude title compound which was purified by HPLC with TFA providing the product as the trifluoroacetic acid (30 mg, 22%). ¹H NMR (300 MHz, DMSO-d₆) δ ppm: 0.97 (t, J=7.35 Hz, 3H) 1.34 (t, J=7.17 Hz, 3H) 1.79-1.87 (m, 2H) 2.40 (s, 3H) 2.98 (t, J=7.54 Hz, 2H) 3.47 (q, J=7.35 Hz, 2H) 6.34 (d, J=7.35 Hz, 1H) 7.14-7.19 (m, 2H) 7.27 (d, 2H) 7.39 (s, 2H) 7.46 (d, 1H) 7.78 (d, J=8.46 Hz, 1H) 8.39 (d, J=6.99 Hz, 1H) 8.92 (d, J=8.82 Hz, 1H); MS (ESI+) m/z 494 (M+H)+.

Example 102

Propane-2-sulfonic acid 4-[2-(7-ethyl-[1,8]naphthyridin-4-ylamino)-4-methyl-phenylsulfanyl]-phenyl ester The product from Example 4 (100 mg, 0.233 mmol) was reacted with isopropyl sulfonyl chloride (40 mg, 0.280 mmol), N,N-diisopropylethylamine (90 mg, 0.70 mmol), and catalytic DMAP in dichloroethane for 18 h giving the crude title compound which was purified by HPLC with TFA providing the product as the trifluoroacetic acid (12 mg, 12%). ¹H NMR (300 MHz, DMSO-d₆) δ ppm: 8.93 (d, J=8.46 Hz, 1H) 8.40 (d, J=7.35 Hz, 1H) 7.79 (d, J=8.82 Hz, 1H) 7.46 (d, 1H) 7.37 (s, 2H) 7.27 (d, 2H) 7.15 (d, J=8.82 Hz, 2H) 6.35 (d, J=6.99 Hz, 1H) 3.66 (m, J=7.72 Hz, 1H) 3.03 (q, J=7.72 Hz, 2H) 2.40 (s, 3H) 1.40 (d, 6H) 1.36 (t, 3H); MS (ESI+) m/z 494 (M+H)+.

Example 103

Phenyl-methanesulfonic acid 4-[2-(7-ethyl-[1,8]naphthyridin-4-ylamino)-4-methyl-phenylsulfanyl]-phenyl ester The product from Example 4 (98 mg, 0.228 mmol) was reacted with benzyl sulfonyl chloride (43 mg, 0.228 mmol), N,N-diisopropylethylamine (88 mg, 0.686 mmol), and catalytic DMAP in dichloroethane for 18 h giving the crude title compound which was purified by HPLC with TFA providing the product as the trifluoroacetic acid (35 mg, 23%). ¹H NMR (300 MHz, DMSO-d₆) δ ppm: 1.35 (t, J=7.54 Hz, 3H) 2.39 (s, 3H) 3.03 (q, J=7.72 Hz, 2H) 4.94 (s, 2H) 6.33 (d, J=6.99 Hz, 1H) 7.07 (d, J=8.82 Hz, 2H) 7.25 (d, J=8.82 Hz, 2H) 7.38-7.49 (m, 8H) 7.79 (d, J=8.82 Hz, 1H) 8.39 (d, J=6.99 Hz, 1H) 8.91 (d, J=8.82 Hz, 1H); MS (ESI+) m/z 542 (M+H)+.

Example 104

N-{4-[4-Methyl-2-(7-methyl-[1,8]naphthyridin-4-ylamino)-phenoxymethyl]-phenyl}-acetamide Example 104a 4-Methyl-2-(7-methyl-[1,8]naphthyridin-4-ylamino)-phenol The product from Example 1d (893 mg, 5 mmol) and 2-Amino-4-methyl-phenol (616 mg, 5 mmol) in ethanol (20 mL) were refluxed for 4 hours. The mixture was cooled to room temperature and evaporated. The residue was triturated with hexane/ethyl acetate (3:1) to give the title compound in quantitative yield as the hydrochloride salt.

Example 104b (2-Hydroxy-5-methyl-phenyl)-(7-methyl-[1,8]naphthyridin-4-yl)-carbamic acid tert-butyl ester To a mixture of Example 104A (1.51 g, 5 mmol) and di-tert-butyl dicarbonate (2.4 g, 11 mmol) in 20 mL anhydrous THF was added NaOH (40 mL, 1N, 40 mmol). The solution was stirred at room temperature for 40 hours and poured into water, neutralized with citric acid and extracted with ethyl acetate. The organic layer was dried over magnesium sulfate, filtered and concentrated. The residue was purified by chromatography on silica eluting with 2% methanol in dichloromethane to give the title compound (1.70 g, 93%).

Example 104c

N-{4-[4-Methyl-2-(7-methyl-[1,8]naphthyridin-4-ylamino)-phenoxymethyl]-phenyl}-acetamide A solution of Example 104B (37 mg, 0.1 mmol), N-(4-chloromethyl-phenyl)-acetamide (22 mg, 0.12 mmol), cesium carbonate (130 mg, 0.4 mmol) and tetrabutylammonium iodide (0.001 g) in DMF (1 ml) was stirred at room temperature for 16 hours. The mixture was poured into water and extracted by ethyl acetate. The organic layer was dried with magnesium sulfate, filtered and concentrated under vacuum giving the title compound. The residue was added dichloromethane (2 mL) and trifluoroacetic acid (2 mL) and stirred at room temperature for 2 hours. The solvent was evaporated and the crude residue was purified by chromatography on silica eluting with 2% methanol in dichloromethane to 5% methanol in dichloromethane to give the title compound as a trifluoroacetic acid salt (11 mg, 21%). $^1$H NMR (300 MHz, DMSO-d$_6$) δ ppm 2.00 (s, 3H) 2.31 (s, 3H) 2.74 (s, 3H) 5.05 (s, 2H) 6.36 (d, J=6.99 Hz, 1H) 7.12 (d, J=8.46 Hz, 2H) 7.25 (m, 3H) 7.40 (d, J=8.46 Hz, 2H) 7.73 (d, J=8.46 Hz, 1H) 8.43 (d, J=6.99 Hz, 1H) 8.98 (d, J=8.46 Hz, 1H) 9.89 (s, 1H) 10.65 (s, 1H) 14.25 (s, 1H); MS (ESI+) m/z 413 (M+H)+.

Example 105

2-{5-[2-(4-Acetylamino-phenylsulfanyl)-5-methyl-phenylamino]-[1,8]naphthyridin-2-yl}-propionic acid ethyl ester To a slurry of sodium hydride (95%, 0.025 g, 1.0 mmol) in 5 mL anhydrous THF at 0° C. under an atmosphere of N$_2$ was added 2-methyl-malonic acid diethyl ester (0.174 g, 1.0 mmol) dropwise. The mixture was stirred for 30 minutes at ambient temperature, treated with the product from Example 24a (0.047 g, 1.0 mmol), microwave at 120° C. for 1 hour, cooled, partitioned between ethyl acetate and water and neutralized with 1M HCl. The aqueous layer was extracted by ethyl acetate and the combined organic layers were dried over Na$_2$SO$_4$, filtered and concentrated under vacuum giving the crude title compound. The residue was purified by chromatography on silica eluting with 1% methanol in dichloromethane to give the title compound (0.031 g, 62%). $^1$H NMR (300 MHz, DMSO-D6) δ ppm 1.14 (t, J=7.17 Hz, 3H) 1.52 (d, J=7.35 Hz, 3H) 2.04 (s, 3H) 2.30 (s, 3H) 4.10 (m, 3H) 6.17 (s, br, 1H) 7.04 (m, 3H) 7.26 (d, J=8.82 Hz, 2H) 7.48 (d, J=7.35 Hz, 1H) 7.57 (d, J=8.46 Hz, 2H) 8.45 (d, J=8.46 Hz, 1H) 8.78 (d, J=8.82 Hz, 1H) 9.11 (s, 1H) 10.05 (s, 1H); (ESI+) m/z 501 (M+H)+.

Example 106

N-{4-[4-Bromo-2-(7-methyl-[1,8]naphthyridin-4-ylamino)-phenylsulfanyl]-phenyl}-acetamide Example 106a N-[4-(4-Bromo-2-nitro-phenylsulfanyl)-phenyl]-acetamide A mixture of 2-fluoro-4-bromo nitro benzene (0.875 g, 3.9 mmol), 4-Acetamido thiophenol (0.797 g, 4.29 mmol) and cesium carbonate (1.4 g, 4.29 mmol) in DMF (8 mL) was heated 2.5 h at 100° C. The mixture was cooled, poured onto ice and the resulting solid is collected by filtration and dried under vacuum leaving the title compound as a yellow solid (1.4 g, 100%).

Example 106b

N-[4-(2-Amino-4-bromo-phenylsulfanyl)-phenyl]-acetamide

A solution of the product of Example 106a (1.4 g, 3.9 mmol), iron powder (0.874 g, 15.6 mmol) and ammonium chloride (0.253 g, 4.68 mmol) in a methanol (6 mL), THF (6 mL), and water (2 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate. The combined extracts were washed with 10% sodium chloride then dried over magnesium sulfate, filtered and concentrated under vacuum to provide the title compound (1.2 g, 92%).

Example 106c

N-{4-[4-Bromo-2-(7-methyl-[1,8]naphthyridin-4-ylamino)-phenylsulfanyl]-phenyl}-acetamide The product from Example 1d (106 mg, 0.59 mmol) was reacted in ethanol (2 mL) with the product from Example 106b (200 mg, 0.59 mmol) for 18 h following the procedure from Example 1g giving the crude title compound which was purified by HPLC with TFA providing the product as a trifluoroacetic acid salt (53 mg, 19%). $^1$H NMR (300 MHz, DMSO-d$_6$) δ ppm: 2.05 (s, 3H) 2.77 (s, 3H), 6.41 (d, J=6.99 Hz, 1H), 7.02 (d, J=8.82 Hz, 1H), 7.33 (d, J=8.46 Hz, 2H), 7.58 (d, J=8.82 Hz, 2H), 7.65 (dd, J=8.46, 2.21 Hz, 1H) 7.77 (d, J=2.21 Hz, 1H), 7.81 (d, J=8.82 Hz, 1H), 8.48 (d, J=6.99 Hz, 1H), 8.96 (d, J=8.82 Hz, 1H), 10.11 (s, 1H), 11.06 (s, 1H), 14.53 (s, 1H); MS (DCI/NH3) m/z 479 (M+H)+.

Example 107

N-{4-[2-(7-Hydrazino-[1,8]naphthyridin-4-ylamino)-4-methyl-phenylsulfanyl]-phenyl}-acetamide The title compound was prepared according to the procedure of Example 47 substituting hydrazine hydrate (0.050 g, 1.0 mmol) for morpholine. The crude product was purified by HTP using HPLC with TFA to give the title compound as the trifluoroacetic acid salt (0.0125 g, 19%). $^1$H NMR (300 MHz, DMSO-d$_6$) δ ppm: 2.04 (s, 3H), 2.33 (s, 3H), 6.13 (d, J=7.35 Hz, 1H, 7.06 (d, J=8.09 Hz, 1H), 7.09-7.19 (m, 1H), 7.19-7.32 (m, 4H), 7.57 (d, J=8.82 Hz, 2H), 8.10 (d, J=6.99 Hz, 1H), 8.62 (d, J=9.56 Hz, 1H), 10.09 (s, 1H), 10.53 (s, 1H), 13.64 (s, 1H); MS (ESI+) m/z 431 (M+H)$^+$;

Example 108

N-(4-{2-[7-(2-Dimethylamino-ethoxy)-[1,8]naphthyridin-4-ylamino]-4-methyl-phenylsulfanyl}-phenyl)-acetamide The title compound was prepared according to the procedure of Example 27 substituting N,N-dimethylethanolamine (0.044 g, 0.5 mmol) for diethyl malonate. The crude product was purified by HPLC with TFA to give the title compound as a trifluoroacetic acid salt (0.05 g, 70%). $^1$H NMR (300 MHz, DMSO-d$_6$) δ ppm: 2.04 (s, 3H), 2.35 (s, 3H), 2.92 (s, 6H), 3.64-3.68 (m, 2H), 4.73-4.86 (m, 2H), 6.31 (d, J=6.99 Hz, 1H), 7.14 (d, J=8.82 Hz, 1H), 7.24 (d, J=8.46 Hz, 2H), 7.27-7.32 (m, 2H), 7.36 (d, J=8.82 Hz, 1H), 7.51 (d, J=8.46 Hz, 2H), 8.33 (d, J=6.99 Hz, 1H), 8.95 (d, J=9.19 Hz, 1H), 9.87 (s, 1H), 10.07 (s, 1H), 10.88 (s, 1H), 14.23 (s, 1H); MS (ESI+) m/z 488 (M+H)$^+$;

Example 109

N-(4-{2-[7-(2-Methoxy-ethylamino)-[1,8]naphthyridin-4-ylamino]-4-methyl-phenylsulfanyl}-phenyl)-acetamide The title compound was prepared according to the procedure of Example 47 substituting 2-methoxyethylamine (75 mg, 1.0 mmol) for morpholine. The crude product was purified by HPLC with TFA to give the title compound as a trifluoroacetic acid salt (10 mg, 17%). $^1$H NMR (300 MHz, DMSO-d$_6$) δ ppm: 2.04 (s, 3H), 2.33 (s, 3H), 3.31 (s, 3H), 3.56 (t, J=4.96 Hz, 2H), 3.60-3.67 (m, 2H), 6.05 (d, J=6.99 Hz, 1H), 6.95 (d, J=9.19 Hz, 1H), 7.05 (d, J=8.09 Hz, 1H), 7.20-7.31 (m, J=7.91, 7.91 Hz, 4H), 7.56 (d, J=8.46 Hz, 2H), 7.96-8.11 (m, 1H), 8.33-8.49 (m, 2H), 10.07 (s, 1H), 10.32 (s, 1H), 13.42 (d, J=5.88 Hz, 1H); MS (ESI+) m/z 474 (M+H)$^+$.

Example 110

(7-Isobutyl-[1,8]naphthyridin-4-yl)-[2-(4-methoxy-phenylsulfanyl)-5-methyl-phenyl]-amine The product from Example 12d (60 mg, 0.271 mmol) was reacted with the product from Example 50b (66 mg, 0.271 mmol) for 25 h giving following the procedure from Example 1g the crude title compound that was triturated with 3:1 ether/THF providing the title compound as a hydrochloride salt (121 mg, 96%). $^1$H NMR (300 MHz, DMSO-d$_6$) δ ppm: 0.97 (d, J=6.62 Hz, 6H) 2.24 (m, J=6.62 Hz, 1H) 2.34 (s, 3H) 2.89 (d, J=7.35 Hz, 2H) 3.72 (s, 3H) 6.27 (d, J=6.99 Hz, 1H) 6.84 (d, J=8.46 Hz, 2H) 7.10 (d, J=8.09 Hz, 1H) 7.23-7.32 (m, 4H) 7.81 (d, J=8.46 Hz, 1H) 8.41 (d, J=6.99 Hz, 1H) 9.07 (d, J=8.46 Hz, 1H) 11.09 (br s, 1H) 14.40 (br s, 1H); MS (ESI+) m/z 430 (M−Cl)+; (ESI−) m/z 428 (M−HCl)−.

Example 111

{5-[2-(4-Amino-phenylsulfanyl)-5-methyl-phenylamino]-[1,8]naphthyridin-2-yl}-cyano-acetic acid ethyl ester The product from Example 30 (19 mg, 0.037 mmol), 2 mL of ethanol and 1 M hydrochloric acid (1.5 mL) were combined and heated at 90° C. for 3 h, cooled and concentrated under vacuum giving the title compound. The crude product was purified by HPLC with TFA to give the title compound as a trifluoroacetic acid salt (10 mg, 46%). $^1$H NMR (300 MHz, DMSO-d$_6$) δ ppm: 1.28 (t, J=6.99 Hz, 3H), 2.28 (s, 3H), 4.25 (q, J=7.11 Hz, 2H), 6.14 (d, J=5.88 Hz, 1H), 6.67 (d, J=8.46 Hz, 2H), 6.86 (d, J=7.72 Hz, 1H), 6.98-7.28 (m, 5H), 8.15 (d, J=5.88 Hz, 1H), 8.65 (d, J=9.56 Hz, 1H), 9.49 (s, 1H), 13.14 (s, 1H); MS (ESI+) m/z 470 (M+H)$^+$.

Example 112

N-{4-[2-(7-Isobutyl-[1,8]naphthyridin-4-ylamino)-4-methyl-phenylsulfanyl]-phenyl}-acetamide The product form Example 12d (50 mg, 0.226 mmol) was reacted with the product from Example 18b (62 mg, 0.226 mmol) for 18 h following the procedure from Example 1g giving the crude title compound which was purified by HPLC with TFA providing the product as a trifluoroacetic acid (35 mg, 33%). $^1$H NMR (300 MHz, DMSO-d$_6$) δ ppm: 0.97 (d, J=6.62 Hz, 7H), 2.03 (s, 3H), 2.23 (s, 1H), 2.35 (s, 3H), 2.89 (d, J=7.35 Hz, 2H), 6.31 (d, J=7.35 Hz, 1H), 7.14 (d, J=8.09 Hz, 1H), 7.21-7.33 (m, 4H), 7.50 (d, J=8.46 Hz, 2H), 7.80 (d, J=8.82 Hz, 1H), 8.41 (d, J=6.99 Hz, 1H), 8.99 (d, J=8.82 Hz, 1H), 10.04 (s, 1H); MS (ESI+) m/z 457 (M+H−TFA)+; (ESI−) m/z 455 (M−H−TFA)−.

Example 113

N-Methyl-4-[4-methyl-2-(7-propyl-[1,8]naphthyridin-4-ylamino)-phenylsulfanyl]-benzamide The product from Example 85b (0.155 g, 0.57 mmol) was reacted with the product from Example 2g as a 3.15M solution in ethanol (0.18 mL, 0.57 mmol) for 24 h following the procedure from Example 1g giving the crude title compound which was purified by HPLC with TFA providing the product as a trifluoroacetic acid salt (0.180 g, 56%). $^1$H NMR (300 MHz, DMSO-d$_6$) δ ppm: 0.97 (t, J=7.35 Hz, 3H) 1.72-1.91 (m, 2H) 2.41 (s, 3H) 2.75 (d, J=4.41 Hz, 3H) 2.97 (t, J=7.35 Hz, 2H) 6.36 (d, J=6.99 Hz, 1H) 7.20 (d, J=8.46 Hz, 2H) 7.33-7.47 (m, 2H) 7.50 (d, 1H) 7.63 (d, J=8.46 Hz, 2H) 7.77 (d, J=8.82 Hz, 1H) 8.30-8.44 (m, J=6.62, 6.62 Hz, 2H) 8.91 (d, J=8.82 Hz, 1H) 10.86-11.09 (s, 1H); MS (ESI+) m/z 443.2 (M+H)+; (ESI−) m/z 441.2 (M−H)−.

Example 114

N-Methyl-3-[4-methyl-2-(7-propyl-[1,8]naphthyridin-4-ylamino)-phenylsulfanyl]-benzamide The product from Example 87b (0.155 g, 0.57 mmol) was reacted with the product from Example 2g as a 3.15M solution in ethanol (0.18 mL, 0.57 mmol) for 24 h following the procedure from Example 1g giving the crude title compound which was purified by HPLC with TFA providing the product as a trifluoroacetic acid salt (0.042 g, 13%). $^1$H NMR (300 MHz, DMSO-d$_6$) δ ppm: 0.98 (t, J=7.35 Hz, 3H) 1.76-1.91 (m, 2H) 2.39 (s, 3H) 2.70 (d, J=4.41 Hz, 3H) 2.91-3.04 (m, 2H) 6.27 (d, J=6.99 Hz, 1H) 7.18-7.42 (m, 4H) 7.42-7.51 (m, 1H) 7.55-7.63 (m, 2H) 7.76 (d, J=8.82 Hz, 1H) 8.28-8.41 (m, J=6.99 Hz, 2H) 8.88 (d, J=8.46 Hz, 1H) 10.95 (s, 1H); MS (ESI+) m/z 443.2 (M+H)+; (ESI−) m/z 441.2 (M−H)−.

Example 115

{4-[4-Methyl-2-(7-propyl-[1,8]naphthyridin-4-ylamino)-phenylsulfanyl]-phenyl}-methanol Example 115a

[4-(4-Methyl-2-nitro-phenylsulfanyl)-phenyl]-methanol

The product from Example 84b (0.5 g, 1.73 mmol) was dissolved in THF (15 mL) and cooled in an ice bath. To the cold solution under nitrogen was added diborane as a 1.0M solution in THF (3.6 mL, 3.6 mmol) and the resulting mixture allowed to warm to room temperature and stir overnight. The crude product was isolated by extractive workup (ether/water) and dried with MgSO4, filtered and concentrated under vacuum giving the crude title compound. Purification by flash chromatography on silica gel gave the alcohol as a bright yellow solid (0.392 g, 82%).

Example 115b

[4-(2-Amino-4-methyl-phenylsulfanyl)-phenyl]-methanol

The product from Example 115a (0.389 g, 1.41 mmol) was reacted with stannous chloride (1.4 g, 7.05 mmol) as described in Example 1f to give the title compound in quantitative yield as an orange oil.

Example 115c

{4-[4-Methyl-2-(7-propyl-[1,8]naphthyridin-4-ylamino)-phenylsulfanyl]-phenyl}-methanol The product from Example 2g as a 3.15M solution in ethanol (0.08 mL, 0.25 mmol) was reacted with the product from Example 115b (0.061 g, 0.25 mmol) for 18.5 h following the procedure from Example 1g giving the crude title compound which was purified by HPLC with TFA providing the product as a trifluoroacetic acid salt (0.0195 g, 14%). $^1$H NMR (300 MHz, DMSO-d$_6$) δ ppm: 0.98 (t, J=7.35 Hz, 3H) 1.75-1.93 (m, 2H) 2.31-2.42 (s, 3H) 2.91-3.08 (m, 2H) 4.42 (s, 2H) 6.30 (d, J=6.99 Hz, 1H) 7.11-7.42 (m, 7H) 7.81 (d, J=8.46 Hz, 1H) 8.39 (d, J=6.99 Hz, 1H) 8.98 (d, J=8.82 Hz, 1H) 11.01 (s, 1H); MS (ESI+) m/z 416.2 (M+H)+, (ESI−) m/z 414.3 (M−H)−.

Example 116

4-[4-(4-Bromo-benzyloxy)-2-(7-methyl-pyrido[2,3-d]pyrimidin-4-ylamino)-phenylsulfanyl]-phenol Example 116a 4-[2-Amino-4-(4-bromo-benzyloxy)-phenylsulfanyl]-phenol A solution of 4-chloro-3-nitro-phenol was reacted with 1-Bromo-4-bromomethyl-benzene using the conditions described in Example 237C to provide 4-(4-Bromo-benzyloxy)-1-chloro-2-nitro-benzene which was treated sequentially using the procedures from Examples 237D and 237E to provide the title product.

Example 116b

4-[4-(4-Bromo-benzyloxy)-2-(7-methyl-pyrido[2,3-d]pyrimidin-4-ylamino)-phenylsulfanyl]-phenol The product of Example 116A was reacted with the product of Example 237B using the procedure of Example 237F substituting the product of Example 116A for the product of Example 237E to provide the crude title compound which was purified by HPLC with TFA to provide the title compound as a trifluoroacetic acid salt (19 mg, 17%). $^1$H NMR (300 MHz, DMSO-D6) δ ppm: 2.72 (s, 3H) 5.13 (s, 2H) 6.63 (m, 2H) 7.03 (dd, J=8.82, 2.57 Hz, 1H) 7.10 (m, 2H) 7.21 (d, J=8.46 Hz, 2H) 7.40 (m, 2H) 7.54 (d, J=8.09 Hz, 1H) 7.66 (s, 1H) 7.73 (d, J=8.46 Hz, 1H) 8.72 (s, 1H) 8.84 (d, J=8.46 Hz, 1H) 9.69 (s, 1H) 11.08 (m, 1H); MS (ESI+) m/z 545, 547 (M+H)+.

Example 117

N-{4-[4-Hydroxy-2-(7-propyl-[1,8]naphthyridin-4-ylamino)-phenylsulfanyl]-phenyl}-acetamide The product from Example 2g (35 mg, 0.17 mmol) was reacted in ethanol (1 mL) with the product from Example 232B (46 mg, 0.17 mmol) for 18 h following the procedure from Example 1g giving the crude title compound which was purified by HPLC with TFA providing the product as a trifluoroacetic acid salt (15 mg, 20%). $^1$H NMR (300 MHz, DMSO-d$_6$) δ ppm: 0.97 (t, J=7.35 Hz, 3H) 1.72-1.92 (m, 2H) 2.01 (s, 3H) 2.98 (t, J=7.35 Hz, 2H) 6.30 (d, J=7.35 Hz, 1H) 6.89 (d, J=2.57 Hz, 1H) 6.91-6.98 (m, 1H) 7.04 (s, 2H) 7.38 (d, J=8.82 Hz, 3H) 7.78 (d, J=8.82 Hz, 1H) 8.34 (d, J=6.99 Hz, 1H) 8.93 (d, J=8.82 Hz, 1H) 9.94 (s, 1H) 10.28 (s, 1H) 10.94 (s, 1H) 14.30 (s, 1H); MS (ESI+) m/z 445 (M+H)+.

Example 118

[2-(2,5-Dimethyl-furan-3-ylsulfanyl)-5-methyl-phenyl]-(7-isobutyl-[1,8]naphthyridin-4-yl)-amine The product form Example 12d (80 mg, 0.362 mmol) was reacted with the product from Example 91b (85 mg, 0.362 mmol) for 18 h following the procedure from Example 1g giving the crude title compound which was purified by HPLC with TFA providing the product as a trifluoroacetic acid (28 mg, 19%). $^1$H NMR (300 MHz, DMSO-d$_6$) δ ppm: 0.97 (d, J=6.62 Hz, 6H), 2.14 (d, J=13.97 Hz, 6H), 2.19-2.30 (m, 1H), 2.33 (s, 3H), 2.90 (d, J=7.35 Hz, 2H), 5.97 (s, 1H), 6.28 (d, J=7.35 Hz, 1H), 7.08 (d, J=8.09 Hz, 1H), 7.21-7.35 (m, 2H), 7.83 (d, J=8.82 Hz, 1H), 8.46 (d, J=6.99 Hz, 1H), 9.05 (d, J=8.82 Hz, 1H), 11.02 (br. S., 1H); MS (ESI+) m/z 418 (M+H−TFA)+.

Example 119

N-{4-[4-(2-Methyl-benzyloxy)-2-(7-propyl-[1,8] naphthyridin-4-ylamino)-phenylsulfanyl]-phenyl}-acetamide Example 119a N-{4-[2-Amino-4-(2-methyl-benzyloxy)-phenylsulfanyl]-phenyl}-acetamide A mixture of the product from Example 232b (28 mg, 0.085 mmol), 2-methylbenzyl bromide (13 mg, 0.096 mmol)

and potassium carbonate (13 mg, 0.09 mmol) in DMF (1 mL) was stirred at room temperature 15 hr. The next day, the reaction mixture was poured onto ice and the solid collected by filtration providing the title compound (32 mg, 100%).

Example 119b

N-{4-[4-(2-Methyl-benzyloxy)-2-(7-methyl-[1,8] naphthyridin-4-ylamino)-phenylsulfanyl]-phenyl}-acetamide The product from Example 1d (18 mg, 0.085 mmol) was reacted in ethanol (1 mL) with the product from Example 119a (32 mg, 0.085 mmol) for 18 h following the procedure from Example 1g giving the crude title compound which was purified by HPLC with TFA providing the product as a trifluoroacetic acid salt (23 mg, 42%). $^1$H NMR (300 MHz, DMSO-$d_6$) δ ppm: 0.97 (t, J=7.35 Hz, 3H) 1.69-1.94 (m, 2H) 2.02 (s, 3H) 2.32 (s, 3H) 2.99 (t, J=7.35 Hz, 2H) 5.14 (s, 2H) 6.32 (d, J=6.99 Hz, 1H) 6.98-7.30 (m, 7H) 7.41 (dd, J=11.40, 8.82 Hz, 4H) 7.80 (d, J=8.82 Hz, 1H) 8.38 (d, J=6.99 Hz, 1H) 8.97 (d, J=8.46 Hz, 1H) 9.98 (s, 1H) 11.02 (s, 1H) 14.37 (s, 1H); MS (ESI+) m/z 549 (M+H)+.

Example 120

N-{4-[4-(3-Methyl-benzyloxy)-2-(7-propyl-[1,8] naphthyridin-4-ylamino)-phenylsulfanyl]-phenyl}-acetamide

Example 120a

N-{4-[2-Amino-4-(3-methyl-benzyloxy)-phenylsulfanyl]-phenyl}-acetamide

A mixture of the product from Example 232b (28 mg, 0.085 mmol), 3-methylbenzyl bromide (13 mg, 0.096 mmol) and potassium carbonate (13 mg, 0.09 mmol) in DMF (1 mL) was stirred at room temperature 15 hr. The next day, the reaction mixture was poured onto ice and the solid collected by filtration providing the tile compound (32 mg, 100%).

Example 120b

N-{4-[4-(3-Methyl-benzyloxy)-2-(7-methyl-[1,8] naphthyridin-4-ylamino)-phenylsulfanyl]-phenyl}-acetamide The product from Example 1d (18 mg, 0.085 mmol) was reacted in ethanol (1 mL) with the product from Example 120a (32 mg, 0.085 mmol) for 18 h following the procedure from Example 1g giving the crude title compound which was purified by HPLC with TFA providing the product as a trifluoroacetic acid salt (14 mg, 26%). $^1$H NMR (300 MHz, DMSO-$d_6$) δ ppm: 0.97 (t, J=7.35 Hz, 3H) 1.62-1.93 (m, 2H) 2.02 (s, 3H) 2.31 (s, 3H) 2.99 (t, J=7.35 Hz, 2H) 5.11 (s, 2H) 6.30 (d, J=6.99 Hz, 1H) 6.97-7.33 (m, 8H) 7.34-7.50 (m, 3H) 7.80 (d, J=8.82 Hz, 1H) 8.36 (d, J=6.99 Hz, 1H) 8.97 (d, J=8.82 Hz, 1H) 9.97 (s, 1H) 11.01 (s, 1H) 14.36 (s, 1H); MS (ESI+) m/z 549 (M+H)+.

Example 121

(5-Bromo-2-phenylsulfanyl-phenyl)-(7-methyl-[1,8] naphthyridin-4-yl)-amine

Example 121a

5-Bromo-2-phenylsulfanyl-phenylamine

A solution of the 4-bromo-2-nitrophenol (10.0 g, 45.9 mmol) and Et$_3$N (14.0 mL, 137.6 mmol) in 100 mL of CH$_2$Cl$_2$ under a N$_2$ atmosphere was treated with trifluoromethanesulfonic anhydride (8.5 mL, 50.5 mmol) at 0° C. for 30 min. Quenched by addition of MeOH. Washed sequentially with 10% citric acid, 0.5 m KOH and water. Dried over MgSO$_4$, filtered and concentrated under vacuum giving the title compound which was purified by silica gel column chromatography eluting with CH$_2$Cl$_2$ giving an amber oil (15.2 g, 95%).

Example 121b (4-bromo-2-nitrophenyl)(phenyl)sulfane

The product from Example 121a (15.2 g, 43.4 mmol) and benzenethiol (4.4 mL, 43.4 mmol) in 100 mL of EtOH was treated with Na$_2$CO$_3$ and heated overnight under reflux. Cooled to room temperature and quenched with water. Extracted with EtOAc. Dried over MgSO$_4$, filtered and concentrated under vacuum giving the title compound, which was purified by silica gel column chromatography eluting with 5% EtOAc/hexane giving a yellow oil (13.3 g, 99%).

Example 121c 5-bromo-2-(phenylthio)benzenamine

The product from Example 121b (2.0 g, 6.45 mmol) was reduced with SnCl$_2$ following the procedure from Example 1f giving the title compound as a clear oil (1.8 g, 100%).

Example 121d (5-Bromo-2-phenylsulfanyl-phenyl)-(7-methyl-[1,8] naphthyridin-4-yl)-amine The product from Example 1d (278 mg, 1.56 mmol) was reacted with the product from Example 121c (437 mg, 1.56 mmol) for 18 h following the procedure from Example 1g giving the crude title compound which was purified by HPLC with TFA providing the product as a trifluoroacetic acid (129 mg, 15%). $^1$H NMR (300 MHz, DMSO-$d_6$) δ ppm: 2.77 (s, 3H) 6.43 (d, J=6.99 Hz, 1H) 7.20 (d, J=8.46 Hz, 1H) 7.34 (s, 5H) 7.69 (dd, J=8.82, 2.21 Hz, 1H) 7.81 (m, 2H) 8.47 (d, J=6.99 Hz, 1H) 8.95 (d, J=8.46 Hz, 1H); MS (ESI+) m/z 422 (M+H−TFA)+.

Example 122

4-[4-Methyl-2-(7-methyl-[1,8]naphthyridin-4-ylamino)-phenoxy]-phenol

Example 122a 4-(4-methyl-2-nitrophenoxy)phenol

A solution of hydroquinone (3.2 g, 29.0 mmol) and K$_2$CO$_3$ (8.0 g, 54.0 mmol) in 40 mL of DMF was heated at 100° C. with 1-fluoro-4-methyl-2-nitrobenzene (3.0 g, 19.3 mmol) with stirring for 24 hours. Cooled to room temperature and diluted with EtOAc. Washed with water and dried the organic layer over MgSO$_4$. Filtered and concentrated under vacuum giving the title compound, which was purified by silica gel

Example 122b 4-(2-amino-4-methylphenoxy)phenol

The product from Example 122a (1.89 g, 7.71 mmol) was reduced with SnCl$_2$ following the procedure from Example 1f giving the title compound as a white solid (1.42 g, 86%).

Example 122c 4-(4-methyl-2-(7-methyl-1,8-naphthyridin-4-ylamino)phenoxy)phenol The product from Example 1d (278 mg, 1.56 mmol) was reacted with the product from Example 122b (336 mg, 1.56 mmol) for 18 h following the procedure from Example 1g giving the crude title compound which was purified by HPLC with TFA providing the product as a trifluoroacetic acid (226 mg, 31%). $^1$H NMR (300 MHz, DMSO-d$_6$) δ ppm: 2.34 (s, 3H) 2.74 (s, 3H) 6.56 (d, J=6.99 Hz, 1H) 6.64-6.71 (m, 2H) 6.75-6.81 (m, 2H) 6.89 (d, J=8.46 Hz, 1H) 7.26 (dd, J=8.46, 1.84 Hz, 1H) 7.31 (s, 1H) 7.76 (d, J=8.82 Hz, 1H) 8.48 (d, J=6.99 Hz, 1H) 8.95 (d, J=8.46 Hz, 1H) 9.34 (s, 1H) 10.91 (s, 1H) 14.36 (s, 1H); MS (ESI+) m/z 358 (M+H−TFA)+.

Example 123

Bis-[3-(7-methyl-[1,8]naphthyridin-4-ylamino)-4-phenylsulfanyl-benzyl]-carbamic acid tert-butyl ester The product from Example 1d (556 mg, 3.12 mmol) was reacted with the product from Example 90c (1.032 g, 3.12 mmol) for 18 h following the procedure from Example 1g giving the crude title compound which was purified by HPLC with TFA providing the product as a trifluoroacetic acid (228 mg, 31%). $^1$H NMR (300 MHz, DMSO-d$_6$) δ ppm: 1.35 (s, 9H) 2.76 (s, 6H) 4.45 (s, 4H) 6.28 (d, J=6.99 Hz, 2H) 7.20-7.31 (m, 12H) 7.34 (s, 4H) 7.77 (d, J=8.82 Hz, 2H) 8.40 (d, J=6.99 Hz, 2H) 8.90 (d, J=8.82 Hz, 2H) 11.00 (s, 2H) 14.40 (s, 2H); MS (ESI+) m/z 829 (M+H−TFA)+.

Example 124

(5-Bromo-2-phenoxy-phenyl)-(7-propyl-[1,8]naphthyridin-4-yl)-amine

Example 124a 4-bromo-2-nitro-1-phenoxybenzene

A solution of phenol (2.35 g, 25.0 mmol) and K$_2$CO$_3$ (9.4 g, 68.1 mmol) in 40 mL of DMF was heated at 100° C. with 4-bromo-1-fluoro-2-nitrobenzene (5.0 g, 22.7 mmol) with stirring for 24 hours. Cooled to room temperature and diluted with EtOAc. Washed with water and dried the organic layer over MgSO$_4$. Filtered and concentrated under vacuum giving the title compound, which was purified by silica gel column chromatography eluting with 15% EtOAc/hexane giving a yellow oil (6.6 g, 99%).

Example 124b 5-bromo-2-phenoxybenzenamine

The product from Example 124a (6.6 g, 22.5 mmol) was reduced with SnCl$_2$ following the procedure from Example 1f giving the title compound as a brown oil (5.9 g, 100%).

Example 124c

N-(5-bromo-2-phenoxyphenyl)-7-propyl-1,8-naphthyridin-4-amine

The product from Example 2g (275 mg, 1.33 mmol) was reacted with the product from Example 124b (351 mg, 1.33 mmol) for 18 h following the procedure from Example 1g giving the crude title compound which was purified by HPLC with TFA providing the product as a trifluoroacetic acid (470 mg, 65%). $^1$H NMR (300 MHz, DMSO-d$_6$) δ ppm: 0.95 (t, J=7.35 Hz, 3H) 1.72-1.93 (m, 2H) 2.91-3.02 (m, 2H) 6.70 (d, J=6.99 Hz, 1H) 6.97 (d, J=7.72 Hz, 2H) 7.10 (t, J=8.27 Hz, 2H) 7.27-7.36 (m, 2H) 7.68 (dd, J=8.82, 2.57 Hz, 1H) 7.78 (d, J=8.46 Hz, 1H) 7.82 (d, J=2.57 Hz, 1H) 8.52 (d, J=6.99 Hz, 1H) 8.89 (d, J=8.82 Hz, 1H) 10.90 (s, 1H) 14.49 (s, 1H); MS (ESI+) m/z 436 (M+H−TFA)+.

Example 125

(5-Bromo-2-phenoxy-phenyl)-(7-methyl-[1,8]naphthyridin-4-yl)-amine

The product from Example 1d (278 mg, 1.56 mmol) was reacted with the product from Example 124b (412 mg, 1.56 mmol) for 18 h following the procedure from Example 1g giving the crude title compound which was purified by HPLC with TFA providing the product as a trifluoroacetic acid (206 mg, 25%). $^1$H NMR (300 MHz, DMSO-d$_6$) δ ppm: 2.73 (s, 3H) 6.69 (d, J=7.35 Hz, 2H) 6.96 (d, J=7.72 Hz, 2H) 7.05-7.15 (m, 3H) 7.24-7.36 (m, 2H) 7.68 (dd, J=8.82, 2.57 Hz, 1H) 7.75 (d, J=8.46 Hz, 1H) 7.82 (d, J=2.21 Hz, 1H) 8.52 (d, J=6.99 Hz, 1H) 8.86 (d, J=8.82 Hz, 1H) 10.93 (s, 1H) 14.49 (s, 1H); MS (ESI+) m/z 408 (M+H−TFA)+.

Example 126

4-[4-Chloro-2-(7-methyl-[1,8]naphthyridin-4-ylamino)-phenoxy]-N-(2-methoxy-ethyl)-benzamide

Example 126a

Methyl 4-(4-chloro-2-nitrophenoxy)benzoate

A mixture of 1,4-dichloro-2-nitrobenzene (20.0 g, 104.2 mmol) and methyl 4-hydroxybenzoate (15.85 g, 104.2 mmol) in 150 mL of EtOH was treated with Na$_2$CO$_3$ and heated overnight under reflux. Cooled to room temperature and quenched with water. Extracted with EtOAc. Dried over MgSO$_4$, filtered and concentrated under vacuum giving the title compound, which was purified by silica gel column chromatography eluting with 10% EtOAc/hexane giving the title compound as a yellow solid (29.6 g, 92%).

Example 126b 4-(4-chloro-2-nitrophenoxy)benzoic acid

The compound from Example 126a (29.6 g, 96.2 mmol) in 200 mL of MeOH was treated with aqueous LiOH (1 M) and heated under reflux for 1 hour. Cooled to room temperature and acidified with aqueous HCl (1 M). Precipitate was filtered, washed with $H_2O$ and air-dried giving the title compound as a yellow solid (28.2 g, 100%).

Example 126c 4-(4-chloro-2-nitrophenoxy)benzoyl chloride

The product from Example 126b (4.0 g, 13.6 mmol) in 40 mL of $CH_2Cl_2$ was treated with oxalyl chloride (3.5 g, 27.2 mmol) and DMF (catalytic amount). Mixture was stirred for 12 hours. Mixture was concentrated under vacuum giving the title compound as a yellow oil (4.2 g, 100%).

Example 126d 4-(4-chloro-2-nitrophenoxy)-N-(2-methoxyethyl)benzamide

The compound from Example 126c (1.0 g, 3.2 mmol) in $CH_2Cl_2$ was added to a mixture of 2-methoxyethanamine (722 mg, 9.61 mmol) in $CH_2Cl_2$. Mixture was stirred for 12 hours. Mixture was concentrated under vacuum giving the title compound, which was purified by silica gel column chromatography eluting with 50% EtOAc/hexane giving the title compound as a yellow oil (1.1 g, 100%).

Example 126e 4-(2-Amino-4-chlorophenoxy)-N-(2-methoxyethyl)benzamide

The product from Example 126d (1.0 g, 2.85 mmol) was reduced with $SnCl_2$ following the procedure from Example 1f giving the title compound as a clear oil (900 mg, 100%).

Example 126f 4-(4-chloro-2-(7-methyl-1,8-naphthyridin-4-ylamino)phenoxy)-N-(2-methoxyethyl)benzamide The product from Example 1d (111 mg, 0.62 mmol) was reacted with the product from Example 126e (200 mg, 0.62 mmol) for 18 h following the procedure from Example 1g giving the crude title compound which was purified by HPLC with TFA providing the product as a trifluoroacetic acid (89.4 mg, 25%). $^1$H NMR (300 MHz, DMSO-$D_6$) δ ppm: 2.73 (s, 3H) 3.25 (s, 3H) 3.32-3.50 (m, 4H) 6.72 (d, J=6.99 Hz, 1H) 6.97 (d, J=8.82 Hz, 2H) 7.30 (d, J=8.82 Hz, 1H) 7.61 (dd, J=8.82, 2.57 Hz, 1H) 7.70-7.80 (m, 4H) 8.42 (t, J=5.15 Hz, 1H) 8.53 (d, J=6.99 Hz, 1H) 8.82 (d, J=8.82 Hz, 1H) 10.90 (s, 1H) 14.54 (s, 1H); MS (ESI+) m/z 463 (M+H−TFA)+.

Example 127

4-[4-Chloro-2-(7-methyl-[1,8]naphthyridin-4-ylamino)-phenoxy]-N-propyl-benzamide Example 127a 4-(4-chloro-2-nitrophenoxy)-N-propylbenzamide The product from Example 126c (1.0 g, 3.2 mmol) was reacted with propan-1-amine (568 mg, 9.61 mmol) for 12 h following the procedure from Example 126d giving the title compound (1.02 g, 100%).

Example 127b 4-(2-amino-4-chlorophenoxy)-N-propylbenzamide

The product from Example 127a (1.0 g, 2.99 mmol) was reduced with $SnCl_2$ following the procedure from Example 1f giving the title compound as a clear oil (834 mg, 92%).

Example 127c 4-(4-chloro-2-(7-methyl-1,8-naphthyridin-4-ylamino)phenoxy)-N-propylbenzamide The product from Example 1d (111 mg, 0.62 mmol) was reacted with the product from Example 127b (190 mg, 0.62 mmol) for 18 h following the procedure from Example 1g giving the crude title compound which was purified by HPLC with TFA providing the product as a trifluoroacetic acid (45.9 mg, 13%). $^1$H NMR (300 MHz, DMSO-$d_6$) δ ppm: 0.86 (t, J=7.54 Hz, 3H) 1.39-1.60 (m, 2H) 2.72 (s, 3H) 3.08-3.26 (m, 2H) 6.72 (d, J=6.99 Hz, 1H) 6.96 (d, J=8.82 Hz, 2H) 7.29 (d, J=8.82 Hz, 1H) 7.61 (dd, J=8.82, 2.57 Hz, 1H) 7.69-7.80 (m, 4H) 8.34 (t, J=5.52 Hz, 1H) 8.53 (d, J=6.99 Hz, 1H) 8.82 (d, J=8.46 Hz, 1H) 10.91 (s, 1H) 14.55 (s, 1H); MS (ESI+) m/z 447 (M+H−TFA)+.

Example 128

4-[4-Chloro-2-(7-methyl-[1,8]naphthyridin-4-ylamino)-phenoxy]-N-methoxy-N-methyl-benzamide Example 128a 4-(4-chloro-2-nitrophenoxy)-N-methoxy-N-methyl-benzamide The product from Example 126c (1.0 g, 3.20 mmol) was reacted with N-methoxymethanamine (391 mg, 6.41 mmol) for 12 h following the procedure from Example 126d giving the title compound (1.03 g, 100%).

Example 128b 4-(2-amino-4-chlorophenoxy)-N-methoxy-N-methylbenzamide

The product from Example 128a (1.0 g, 2.97 mmol) was reduced with $SnCl_2$ following the procedure from Example 1f giving the title compound as a clear oil (911 mg, 100%).

Example 128c 4-(4-chloro-2-(7-methyl-1,8-naphthyridin-4-ylamino)phenoxy)-N-methoxy-N-methylbenzamide The product from Example 1d (111 mg, 0.62 mmol) was reacted with the product from Example 128b (192 mg, 0.62 mmol) for 18 h following the procedure from Example 1g giving the crude title compound which was purified by HPLC with TFA providing the product as a trifluoroacetic acid (50.9 mg, 15%). $^1$H NMR (300 MHz, DMSO-$d_6$) δ ppm: 2.72 (s, 3H) 3.19 (s, 3H) 3.42 (s, 3H) 6.71 (d, J=6.99 Hz, 1H) 6.94 (d, J=8.82 Hz, 2H) 7.36 (d, J=8.82 Hz, 1H) 7.50 (d, J=8.82 Hz, 2H) 7.63 (dd, J=8.82, 2.57 Hz, 1H) 7.72 (d, J=8.82 Hz, 1H)

7.75 (d, J=2.57 Hz, 1H) 8.53 (d, J=6.99 Hz, 1H) 8.81 (d, J=8.46 Hz, 1H) 10.88 (s, 1H) 14.46 (s, 1H); MS (ESI+) m/z 449 (M+H−TFA)+.

Example 129

4-[4-Chloro-2-(7-methyl-[1,8]naphthyridin-4-ylamino)-phenoxy]-N,N-diethyl-benzamide

Example 129a 4-(4-chloro-2-nitrophenoxy)-N,N-diethylbenzamide

The compound from Example 126c (1.0 g, 3.2 mmol) in $CH_2Cl_2$ was added to a mixture of diethylamine (469 mg, 6.41 mmol) in $CH_2Cl_2$. Mixture was stirred for 12 hours. Mixture was concentrated under vacuum giving the title compound, which was purified by silica gel column chromatography eluting with 50% EtOAc/hexane giving a yellow oil (1.1 g, 100%).

Example 129b 4-(2-amino-4-chlorophenoxy)-N,N-diethylbenzamide

The product from Example 129a (1.0 g, 2.87 mmol) was reduced with $SnCl_2$ following the procedure from Example 1f giving the title compound as a clear oil (772 mg, 85%).

Example 129c 4-(4-chloro-2-(7-methyl-1,8-naphthyridin-4-ylamino)phenoxy)-N,N-diethylbenzamide The product from Example 1d (111 mg, 0.62 mmol) was reacted with the product from Example 129b (199 mg, 0.62 mmol) for 18 h following the procedure from Example 1g giving the crude title compound which was purified by HPLC with TFA providing the product as a trifluoroacetic acid (49.2 mg, 14%). $^1$H NMR (300 MHz, DMSO-$d_6$) δ ppm: 1.01 (s, 6H) 2.73 (s, 3H) 3.35 (s, 1H) 3.53-3.81 (m, 4H) 6.70 (d, J=7.35 Hz, 1H) 6.93 (d, J=8.46 Hz, 2H) 7.22 (d, J=8.82 Hz, 2H) 7.34 (d, J=8.82 Hz, 1H) 7.62 (dd, J=8.82, 2.57 Hz, 1H) 7.73 (d, J=6.25 Hz, 1H) 7.75 (s, 1H) 8.53 (d, J=6.99 Hz, 1H) 8.82 (d, J=8.82 Hz, 1H) 10.92 (s, 1H) 14.55 (s, 1H); MS (ESI+) m/z 461 (M+H−TFA)+.

Example 130

4-[4-Chloro-2-(7-propyl-[1,8]naphthyridin-4-ylamino)-phenoxy]-N-propyl-benzamide The product from Example 2g (75 mg, 0.36 mmol) was reacted with the product from Example 127b (111 mg, 0.36 mmol) for 18 h following the procedure from Example 1g giving the crude title compound which was purified by HPLC with TFA providing the product as a trifluoroacetic acid (25.8 mg, 12%). $^1$H NMR (300 MHz, DMSO-$d_6$) δ ppm: 0.86 (t, J=7.35 Hz, 3H) 0.95 (t, J=7.35 Hz, 3H) 1.37-1.56 (m, 2H) 1.72-1.88 (m, 2H) 2.96 (t, J=7.54 Hz, 2H) 3.08-3.22 (m, 2H) 6.72 (d, J=6.99 Hz, 1H) 6.97 (d, J=8.82 Hz, 2H) 7.29 (d, J=8.82 Hz, 1H) 7.61 (dd, J=8.82, 2.57 Hz, 1H) 7.75 (d, J=8.82 Hz, 4H) 8.34 (t, J=5.70 Hz, 1H) 8.52 (d, J=6.99 Hz, 1H) 8.85 (d, J=8.82 Hz, 1H) 10.90 (s, 1H) 14.55 (s, 1H); MS (ESI+) m/z 475 (M+H−TFA)+.

Example 131

4-[4-Chloro-2-(7-propyl-[1,8]naphthyridin-4-ylamino)-phenoxy]-N-(2-methoxy-ethyl)-benzamide The product from Example 2g (75 mg, 0.36 mmol) was reacted with the product from Example 126e (116 mg, 0.36 mmol) for 18 h following the procedure from Example 1g giving the crude title compound which was purified by HPLC with TFA providing the product as a trifluoroacetic acid (101.7 mg, 46%). $^1$H NMR (300 MHz, DMSO-$d_6$) δ ppm: 0.95 (t, J=7.35 Hz, 3H) 1.70-1.90 (m, 2H) 2.90-3.01 (m, 2H) 3.24 (s, 3H) 3.32-3.47 (m, 4H) 6.73 (d, J=6.99 Hz, 1H) 6.98 (d, J=8.82 Hz, 2H) 7.29 (d, J=8.82 Hz, 1H) 7.61 (dd, J=8.82, 2.57 Hz, 1H) 7.71-7.81 (m, 4H) 8.42 (t, J=4.78 Hz, 1H) 8.53 (d, J=6.99 Hz, 1H) 8.85 (d, J=8.82 Hz, 1H) 10.92 (s, 1H) 14.57 (s, 1H); MS (ESI+) m/z 491 (M+H−TFA)+.

Example 132

4-[4-Chloro-2-(7-propyl-[1,8]naphthyridin-4-ylamino)-phenoxy]-N-methoxy-N-methyl-benzamide The product from Example 2g (75 mg, 0.36 mmol) was reacted with the product from Example 128b (111 mg, 0.36 mmol) for 18 h following the procedure from Example 1g giving the crude title compound which was purified by HPLC with TFA providing the product as a trifluoroacetic acid (76.3 mg, 36%). $^1$H NMR (300 MHz, DMSO-$d_6$) δ ppm: 0.88-1.03 (m, 3H) 1.70-1.91 (m, 2H) 2.88-3.00 (m, 2H) 3.18 (s, 3H) 3.42 (s, 3H) 6.71 (d, J=7.35 Hz, 1H) 6.94 (d, J=8.82 Hz, 2H) 7.36 (d, J=8.82 Hz, 1H) 7.50 (d, J=8.82 Hz, 2H) 7.59-7.66 (m, 1H) 7.71-7.79 (m, 2H) 8.53 (d, J=6.99 Hz, 1H) 8.84 (d, J=8.82 Hz, 1H) 10.89 (s, 1H) 14.54 (s, 1H); MS (ESI+) m/z 477 (M+H−TFA)+.

Example 133

4-[4-Chloro-2-([1,8]naphthyridin-4-ylamino)-phenoxy]-N-ethyl-N-methyl-benzamide

Example 133a 4-(4-chloro-2-nitrophenoxy)-N-ethyl-N-methylbenzamide

The compound from Example 126c (1.0 g, 3.2 mmol) in $CH_2Cl_2$ was added to a mixture of N-methylethanamine (379 mg, 6.41 mmol) in $CH_2Cl_2$. Mixture was stirred for 12 hours. Mixture was concentrated under vacuum giving the title compound, which was purified by silica gel column chromatography eluting with 50% EtOAc/hexane giving a yellow oil (1.03 g, 100%).

Example 133b 4-(2-amino-4-chlorophenoxy)-N-ethyl-N-methylbenzamide

The product from Example 133a (1.0 g, 2.99 mmol) was reduced with $SnCl_2$ following the procedure from Example 1f giving the title compound as a clear oil (751 mg, 83%).

Example 133c

4-(2-(1,8-naphthyridin-4-ylamino)-4-chlorophenoxy)-N-ethyl-N-methylbenzamide

The product from Example 16c (100 mg, 0.61 mmol) was reacted with the product from Example 133b (185 mg, 0.61 mmol) for 18 h following the procedure from Example 1g giving the crude title compound which was purified by HPLC with TFA providing the product as a trifluoroacetic acid (141 mg, 42%). $^1$H NMR (300 MHz, DMSO-$d_6$) δ ppm: 0.86-1.18 (m, 3H) 2.62-2.92 (m, 5H) 6.76 (d, J=7.35 Hz, 1H) 6.94 (d, J=8.82 Hz, 2H) 7.25 (d, J=8.09 Hz, 2H) 7.34 (d, J=8.82 Hz, 1H) 7.63 (dd, J=8.82, 2.57 Hz, 1H) 7.75 (d, J=2.57 Hz, 1H) 7.85 (dd, J=8.46, 4.41 Hz, 1H) 8.61 (d, J=6.99 Hz, 1H) 8.96 (dd, J=8.64, 1.29 Hz, 1H) 9.14 (dd, J=4.23, 1.29 Hz, 1H) 11.06 (s, 1H) 14.74 (s, 1H); MS (ESI+) m/z 433 (M+H−TFA)+.

Example 134

4-[4-(4-Bromo-benzyloxy)-2-(7-methyl-[1,8]naphthyridin-4-ylamino)-phenylsulfanyl]-phenol

The product from Example 1d (100 mg, 0.559 mmol) was reacted with the product from Example 116A (224 mg, 0.559 mmol) for 18 h following the procedure from Example 1g giving the crude title compound which was purified by HPLC with TFA providing the product as a trifluoroacetic acid (129 mg, 61%). $^1$H NMR (300 MHz, DMSO-$d_6$) δ ppm: 2.76 (s, 3H) 5.12 (s, 2H) 6.26 (d, J=6.99 Hz, 1H) 6.65 (d, J=8.45 HZ, 2H) 7.07-7.25 (m, 5H) 7.39 (d, J=8.45 Hz, 2H) 7.60 (d, J=8.45 Hz, 2H) 7.81 (d, J=8.45 Hz, 1H) 8.39 (d, J=7.35 Hz, 1H) 8.99 (d, J=8.45 Hz, 1H) 9.78 (s, 1H) 11.05 (br s, 1H) 14.40 (br s, 1H); MS (ESI+) m/z 544, 546 (M+H−TFA)+; (ESI−) m/z 542, 544 (M−H−TFA)−.

Example 135

4-[4-(3-Bromo-benzyloxy)-2-(7-methyl-[1,8]naphthyridin-4-ylamino)-phenylsulfanyl]-phenol

A solution of 4-chloro-3-nitro-phenol was reacted with 1-bromo-3-bromomethyl-benzene using the conditions described in Example 237C to provide 4-(3-Bromo-benzyloxy)-1-chloro-2-nitro-benzene which was treated sequentially using the procedures from Examples 237D and 237E to provide 4-[2-Amino-4-(3-bromo-benzyloxy)-phenylsulfanyl]-phenol.

The product from Example 1d (57 mg, 0.319 mmol) was reacted with 4-[2-Amino-4-(3-bromo-benzyloxy)-phenylsulfanyl]-phenol (128 mg, 0.319 mmol) for 28 h following the procedure from Example 1g giving the crude title compound which was purified by HPLC with TFA providing the product as a trifluoroacetic acid (118 mg, 56%). $^1$H NMR (300 MHz, DMSO-$d_6$) δ ppm: 2.76 (3H) 5.15 (s, 2H) 6.25 (d, J=6.99 Hz, 1H) 6.65 (d, J=8.46 Hz, 2H) 7.06-7.68 (m, 8H) 7.80 (d, J=8.46 Hz, 1H) 8.39 (d, J=6.99 Hz, 1H) 8.99 (d, J=8.45 Hz, 1H) 9.78 (s, 1H) 11.02 (br s, 1H) 14.39 (br s, 1H); MS (ESI+) m/z 544, 546 (M+H−TFA)+; (ESI−) m/z 542, 544 (M−H−TFA)−.

Example 136

4-[4-(3-Bromo-benzyloxy)-2-(7-propyl-[1,8]naphthyridin-4-ylamino)-phenylsulfanyl]-phenol

The product from Example 2g (62 mg, 0.30 mmol) was reacted with 4-[2-Amino-4-(3-bromo-benzyloxy)-phenylsulfanyl]-phenol (120 mg, 0.30 mmol) for 48 h following the procedure from Example 1g giving the crude title compound which was purified by HPLC with TFA providing the product as a trifluoroacetic acid (86 mg, 41%). $^1$H NMR (300 MHz, DMSO-$d_6$) δ ppm: 0.98 (t, J=7.73 Hz, 3H) 1.85 (dt, J=7.73 Hz, 2H) 3.00 (dd, J=7.72 Hz, 2H) 5.15 (s, 2H) 6.27 (d, J=7.35 Hz, 1H) 6.66 (d, J=8.82 Hz, 2H) 7.07-7.69 (m, 7H) 7.65 (s, 1H) 7.83 (d, J=8.82 Hz, 1H) 8.41 (d, J=6.99 Hz, 1H) 9.03 (d, J=8.82 Hz, 1H) 9.81 (s, 1H) 11.05 (br s, 1H) 14.43 (br s, 1H); MS (ESI+) m/z 572, 574 (M+H−TFA)+; (ESI−) m/z 570-572 (M−H−TFA)−.

Example 137

4-[4-(4-Bromo-benzyloxy)-2-([1,8]naphthyridin-4-ylamino)-phenylsulfanyl]-phenol

The product from Example 16c (50 mg, 0.30 mmol) was reacted with the product from Example 116A (120 mg, 0.30 mmol) for 26 h following the procedure from Example 1g giving the crude title compound which was purified by HPLC with TFA providing the product as a trifluoroacetic acid (95 mg, 49%). $^1$H NMR (300 MHz, DMSO-$d_6$) δ ppm: 5.12 (s, 2H) 6.30 (d, J=7.35 Hz, 1H) 6.64 (d, J=8.82 Hz, 2H) 7.08-7.25 (m, 3H) 7.39 (d, J=8.09 Hz, 2H) 7.60 (d, J=8.09 Hz, 2H) 7.91 (dd, J=4.42 Hz, 1H) 8.46 (d, J=6.98 Hz, 1H) 9.12 (d, J=8.46 Hz, 2H) 9.17 (d, J=4.42 Hz, 1H) 9.78 (s, 1H) 11.10 (br s, 1H) 14.49 (br s, 1H); (ESI+) m/z 529, 531 (M+H−TFA)+; (ESI−) m/z 528, 530 (M−H−TFA)−.

Example 138

4-[4-(3-Bromo-benzyloxy)-2-([1,8]naphthyridin-4-ylamino)-phenylsulfanyl]-phenol

The product from Example 16c (50 mg, 0.30 mmol) was reacted with 4-[2-Amino-4-(3-bromo-benzyloxy)-phenylsulfanyl]-phenol (120 mg, 0.30 mmol) for 40 h following the procedure from Example 1g giving the crude title compound which was purified by HPLC with TFA providing the product as a trifluoroacetic acid (87 mg, 45%). $^1$H NMR (300 MHz, DMSO-$d_6$) δ ppm: 5.15 (s, 2H) 6.30 (d, J=6.99 Hz, 1H) 6.66 (d, J=8.83 Hz, 2H) 7.08-7.47 (m, 6H) 7.56 (d, J=7.72 Hz, 1H) 7.65 (m, 1H) 7.92 (dd, J=4.41 Hz, J=8.46 Hz, 1H) 8.18 (d, J=6.99 Hz, 1H) 9.14 (dd, J=8.83 Hz, 1H) 9.17 (dd, J=5.88 Hz, J=1.84 Hz, 1H) 9.80 (s, 1H) 11.16 (br s, 1H) 14.53 (br s, 1H); MS (ESI+) m/z 529, 531 (M+H−TFA)=; (ESI−) m/z 528, 530 (M−H−TFA)−.

Example 139

4-[4-(3-Fluoro-benzyloxy)-2-(7-methyl-[1,8]naphthyridin-4-ylamino)-phenylsulfanyl]-phenol

A solution of 4-chloro-3-nitro-phenol was reacted with 1-bromomethyl-3-fluoro-benzene using the conditions described in Example 237C to provide 1-Chloro-4-(3-fluoro-benzyloxy)-2-nitro-benzene which was treated sequentially using the procedures from Examples 237D and 237E to provide 4-[2-amino-4-(3-fluoro-benzyloxy)-phenylsulfanyl]-phenol.

The product from Example 1d (53 mg, 0.30 mmol) was reacted with 4-[2-amino-4-(3-fluoro-benzyloxy)-phenylsulfanyl]-phenol (102 mg, 0.30 mmol) for 20 h following the procedure from Example 1g giving the crude title compound which was purified by HPLC with TFA providing the product as a trifluoroacetic acid (60 mg, 33%). $^1$H NMR (300 MHz, DMSO-d$_6$) δ ppm: 2.76 (s, 3H) 5.16 (s, 2H) 6.27 (d, J=6.99 Hz, 1H) 6.64 (d, J=8.46 Hz, 2H) 7.03-7.36 (m, 7H) 7.45 (m, J=6.26 Hz, 1H) 7.80 (d, J=8.82 Hz, 1H) 8.39 (d, J=6.98 Hz, 1H) 8.99 (d, J=8.82 Hz, 1H) 9.78 (s, 1H) 11.02 (br s, 1H) 14.39 (br s, 1H); MS (ESI+) m/z, 484 (M+H–TFA)+; (ESI–) m/z, 482 (M–H–TFA)–.

Example 140

4-[4-(4-Fluoro-benzyloxy)-2-(7-methyl-[1,8]naphthyridin-4-ylamino)-phenylsulfanyl]-phenol A solution of 4-chloro-3-nitro-phenol was reacted with 1-Bromomethyl-4-fluoro-benzene using the conditions described in Example 237C to provide 1-Chloro-4-(4-fluoro-benzyloxy)-2-nitro-benzene which was treated sequentially using the procedures from Examples 237D and 237E to provide 4-[2-amino-4-(4-fluoro-benzyloxy)-phenylsulfanyl]-phenol.

The product from Example 1d (53 mg, 0.30 mmol) was reacted with 4-[2-amino-4-(4-fluoro-benzyloxy)-phenylsulfanyl]-phenol (102 mg, 0.30 mmol) for 18 h following the procedure from Example 1g giving the crude title compound which was purified by HPLC with TFA providing the product as a trifluoroacetic acid (115 mg, 64%). $^1$H NMR (300 MHz, DMSO-d$_6$) δ ppm: 2.76 (s, 3H) 5.11 (s, 2H) 6.26 (d, J=6.99 Hz, 1H) 6.65 (d, J=8.46 Hz, 2H) 7.10 (d, J=8.82 Hz, 2H) 7.15-7.27 (m, 4H) 7.49 (m, J=5.88 Hz, 2H) 7.81 (d, J=8.46 Hz, 1H) 8.40 (d, J=6.98 Hz, 1H) 8.98 (d, J=8.46 Hz, 1H) 9.78 (s, 1H) 11.03 (br s, 1H) 14.36 (br s, 1H); MS (ESI+) m/z, 484 (M+H–TFA)+; (ESI–) m/z, 482 (M–H–TFA)–.

Example 141

4-[4-(4-Fluoro-benzyloxy)-2-([1,8]naphthyridin-4-ylamino)-phenylsulfanyl]-phenol The product from Example 16c (50 mg, 0.30 mmol) was reacted with the product from 4-[2-amino-4-(4-fluoro-benzyloxy)-phenylsulfanyl]-phenol (102 mg, 0.30 mmol) for 20 h following the procedure from Example 1g giving the crude title compound which was purified by HPLC with TFA providing the product as a trifluoroacetic acid (99 mg, 56%). $^1$H NMR (300 MHz, DMSO-d$_6$) δ ppm: 5.11 (s, 2H) 6.31 (d, J=6.99 Hz, 1H) 6.64 (d, J=8.45 Hz, 2H) 7.08-7.27 (m, 6H) 7.50 (m, J=5.51 Hz, 2H) 7.91 (d, J=4.41 Hz, 1H) 8.47 (d, J=6.98 Hz, 1H) 9.13 (dd, J=1.47 Hz, J=8.45 Hz, 1H) 9.17 (dd, J=1.47 Hz, J=4.05 Hz, 1H) 9.79 (s, 1H) 11.14 (br s, 1H) 14.50 (br s, 1H); MS (ESI+) m/z, 470 (M+H–TFA)+; (ESI–) m/z, 468 (M–H–TFA)–.

Example 142

4-[4-(3-Fluoro-benzyloxy)-2-([1,8]naphthyridin-4-ylamino)-phenylsulfanyl]-phenol The product from Example 16c (50 mg, 0.30 mmol) was reacted with 4-[2-amino-4-(3-fluoro-benzyloxy)-phenylsulfanyl]-phenol (102 mg, 0.30 mmol) for 22 h following the procedure from Example 1g giving the crude title compound which was purified by HPLC with TFA providing the product as a trifluoroacetic acid (75 mg, 43%). $^1$H NMR (300 MHz, DMSO-d$_6$) δ ppm: 5.16 (s, 2H) 6.31 (d, J=7.36 Hz, 1H) 6.64 (d, J=8.82 Hz, 2H) 7.09-7.28 (m, 6H) 7.29 (2, 1H) 7.44 (m, J=6.61 Hz, 1H) 7.93 (dd, J=4.41 Hz, 1H) 8.47 (d, J=6.98 Hz, 1H) 9.14 (dd, J=1.47 Hz, J=8.46 Hz, 1H) 9.18 (dd, J=1.47 Hz, J=4.41 Hz, 1H) 9.79 (s, 1H) 11.16 (br s, 1H) 14.52 (br s, 1H); MS (ESI+) m/z, 470 (M+H–TFA)+; (ESI–) m/z, 468 (M–H–TFA)–.

Example 143

4-[4-(4-Chloro-benzyloxy)-2-(7-propyl-[1,8]naphthyridin-4-ylamino)-phenylsulfanyl]-phenol Example 143a 4-[2-Amino-4-(4-chloro-benzyloxy)-phenylsulfanyl]-phenol A solution of 4-chloro-3-nitro-phenol was reacted with 1-chloro-4-brommethyl benzene using the conditions described in Example 237C to provide 4-(4-chloro-benzyloxy)-1-chloro-2-nitro-benzene which was treated sequentially using the procedures from Examples 237D and 237E to provide the title compound.

Example 143b

4-[4-(4-Chloro-benzyloxy)-2-(7-propyl-[1,8]naphthyridin-4-ylamino)-phenylsulfanyl]-phenol The product from Example 2g (85 mg, 0.41 mmol) was reacted with the product from Example 143a (146 mg, 0.41 mmol) for 26 h following the procedure from Example 1g giving the crude title compound which was purified by HPLC with TFA providing the product as a trifluoroacetic acid (89 mg, 68%). $^1$H NMR (300 MHz, DMSO-d$_6$) δ ppm: 0.98 (t, J=7.35 Hz, 3H) 1.83 (sext, J=7.35 Hz, 2H) 3.00 (dd, J=7.35 Hz, 2H) 5.13 (s, 2H) 6.27 (d, J=6.99 Hz, 1H) 6.64 (d, J=8.82 Hz, 2H) 7.05-7.25 (m, J=8.45 Hz, 4H) 7.48 (m, 4H) 7.83 (d, J=8.45 Hz, 1H) 8.40 (d, J=6.99 Hz, 1H) 9.00 (d, J=8.46 Hz, 1H) 9.78 (s, 1H) 11.03 (br s, 1H) 14.40 (br s, 1H); MS (ESI+) m/z, 528, 530 (M+H–TFA)+; (ESI–) m/z, 526, 528 (M–H–TFA)–.

Example 144

4-[4-(3-Chloro-benzyloxy)-2-(7-propyl-[1,8]naphthyridin-4-ylamino)-phenylsulfanyl]-phenol Example 144a 4-[2-Amino-4-(3-chloro-benzyloxy)-phenylsulfanyl]-phenol A solution of 4-chloro-3-nitro-phenol was reacted with 1-chloro-3-bromomethyl benzene using the conditions described in Example 237C to provide 4-(3-chloro-benzyloxy)-1-chloro-2-nitro-benzene which was treated sequentially using the procedures from Examples 237D and 237E to provide the title compound.

Example 144b

4-[2-Amino-4-(3-chloro-benzyloxy)-phenylsulfanyl]-phenol

The product from Example 2g (85 mg, 0.41 mmol) was reacted with the product from Example 144a (146 mg, 0.41 mmol) for 24 h following the procedure from Example 1g giving the crude title compound which was purified by HPLC with TFA providing the product as a trifluoroacetic acid (85 mg, 65%). ¹H NMR (300 MHz, DMSO-d₆) δ ppm: 0.98 (t, J=7.32 Hz, 3H) 1.85 (sext, J=7.35 Hz, 2H) 3.00 (dd, J=7.72 Hz, 2H) 5.15 (s, 2H) 6.26 (d, J=6.99 Hz, 1H) 6.65 (d, J=8.83 Hz, 2H) 7.07-7.25 (m, 5H) 7.35-7.54 (m, 3H) 7.83 (d, J=8.46 Hz, 1H) 8.40 (d, J=7.36 Hz, 1H) 9.02 (d, J=8.46 Hz, 1H) 9.79 (s, 1H) 11.02 (br s, 1H) 14.39 (br s, 1H); MS (ESI+) m/z, 528, 530 (M+H−TFA)+; (ESI−) m/z, 526, 528 (M−H−TFA)−.

Example 145

4-[4-(3-Fluoro-benzyloxy)-2-(7-propyl-[1,8]naphthyridin-4-ylamino)-phenylsulfanyl]-phenol The product from Example 2g (85 mg, 0.41 mmol) was reacted with 4-[2-amino-4-(3-fluoro-benzyloxy)-phenylsulfanyl]-phenol (141 mg, 0.41 mmol) for 24 h following the procedure from Example 1g giving the crude title compound which was purified by HPLC with TFA providing the product as a trifluoroacetic acid (95 mg, 37%). ¹H NMR (300 MHz, DMSO-d₆) δ ppm: 0.98 (t, J=7.36 Hz, 3H) 1.85 (sext, J=7.72 Hz, 2H) 3.00 (dd, J=7.36 Hz, 2H) 5.16 (s, 2H) 6.27 (d, J=7.35 Hz, 1H) 6.66 (d, J=8.83 Hz, 2H) 7.09-7.34 (m, 7H) 7.43 (m, J=6.25 Hz, 1H) 7.83 (d, J=8.83 Hz, 1H) 8.40 (d, J=6.99 Hz, 1H) 9.03 (d, J=8.83 Hz, 1H) 9.80 (s, 1H) 11.04 (br s, 1H) 14.45 (br s, 1H); MS (ESI+) m/z, 512 (M+H−TFA)+; (ESI−) m/z, 510 (M−H−TFA)−.

Example 146

4-[4-(3-Chloro-benzyloxy)-2-([1,8]naphthyridin-4-ylamino)-phenylsulfanyl]-phenol The product from Example 16c (50 mg, 0.30 mmol) was reacted with the product from Example 144a (107 mg, 0.30 mmol) for 18 h following the procedure from Example 1g giving the crude title compound which was purified by HPLC with TFA providing the product as a trifluoroacetic acid (109 mg, 60%). ¹H NMR (300 MHz, DMSO-d₆) δ ppm: 2.77 (s, 3H) 5.16 (s, 2H) 6.25 (d, J=6.98 Hz, 1H) 6.66 (d, J=8.83 Hz, 2H) 7.07-7.25 (m, J=8.46 Hz, 5H) 7.38-7.53 (m, 3H) 7.80 (d, J=8.45 Hz, 1H) 8.40 (d, J=6.99 Hz, 1H) 8.99 (d, J=8.83 HZ, 1H) 9.79 (s, 1H) 11.02 (br s, 1H) 14.38 (br s, 1H); MS (ESI+) m/z 500 (M+H−TFA)+; (ESI−) m/z 498 (M−H−TFA)−.

Example 147

4-[4-(4-Chloro-benzyloxy)-2-([1,8]naphthyridin-4-ylamino)-phenylsulfanyl]-phenol The product from Example 16c (50 mg, 0.30 mmol) was reacted with the product from Example 143a (107 mg, 0.30 mmol) for 24 h following the procedure from Example 1g giving the crude title compound which was purified by HPLC with TFA providing the product as a trifluoroacetic acid (50 mg, 27%). ¹H NMR (300 MHz, DMSO-d₆) δ ppm: 5.14 (s, 2H) 6.31 (d, J=7.36 Hz, 1H) 6.64 (d, J=8.82 Hz, 2H) 7.05-7.40 (m, J=8.46 Hz, 4H) 7.46 (m, J=5.52 Hz, 3H) 7.93 (m, J=4.41 Hz, 1H) 8.48 (d, J=6.98 Hz, 1H) 9.17 (m, J=1.47 Hz, J=5.88 Hz, 3H) 9.79 (s, 1H) 11.15 (br s, 1H) 14.54 (br s, 1H); MS (ESI+) m/z, 486 (M+H−TFA)+; (ESI−) m/z, 484 (M−H−TFA)−.

Example 148

4-[4-(3-Chloro-benzyloxy)-2-(7-methyl-[1,8]naphthyridin-4-ylamino)-phenylsulfanyl]-phenol The product from Example 1d (71 mg, 0.40 mmol) was reacted with the product from Example 144a (143 mg, 0.41 mmol) for 24 h following the procedure from Example 1g giving the crude title compound which was purified by HPLC with TFA providing the product as a trifluoroacetic acid (122 mg, 49%). ¹H NMR (300 MHz, DMSO-d₆) δ ppm: 2.77 (s, 3H) 5.16 (s, 2H) 6.25 (d, J=6.98 Hz, 1H) 6.66 (d, J=8.83 Hz, 2H) 7.07-7.25 (m, J=8.46 Hz, 5H) 7.38-7.53 (m, 3H) 7.80 (d, J=8.45 Hz, 1H) 8.40 (d, J=6.99 Hz, 1H) 8.99 (d, J=8.83 HZ, 1H) 9.79 (s, 1H) 11.02 (br s, 1H) 14.38 (br s, 1H); MS (ESI+) m/z 500 (M+H−TFA)+; (ESI−) m/z 498 (M−H−TFA)−.

Example 149

4-[4-Benzyloxy-2-([1,8]naphthyridin-4-ylamino)-phenylsulfanyl]-phenol

A solution of 4-chloro-3-nitro-phenol was reacted with Bromomethyl-benzene using the conditions described in Example 237C to provide 4-benzyloxy-1-chloro-2-nitrobenzene which was treated sequentially using the procedures from Examples 237D and 237E to provide 4-(2-amino-4-benzyloxy-phenylsulfanyl)-phenol.

The product from Example 16c (100 mg, 0.559 mmol) was reacted with 4-(2-amino-4-benzyloxy-phenylsulfanyl)-phenol (224 mg, 0.559 mmol) for 18 h following the procedure from Example 1g giving the crude title compound which was purified by HPLC with TFA providing the product as a trifluoroacetic acid (mg, %). ¹H NMR (300 MHz, DMSO-d₆) δ ppm: 5.14 (s, 2H), 6.31 (d, J=6.99 Hz, 1H), 6.61-6.69 (m, 2H), 7.08-7.23 (m, 5H), 7.32-7.46 (m, 5H), 7.92 (dd, J=8.46, 4.41 Hz, 1H), 8.47 (d, J=6.99 Hz, 1H), 9.10-9.21 (m, 2H), 9.77 (s, 1H), 11.14 (s, 1H); MS (ESI+) m/z 452 (M+H−TFA)+; (ESI−) m/z 450 (M−H−TFA)−.

Example 150

4-[4-(4-Chloro-benzyloxy)-2-(7-methyl-[1,8]naphthyridin-4-ylamino)-phenylsulfanyl]-phenol The product from Example 1d (100 mg, 0.559 mmol) was reacted with the product from Example 143a (224 mg, 0.559 mmol) for 18 h following the procedure from Example 1g giving the crude title compound which was purified by HPLC with TFA providing the product as a trifluoroacetic acid (mg, %). ¹H NMR (300 MHz, DMSO-d₆) δ ppm: 2.77 (s, 3H), 5.16 (s, 2H), 6.26 (d, J=6.99 Hz, 1H), 6.65 (d, J=8.46 Hz, 2H), 7.09-7.24 (m, 5H), 7.37-7.44 (m, 3H), 7.51 (s, 1H), 7.81 (d, J=8.82 Hz, 1H), 8.40 (d, J=6.99 Hz, 1H), 8.99 (d, J=8.82 Hz, 1H), 9.80 (s, 1H), 11.04 (s, 1H); MS (ESI+) m/z 500 (M+H−TFA)+; (ESI−) m/z 498 (M−H−TFA)−.

Example 151

4-[4-Benzyloxy-2-(7-methyl-[1,8]naphthyridin-4-ylamino)-phenylsulfanyl]-phenol

The product form Example 1d (50 mg, 0.280 mmol) was reacted with 4-(2-amino-4-benzyloxy-phenylsulfanyl)-phenol (91 mg, 0.280 mmol) for 18 h following the procedure from Example 1g giving the crude title compound which was purified by HPLC with TFA providing the product as a trifluoroacetic acid (22 mg, 17%). ¹H NMR (300 MHz, DMSO-d₆) δ ppm: 2.76 (s, 3H), 5.13 (s, 2H), 6.26 (d, J=6.99 Hz, 1H), 6.65 (d, J=8.46 Hz, 2H), 7.08-7.22 (m, 5H), 7.32-7.46 (m, H), 7.80 (d, J=8.46 Hz, 1H), 8.39 (d, J=6.99 Hz, 1H), 8.99 (d, J=8.46 Hz, 1H), 9.78 (s, 1H), 11.01 (s, 1H); MS (ESI+) m/z 466 (M+H−TFA)+; (ESI−) m/z 464 (M−H−TFA)−.

Example 152

4-[4-Benzyloxy-2-(7-propyl-[1,8]naphthyridin-4-ylamino)-phenylsulfanyl]-phenol

The product form Example 2g (50 mg, 0.241 mmol) was reacted with 4-(2-amino-4-benzyloxy-phenylsulfanyl)-phenol (78 mg, 0.241 mmol) for 18 h following the procedure from Example 1g giving the crude title compound which was purified by HPLC with TFA providing the product as a trifluoroacetic acid (2 mg, 2%). $^1$H NMR (300 MHz, DMSO-$d_6$) δ ppm: 0.98 (t, J=7.35 Hz, 3H), 1.78-1.91 (m, J=7.43, 7.43, 7.43, 7.43, 7.43 Hz, 2H), 3.00 (t, J=7.54 Hz, 2H), 5.13 (s, 2H), 6.27 (d, J=6.99 Hz, 1H), 6.65 (d, J=8.82 Hz, 2H), 7.09-7.23 (m, 5H), 7.32-7.46 (m, 5H), 7.82 (d, J=8.82 Hz, 1H), 8.39 (d, J=6.99 Hz, 1H), 9.02 (d, J=8.82 Hz, 1H), 9.78 (s, 1H), 11.00 (s, 1H); MS (ESI+) m/z 494 (M+H−TFA)+; (ESI−) m/z 492 (M−H−TFA)−.

Example 153

N-{4-[4-(3-Methoxy-benzyloxy)-2-(7-propyl-[1,8]naphthyridin-4-ylamino)-phenylsulfanyl]-phenyl}-acetamide

Example 153a

N-{4-[2-Amino-4-(3-methoxy-benzyloxy)-phenylsulfanyl]-phenyl}-acetamide

A mixture of the product from Example 232B (28 mg, 0.085 mmol), 3-methoxybenzyl bromide (19 mg, 0.096 mmol) and potassium carbonate (13 mg, 0.09 mmol) in DMF (1 mL) was stirred at room temperature 15 h. The next day, the reaction mixture was poured onto ice and the solid collected by filtration providing the title compound (33 mg, 100%).

Example 153b

N-{4-[4-(3-Methoxy-benzyloxy)-2-(7-propyl-[1,8]naphthyridin-4-ylamino)-phenylsulfanyl]-phenyl}-acetamide

The product from Example 1d (18 mg, 0.085 mmol) was reacted in ethanol (1 mL) with the product from Example 153a (33 mg, 0.085 mmol) for 18 h following the procedure from Example 1g giving the crude title compound which was purified by HPLC with TFA providing the product as a trifluoroacetic acid salt (14 mg, 30%). $^1$H NMR (300 MHz, DMSO-$d_6$) δ ppm: 0.97 (t, J=7.35 Hz, 3H) 1.69-1.93 (m, 2H) 2.02 (s, 3H) 2.99 (t, J=6.99 Hz, 2H) 3.75 (s, 3H) 5.13 (s, 2H) 6.29 (d, J=7.35 Hz, 1H) 6.91 (dd, J=8.09, 2.57 Hz, 1H) 6.95-7.05 (m, 2H) 7.13 (d, J=8.82 Hz, 2H) 7.16-7.24 (m, 2H) 7.31 (t, J=8.09 Hz, 1H) 7.38 (d, J=8.46 Hz, 1H) 7.42 (d, J=8.82 Hz, 2H) 7.80 (d, J=8.82 Hz, 1H) 8.35 (d, J=6.99 Hz, 1H) 8.97 (d, J=8.82 Hz, 1H) 9.97 (s, 1H) 11.00 (s, 1H) 14.36 (s, 1H); MS (ESI+) m/z 565 (M+H)+.

Example 154

N-{4-[4-(3-Bromo-benzyloxy)-2-(7-propyl-[1,8]naphthyridin-4-ylamino)-phenylsulfanyl]-phenyl}-acetamide

Example 154a

N-{4-[2-Amino-4-(3-bromo-benzyloxy)-phenylsulfanyl]-phenyl}-acetamide

A mixture of the product from Example 232B (28 mg, 0.085 mmol), 3-bromobenzyl bromide (24 mg, 0.096 mmol) and potassium carbonate (13 mg, 0.09 mmol) in DMF (1 mL) was stirred at room temperature 15 hr. The next day, the reaction mixture was poured onto ice and the solid collected by filtration providing the title compound (37 mg, 100%).

Example 154b

N-{4-[4-(3-Bromo-benzyloxy)-2-(7-methyl-[1,8]naphthyridin-4-ylamino)-phenylsulfanyl]-phenyl}-acetamide

The product from Example 1d (18 mg, 0.085 mmol) was reacted in ethanol (1 mL) with the product from Example 154a (37 mg, 0.085 mmol) for 18 h following the procedure from Example 1g giving the crude title compound which was purified by HPLC with TFA providing the product as a trifluoroacetic acid salt (15 mg, 30%). $^1$H NMR (300 MHz, DMSO-$d_6$) δ ppm: 0.97 (t, J=7.35 Hz, 3H) 1.65-1.90 (m, 2H) 2.02 (s, 3H) 2.99 (t, J=7.54 Hz, 2H) 5.17 (s, 2H) 6.29 (d, J=6.99 Hz, 1H) 7.14 (d, J=8.82 Hz, 2H) 7.17-7.27 (m, 2H) 7.28-7.40 (m, 3H) 7.42 (d, J=8.46 Hz, 2H) 7.55 (d, J=7.72 Hz, 1H) 7.66 (s, 1H) 7.80 (d, J=8.46 Hz, 1H) 8.37 (d, J=6.99 Hz, 1H) 8.97 (d, J=8.82 Hz, 1H) 9.98 (s, 1H) 11.00 (s, 1H) 14.37 (s, 1H); MS (ESI+) m/z 613 (M+H)+.

Example 155

N-{4-[4-(3-Nitro-benzyloxy)-2-(7-propyl-[1,8]naphthyridin-4-ylamino)-phenylsulfanyl]-phenyl}-acetamide

Example 155a

N-{4-[2-Amino-4-(3-nitro-benzyloxy)-phenylsulfanyl]-phenyl}-acetamide

A mixture of the product from Example 232B (28 mg, 0.085 mmol), 3-nitrobenzyl bromide (21 mg, 0.096 mmol) and potassium carbonate (13 mg, 0.09 mmol) in DMF (1 mL) was stirred at room temperature 15 hr. The next day, the reaction mixture was poured onto ice and the solid collected by filtration providing the title compound (34 mg, 100%).

Example 155b

N-{4-[2-(7-Methyl-[1,8]naphthyridin-4-ylamino)-4-(3-nitro-benzyloxy)-phenylsulfanyl]-phenyl}-acetamide

The product from Example 1d (18 mg, 0.085 mmol) was reacted in ethanol (1 mL) with the product from Example 155a (34 mg, 0.085 mmol) for 18 h following the procedure from Example 1g giving the crude title compound which was purified by HPLC with TFA providing the product as a trifluoroacetic acid salt (13 mg, 29%). $^1$H NMR (300 MHz, DMSO-$d_6$) δ ppm: 0.98 (t, J=7.35 Hz, 3H) 1.72-1.92 (m, 2H) 2.02 (s, 3H) 2.99 (t, J=7.54 Hz, 2H) 5.32 (s, 2H) 6.30 (d, J=6.99 Hz, 1H) 7.15 (d, J=8.46 Hz, 2H) 7.19-7.25 (m, 1H) 7.27 (d, J=2.57 Hz, 1H) 7.38 (d, J=8.82 Hz, 1H) 7.43 (d, J=8.46 Hz, 2H) 7.72 (t, J=7.91 Hz, 1H) 7.81 (d, J=8.82 Hz, 1H) 7.91 (d, J=7.72 Hz, 1H) 8.22 (d, J=8.82 Hz, 1H) 8.32 (d, J=7.35 Hz, 1H) 8.97 (d, J=8.82 Hz, 1H) 9.98 (s, 1H) 11.01 (s, 1H) 14.37 (s, 1H); MS (ESI+) m/z 580 (M+H)+.

Example 156

N-{4-[4-(4-Cyano-benzyloxy)-2-(7-propyl-[1,8]naphthyridin-4-ylamino)-phenylsulfanyl]-phenyl}-acetamide

Example 156a

N-{4-[2-Amino-4-(4-cyano-benzyloxy)-phenylsulfanyl]-phenyl}-acetamide

A mixture of the product from Example 232B (28 mg, 0.085 mmol), 4-cyanobenzyl bromide (19 mg, 0.096 mmol) and potassium carbonate (13 mg, 0.09 mmol) in DMF (1 mL) was stirred at room temperature 15 hr. The next day, the reaction mixture was poured onto ice and the solid collected by filtration providing the title compound (33 mg, 100%).

Example 156b

N-{4-[4-(4-Cyano-benzyloxy)-2-(7-methyl-[1,8]naphthyridin-4-ylamino)-phenylsulfanyl]-phenyl}-acetamide The product from Example 1d (18 mg, 0.085 mmol) was reacted in ethanol (1 ml) with the product from Example 156a (33 mg, 0.085 mmol) for 18 h following the procedure from Example 1g giving the crude title compound which was purified by HPLC with TFA providing the product as a trifluoroacetic acid salt (12 mg, 21%). $^1$H NMR (300 MHz, DMSO-$d_6$) δ ppm: 0.97 (t, J=7.35 Hz, 3H) 1.69-1.92 (m, 2H) 2.02 (s, 3H) 2.99 (t, J=7.54 Hz, 2H) 5.27 (s, 2H) 6.30 (d, J=6.99 Hz, 1H) 7.14 (d, J=8.82 Hz, 2H) 7.17-7.27 (m, 2H) 7.37 (d, J=8.46 Hz, 1H) 7.42 (d, J=8.82 Hz, 2H) 7.64 (d, J=8.09 Hz, 2H) 7.81 (d, J=8.82 Hz, 1H) 7.89 (d, J=8.46 Hz, 2H) 8.38 (d, J=6.99 Hz, 1H) 8.97 (d, J=8.82 Hz, 1H) 9.98 (s, 1H) 11.01 (s, 1H) 14.38 (s, 1H); MS (ESI+) m/z 560 (M+H)+.

Example 157

N-{4-[4-(2-Bromo-benzyloxy)-2-(7-propyl-[1,8]naphthyridin-4-ylamino)-phenylsulfanyl]-phenyl}-acetamide

Example 157a

N-{4-[2-Amino-4-(2-bromo-benzyloxy)-phenylsulfanyl]-phenyl}-acetamide

A mixture of the product from Example 232B (56 mg, 0.17 mmol), 2-bromobenzyl bromide (26 1, 0.17 mmol) and potassium carbonate (26 mg, 0.19 mmol) in DMF (1 mL) was stirred at room temperature 15 hr. The next day, the reaction mixture was poured onto ice and the solid collected by filtration providing the title compound (75 mg, 100%).

Example 157b

N-{4-[4-(2-Bromo-benzyloxy)-2-(7-propyl-[1,8]naphthyridin-4-ylamino)-phenylsulfanyl]-phenyl}-acetamide The product from Example 2g (35 mg, 0.17 mmol) was reacted in ethanol (1 mL) with the product from Example 157a (75 mg, 0.17 mmol) for 18 h following the procedure from Example 1g giving the crude title compound which was purified by HPLC with TFA providing the product as a trifluoroacetic acid salt (18 mg, 29%). $^1$H NMR (300 MHz, DMSO-$d_6$), δ ppm: 0.97 (t, J=7.35 Hz, 3H), 1.72-1.92 (m, 2H) 2.02 (s, 3H), 2.99 (t, J=7.35 Hz, 2H), 5.17 (s, 2H), 6.33 (d, J=6.99 Hz, 1H), 7.16 (d, J=8.46 Hz, 2H), 7.18-7.28 (m, 2H), 7.28-7.51 (m, 5H), 7.60 (dd, J=7.54, 1.65 Hz, 1H), 7.69 (d, J=6.99 Hz, 1H), 7.81 (d, J=8.82 Hz, 1H), 8.39 (d, J=6.99 Hz, 1H), 8.97 (d, J=8.82 Hz, 1H), 9.99 (s, 1H), 11.02 (s, 1H), 14.37 (s, 1H): MS (ESI+) m/z 613M+H)+.

Example 158

N-{4-[4-(4-Bromo-benzyloxy)-2-(7-propyl-[1,8]naphthyridin-4-ylamino)-phenylsulfanyl]-phenyl}-acetamide

Example 158a

N-{4-[2-Amino-4-(4-bromo-benzyloxy)-phenylsulfanyl]-phenyl}-acetamide

A mixture of the product from Example 232B (28 mg, 0.085 mmol), 4-bromobenzyl bromide (24 mg, 0.096 mmol) and potassium carbonate (13 mg, 0.09 mmol) in DMF (1 mL) was stirred at room temperature 15 hr. The next day, the reaction mixture was poured onto ice and the solid collected by filtration providing the title compound (37 mg, 100%).

Example 158b

N-{4-[4-(4-Bromo-benzyloxy)-2-(7-methyl-[1,8]naphthyridin-4-ylamino)-phenylsulfanyl]-phenyl}-acetamide The product from Example 1d (18 mg, 0.085 mmol) was reacted in ethanol (1 mL) with the product from Example 158a (37 mg, 0.085 mmol) for 18 h following the procedure from Example 1g giving the crude title compound which was purified by HPLC with TFA providing the product as a trifluoroacetic acid salt (26 mg, 42%). $^1$H NMR (300 MHz, DMSO-$d_6$) δ ppm: 0.97 (t, J=7.35 Hz, 3H) 1.67-1.92 (m, 2H) 2.02 (s, 3H) 2.99 (t, J=7.54 Hz, 2H) 5.14 (s, 2H) 6.30 (d, J=6.99 Hz, 1H) 7.14 (d, J=8.46 Hz, 2H) 7.16-7.26 (m, 2H) 7.31-7.49 (m, 5H) 7.53-7.66 (m, 2H) 7.80 (d, J=8.46 Hz, 1H) 8.37 (d, J=6.99 Hz, 1H) 8.97 (d, J=8.82 Hz, 1H) 9.97 (s, 1H) 11.00 (s, 1H) 14.37 (s, 1H); MS (ESI+) m/z 615 (M+H)+.

Example 159

N-{4-[4-Chloro-2-(7-methyl-[1,8]naphthyridin-4-ylamino)-phenoxy]-phenyl}-acetamide

Example 159a

N-[4-(4-Chloro-2-nitro-phenoxy)-phenyl]-acetamide

A mixture of 2-Fluoro-5-Chloro Nitro benzene (0.5 g, 2.85 mmol), 4-Acetamidophenol (0.45 g, 3.00 mmol) and cesium carbonate (0.98 g, 3.00 mmol) in DMSO (5 mL) was heated 6 hr at 90° C. The mixture was cooled, diluted with ethyl acetate (100 mL) and the organic layer washed with water, 20% aqueous potassium hydroxide solution and aqueous 10% sodium chloride solution, then dried over anhydrous sodium sulfate. The drying agent was filtered and the solvent concentrated under vacuum leaving the title compound as a tan solid (0.71 g, 81%).

Example 159b

N-[4-(2-Amino-4-chloro-phenoxy)-phenyl]-acetamide

The product from Example 159A was reduced with Fe and NH$_4$Cl following the procedure from Example 237E to give the title compound.

Example 159c

N-{4-[4-Chloro-2-(7-methyl-[1,8]naphthyridin-4-ylamino)-phenoxy]-phenyl}-acetamide The product form Example 1d (50 mg, 0.280 mmol) was reacted with the product from Example 159B (77 mg, 0.280 mmol) for 18 h following the procedure from Example 1g giving the crude title compound which was purified by HPLC with TFA providing the product as a trifluoroacetic acid (25 mg, 17%). $^1$H NMR (300 MHz, DMSO-d$_6$) δ ppm: 1.92-2.11 (m, 3H) 2.74 (s, 3H) 6.69 (d, J=6.99 Hz, 1H) 6.87-6.99 (m, 2H) 7.07 (d, J=9.19 Hz, 1H) 7.45-7.57 (m, 3H) 7.69 (d, J=2.57 Hz, 1H) 7.77 (d, J=8.82 Hz, 1H) 8.52 (d, J=6.99 Hz, 1H) 8.91 (d, J=8.46 Hz, 1H) 9.93 (s, 1H) 10.92 (s, 1H) 14.50 (s, 1H); MS (ESI+) m/z 419 (M+H)+, (ESI−) m/z 417 (M−H)−.

Example 160

[2-(3,4-Dimethyl-phenylsulfanyl)-5-methyl-phenyl]-(7-propyl-[1,8]naphthyridin-4-yl)-amine The product form Example 2g (70 mg, 0.338 mmol) was reacted with the product from Example 4c substituting 3,4-dimethylbenzenthiol for 4-mercaptophenol for 20 h following the procedure from Example 1g giving the crude title compound that was triturated with 4:1 ether/THF providing the title compound as a hydrochloride salt (135 mg, 88%). $^1$H NMR (300 MHz, DMSO-d$_6$) δ ppm: 0.99 (t, J=7.35 Hz, 3H) 1.82 (m, J=7.35 HZ, 2H) 1.93 (s, 3H) 2.05 (s, 3H) 2.36 (s, 3H) 2.99 (q, J=7.35 Hz, 2H) 6.20 (d, J=6.99 Hz, 1H) 6.94 (m, 3H) 7.32 (m, 2H) 7.34 (s, 1H) 7.80 (d, J=8.82 Hz, 1H) 8.33 (d, J=7.35 Hz, 1H) 8.97 (d, J=8.82 Hz, 1H) 10.96 (br s, 1H) 14.29 (br s, 1H); MS (ESI+) m/z 414 (M−Cl)+; (ESI−) m/z 412 (M−HCl)−.

Example 161

(7-Ethyl-[1,8]naphthyridin-4-yl)-[2-(4-methoxy-phenylsulfanyl)-5-methyl-phenyl]-amine The product from Example 3f (79 mg, 0.41 mmol) was reacted with the product from Example 50b (88 mg, 0.41 mmol) for 23 h giving following the procedure from Example 1g providing the crude title compound that was triturated with 3:1 ether/THF to give the title compound (162 mg, 90%). $^1$H NMR (300 MHz, DMSO-d$_6$) δ ppm: 1.37 (t, J=7.35 Hz, 3H) 2.34 (s, 3H) 3.05 (q, J=7.35 Hz, 2H) 3.72 (s, 3H) 6.27 (d, J=6.98 Hz, 1H) 6.85 (m, J=8.82 Hz, J=2.20 Hz, 2H) 7.10 (d, J=8.09 Hz, 1H) 7.23-7.32 (m, 4H) 7.83 (d, J=8.83 Hz, 1H) 8.41 (d, J=6.98 Hz, 1H) 9.11 (d, J=8.83 Hz, 1H) 11.16 (br s, 1H) 14.39 (br s, 1H); MS (ESI+) m/z 402 (M−Cl)+; (ESI−) m/z 400 (M−HCl)−.

Example 162

4-[4-Chloro-2-(7-propyl-[1,8]naphthyridin-4-ylamino)-phenoxy]-N-methyl-benzamide

Example 162a 4-(4-Chloro-2-nitro-phenoxy)-N-methyl-benzamide

The product from Example 126c (225 mg, 0.72 mmol) was reacted with methylamine (1.0 mL, 2.0 mmol) in THF (20 mL) at room temperature. The THF was removed under reduced pressure. The crude residue was purified by flash chromatography eluting with hexanes/ethyl acetate (30:70) to give the title compound (110 mg, 50%).

Example 162b 4-(2-Amino-4-chloro-phenoxy)-N-methyl-benzamide

The product from Example 162a (200 mg, 0.65 mmol) was reacted with SnCl$_2$ as described in Example 1f to give the title compound (100 mg, 55%).

Example 162c

4-[4-Chloro-2-(7-propyl-[1,8]naphthyridin-4-ylamino)-phenoxy]-N-methyl-benzamide The product from Example 2g (64 mg, 0.31 mmol) was reacted with Example 162b (85.0 mg, 0.31 mmol) in ethanol (5 mL) at 85° C. in a sealed tube for 18 h giving the crude title compound which was purified by HPLC with TFA providing the product as the trifluoroacetic acid (25 mg, 31%). $^1$H NMR (300 MHz, DMSO-d$_6$) δ ppm: 8.85 (d, J=8.82 Hz, 1H) 8.53 (d, J=7.35 Hz, 1H) 8.33 (d, J=4.17 Hz, 1H) 7.71-7.78 (m, 4H) 7.61 (dd, J=8.82, 2.57 Hz, 1H) 7.29 (d, 1H) 6.97 (d, J=8.82 Hz, 2H) 6.73 (d, J=6.99 Hz, 1H) 2.93-3.00 (t, 2H) 2.71 (d, 3H) 1.76-1.87 (m, 2H) 0.95 (t, J=7.35 Hz, 3H); MS (ESI+) m/z 561 (M+H)+.

Example 163

1-{4-[4-Chloro-2-(7-propyl-[1,8]naphthyridin-4-ylamino)-phenoxy]-phenyl}-ethanone oxime

Example 163a

1-[4-(2-Amino-4-chloro-phenoxy)-phenyl]-ethanone

The product form Example 164a (1.0 g, 3.4 mmol) was reacted with SnCl$_2$ as described in Example 1f to give the title compound (0.70 g, 78%).

Example 163b

1-[4-(2-Amino-4-chloro-phenoxy)-phenyl]-ethanone oxime

To the product from Example 163a (150 mg, 0.57 mmol) in ethanol (15 mL) was added hydroxylamine hydrochloride (41.8 mg, 0.60 mmol), and disopropylethylamine (82 mg, 0.63 mmol). The reaction was heated at 60° C. for 3 h. The reaction was cooled and poured into water. The solution was extracted with ethyl ether. The organic layer washed with water, brine, and dried over sodium sulfate, filtered and concentrated under vacuum giving the title compound (65 mg, 42%).

Example 163c

1-{4-[4-Chloro-2-(7-propyl-[1,8]naphthyridin-4-ylamino)-phenoxy]-phenyl}-ethanone oxime The product from Example 2g (45 mg, 0.217 mmol) was reacted with Example 163b (60.0 mg, 0.217 mmol) in ethanol (10 mL) at 85° C. in a sealed tube for 18 h giving the crude title compound which was purified by HPLC with TFA providing the product as the trifluoroacetic acid (25 mg, 31%). $^1$H NMR (500 MHz, DMSO-$d_6$) δ ppm: 0.98 (t, J=7.32, 2.44 Hz, 3H) 1.81-1.88 (m, 2H) 2.09 (s, 3H) 2.99 (t, 2H) 6.74 (d, J=7.32 Hz, 1H) 6.97 (d, J=9.28 Hz, 2H) 7.26 (d, J=9.28 Hz, 1H) 7.56 (d, J=8.79 Hz, 2H) 7.61 (dd, J=9.03, 2.69 Hz, 1H) 7.75 (d, J=2.44 Hz, 1H) 7.77-7.79 (m, 1H) 8.57 (d, J=6.84 Hz, 1H) 8.93 (d, J=8.30 Hz, 1H); MS (ESI+) m/z 447 (M+H)+.

Example 164

1-{4-[4-Chloro-2-(7-propyl-[1,8]naphthyridin-4-ylamino)-phenoxy]-phenyl}-ethanol

Example 164a

1-[4-(4-Chloro-2-nitro-phenoxy)-phenyl]-ethanone

1-Bromo-4-chloro-2-nitrobenzene (5 g, 21.2 mmol) was added to a solution of 4-hydroxyacetophenone (2.87 g, 21.1 mmol), and $K_2CO_3$ (7.28 g, 0.052 mol) in DMF (50 mL). The mixture was heated at 80° C. for 15 h. The reaction was poured into water. The aqueous phase was extracted with ethyl acetate (2×) and the combined phases were washed with water, brine, and dried over sodium sulfate, filtered and concentrated under vacuum giving the crude title compound. The crude product was purified by flash chromatography eluting with (hexanes/ethyl acetate 70:30) to give the title compound (4.8 g, 77.8%).

Example 164b

1-[4-(4-Chloro-2-nitro-phenoxy)-phenyl]-ethanol

The product from Example 164a (0.7 g, 2.4 mmol) was added to ethanol (30 mL) and sodium borohydride (115 g, 3.11 mmol) was added portion wise. The reaction was stirred for 1 h and then the excess sodium borohydride was destroyed by drop wise addition of acetic acid. The reaction was poured onto ice/water and extracted with ethyl acetate. The organic phase washed with water, brine, and dried over sodium sulfate, filtered and concentrated under vacuum giving the title compound (0.634 g, 90%).

Example 164c

1-[4-(2-Amino-4-chloro-phenoxy)-phenyl]-ethanol

The product form Example 164b (0.58 g, 1.9 mmol) was reduced with $SnCl_2$ as described in Example 1f to give the title compound (0.36 g, 70%).

Example 164d

Example 164 1-{4-[4-Chloro-2-(7-propyl-[1,8]naphthyridin-4-ylamino)-phenoxy]-phenyl}-ethanol The product from Example 2g (125 mg, 0.60 mmol) was reacted with Example 164c (160 mg, 0.60 mmol) in ethanol (10 mL) at 85° C. in a sealed tube for 18 h giving the crude title compound which was purified by HPLC with TFA providing the product as the trifluoroacetic acid (40 mg, 12%). $^1$H NMR (300 MHz, DMSO-$d_6$) δ ppm: 8.91 (d, J=8.82 Hz, 1H) 8.52 (d, J=6.99 Hz, 1H) 7.78 (d, J=8.82 Hz, 1H) 7.70 (d, J=2.57 Hz, 1H) 7.56 (dd, J=8.82, 2.57 Hz, 1H) 7.23 (d, J=8.46 Hz, 2H) 7.12 (d, J=8.82 Hz, 1H) 6.87-6.94 (m, 2H) 6.69 (d, J=6.99 Hz, 1H) 4.63 (q, J=6.25 Hz, 1H) 2.97 (t, J=7.54 Hz, 2H) 1.75-1.88 (m, J=7.35, 7.35, 7.35, 7.35 Hz, 2H) 1.19 (d, J=6.25 Hz, 3H) 0.95 (t, J=7.35 Hz, 3H); ); MS (ESI−) m/z 432 (M−H)−.

Example 165

Propane-2-sulfonic acid 4-[4-chloro-2-(7-methyl-[1,8]naphthyridin-4-ylamino)-phenoxy]-phenyl ester

Example 165a

4-Chloro-1-(4-methoxy-phenoxy)-2-nitro-benzene

1-Bromo-4-chloro-2-nitrobenzene (10 g, 42.2 mmol) was added to a solution of 4-methoxyphenol (5.3 g, 42.2 mmol), and $K_2CO_3$ (14.5 g, 105 mmol) in DMF (50 mL). The mixture was heated at 80° C. for 16 h. The reaction was poured into water. The aqueous phase was extracted with ethyl acetate and the combined phases were washed with water, brine, and dried over sodium sulfate, filtered and concentrated under vacuum giving the crude title compound. The crude product was purified by silica gel chromatography eluting with (hexanes/ethyl acetate 90:10) to give the title compound (8.0 g, 67%).

Example 165b 4-(4-Chloro-2-nitro-phenoxy)-phenol

To Example 165a (0.98 g, 3.5 mmol) in $CH_2Cl_2$ (20 mL) was added boron tribromide (0.95 g, 3.90 mmol). The reaction was stirred for 18 h. Methanol was added to destroy excess boron tribromide. The reaction was poured into water and extracted with methylene chloride. The phases were separated. The organic phase washed with water, brine, and dried over sodium sulfate, filtered and concentrated under vacuum giving the crude title compound. The crude product was purified by silica gel chromatography eluting with (hexanes/ethyl acetate 90:10) to give the title compound (0.57, 60%).

Example 165c 4-(2-Amino-4-chloro-phenoxy)-phenol

The product from Example 165b (1.0 g, 3.7 mmol) was reacted with $SnCl_2$ as described in Example 1f to give the title compound (0.7 g, 78%).

Example 165d

4-[4-Chloro-2-(7-methyl-[1,8]naphthyridin-4-ylamino)-phenoxy]-phenol

The product from Example 1d (80 mg, 4.5 mmol) was reacted with the product from Example 165c (106 mg, 4.5 mmol) in ethanol (15 mL) at 85° C. in a sealed tube for 18 h giving the crude title compound which was purified by HPLC with TFA providing the product as the trifluoroacetic acid (40 mg, 18%).

Example 165e

Propane-2-sulfonic acid 4-[4-chloro-2-(7-methyl-[1,8]naphthyridin-4-ylamino)-phenoxy]-phenyl ester The product from Example 165d (43 mg, 0.085 mmol) was reacted with isopropylsulfonyl chloride (14.5 mg, 0.102 mmol), N,N-diisopropylethylamine (33 mg, 0.255 mmol), and catalytic DMAP in $CH_2Cl_2$ for 18 h giving the crude title compound which was purified by HPLC with TFA providing the product as the trifluoroacetic acid (16 mg, 31%). $^1H$ NMR (300 MHz, DMSO-$d_6$) δ ppm: 1.38 (d, J=6.99 Hz, 6H) 2.73 (s, 3H) 3.54-3.65 (m, 1H) 6.69 (d, J=6.99 Hz, 1H) 7.01 (d, J=9.19 Hz, 2H) 7.20 (d, J=9.19 Hz, 2H) 7.27 (d, J=8.82 Hz, 1H) 7.60 (dd, J=8.82, 2.57 Hz, 1H) 7.70-7.75 (m, 2H) 8.51 (d, J=6.99 Hz, 1H) 8.81 (d, J=8.82 Hz, 1H); MS (ESI+) m/z 484 (M+H)+.

Example 166

4-[4-Chloro-2-(7-methyl-[1,8]naphthyridin-4-ylamino)-phenoxy]-N-methyl-benzamide The product from Example 1d (100 mg, 0.562 mmol) was reacted with Example 162b (155.0 mg, 0.562 mmol) in ethanol (5 mL) at 85° C. in a sealed tube for 18 h giving the crude title compound which was purified by HPLC with TFA providing the product as the trifluoroacetic acid (40 mg, 13%). $^1H$ NMR (300 MHz, DMSO-$d_6$) δ ppm: 8.82 (d, J=8.46 Hz, 1H) 8.53 (d, J=6.99 Hz, 1H) 8.33 (d, J=4.41 Hz, 1H) 7.71-7.78 (m, 4H) 7.61 (dd, J=8.82, 2.57 Hz, 1H) 7.30 (d, J=8.82 Hz, 1H) 6.96 (d, J=8.82 Hz, 2H) 6.72 (d, J=6.99 Hz, 1H) 2.71-2.77 (m, 6H); MS (ESI+) m/z 419 (M+H)+.

Example 167

[2-(4-Aminomethyl-phenoxy)-5-chloro-phenyl]-(7-methyl-[1,8]naphthyridin-4-yl)-amine

Example 167a 4-(4-Chloro-2-nitro-phenoxy)-benzonitrile

1-Bromo-4-chloro-2-nitrobenzene (10 g, 42.3 mmol) was added to a solution of 4-cyanophenol (5.0 g, 42.3 mmol), and $K_2CO_3$ (14.6 g, 0.10 mol) in DMF (50 mL). The mixture was heated at 80° C. for 15 hr. The reaction was poured into water. The aqueous phase was extracted with ethyl acetate and the combined organic phases were washed with water, brine, and dried over sodium sulfate. The organic phase was filtered and concentrated under vacuum. The residue was purified by flash chromatography eluting with (hexanes/ethyl acetate 4:1) to give the product (9.0 g, 77.8%).

Example 167b 4-(2-Amino-4-chloro-phenoxy)-benzonitrile

To the product from Example 116a (0.5 g, 1.8 mmol) in absolute ethanol (20 mL) was added $BiCl_3$ (0.86 g, 27.3 mmol), and $NaBH_4$ (0.55 g, 14.6 mmol) while cooling in an ice/water bath. The mixture was stirred for 20 h. The reaction was filtered through celite to remove bismuth. The solution was concentrated under reduced pressure. The residue was treated with 5% HCl for 15 h and than made basic with ammonium hydroxide (pH=10). The solution was extracted with ethyl acetate. The ethyl acetate layer washed with water, brine, and dried over sodium sulfate, filtered and concentrated under vacuum giving the title compound as a solid (0.34 g, 77%).

Example 167c

4-[4-Chloro-2-(7-methyl-[1,8]naphthyridin-4-ylamino)-phenoxy]-benzonitrile

The product from Example 1d (100 mg, 0.408 mmol) was reacted with Example 167b (100 mg, 0.408 mmol) in ethanol (10 mL) at 85° C. in a sealed tube for 18 h giving the crude title compound which was purified by HPLC with TFA providing the product as the trifluoroacetic acid (125 mg, 44%).

Example 167d

[2-(4-Aminomethyl-phenoxy)-5-chloro-phenyl]-(7-methyl-[1,8]naphthyridin-4-yl)-amine The product of Example 167c (88 mg, 0.175 mmol) was reacted with lithium aluminum hydride (13.3 mg, 0.351 mmol) in THF (5 mL) at 60° C. for 15 h giving the crude title compound which was purified by HPLC with TFA providing the product as the trifluoroacetic acid (15 mg, 14%). $^1H$ NMR (300 MHz, DMSO-$d_6$) δ ppm: 11.04 (s, 1H) 8.92 (d, J=8.82 Hz, 1H) 8.54 (d, J=6.99 Hz, 1H) 8.18 (s, 2H) 7.72-7.80 (m, 2H) 7.59 (dd, J=9.01, 2.76 Hz, 1H) 7.40 (d, J=8.82 Hz, 2H) 6.99-7.12 (m, 3H) 6.74 (d, J=6.99 Hz, 1H) 3.97 (q, J=5.52 Hz, 2H) 2.74 (s, 3H); MS (ESI+) m/z 391 (M+H)+.

Example 168

3-[4-Chloro-2-(7-propyl-[1,8]naphthyridin-4-ylamino)-phenoxy]-N,N-dimethyl-benzamide

Example 168a 3-(4-Chloro-2-nitro-phenoxy)-benzoic acid

To a solution of DMF (50 mL) was added 1-bromo-2-nitro-4-chloro-benzene (10.0 g, 42.2 mmol), 3-hydxoxybenzoic acid (5.8 g, 42.0 mmol), and $K_2CO_3$ (17.5 g, 0.13 mol). The solution was heated to 85° C. and stirred overnight. The reaction was poured into distill water and extracted with ethyl acetate. The combined organic layers were washed with distilled water, brine, and dried over $Na_2SO_4$, filtered and concentrated under vacuum giving a crude oil. This oil was purified by silica gel column chromatography eluting with CH$_2$Cl$_2$/MeOH (90:10) to give the title compound (7.4 gm, 60

Example 168b 3-(4-Chloro-2-nitro-phenoxy)-benzoyl chloride

The product from Example 168a (2.0 g. 6.8 mmol) was treated with oxalyl chloride (9.0 g, 13.6 mmol) and catalytic DMF at 60° C. for 5 h. The excess oxalyl chloride was removed under vacuum. The residue was chased with benzene to give the desired product (2.2 g, 94%).

Example 168c 3-(4-Chloro-2-nitro-phenoxy)-N,N-dimethyl-benzamide

To the product from Example 168b (2.0 g, 6.4 mmol) in THF (25 mL) was added dimethylamine (0.6 g, 13.3 mmol) and the reaction stirred for 16 h. The reaction was poured into water and extracted with ethyl acetate. The organic layer washed with 5% HCL, water, brine, and dried over sodium sulfate, filtered and concentrated under vacuum giving the title compound (1.9 g, 87%).

Example 168d 3-(2-Amino-4-chloro-phenoxy)-N,N-dimethyl-benzamide

The product from Example 168c (1.5 g, 4.6 mmol) was reacted with SnCl$_2$ as described in Example 1f to give the title compound (0.91 g, 68%).

Example 168e

3-[4-Chloro-2-(7-propyl-[1,8]naphthyridin-4-ylamino)-phenoxy]-N,N-dimethyl-benzamide The product from Example 2g (177 mg, 0.86 mmol) was reacted with the product from Example 168d (249 mg, 0.86 mmol) in ethanol (5 mL) at 85° C. in a sealed tube for 18 h giving the crude title compound which was purified by HPLC with TFA providing the product as the trifluoroacetic acid (100 mg, 20.2%). $^1$H NMR (500 MHz, DMSO-D6) δ ppm: 8.86 (d, J=8.79 Hz, 1H) 8.52 (d, J=6.84 Hz, 1H) 7.74 (d, 1H) 7.72 (d, 1H) 7.60 (dd, J=8.79, 2.93 Hz, 1H) 7.28-7.33 (m, 1H) 7.27 (d, 2H) 7.06 (d, J=7.81 Hz, 1H) 6.99 (dd, J=8.06, 2.69 Hz, 1H) 6.71 (d, J=6.84 Hz, 1H) 2.96 (t, 2H) 2.91 (s, 3H) 2.70 (s, 3H) 1.79-1.86 (m, 2H) 0.96 (t, J=7.49 Hz, 3H); MS (ESI+) m/z 461 (M+H)+.

Example 169

3-[4-Chloro-2-(7-propyl-[1,8]naphthyridin-4-ylamino)-phenoxy]-benzoic acid ethyl ester

Example 169a 3-(4-Chloro-2-nitro-phenoxy)-benzoic acid ethyl ester

To the product from Example 168a (2.0 g, 6.8 mmol) in ethanol (50 mL) with cooling, was bubbled HCl gas for 10 h. The excess ethanol was removed under vacuum. The solid was taken up in ethyl acetate. The organic layer washed with saturated NaHCO$_3$, water, brine, and dried over sodium sulfate, filtered and concentrated under vacuum giving the title compound (2.0 g, 91%).

Example 169b 3-(2-Amino-4-chloro-phenoxy)-benzoic acid ethyl ester

The product from Example 169a (1.5 g, 4.7 mmol) was reacted with SnCl$_2$ as described in Example 1f to give the title compound (1.0 g, 73%).

Example 169c

3-[4-Chloro-2-(7-propyl-[1,8]naphthyridin-4-ylamino)-phenoxy]-benzoic acid ethyl ester The product from Example 2g (113 mg, 0.55 mmol) was reacted with Example 169b (160 mg, 0.55 mmol) in ethanol (5 mL) at 85° C. in a sealed tube for 18 h giving the crude title compound which was purified by HPLC with TFA providing the product as the trifluoroacetic acid (200 mg, 63%). $^1$H NMR (300 MHz, DMSO-d$_6$) δ ppm: 8.76 (d, J=8.46 Hz, 1H) 8.54 (d, J=6.99 Hz, 1H) 7.74 (dd, J=5.70, 3.13 Hz, 2H) 7.58-7.65 (m, J=5.70, 5.70, 2.57 Hz, 2H) 7.29-7.43 (m, 3H) 7.20 (dd, J=7.72, 2.21 Hz, 1H) 6.68 (d, J=6.99 Hz, 1H) 4.23 (q, J=6.99 Hz, 2H) 2.96 (t, J=7.54 Hz, 2H) 1.77-1.85 (m, 2H) 1.29 (t, 3H) 0.95 (t, J=7.35 Hz, 3H); MS (ESI+) m/z 461 (M+H)+.

Example 170

1-{3-[4-Chloro-2-(7-propyl-[1,8]naphthyridin-4-ylamino)-phenoxy]-phenyl}-ethanol

Example 170a

1-[3-(4-Chloro-2-nitro-phenoxy)-phenyl]-ethanone

1-Bromo-4-chloro-2-nitrobenzene (10 g, 42.2 mmol) was added to a solution of 3-hydroxyacetophenone (5.5 g, 42.2 mmol), and K$_2$CO$_3$ (11.7 g, 84.6 mmol) in DMF (50 mL). The mixture was heated at 80° C. for 16 h. The reaction was poured into water. The aqueous phase was extracted with ethyl acetate (2×) and the combined phases were washed with water, brine, and dried over sodium sulfate, filtered and concentrated under vacuum giving the title compound. The crude product was purified by flash chromatography eluting with (hexanes/ethyl acetate 70:30) to give the title compound (8.6 g, 70%).

Example 170b

1-[3-(4-Chloro-2-nitro-phenoxy)-phenyl]-ethanol

To the product from Example 170a (1.8 g, 6.2 mmol) in ethanol (50 mL) was added sodium borohydride (0.32 g, 8.64 mmol) portion wise. The reaction was stirred at room temperature for 16 h. The excess sodium borohydride was destroyed by addition of acetic acid. The reaction was poured onto ice/water and extracted with ethyl acetate. The organic phase washed with water, brine, and dried over sodium sulfate, filtered and concentrated under vacuum giving the title compound. The crude residue was purified by silica gel chromatography eluting with (hexanes/ethyl acetate/methanol (75:15:5) to give the desired product (0.98 g, 54%).

Example 170c

1-[3-(2-Amino-4-chloro-phenoxy)-phenyl]-ethanol

The product from Example 170b (0.98 g, 3.3 mmol) was reduced with SnCl$_2$ as described in Example 1f to give the title compound (0.61 g, 70%).

Example 170d

1-{3-[4-Chloro-2-(7-propyl-[1,8]naphthyridin-4-ylamino)-phenoxy]-phenyl}-ethanol The product from Example 2g (140 mg, 0.68 mmol) was reacted with Example 170c (178 mg, 0.68 mmol) in ethanol (5 mL) at 85° C. in a sealed tube for 18 h giving the crude title compound which was purified by HPLC with TFA providing the product as the trifluoroacetic acid (110 mg, 30%). $^1$H NMR (300 MHz, DMSO-d$_6$) δ ppm: 8.86 (d, J=8.46 Hz, 1H) 8.53 (d, J=7.35 Hz, 1H) 7.77 (d, J=8.82 Hz, 1H) 7.71 (d, J=2.57 Hz, 1H) 7.58 (dd, J=8.82, 2.57 Hz, 1H) 7.17-7.22 (d, 2H) 7.01 (d, J=7.72 Hz, 1H) 6.87 (s, 1H) 6.78 (dd, J=7.54, 2.02 Hz, 1H) 6.68 (d, J=6.99 Hz, 1H) 4.55-4.62 (q, J=6.62 Hz, 1H) 2.96 (t, J=7.54 Hz, 2H) 1.76-1.86 (m, 2H) 1.12 (d, J=6.62 Hz, 3H) 0.95 (t, J=7.35 Hz, 3H); MS (ESI+) m/z 434 (M+H)+.

Example 171

3-[4-Chloro-2-(7-propyl-[1,8]naphthyridin-4-ylamino)-phenoxy]-benzamide

Example 171a 3-(4-Chloro-2-nitro-phenoxy)-benzamide

The product from Example 168b (1.8 g, 6.13 mmol) was added to cold NH$_4$OH (15 mL) and stirred for 1 h. The reaction was poured into water and extracted with ethyl acetate. The organic layer washed with water, brine, and dried over sodium sulfate, filtered and concentrated under vacuum to gave the title compound (1.66 g, 92%).

Example 171b 3-(2-Amino-4-chloro-phenoxy)-benzamide

The product from Example 171a (0.56 g, 1.9 mmol) was reacted with SnCl$_2$ following the procedure described in Example 1f to give the title compound (0.60 g, 83%).

Example 171c

3-[4-Chloro-2-(7-propyl-[1,8]naphthyridin-4-ylamino)-phenoxy]-benzamide

The product from Example 2g (140 mg, 0.68 mmol) was reacted with the product from Example 171b (178 mg, 0.68 mmol) in ethanol (5 mL) at 85° C. in a sealed tube for 18 h giving the crude title compound which was purified by HPLC with TFA providing the product as the trifluoroacetic acid (110 mg, 30%). $^1$H NMR (500 MHz, DMSO-d$_6$) δ ppm: 8.81 (d, J=8.54 Hz, 1H) 8.45 (d, J=7.32 Hz, 1H) 6.76-6.79 (m, 2H) 6.64 (d, J=8.54 Hz, 2H) 6.44 (s, 1H) 6.37 (t, J=7.93 Hz, 1H) 6.31 (d, J=8.54 Hz, 1H) 7.16 (dd, J=7.93, 2.44 Hz, 1H) 6.84 (d, J=7.32 Hz, 1H) 2.95 (t, J=7.32 Hz, 2H) 1.80 (m, 2H) 0.95 (t, J=7.32 Hz, 3H); MS (ESI+) m/z 433 (M+H)+.

Example 172

3-[4-Chloro-2-(7-propyl-[1,8]naphthyridin-4-ylamino)-phenoxy]-N-ethyl-benzamide

Example 172a

To the product from Example 168b (1.6 g, 5.1 mmol) in THF (25 mL) was added ethylamine (0.4 g, 8.0 mmol) and the reaction stirred for 16 h. The reaction was poured into water and extracted with ethyl acetate. The organic layer washed with 5% HCl, water, brine, and dried over sodium sulfate, filtered and concentrated under vacuum giving the title compound (1.4 g, 85%).

Example 172b 3-(2-Amino-4-chloro-phenoxy)-N-ethyl-benzamide

The product from Example 172a (0.90 g, 2.8 mmol) was reacted with SnCl$_2$ as described in Example 1f to give the title compound (0.65 g, 81%).

Example 172c

3-[4-Chloro-2-(7-propyl-[1,8]naphthyridin-4-ylamino)-phenoxy]-N-ethyl-benzamide

The product from Example 2g (128 mg, 0.62 mmol) was reacted with Example 172b (180 mg, 0.62 mmol) in ethanol (10 mL) at 85° C. in a sealed tube for 18 h giving the crude title compound which was purified by HPLC with TFA providing the product as the trifluoroacetic acid (70 mg, 20%). $^1$H NMR (500 MHz, DMSO-d$_6$) δ ppm: 8.84 (d, J=8.82 Hz, 1H) 8.53 (d, J=7.26 Hz, 1H) 8.39 (t, J=5.45 Hz, 1H) 7.72-7.76 (m, 2H) 7.60 (dd, J=8.82, 2.59 Hz, 1H) 7.54 (d, J=7.78 Hz, 1H) 7.32-7.36 (m, 2H) 7.25 (d, J=8.82 Hz, 1H) 7.09 (dd, J=7.78, 2.59 Hz, 1H) 6.70 (d, J=7.26 Hz, 1H) 3.19-3.25 (m, 2H) 2.96 (t, J=7.52 Hz, 2H) 1.79-1.84 (m, 2H) 1.08 (t, J=7.00 Hz, 3H) 0.95 (t, J=7.52 Hz, 3H); MS (ESI+) m/z 461 (M+H)+.

Example 173

3-[4-Chloro-2-(7-propyl-[1,8]naphthyridin-4-ylamino)-phenoxy]-N-phenyl-benzamide Example 173a To the product from Example 168b (0.81 g, 2.6 mmol) in THF (25 mL) was added benzyl amine (0.25 g, 2.6 mmol), and N,N-diisopropylethylamine (0.67 g, 5.2 mmol). The reaction was stirred for 16 h. The reaction was poured into water and extracted with ethyl acetate. The organic layer was washed with 5% HCl, water, brine, and dried over sodium sulfate, filtered and concentrated under vacuum giving the title compound (0.8 g, 85%).

Example 173b 3-(2-Amino-4-chloro-phenoxy)-N-phenyl-benzamide

The product from Example 173a (0.84 g, 2.3 mmol) was reacted with SnCl$_2$ as described in Example 1f to give the desired product (0.60 g, 77%).

Example 173c

3-[4-Chloro-2-(7-propyl-[1,8]naphthyridin-4-ylamino)-phenoxy]-N-phenyl-benzamide The product from Example 2g (131 mg, 0.63 mmol) was reacted with Example 173b (214 mg, 0.63 mmol) in ethanol (10 mL) at 85° C. in a sealed tube for 18 h giving the crude title compound which was purified by HPLC with TFA providing the product as the trifluoroacetic acid (125 mg, 31%). $^1$H NMR (300 MHz, DMSO-$d_6$) δ ppm: 10.11 (s, 1H) 8.80 (d, J=8.82 Hz, 1H) 8.53 (d, J=6.99 Hz, 1H) 7.67-7.75 (m, 4H) 7.58-7.67 (m, 2H) 7.40-7.46 (m, 2H) 7.30-7.37 (m, 3H) 7.08-7.18 (m, 2H) 6.70 (d, J=7.35 Hz, 1H) 2.92 (t, 2H) 1.73-1.82 (m, 2H) 0.92 (t, J=7.35 Hz, 3H); MS (ESI+) m/z 509 (M+H)+.

Example 174

3-[4-Chloro-2-(7-propyl-[1,8]naphthyridin-4-ylamino)-phenoxy]-N-(3-hydroxy-phenyl)-benzamide

Example 174a

N-[3-(tert-Butyl-dimethyl-silanyloxy)-phenyl]-3-(4-chloro-2-nitro-phenoxy)-benzamide To the product from Example 168b (1.3 g, 4.2 mmol) in THF (25 mL) was added 3-(tert-Butyl-dimethyl-silanyloxy)-phenylamine (1.0 g, 4.2 mmol), and N,N-diisopropylethylamine (0.67 g, 5.2 mmol). The reaction was stirred for 16 h. The reaction was poured into water and extracted with ethyl acetate. The organic layer washed with 5% HCL, water, brine, and dried over sodium sulfate, filtered and concentrated under vacuum giving the title compound (1.3 g, 85%).

Example 174b 3-(4-Chloro-2-nitro-phenoxy)-N-(3-hydroxy-phenyl)-benzamide

To the product from Example 174a (1.5 g, 3.0 mmol) in THF (25 mL) was added tetrabutylammonium fluoride (0.94 g, 3.6 mmol). The reaction was stirred for 16 h. The reaction was poured into water and extracted with ethyl acetate. The organic layer washed with water, brine, and dried over sodium sulfate, filtered and concentrated under vacuum giving the title compound (1.0 g, 86%).

Example 174c 3-(2-Amino-4-chloro-phenoxy)-N-(3-hydroxy-phenyl)-benzamide

The product from Example 174b (1.0 g, 2.6 mmol) was reacted with SnCl$_2$ as described in Example 1f to give the title compound (0.71 g, 84%).

Example 174d

3-[4-Chloro-2-(7-propyl-[1,8]naphthyridin-4-ylamino)-phenoxy]-N-(3-hydroxy-phenyl)-benzamide The product from Example 2g (144 mg, 0.70 mmol) was reacted with Example 174c (247 mg, 0.70 mmol) in ethanol (10 mL) at 85° C. in a sealed tube for 18 h giving the crude title compound which was purified by HPLC with TFA providing the product as the trifluoroacetic acid (123 mg, 27%). $^1$H NMR (300 MHz, DMSO-$d_6$) δ ppm: 10.02 (s, 1H) 9.45 (s, 1H) 8.81 (d, J=8.82 Hz, 1H) 8.53 (d, J=7.35 Hz, 1H) 7.74 (m, 2H) 7.69 (d, 2H) 7.61 (dd, 1H) 7.43 (s, 2H) 7.33 (s, 2H) 7.17 (m, 1H) 7.12 (s, 2H) 6.71 (d, J=6.99 Hz, 1H) 6.52 (m, 1H) 2.93 (t, J=7.54 Hz, 2H) 1.72-1.86 (m, 2H) 0.93 (t, J=7.35 Hz, 3H); MS (ESI+) m/z 525 (M+H)+.

Example 175

3-[4-Chloro-2-(7-propyl-[1,8]naphthyridin-4-ylamino)-phenoxy]-N-propyl-benzamide

Example 175a 3-(4-Chloro-2-nitro-phenoxy)-N-propyl-benzamide

To Example 168b (1.0 g, 3.2 mmol) in THF (25 mL) was added n-propylamine (0.38 g, 6.4 mmol) and the reaction stirred for 16 h. The reaction was poured into water and extracted with ethyl acetate. The organic layer washed with 5% HCl, water, brine, and dried over sodium sulfate, filtered and concentrated under vacuum giving the title compound (0.88 g, 82%).

Example 175b 3-(2-Amino-4-chloro-phenoxy)-N-propyl-benzamide

The product from Example 175a (0.88 g, 2.6 mmol) was reacted with SnCl$_2$ as described in Example 1f to give the title compound (0.61 g, 76%).

Example 175c

3-[4-Chloro-2-(7-propyl-[1,8]naphthyridin-4-ylamino)-phenoxy]-N-propyl-benzamide The product from Example 2g (110 mg, 0.53 mmol) was reacted with Example 175b (162 mg, 0.53 mmol) in ethanol (10 mL) at 85° C. in a sealed tube for 18 h giving the crude title compound which was purified by HPLC with TFA providing the product as the trifluoroacetic acid (50 mg, 16%). $^1$H NMR (300 MHz, DMSO-$d_6$) δ ppm: 0.85 (t, J=7.54 Hz, 3H) 0.95 (t, J=7.35 Hz, 3H) 1.42-1.54 (m, 2H) 1.75-1.88 (m, 2H) 2.96 (t, J=7.54 Hz, 2H) 3.15 (q, 2H) 6.69 (d, J=6.99 Hz, 1H) 7.09 (dd, J=7.54, 2.39 Hz, 1H) 7.26 (d, J=8.82 Hz, 1H) 7.32-7.36 (m, 2H) 7.54 (d, J=8.09 Hz, 1H) 7.60 (dd, J=8.82, 2.57 Hz, 1H) 7.72-7.77 (m, 2H) 8.39 (t, J=5.70 Hz, 1H) 8.52 (d, J=7.35 Hz, 1H) 8.82 (d, J=8.82 Hz, 1H); MS (ESI+) m/z 475 (M+H)+.

Example 176

{3-[4-Chloro-2-(7-methyl-[1,8]naphthyridin-4-ylamino)-phenoxy]-phenyl}-methanol

Example 176a 3-(4-Chloro-2-nitro-phenoxy)-benzaldehyde

To a solution of DMF (50 mL) was added 1-bromo-2-nitro-4-chloro-benzene (10.0 g, 42.2 mmol), 3-hydroxybenzaldehyde (5.2 g, 42.2 mmol), and K$_2$CO$_3$ (11.5 g, 84.6 mmol). The solution was heated to 85° C. and stirred overnight. The reaction was poured into distill water and extracted with ethyl acetate. The combined organic layers were washed with distilled water, brine, and dried over Na₂SO₄, filtered and concentrated under vacuum giving the crude title compound. This solid was purified by silica gel column chromatography eluting with hexanes/ethyl acetate (4:1) to give the title compound (4.4 gm, 41%).

Example 176b

[3-(4-Chloro-2-nitro-phenoxy)-phenyl]-methanol

To the product from Example 176a (2.0 g. 7.2 mmol) in ethanol (25 mL) was added sodium borohydride (0.32 g, 8.6 mmol). The reaction was stirred for 4 h. The excess sodium borohydride was destroyed by the addition of acetic acid. The reaction was poured into water and extracted with ethyl acetate. The organic layer was separated and washed with water, brine, and dried over sodium sulfate, filtered and concentrated under vacuum giving the title compound (1.9 g, 94%).

Example 176c

[3-(2-Amino-4-chloro-phenoxy)-phenyl]-methanol

The product from Example 176b (1.9 g, 6.8 mmol) was reacted with SnCl₂ as described in Example 1f to give the title compound (1.4 g, 83%).

Example 176d

{3-[4-Chloro-2-(7-methyl-[1,8]naphthyridin-4-ylamino)-phenoxy]-phenyl}-methanol

The product from Example 1d (110 mg, 0.62 mmol) was reacted with Example 176c (153 mg, 0.62 mmol) in ethanol (10 mL) at 85° C. in a sealed tube for 18 h giving the crude title compound which was purified by HPLC with TFA providing the product as the trifluoroacetic acid (50 mg, 16%). ¹H NMR (300 MHz, DMSO-d₆) δ ppm: 8.96-9.00 (m, 1H) 8.52 (d, J=6.99 Hz, 1H) 7.70-7.74 (m, 2H) 7.57 (dd, J=9.01, 2.39 Hz, 1H) 7.15-7.25 (m, 2H) 7.00 (d, J=7.72 Hz, 1H) 6.88 (s, 1H) 6.82 (dd, 1H) 6.68 (d, J=6.99 Hz, 1H) 4.37 (s, 2H) 2.74 (s, 3H); MS (ESI+) m/z 392 (M+H)+.

Example 177

1-{3-[4-Chloro-2-(7-methyl-[1,8]naphthyridin-4-ylamino)-phenoxy]-phenyl}-ethanol The product from Example 1d (125 mg, 0.70 mmol) was reacted with Example 170c (184 mg, 0.70 mmol) in ethanol (10 mL) at 85° C. in a sealed tube for 18 h giving the crude title compound which was purified by HPLC with TFA providing the product as the trifluoroacetic acid (59 mg, 16%). ¹H NMR (300 MHz, DMSO-d₆) δ ppm: 1.15 (d, J=6.25 Hz, 3H) 2.62 (s, 3H) 4.60 (q, J=6.37 Hz, 1H) 6.64 (d, J=7.35 Hz, 1H) 6.73-6.79 (m, 1H) 6.89 (s, 1H) 7.01 (d, J=7.72 Hz, 1H) 7.16 (t, J=8.09 Hz, 2H) 7.56 (dd, J=8.82, 2.57 Hz, 1H) 7.68-7.72 (m, 2H) 8.53 (d, J=6.99 Hz, 1H) 9.18 (d, J=8.46 Hz, 1H); MS (ESI+) m/z 406 (M+H)+.

Example 178

3-[4-Chloro-2-(7-methyl-[1,8]naphthyridin-4-ylamino)-phenoxy]-N-(3-hydroxy-phenyl)-benzamide The product from Example 1d (125 mg, 0.70 mmol) was reacted with Example 174c (237 mg, 0.70 mmol) in ethanol (10 mL) at 85° C. in a sealed tube for 18 h giving the crude title compound which was purified by HPLC with TFA providing the product as the trifluoroacetic acid (120 mg, 28%). ¹H NMR (300 MHz, DMSO-d₆) δ ppm: 10.00 (s, 1H) 8.81 (d, J=8.46 Hz, 1H) 8.55 (d, J=6.99 Hz, 1H) 7.72-7.75 (m, 2H) 7.65-7.71 (m, 1H) 7.62 (dd, J=9.01, 2.76 Hz, 1H) 7.42 (s, 2H) 7.30 (d, J=8.82 Hz, 1H) 7.26 (s, 1H) 7.16 (dd, J=7.35, 2.57 Hz, 1H) 7.10 (d, J=5.52 Hz, 2H) 6.71 (d, J=6.99 Hz, 1H) 6.48-6.55 (m, 1H) 2.69 (s, 3H); MS (ESI-) m/z 495 (M-H)-.

Example 179

[5-Chloro-2-(4-isopropyl-phenoxy)-phenyl]-(7-methyl-[1,8]naphthyridin-4-yl)-amine Example 179a 4-Chloro-1-(4-isopropyl-phenoxy)-2-nitro-benzene 1-Bromo-4-chloro-2-nitrobenzene (12 g, 50.7 mmol) was added to a solution of 4-isopropylphenol (8.3 g, 60.8 mmol), and K₂CO₃ (14.0 g, 101 mmol) in DMF (70 mL). The mixture was heated at 80° C. for 16 h. The reaction was poured into water. The aqueous phase was extracted with ethyl acetate and the combined phases were washed with water, brine, and dried over sodium sulfate, filtered and concentrated under vacuum giving the crude title compound. The crude product was purified by silica gel chromatography eluting with (hexanes/ethyl acetate 90:10) to give the title compound (13.5 g, 92%).

Example 179b

5-Chloro-2-(4-isopropyl-phenoxy)-phenylamine

The product from Example 179a (13.7 g, 46.8 mmol) was reacted with SnCl₂ as described in Example 1f to give the title compound (10.3 g, 84.4%).

Example 179

[5-Chloro-2-(4-isopropyl-phenoxy)-phenyl]-(7-methyl-[1,8]naphthyridin-4-yl)-amine The product from Example 1d (120 mg, 0.67 mmol) was reacted with Example 179b (175 mg, 0.67 mmol) in ethanol (10 mL) at 85° C. in a sealed tube for 18 h giving the crude title compound which was purified by HPLC with TFA providing the product as the trifluoroacetic acid (60 mg, 17%). ¹H NMR (300 MHz, DMSO-d₆) δ ppm: 8.86 (d, J=8.46 Hz, 1H) 8.51 (d, J=7.35 Hz, 1H) 7.75 (d, 1H) 7.70 (d, 1H) 7.55 (dd, J=7.87, 1H) 7.14 (m, 3H) 6.89 (d, J=8.64, 2.76 Hz, 2H) 6.67 (d, J=6.98 Hz, 1H) 2.79 (m, 1H) 2.73 (s, 3H) 1.09 (d, J=6.99 Hz, 6H); MS (ESI+) m/z 404 (M+H)+.

Example 180

{2-[3-(1-Azido-ethyl)-phenoxy]-5-chloro-phenyl}-(7-propyl-[1,8]naphthyridin-4-yl)-amine Example 180a 2-[3-(1-Azido-ethyl)-phenoxy]-5-chloro-phenylamine To the product from Example 170c in toluene (25 mL) was added diphenylphosphoryl azide (1.72 g, 6.23 mmol), followed by 1,8-diazabicyclo[4.3.0]undec-7-ene (0.95 g, 6.2 mmol). The mixture was stirred at 25° C. for 18 h. The reaction was poured into water and extracted with ethyl acetate. The combined organic layers were washed with water, brine, dried over sodium sulfate, filtered and concentrated under vacuum giving the title compound. The crude product was purified on silica gel, eluting with hexanes/ethyl acetate/methanol (85:17:3) to provide the title compound (700 mg, 50%).

Example 180b

{2-[3-(1-Azido-ethyl)-phenoxy]-5-chloro-phenyl}-(7-propyl-[1,8]naphthyridin-4-yl)-amine The product from Example 2g (130 mg, 0.63 mmol) was reacted with Example 180a (181 mg, 0.63 mmol) in ethanol (10 mL) at 85° C. in a sealed tube for 18 h giving the crude title compound which was purified by HPLC with TFA providing the product as the trifluoroacetic acid (11 mg, 11%). $^1$H NMR (500 MHz, DMSO-d$_6$) δ ppm: 0.91 (t, J=7.42 Hz, 3H) 1.23 (d, J=6.59 Hz, 3H) 1.74-1.81 (m, 2H) 2.91 (t, J=7.69 Hz, 2H) 4.61 (q, J=6.59 Hz, 1H) 6.67 (d, J=7.14 Hz, 1H) 6.82 (s, 2H) 6.99 (d, J=7.14 Hz, 1H) 7.21 (d, J=8.79 Hz, 2H) 7.52 (dd, J=8.79 Hz, 1H) 7.64 (d, J=2.75 Hz, 1H) 7.65 (d, J=8.79 Hz, 1H) 8.48 (d, J=6.04 Hz, 1H) 8.81 (d, J=8.79 Hz, 1H); MS (ESI+) m/z 459 (M+H)+.

Example 181

3-[4-Fluoro-2-(7-propyl-[1,8]naphthyridin-4-ylamino)-phenoxy]-N,N-dimethyl-benzamide

Example 181a 3-(4-Fluoro-2-nitro-phenoxy)-benzoic acid ethyl ester 2,5-Difluoronitrobenzene (5.0 g, 31.4 mmol), ethyl 3-hydroxybenzoate (5.2 g, 31.4 mmol), and K$_2$CO$_3$ (8.7 g, 62.8 mmol) were added to DMF (50 mL). The solution was heated to 85° C. and stirred for 16 h. The reaction was cooled. The reaction was poured into distilled water and extracted with ethyl acetate. The combined organic layers were washed with distilled water, brine, and dried over sodium sulfate, filtered and concentrated under vacuum giving the crude title compound. The crude product was purified by silica gel column chromatography eluting with hexanes/ethyl acetate (90:10) to give the title compound (7.0 g, 73%).

Example 181b 3-(4-Fluoro-2-nitro-phenoxy)-benzoic acid

The product from Example 181a (3.0 g, 9.8 mmol) was added to a solution of THF/H$_2$O (5:1). Lithium hydroxide monohydrate (0.82 g, 19.5 mmol) was added in one portion. The solution was warmed to 60° C. for 2 h. The reaction was cooled. Distilled water was added. The pH was adjusted to 4.0 with 10% HCl. The mixture was extracted with ethyl acetate. The combined organic phases were washed with water, saturated NaHCO$_3$, water, brine, and dried over sodium sulfate, filtered and concentrated under vacuum giving the title compound (2.65 g, 97%).

Example 181c 3-(4-Fluoro-2-nitro-phenoxy)-benzoyl chloride

The product from Example 181b (1.6 g, 5.6 mmol) was treated with oxalyl chloride (0.86 g, 6.7 mmol) and catalytic DMF at room temperature for 6 h. The excess oxalyl chloride was removed under vacuum. The residue was chased with benzene to \give the title compound (1.66 g, 94%).

Example 181d 3-(4-Fluoro-2-nitro-phenoxy)-N,N-dimethyl-benzamide

The product from Example 181c (1.0 g, 3.4 mmol) was added to THF (25 mL) and dimethylamine (0.31 g, g, 6.8 mmol) was added. The reaction was stirred at room temperature for 16 h. The reaction was poured onto ice/water and extracted with ethyl acetate. The organic phase was washed with 5% HCl, water, brine, and dried over sodium sulfate, filtered and concentrated under vacuum giving the title compound (0.90 g, 87%).

Example 181e 3-(2-Amino-4-fluoro-phenoxy)-N,N-dimethyl-benzamide

The product from Example 181d (1.1 g, 3.4 mmol) was reduced with SnCl$_2$ as described in Example 1f to give the title compound (0.88 g, 88%).

Example 181f

3-[4-Fluoro-2-(7-propyl-[1,8]naphthyridin-4-ylamino)-phenoxy]-N,N-dimethyl-benzamide The product from Example 2g (110 mg, 0.53 mmol) was reacted with Example 181e (154 mg, 0.53 mmol) in ethanol (10 mL) at 85° C. in a sealed tube for 18 h giving the crude title compound which was purified by HPLC with TFA providing the product as the trifluoroacetic acid (65 mg, 20%). $^1$H NMR (300 MHz, DMSO-d$_6$) δ ppm: 0.95 (t, J=7.35 Hz, 3H) 1.74-1.87 (m, 2H) 2.66 (s, 3H) 2.90 (s, 3H) 2.96 (t, 2H) 6.71 (d, J=6.99 Hz, 1H) 6.82 (s, 1H) 6.91 (dd, J=8.27, 1.65 Hz, 1H) 7.01 (d, J=7.72 Hz, 1H) 7.27 (t, J=7.91 Hz, 1H) 7.36-7.45 (m, 2H) 7.56 (dd, J=8.82, 2.94 Hz, 1H) 7.75 (d, J=8.46 Hz, 1H) 8.52 (d, J=6.99 Hz, 1H) 8.83 (d, J=8.46 Hz, 1H); MS (ESI+) m/z 445 (M+H)+.

Example 182

{2-[4-(1-Amino-ethyl)-phenoxy]-5-chloro-phenyl}-(7-methyl-[1,8]naphthyridin-4-yl)-amine

Example 182a

1-[4-(1-Azido-ethyl)-phenoxy]-4-chloro-2-nitro-benzene

To the product from Example 164b (0.30 g, 1.0 mmol) in toluene (20 mL) was added diphenylphosphoryl azide (0.36 g 6.26 mmol), followed by 1,8-diazabicyclo[4.3.0]undec-7-ene (0.19 g, 1.3 mmol). The mixture is stirred at 25° C. for 18 h. The reaction was poured into water and extracted with ethyl acetate. The combined organic layers are washed with 5% HCl, sat. NaCl (1×), dried over sodium sulfate, filtered and concentrated under vacuum giving the crude title compound. The crude product was purified by silica gel chromatography, eluting with hexanes/ethyl acetate/methanol (85:15:5) to provide the title compound (300 mg, 94%).

Example 182b

{1-[4-(4-Chloro-2-nitro-phenoxy)-phenyl]-ethyl}-carbamic acid benzyl ester

To the product form Example 182a (1.3 g 4.1 mmol) in THF (20 mL) was added trimethylphosphine (4.7 g, 5.4 mmol). After the mixture was stirred for 30 minute at room temperature, the reaction mixture was treated with benzyl chloroformate (0.85 g, 5.0 mmol) and stirred 18 h. The reaction is poured into 0.1 M potassium phosphate buffer, pH=7.0 and extracted with methylene chloride. The organic layer washed with water, brine, dried over sodium sulfate, filtered and concentrated under vacuum giving the crude title compound. The residue is treated with cold ethyl ether. The resulting white precipitate was collected to give the title compound (1.9 g, 74

Example 182c

{1-[4-(2-Amino-4-chloro-phenoxy)-phenyl]-ethyl}-carbamic acid benzyl ester

The product from Example 182b (1.0 g, 2.34 mmol) was reacted with $SnCl_2$ as described in Example 237E to give the title compound (0.75 g, 80%).

Example 182d

{2-[4-(1-Amino-ethyl)-phenoxy]-5-chloro-phenyl}-(7-methyl-[1,8]naphthyridin-4-yl)-amine The product from Example 1d (120 mg, 0.67 mmol) was reacted with Example 182b (266 mg, 0.67 mmol) in ethanol (10 mL) at 85° C. in a sealed tube for 18 h. The ethanol was then removed under vacuum. The crude compound was then treated with excess 48% HBr for 10 h. The excess HBr was removed under vacuum and the crude residue purified by HPLC with TFA providing the title compound as the trifluoroacetic acid (15 mg, 17%). $^1$H NMR (300 MHz, DMSO-$d_6$) δ ppm: 1.38 (d, J=6.62 Hz, 3H) 2.74 (s, 3H) 4.36 (q, 1H) 6.72 (d, J=6.99 Hz, 1H) 7.03 (d, J=8.82 Hz, 2H) 7.13 (d, J=8.82 Hz, 1H) 7.39 (d, J=8.82 Hz, 2H) 7.59 (dd, J=8.82, 2.57 Hz, 1H) 7.72-7.78 (m, 2H) 8.24 (s, 2H) 8.53 (d, J=7.35 Hz, 1H) 8.88 (d, J=8.82 Hz, 1H); MS (ESI−) m/z 403 (M−H)−.

Example 183

N-{4-[2-(7-Methyl-[1,8]naphthyridin-4-ylamino)-4-trifluoromethyl-phenylsulfanyl]-phenyl}-acetamide

Example 183a

N-[4-(2-Nitro-4-trifluoromethyl-phenylsulfanyl)-phenyl]-acetamide

The title compound was prepared from 1-Chloro-2-nitro-4-trifluoromethyl-benzene (250 mg, 1.10 mmol), N-(4-Mercapto-phenyl)-acetamide (185 mg, 1.10 mmol), and $K_2CO_3$ (268 mg, 1.94 mmol) heated in DMF at 100° C. for 16 hrs. Reaction mixture was then cooled to room temperature and diluted with water and extracted with ethyl acetate (350 mg, 88%).

Example 183b

N-[4-(2-Amino-4-trifluoromethyl-phenylsulfanyl)-phenyl]-acetamide

The product from Example 183a (350 mg, 0.985 mmol), and Pt(IV)O$_2$ (4 mg, 0.2 mmol) were placed in a 50 ml round bottom flask and dissolved in 1 ml of EtOH and 1 ml of THF. Reaction mixture placed under vacuum and backfilled with $H_2$ using a balloon. Balloon was left on overnight and the next day the reaction mixture was purged and backfilled with $N_2$, filtered and concentrated under vacuum giving the title compound (260 mg, 80%).

Example 183c

N-{4-[2-(7-Methyl-[1,8]naphthyridin-4-ylamino)-4-trifluoromethyl-phenylsulfanyl]-phenyl}-acetamide The product form Example 1d (50 mg, 0.280 mmol) was reacted with the product from Example 183b (91 mg, 0.280 mmol) for 18 h following the procedure from Example 1g giving the crude title compound which was purified by HPLC with TFA providing the product as a trifluoroacetic acid (18 mg, 16%). $^1$H NMR (300 MHz, DMSO-$d_6$) δ ppm: 2.07 (s, 3H), 2.78 (s, 3 H), 6.43 (d, J=6.99 Hz, 1H), 7.09-7.15 (m, 1H), 7.44 (d, J=8.46 Hz, 2H), 7.68 (d, J=8.46 Hz, 2H), 7.78 (dd, J=8.64, 1.65 Hz, 1H), 7.84 (d, J=8.82 Hz, 1H), 7.92 (d, J=1.84 Hz, 1H), 8.52 (d, J=7.35 Hz, 1H), 9.00 (d, J=8.46 Hz, 1H), 10.19 (s, 1H), 11.12 (s, 1H); MS (ESI+) m/z 469 (M+H−TFA)+; (ESI−) m/z 467 (M−H−TFA)−.

Example 184

[5-Methyl-2-(1H-[1,2,4]triazol-3-ylsulfanyl)-phenyl]-(7-propyl-[1,8]naphthyridin-4-yl)-amine

Example 184a

5-Methyl-2-(1H-[1,2,4]triazol-3-ylsulfanyl)-phenylamine

The title compound was prepared from 1-Chloro-4-methyl-2-nitro-benzene (3.00 g, 17.5 mmol), 1H-[1,2,4]Triazole-3-thiol (1.94 g, 19.2 mmol), and $K_2CO_3$ (4.22 g, 30.6 mmol) heated in DMF at 100° C. for 16 hrs. Reaction mixture was then cooled to room temperature and diluted with water and extracted with ethyl acetate. Dried over $Na_2SO_4$, filtered and concentrated under vacuum giving the title compound (1.1 g, 26%).

Example 184b

5-Methyl-2-(1H-[1,2,4]triazol-3-ylsulfanyl)-phenylamine

The product form Example 184a was reduced with $SnCl_2$ following the procedure from Example 1f to give the title compound.

Example 184c

[5-Methyl-2-(1H-[1,2,4]triazol-3-ylsulfanyl)-phenyl]-(7-propyl-[1,8]naphthyridin-4-yl)-amine The product form Example 2g (60 mg, 0.290 mmol) was reacted with the product from Example 184b (60 mg, 0.290 mmol) for 18 h following the procedure from Example 1g giving the crude title compound which was purified by HPLC with TFA providing the product as a trifluoroacetic acid (17 mg, 16%). $^1$H NMR (300 MHz, DMSO-d$_6$) δ ppm: 0.98 (t, J=7.35 Hz, 3H), 1.78-1.91 (m, 2H), 2.38 (s, 3H), 2.99 (t, 2H), 6.33 (d, J=6.99 Hz, 1H), 7.29-7.39 (m, 2H), 7.46 (d, J=8.09 Hz, 1H), 7.83 (d, J=8.82 Hz, 1H), 8.44 (d, J=6.99 Hz, 1H), 9.00 (d, J=8.46 Hz, 1H), 11.07 (s, 1H), 14.16-14.55 (m, 2H); MS (ESI+) m/z 377 (M+H−TFA)+; (ESI−) m/z 375 (M−H−TFA)−.

Example 185

[2-(2-Amino-phenylsulfanyl)-5-methyl-phenyl]-(7-propyl-[1,8]naphthyridin-4-yl)-amine Example 185a 2-(4-Methyl-2-nitro-phenylsulfanyl)-phenylamine The title compound was prepared from 1-Chloro-4-methyl-2-nitro-benzene (3.00 g, 17.5 mmol), 2-Amino-benzenethiol (2.41 g, 19.23 mmol), and K$_2$CO$_3$ (4.22 g, 30.6 mmol) heated in DMF at 100° C. for 16 hrs. Reaction mixture was then cooled to room temperature and diluted with water and extracted with ethyl acetate. (0.990 g, 21%)

Example 185b

N-[2-(4-Methyl-2-nitro-phenylsulfanyl)-phenyl]-acetamide

The material from Example 185a (0.990 3.80 mmol) was dissolved in CH$_2$Cl$_2$ to which acetyl chloride (0.328 g, 4.183 mmol) was added. Reaction mixture stirred at room temperature for 1 hr at which time the title compound was collected by filtration (910 mg, 79%).

Example 185c

N-[2-(2-Amino-4-methyl-phenylsulfanyl)-phenyl]-acetamide

The product form Example 185b was reduced with SnCl$_2$ following the procedure from Example 1f to give the title compound.

Example 185d

N-{2-[4-Methyl-2-(7-propyl-[1,8]naphthyridin-4-ylamino)-phenylsulfanyl]-phenyl}-acetamide The product form Example 2g (150 mg, 0.726 mmol) was reacted with the product from Example 185c (198 mg, 0.726 mmol) for 42 h following the procedure from Example 1g giving the crude title compound which was purified by HPLC with TFA providing the product as a trifluoroacetic acid (150 mg, 46%)

Example 185e

[2-(2-Amino-phenylsulfanyl)-5-methyl-phenyl]-(7-propyl-[1,8]naphthyridin-4-yl)-amine The product from Example 185d was dissolved in 50% HCl:H2O and heated to 100° C. for 1 hr. Reaction mixture was then cooled to room temperature, made basic with 2N NaOH, and extracted with CH$_2$Cl$_2$. Dried over Na$_2$SO$_4$, filtered and concentrated under vacuum giving the crude title compound. Purified by HPLC with TFA providing the product as a trifluoroacetic acid (87 mg, 64%). $^1$H NMR (300 MHz, DMSO-d$_6$) δ ppm: 0.98 (t, J=7.35 Hz, 3H), 1.79-1.92 (m, J=7.43, 7.43, 7.43, 7.43, 7.43 Hz, 2H), 2.32 (s, 3H), 3.00 (t, J=7.54 Hz, 2H), 6.34 (d, J=6.99 Hz, 1H), 6.49 (t, J=7.54 Hz, 1H), 6.68 (d, J=6.99 Hz, 1H), 6.92 (d, J=8.09 Hz, 1H), 7.05-7.13 (m, 1H), 7.15-7.20 (m, 1H), 7.24 (d, J=8.46 Hz, 1H), 7.28 (s, 1H), 7.84 (d, J=8.82 Hz, 1H), 8.42 (d, J=6.99 Hz, 1H), 9.06 (d, J=8.82 Hz, 1H); MS (ESI+) m/z 401 (M+H−TFA)+; (ESI−) m/z 399 (M−H−TFA)−.

Example 186

N-{3-[3-Methyl-5-(7-propyl-[1,8]naphthyridin-4-ylamino)-phenylsulfanyl]-phenyl}-acetamide Example 186a 3-Amino-benzenethiol copper 3-Amino-benzenethiol (2.00 g, 15.98 mmol) was treated to the conditions described in 187a to provide the title compound (3.67 g, 100%).

Example 186b 3-(3-Methyl-5-nitro-phenylsulfanyl)-phenylamine

The title compound was prepared following the procedure from Example 187d using Example 187c (400 mg, 1.85 mmol), and Example 186a (348 mg, 1.85 mmol) providing the title compound (300 mg, 62%).

Example 186c

N-[3-(3-Methyl-5-nitro-phenylsulfanyl)-phenyl]-acetamide

The title compound was prepared following the procedure of Example 185b using Example 186b (115 mg, 0.442 mmol) and acetyl chloride (52 mg, 0.663 mmol) to provide (130 mg, 97%).

Example 186d

N-[3-(3-Amino-5-methyl-phenylsulfanyl)-phenyl]-acetamide

The title compound was obtained following the procedure from Example 183b using the product from Example 186c (130 mg, 0.430 mmol), and PtO$_2$ (2 mg, 0.009 mmol) to provide (73 mg, 62%).

Example 186f

N-{3-[3-Methyl-5-(7-propyl-[1,8]naphthyridin-4-ylamino)-phenylsulfanyl]-phenyl}-acetamide The product form Example 2g (70 mg, 0.338 mmol) was reacted with the product from Example 186d (73 mg, 0.338 mmol) for 16 h following the procedure from Example 1g giving the crude title compound which was purified by HPLC with TFA providing the product as a trifluoroacetic acid (14 mg, 10%). $^1$H NMR (300 MHz, DMSO-d$_6$) δ ppm: 0.96 (t, J=7.35 Hz, 3H), 1.75-1.89 (m, 2H), 2.03 (s, 3H), 2.36 (s, 3H), 2.98 (t, J=7.54 Hz, 2H), 6.85 (d, J=7.35 Hz, 1H), 7.06-7.14 (m, 2H), 7.22 (s, 2H), 7.35 (t, J=7.91 Hz, 1H), 7.47 (d, 1H), 7.76-7.82 (m, 2H), 8.45 (d, J=7.35 Hz, 1H), 8.98 (d, J=8.82 Hz, 1H), 10.07 (s, 1H), 10.97 (s, 1H); MS (ESI+) m/z 443 (M+H−TFA)+; (ESI−) m/z 441 (M−H−TFA)−.

Example 187

N-{4-[3-Methyl-5-(7-propyl-[1,8]naphthyridin-4-ylamino)-phenylsulfanyl]-phenyl}-acetamide Example 187a N-(4-Mercapto-phenyl)-acetamide copper N-(4-Mercapto-phenyl)-acetamide (1.00 g, 5.98 mmol) and $Cu_2O$ (385 mg, 27.0 mmol) were dissolved in EtOH and heated to reflux for 24 hrs. At this time the reaction mixture was cooled to room temperature and the title compound was collected by filtration (1.374 g, 100%).

Example 187b

2-Bromo-4-methyl-6-nitro-phenylamine

The title compound was prepared by dissolving 4-Methyl-2-nitro-phenylamine (20.0 g, 131 mmol) in 200 mL of HOAc. The reaction mixture was then heated to 100° C. until reaction mixture was homogeneous. At this point the reaction mixture was cooled to room temperature and $Br_2$ (25.21 g, 157 mmol) was added drop wise over the course of 10 minutes. An orange solid formed, and upon completion of the addition the reaction mixture was diluted with water and the title compound collected by filtration (29 g, 96%).

Example 187c

1-Bromo-3-methyl-5-nitro-benzene

The title compound was prepared from Example 187b (10.0 g, 43.2 mmol) dissolved in 60 mL of MeOH and 8 mL of $H_2SO_4$ (concd). This mixture was heated to 85° C. at which time $NaNO_2$ (7.466 g, 108.2 mmol) was added portion wise so that the reaction mixture did not bubble over. After complete addition the reaction mixture was allowed to stir at 85° C. for another 30 minutes. Reaction mixture was then cooled to room temperature, diluted with water and extracted with $CH_2Cl_2$. Dried over $Na_2SO_4$, filtered and concentrated under vacuum giving the title compound (8.00 g, 85%).

Example 187d

N-[4-(3-Methyl-5-nitro-phenylsulfanyl)-phenyl]-acetamide

The title compound was prepared from Example 187c (400 mg, 1.85 mmol), Example 187a (425 mg, 1.852 mmol), 10 mL of quinoline, and 2 mL of pyridine heated to 170° C. for 22 hrs. At this time the reaction mixture was cooled to room temperature and quenched with 30% HCl and extracted with ether and dried over $Na_2SO_4$, filtered and concentrated under vacuum giving the title compound. Purified by column chromatography on silica gel eluting with 30% ethyl acetate in hexanes (280 mg, 50%).

Example 187e

N-[4-(3-Amino-5-methyl-phenylsulfanyl)-phenyl]-acetamide

The title compound was achieved using the procedure from Example 183b using the product from Example 187d (280 mg, 0.926 mmol), and $PtO_2$ (2 mg, 0.009 mmol) providing the tile compound (240 mg, 95%).

Example 187f

N-{4-[3-Methyl-5-(7-propyl-[1,8]naphthyridin-4-ylamino)-phenylsulfanyl]-phenyl}-acetamide The product form Example 2g (70 mg, 0.338 mmol) was reacted with the product from Example 187e (198 mg, 0.726 mmol) for 16 h following the procedure from Example 1g giving the crude title compound which was purified by HPLC with TFA providing the product as a trifluoroacetic acid (5 mg, 4%). $^1$H NMR (300 MHz, DMSO-$d_6$) δ ppm: 0.96 (t, J=7.35 Hz, 3H), 1.76-1.89 (m, 2H), 2.05 (s, 3H), 2.33 (s, 3H), 2.97 (t, J=7.54 Hz, 2H), 6.80 (d, J=7.35 Hz, 1H), 6.95 (s, 1H), 7.10 (d, J=15.44 Hz, 2H), 7.46 (d, J=8.82 Hz, 2H), 7.67 (d, J=8.82 Hz, 2H), 7.78 (d, J=8.82 Hz, 1H), 8.46 (d, J=6.99 Hz, 1H), 8.96 (d, J=8.46 Hz, 1H), 10.14 (s, 1H), 10.90 (s, 1H); MS (ESI+) m/z 443 (M+H−TFA)+; (ESI−) m/z 441 (M−H−TFA)−.

Example 188

[3-(4-Amino-phenylsulfanyl)-5-methyl-phenyl]-(7-propyl-[1,8]naphthyridin-4-yl)-amine The product from Example 187 (60 mg, 0.136 mmol) was treated to the conditions of Example 185 to provide the title compound (10 mg, 18%). $^1$H NMR (300 MHz, DMSO-$d_6$) δ ppm: 0.96 (t, J=7.35 Hz, 3H), 1.76-1.89 (m, 2H), 2.30 (s, 3H), 2.97 (t, J=7.54 Hz, 2H), 6.65 (d, J=8.46 Hz, 2H), 6.74-6.83 (m, 2H), 6.94 (s, 1H), 7.03 (s, 1H), 7.23 (d, J=8.46 Hz, 2H), 7.78 (d, J=8.82 Hz, 1H), 8.45 (d, J=6.99 Hz, 1H), 8.96 (d, J=8.46 Hz, 1H), 10.90 (s, 1H); MS (ESI+) m/z 401 (M+H−TFA)+.

Example 189

(3-Benzyloxy-phenyl)-(7-propyl-[1,8]naphthyridin-4-yl)-amine

Example 189a

1-Benzyloxy-3-nitro-benzene

3-Nitro-phenol (1.00 g, 7.189 mmol) was treated with benzyl bromide (1.352 g, 7.91 mmol), and $K_2CO_3$ (1.242 g, 8.986 mmol) in DMF. The reaction mixture was heated to 100° C. for 1 hr at which time the reaction mixture was cooled to room temperature, diluted with water and extracted with ethyl

Example 189b

3-Benzyloxy-phenylamine

The title compound was obtained following the procedure from Example 183b using the product from Example 189a (1.600 g, 6.98 mmol), and $PtO_2$ (15 mg, 0.070 mmol) providing (1.00 g, 72%).

Example 189c (3-Benzyloxy-phenyl)-(7-propyl-[1,8]naphthyridin-4-yl)-amine

The product form Example 2g (30 mg, 0.145 mmol) was reacted with the product from Example 189b (29 mg, 0.145 mmol) for 16 h following the procedure from Example 1g giving the crude title compound which was purified by HPLC with TFA providing the product as a trifluoroacetic acid (27 mg, 50%). $^1$H NMR (300 MHz, DMSO-$d_6$) δ ppm: 0.97 (t, J=7.35 Hz, 3H), 1.77-1.90 (m, J=7.35 Hz, 2H), 2.99 (t, J=7.35 Hz, 2H), 5.17 (s, 2H), 6.80 (d, J=6.99 Hz, 1H), 7.06 (dd, J=8.46, 1.10 Hz, 1H), 7.09-7.15 (m, J=3.68 Hz, 2H), 7.37-7.51 (m, 5H), 7.82 (d, J=8.82 Hz, 1H), 8.46 (d, J=7.35 Hz, 1H), 9.03 (d, J=8.82 Hz, 1H), 11.00 (s, 1H); MS (ESI+) m/z 370 (M+H−TFA)+; (ESI−) m/z 368 (M−H−TFA)−.

Example 190

[3-(4-Bromo-benzyloxy)-phenyl]-(7-methyl-[1,8]naphthyridin-4-yl)-amine

Example 190a

1-(4-Bromo-benzyloxy)-3-nitro-benzene

3-Nitro-phenol (1.00 g, 7.189 mmol) was treated with 4-bromo-benzyl bromide (1.976 g, 7.90 mmol) following the procedure of 189a providing the tile compound (2.1 g, 97%).

Example 190b

3-(4-Bromo-benzyloxy)-phenylamine

The title compound was prepared by reduction of the product from Example 190a with $SnCl_2$ following the procedure from Example 1f.

Example 190c

[3-(4-Bromo-benzyloxy)-phenyl]-(7-methyl-[1,8]naphthyridin-4-yl)-amine

The product form Example 1d (50 mg, 0.316 mmol) was reacted with the product from Example 190b (88 mg, 0.316 mmol) for 16 h following the procedure from Example 1g giving the crude title compound which was purified by HPLC with TFA providing the product as a trifluoroacetic acid (80 mg, 60%). $^1$H NMR (300 MHz, DMSO-$d_6$) δ ppm: 2.75 (s, 3H), 5.16 (s, 2H), 6.81 (d, J=7.35 Hz, 1H), 7.04-7.14 (m, 3H), 7.43 (d, J=8.46 Hz, 2H), 7.51 (t, J=8.09 Hz, 1H), 7.62 (d, J=8.46 Hz, 2H), 7.79 (d, J=8.82 Hz, 1H), 8.47 (d, J=6.99 Hz, 1H), 9.00 (d, J=8.46 Hz, 1H), 10.98 (s, 1H); MS (ESI+) m/z 422 (M+H−TFA)+; (ESI−) m/z 419 (M−H−TFA)−.

Example 191

N-{4-[3-Fluoro-5-(7-propyl-[1,8]naphthyridin-4-ylamino)-phenoxy]-phenyl}-acetamide

Example 191a

N-[4-(3-Fluoro-5-nitro-phenoxy)-phenyl]-acetamide

To a solution of N-(4-hydroxyphenyl)acetamide (1.00 g, 6.5 mmol) in DMSO (12 ml) was added 1M t-BuOK/THF solution (7.13 ml, 7.13 mmol) dropwise at room temperature and the mixture was stirred at room temperature for 30 minutes under $N_2$ flow. 1,3-Difluoro-5-nitrobenzene (0.89 ml, 7.8 mmol) was added at room temperature, and then the mixture was stirred at room temperature for 2 hours and at 50° C. for 2 hours under a $N_2$ flow. The reaction mixture was cooled to room temperature, diluted with $H_2O$, and then extracted with EtOAc. The extract washed with $H_2O$ and brine, dried over $MgSO_4$, filtered and concentrated under vacuum giving the title compound as a pale brown solid, which was purified by washing with i-$Pr_2O$ to give the desired product as slightly brown crystal (1.73 g, 92%).

Example 191b

N-[4-(3-Amino-5-fluoro-phenoxy)-phenyl]-acetamide

The product from Example 191a was reduced with Fe and $NH_4Cl$ following the procedure from Example 237E to give the title compound.

Example 191c

N-{4-[3-Fluoro-5-(7-propyl-[1,8]naphthyridin-4-ylamino)-phenoxy]-phenyl}-acetamide The product from Example 3f (150 mg, 0.84 mmol) was reacted with the product from Example 191b (190 mg, 0.84 mmol) for 6 h following the procedure from Example 1g giving the crude title compound which was purified by silica gel column chromatography eluting with 50:1 $CH_2Cl_2$/MeOH providing the title compound (210 mg, 68%). $^1$H NMR (300 MHz, DMSO-$d_6$) δ ppm: 2.40 (s, 3H), 2.68 (s, 3H), 6.62 (d, J=6.9 Hz, 1H), 6.98 (t, J=7.3 Hz, 1H), 7.19 (t, J=7.3 Hz, 2H), 7.36 (s, 1H), 7.38 (d, J=8.3 Hz, 1H), 7.52 (d, J=7.3 Hz, 2H), 7.67 (d, J=8.8 Hz, 1H), 7.78 (d, J=8.3 Hz, 1H), 8.40 (d, J=6.9 Hz, 1H), 8.94 (d, J=8.8 Hz, 1H); MS (ESI+) m/z 369 (M+H)+, (ESI−) m/z 367 (M−H)−.

Example 192

4-[3-Fluoro-5-(7-methyl-[1,8]naphthyridin-4-ylamino)-phenoxy]-N,N-dimethyl-benzamide

Example 192a

4-(3-Fluoro-5-nitro-phenoxy)-benzoic acid methyl ester

To a solution of 4-hydroxybenzoic acid methyl ester (3.00 g, 19.5 mmol) in DMSO (30 ml) was added t-BuOK (2.56 g, 21.5 mmol) at room temperature and the mixture was stirred at room temperature for 30 minutes under $N_2$ flow. 1,3-Difluoro-5-nitrobenzene (2.34 ml, 20.5 mmol) was added dropwise at room temperature. The mixture was heated at 90° C. for 2 hours under $N_2$ flow. The reaction mixture was cooled to room temperature, diluted with H$_2$O, and then extracted with EtOAc. The extract washed with H$_2$O and brine, dried over MgSO$_4$, filtered and concentrated under vacuum giving the title compound as a dark brown oil, which was crystallized with i-Pr$_2$O. The crystals were collected by filtration to give the desired product as pale yellow crystal (1.92 g, 40%). The filtrate gave additional product (1.46 g, 30%) as pale yellow crystal by silica gel column chromatography eluting with 4:1 EtOAc/hexane.

Example 192b

4-(3-Fluoro-5-nitro-phenoxy)-benzoic acid

The product from Example 192a (3.30 g, 11.3 mmol) and 2N NaOH (11.3 ml, 22.7 mmol) in MeOH (33 ml) was refluxed for 30 minutes, and then evaporated. The residue was dissolved in H$_2$O and acidified to pH 2 with 10% HCl under stirring. The precipitate was collected by filtration, washed with H$_2$O, and dried in vacuum overnight to give the title compound as a slightly yellow crystal (3.03 g, 96%).

Example 192c

4-(3-Fluoro-5-nitro-phenoxy)-N,N-dimethyl-benzamide

The product from Example 192b (1.00 g, 3.6 mmol) and SOCl$_2$ (3.97 ml, 54.1 mmol) was refluxed for 1 hour. Excess SOCl$_2$ was removed under reduced pressure to give the corresponding acid chloride as pale brown oil. To a solution of 2N Me$_2$NH/THF solution (18.0 ml, 36.1 mmol) was added a solution of the obtained acid chloride in THF (10 ml) dropwise at 5° C. over 15 minutes. The mixture was stirred at 5° C. for 1 hour and then evaporated. The residue was treated with H$_2$O and the resulting solid was collected by filtration. The solid washed with H$_2$O and dried in vacuum to give the title compound as a pale yellow crystal (1.09 g, 99%).

Example 192d

4-(3-Amino-5-fluoro-phenoxy)-benzoic acid methyl ester

The product from Example 192c was reduced with Fe and NH$_4$Cl following the procedure from Example 237E to give the title compound.

Example 192e

4-[3-Fluoro-5-(7-methyl-[1,8]naphthyridin-4-ylamino)-phenoxy]-N,N-dimethyl-benzamide The product from Example 1d (80 mg, 0.45 mmol) was reacted with the product from Example 192d (130 mg, 0.45 mmol) for 20 h following the procedure from Example 1g giving the crude title compound which was purified by trituration with EtOAc providing the product (150 mg, 79%). $^1$H NMR (300 MHz, DMSO-d$_6$) δ ppm: 2.77 (s, 3H), 2.98 (br-s, 6H), 6.97-7.08 (m, 2H), 7.12 (d, J=7.0 Hz, 1H), 7.18-7.25 (m, 1H), 7.23 (d, J=8.8 Hz, 2H), 7.53 (d, J=8.8 Hz, 2H), 7.79 (d, J=8.5 Hz, 1H), 8.59 (d, J=7.0 Hz, 1H), 9.00 (d, J=8.5 Hz, 1H); MS (ESI+) m/z 417 (M+H)+, (ESI−) m/z 415 (M−H)−.

Example 193

4-[3-Chloro-5-(7-propyl-[1,8]naphthyridin-4-ylamino)-phenoxy]-phenol

Example 193a

1-Chloro-3,5-dinitro-benzene

To a mixture of the t-BuONO (5.41 ml, 41.0 mmol) and CuCl$_2$ (4.41 g, 32.8 mmol) in CH$_3$CN (100 ml) was added 3,5-dinitroaniline (5.00 g, 27.3 mmol) slowly at 58-60° C. After the addition, the mixture was heated at 65° C. for 30 minutes, and then evaporated. The residue was diluted with EtOAc 200 ml, washed with 20% HCl, 10% NaHCO$_3$ and brine. The organic layer was dried over MgSO$_4$ filtered and concentrated under vacuum giving the title compound which was purified by silica gel column chromatography eluting with 10:1 EtOAc/hexane to give the title product as pale yellow crystal (4.60 g, 83%).

Example 193b

4-(3-Chloro-5-nitro-phenoxy)-phenol

The product from Example 193a (1.00 g, 5.0 mmol), hydroquinone (0.50 g, 4.5 mmol) and K$_2$CO$_3$ (0.78 g, 5.6 mmol) in DMF (10 ml) was heated at 110° C. for 3.5 hours. The reaction mixture was cooled to room temperature, diluted with H$_2$O and then extracted with EtOAc. The extract was washed with H$_2$O and brine, dried over MgSO$_4$, filtered and concentrated under vacuum giving the title compound. The residue was treated with i-Pr$_2$O and insoluble material was filtered off. The filtrate was evaporated and purified by silica gel column chromatography eluting with 5:2 EtOAc/hexane to give the title product as pale yellow oil (0.51 g, 43%).

Example 193c

4-(3-Amino-5-chloro-phenoxy)-phenol

The product from Example 192c was reduced with Fe and NH$_4$Cl following the procedure from Example 237E to give the title compound.

Example 193d

4-[3-Chloro-5-(7-propyl-[1,8]naphthyridin-4-ylamino)-phenoxy]-phenol

The product from Example 2g (100 mg, 0.48 mmol) was reacted with the product from Example 134c (140 mg, 0.48 mmol) for 17 h following the procedure from Example 1g giving the crude title compound which was purified by trituration with EtOAc providing the title compound (140 mg, 71%). $^1$H NMR (300 MHz, DMSO-d$_6$) δ ppm: 0.98 (t, J=7.4 Hz, 3H), 1.86 (sextet, J=7.4 Hz, 2H), 3.00 (t, J=7.4 Hz, 2H), 6.87 (d, J=8.8 Hz, 2H), 6.95 (d, J=1.8 Hz, 1H), 6.99-7.07 (m, 2H), 7.04 (d, J=8.8 Hz, 2H), 7.28 (d, J=1.8 Hz, 1H), 7.81 (d, J=8.8 Hz, 1H), 8.57 (d, J=7.0 Hz, 1H), 9.02 (d, J=8.8 Hz, 1H); MS (ESI+) m/z 406, 408 (M+H)+, (ESI−) m/z 404, 406 (M−H)−.

Example 194

N-{4-[3-Chloro-5-(7-propyl-[1,8]naphthyridin-4-ylamino)-phenoxy]-phenyl}-acetamide

Example 194a

N-[4-(3-Chloro-5-nitro-phenoxy)-phenyl]-acetamide

The product from Example 193a (1.06 g, 5.2 mmol), N-(4-hydroxyphenyl)acetamide (0.70 g, 4.5 mmol) and $K_2CO_3$ (0.79 g, 5.7 mmol) in DMF (14 ml) was heated at 110° C. for 6 hours. The reaction mixture was cooled to room temperature, diluted with $H_2O$ and then extracted with EtOAc. The extract washed with $H_2O$ and brine, dried over $MgSO_4$, filtered and concentrated under vacuum giving the crude title compound as a pale brown crystal, which was purified by washing with i-$Pr_2O$ to give the desired product as pale brown crystal (1.28 g, 92%).

Example 194b

N-[4-(3-Amino-5-chloro-phenoxy)-phenyl]-acetamide

The product from Example 192c was reduced with Fe and $NH_4Cl$ following the procedure from Example 237E to give the title compound.

Example 194c

N-{4-[3-Chloro-5-(7-propyl-[1,8]naphthyridin-4-ylamino)-phenoxy]-phenyl}-acetamide The product from Example 2g (100 mg, 0.48 mmol) was reacted with the product from Example 194bc (130 mg, 0.48 mmol) for 22 h following the procedure from Example 1g giving the crude title compound which was purified by trituration with EtOAc providing the product (110 mg, 51%). $^1$H NMR (300 MHz, DMSO-$d_6$) δ ppm: 1.00 (t, J=7.0 Hz, 3H), 1.87 (sextet, J=7.0 Hz, 2H), 2.08 (s, 3H), 3.01 (t, J=7.0 Hz, 2H), 7.01 (s, 1H), 7.07 (d, J=7.0 Hz, 1H), 7.07 (s, 1H), 7.14 (d, J=7.2 Hz, 2H), 7.30 (s, 1H), 7.72 (d, J=7.2 Hz, 2H), 7.76 (d, J=8.7 Hz, 1H), 8.55 (d, J=7.0 Hz, 1H), 9.03 (d, J=8.7 Hz, 1H); MS (ESI+) m/z 447, 449 (M+H)+, (ESI−) m/z 445, 447 (M−H)−.

Example 195

4-[3-Chloro-5-(7-methyl-[1,8]naphthyridin-4-ylamino)-phenoxymethyl]-N-methyl-benzamide

Example 195a 4-(3-Chloro-5-nitro-phenoxymethyl)-benzoic acid methyl ester

The product from Example 13a (2.50 g, 12.3 mmol), 4-hydroxymethylbenzoic acid methyl ester (2.30 g, 13.6 mmol) and $K_2CO_3$ (2.14 g, 15.4 mmol) in DMF (50 mL) was heated at 110° C. for 16 hours. The reaction mixture was cooled to room temperature and diluted with $H_2O$. The precipitate was collected by filtration and washed with $H_2O$ and i-$Pr_2O$ to give the title compound as a pale brown crystal (2.54 g).

Example 195b 4-(3-Chloro-5-nitro-phenoxymethyl)-benzoic acid

The product from Example 195a (2.50 g, 13.5 mmol) and 2N NaOH (7.77 ml, 15.5 mmol) in MeOH (25 mL) was refluxed for 1 hour, and then evaporated. The residue was dissolved in $H_2O$ and acidified to pH 2 with 10% HCl under stirring. The precipitate was collected by filtration, washed with $H_2O$, and dried in vacuum overnight to give the title compound as pale brown crystal (2.30 g, 62%).

Example 195c 4-(3-Chloro-5-nitro-phenoxymethyl)-N-methyl-benzamide

The product from Example 195b (0.70 g, 2.3 mmol) and $SOCl_2$ (2.50 ml, 34.1 mmol) was refluxed for 1 hour. Excess $SOCl_2$ was removed under reduced pressure to give the corresponding acid chloride as pale brown solid. To a solution of 2N $MeNH_2$/THF solution (11.4 mL, 22.8 mmol) was added a solution of the acid chloride obtained above in THF (7 mL) dropwise at 5° C. The mixture was stirred at 5° C. for 1 hour and then evaporated. The residue was treated with $H_2O$, acidified to pH 2 with 10% HCl, and then the resulting solid was collected by filtration. The solid washed with $H_2O$ and i-$Pr_2O$, and dried in vacuum to give the title compound as a pale brown crystal (0.69 g, 95%).

Example 195d 4-(3-Amino-5-chloro-phenoxymethyl)-N-methyl-benzamide

The product from Example 195c was reduced with Fe and $NH_4Cl$ following the procedure from Example 237E to give the title compound.

Example 195e

4-[3-Chloro-5-(7-methyl-[1,8]naphthyridin-4-ylamino)-phenoxymethyl]-N-methyl-benzamide The product from Example 1d (100 mg, 0.56 mmol) was reacted with the product from Example 195d (160 mg, 0.56 mmol) for 15 h following the procedure from Example 1g giving the crude title compound which was purified by trituration with EtOAc providing the product (240 mg, 99%). $^1$H NMR (300 MHz, DMSO-$d_6$) δ ppm: 2.75 (s, 3H), 2.79 (d, J=4.4 Hz, 3H), 5.26 (s, 2H), 6.90 (d, J=7.0 Hz, 1H), 7.14 (br-t, J=1.9 Hz, 1H), 7.18 (br-t, J=1.9 Hz, 1H), 7.20 (br-t, J=1.9 Hz, 1H), 7.53 (d, J=8.5 Hz, 2H), 7.77 (d, J=8.8 Hz, 1H), 7.87 (d, J=8.5 Hz, 2H), 8.47 (br-s, 1H), 8.50 (d, J=7.0 Hz, 1H), 9.08 (d, J=8.8 Hz, 1H), 11.08 (br-s, 1H); MS (ESI+) m/z 433, 435 (M+H)+, (ESI−) m/z 431, 433 (M−H)−.

Example 196

[3-(4-Bromo-benzyloxy)-5-chloro-phenyl]-(7-propyl-[1,8]naphthyridin-4-yl)-amine

Example 196a 1-(4-Bromo-benzyloxy)-3-chloro-5-nitro-benzene

The product from Example 193a (0.75 g, 3.7 mmol), 4-bromobenzyl alcohol (0.77 g, 4.1 mmol) and $K_2CO_3$ (0.64 g, 4.6 mmol) in DMF (15 ml) was heated at 110° C. for 23 hours. The reaction mixture was cooled to room temperature, diluted with $H_2O$, acidified to pH 2 with 10% HCl, and then extracted with EtOAc. The extract washed with $H_2O$ and brine, dried over $MgSO_4$, filtered and concentrated under vacuum giving the crude title compound. The residue was treated with 50 mL of a mixture of n-hexane and EtOAc (3:1) and silica gel. After being stirred at room temperature for 30 minutes, the mixture was filtered through celite. The filtrate was evaporated and the resulting solid washed with i-Pr$_2$O to give the title compound as a pale yellow crystals (0.70 g).

Example 196b 3-(4-Bromo-benzyloxy)-5-chloro-phenylamine

The product from Example 196a was reduced with Fe and NH$_4$Cl following the procedure from Example 237E to give the title compound.

Example 196c

[3-(4-Bromo-benzyloxy)-5-chloro-phenyl]-(7-propyl-[1,8]naphthyridin-4-yl)-amine

The product from Example 2g (100 mg, 0.39 mmol) was reacted with the product from Example 196b (120 mg, 0.39 mmol) for 22 h following the procedure from Example 1g giving the crude title compound which was purified by trituration with EtOAc providing the title compound (1990 mg, 100%). $^1$H NMR (300 MHz, DMSO-d$_6$) δ ppm: 0.96 (t, J=7.4 Hz, 3H), 1.83 (sextet, J=7.4 Hz, 2H), 2.97 (t, J=7.4 Hz, 2H), 5.18 (s, 2H), 6.91 (d, J=6.7 Hz, 1H), 7.05-7.17 (m, 3H), 7.43 (d, J=8.4 Hz, 2H), 7.63 (d, J=8.4 Hz, 2H), 7.73 (d, J=8.5 Hz, 1H), 8.51 (d, J=6.7 Hz, 1H), 9.05 (d, J=8.5 Hz, 1H); MS (ESI+) m/z 482, 484, 486 (M+H)+, (ESI−) m/z 480, 482, 484 (M−H)−.

Example 197

N-{4-[3-Chloro-5-(7-methyl-[1,8]naphthyridin-4-ylamino)-phenoxymethyl]-phenyl}-acetamide Example 197a Acetic acid 4-acetylamino-benzyl ester To a solution of 4-hydroxymethylaniline (2.00 g, 15.9 mmol) in pyridine (20 ml) was added Ac$_2$O (3.76 mL, 39.8 mmol) dropwise over 5 minutes at room temperature and the mixture was allowed to stir for 1 hour and then evaporated. The residue was diluted with H$_2$O (20 mL) and acidified to pH 3 with conc. HCl at 5° C. under stirring. The resulting crystal was collected by filtration, washed with small amount of cold H$_2$O and dried at room temperature in vacuum overnight to give the title compound as a pale brown crystal (2.90 g, 88%).

Example 197b

N-(4-Hydroxymethyl-phenyl)-acetamide

The product from Example 197a (4.00 g, 19.3 mmol) in THF (40 mL) was added aqueous LiOH solution (0.91 g, 21.2 mmol dropwise at room temperature over 10 minutes. The mixture was allowed to stir at room temperature for 27 hours and then evaporated. The aqueous residue was diluted with H$_2$O, adjusted to pH 4 with 10% HCl, and then extracted with EtOAc. The extract was washed with brine, dried over MgSO$_4$, filtered and concentrated under vacuum giving the title compound which was purified by washing with cold EtOAc to give the title compound as colorless crystals (2.92 g, 92%).

Example 197c

N-[4-(3-Chloro-5-nitro-phenoxymethyl)-phenyl]-acetamide

The product from Example 193a (1.00 g, 4.9 mmol), and the product from Example 197b (0.90 g, 5.4 mmol) and K$_2$CO$_3$ (0.86 g, 6.2 mmol) in DMF (20 mL) were heated at 100° C. for 10 hours. The reaction mixture was cooled to room temperature, diluted with H$_2$O. The resulting solid was collected by filtration, washed with H$_2$O, and dried in vacuum to give brown crystal, which was purified by silica gel column chromatography eluting with 5:2 EtOAc/hexane to give the title compound as a dark orange crystal (0.47 g, 30%).

Example 197d

N-[4-(3-Amino-5-chloro-phenoxymethyl)-phenyl]-acetamide

The product from Example 196c was reduced with Fe and NH$_4$Cl following the procedure from Example 237E to give the title compound.

Example 197e

N-{4-[3-Chloro-5-(7-methyl-[1,8]naphthyridin-4-ylamino)-phenoxymethyl]-phenyl}-acetamide The product from Example 1d (70 mg, 0.39 mmol) was reacted with the product from Example 197d (110 mg, 0.39 mmol) for 23 h following the procedure from Example 1g giving the crude title compound which was purified by trituration with EtOAc providing the title compound (140 mg, 82%). $^1$H NMR (300 MHz, DMSO-d$_6$) δ ppm: 2.05 (s, 3H), 2.75 (s, 3H), 5.11 (s, 2H), 6.90 (d, J=7.0 Hz, 1H), 7.12 (br-s, 1H), 7.17 (br-s, 2H), 7.38 (d, J=8.5 Hz, 2H), 7.61 (d, J=8.5 Hz, 2H), 7.78 (d, J=8.9 Hz, 1H), 8.50 (d, J=7.0 Hz, 1H), 9.12 (d, J=8.9 Hz, 1H), 10.06 (s, 1H), 11.17 (br-s, 1H); MS (ESI+) m/z 433, 435 (M+H)+, (ESI−) m/z 431, 433 (M−H)−.

Example 198

(5-Methyl-2-phenoxy-phenyl)-(7-propyl-[1,8]naphthyridin-4-yl)-amine

The product from Example 2g (82 mg, 0.40 mmol) was reacted with the product from Example 42b (88 mg, 0.40 mmol) for 24 h following the procedure from Example 1g giving the crude title compound that was triturated with 3:1 ether/THF providing the title compound as a hydrochloride salt (159 mg, 93%). $^1$H NMR (300 MHz, DMSO-d$_6$) δ ppm: 0.95 (t, J=7.73 Hz, 3H) 1.82 (q, J=7.72 Hz, 2H) 2.97 (dd, J=7.73 Hz, 2H) 6.68 (d, J=6.99 Hz, 1H) 6.99 (d, J=7.72 Hz, 2H) 7.12 (dd, J=8.82 Hz, 2H) 7.30 (dd, J=8.09 Hz, 2H) 7.66 (dd, J=8.82 Hz, J=2.58 Hz, 1H) 7.71 (d, J=2.2 Hz, 1H) 7.77 (d, J=8.82 Hz, 1H) 8.52 (d, J=6.98 Hz, 1H) 9.07 (d, J=8.82 Hz, 1H) 11.26 (br s, 1H) 14.45 (brs, 1H); MS (ESI+) m/z 390 (M−Cl)+; (ESI−) m/z 388 (M−HCl)−.

Example 199

2,2-Dimethyl-N-{3-[4-methyl-2-(7-propyl-[1,8] naphthyridin-4-ylamino)-phenylsulfanyl]-phenyl}-propionamide Example 199a 3-(4-Methyl-2-nitro-phenylsulfanyl)-phenylamine The title compound was prepared from 3-Amino-benzenethiol (5.034 g, 40.21 mmol), 1-Chloro-4-methyl-2-nitrobenzene (4.600 g, 26.81 mmol) and K$_2$CO$_3$ (6.484 g, 46.92 mmol) dissolved in DMF and heated to 100° C. for 16 hrs. At this time the reaction mixture was cooled to room temperature and diluted with water, extracted with ethyl acetate. Dried over Na$_2$SO$_4$, filtered and concentrated under vacuum giving the title compound (2.3 g, 32%).

Example 199b

N-[3-(4-Methyl-2-nitro-phenylsulfanyl)-phenyl]-acetamide

The title compound was prepared using 3-(4-Methyl-2-nitro-phenylsulfanyl)-phenylamine (8.20 g, 31.50 mmol) and acetyl chloride (2.72 g, 34.65 mmol) dissolved in CH$_2$Cl$_2$. This was stirred at room temperature for 2 hrs at which time the title compound was collected by filtration (8.78 g, 92

Example 199c

N-[3-(2-Amino-4-methyl-phenylsulfanyl)-phenyl]-acetamide

The product from Example 199b was reduced with SnCl$_2$ following the procedure from Example 14 to give the title compound.

Example 199d

N-{3-[4-Methyl-2-(7-propyl-[1,8]naphthyridin-4-ylamino)-phenylsulfanyl]-phenyl}-acetamide The title compound was prepared from the product of Example 2g (750 mg, 3.63 mmol), and the product of Example 199c (988 mg, 3.63 mmol) combined in 10 mL of EtOH and heated to 80° C. for 40 hrs. After cooling to room temperature the solvent was removed under vacuum giving the title compound (1.2 g, 74%).

Example 199e

[2-(3-Amino-phenylsulfanyl)-5-methyl-phenyl]-(7-propyl-[1,8]naphthyridin-4-yl)-amine The title compound was prepared by treating the product of Example 199d (1.20 g, 2.71 mmol) with 10 mL of a 50% solution of HCl in water. This reaction mixture was heated to 100° C. for 1 hr. At this time the reaction mixture was cooled to room temperature and made basic with 2N NaOH. This was then extracted with CH$_2$Cl$_2$, which was then dried over Na$_2$SO$_4$, filtered and concentrated under vacuum giving the title compound (720 mg, 66%).

Example 199f 2,2-Dimethyl-N-{3-[4-methyl-2-(7-propyl-[1,8]naphthyridin-4-ylamino)-phenylsulfanyl]-phenyl}-propionamide The title compound was prepared using 2,2-Dimethyl-propionic acid (26 mg, 0.16 mmol) as the acid in the procedure for Example 74 providing the title compound (3 mg, 5%). $^1$H NMR (500 MHz, DMSO-D$_2$O) δ ppm: 0.97 (t, J=7.48 Hz, 3H), 1.16 (s, 9H), 1.79-1.86 (m, 2H), 2.39 (s, 3H), 2.94-3.00 (m, 2H), 6.31 (d, J=7.02 Hz, 1H), 6.87 (d, J=8.24 Hz, 1H), 7.07 (t, J=7.93 Hz, 1H), 7.33-7.38 (m, 3H), 7.43-7.49 (m, 1H), 7.57-7.61 (m, 1H), 7.72 (d, J=8.85 Hz, 1H), 8.28 (d, J=7.02 Hz, 1H), 8.86 (d, J=8.85 Hz, 1H), 9.10 (s, 1H); MS (ESI+) m/z 485 (M+TFA+H)+; (ESI−) m/z 483 (M+TFA−H).
).

Example 200

2,5-Dimethyl-furan-3-carboxylic acid {3-[4-methyl-2-(7-propyl-[1,8]naphthyridin-4-ylamino)-phenylsulfanyl]-phenyl}-amide The title compound was prepared using 2,5-Dimethyl-furan-3-carboxylic acid (26 mg, 0.16 mmol) as the acid in the procedure for Example 74 providing the title compound (3 mg, 5%). $^1$H NMR (500 MHz, DMSO-D$_2$O) δ ppm: 0.93 (t, J=7.32 Hz, 3H), 1.70-1.77 (m, 2H), 2.26 (s, 3H), 2.39 (s, 3H), 2.47 (s, 3H), 2.82-2.86 (m, 2H), 6.27 (d, J=7.02 Hz, 1H), 6.53 (s, 1H), 6.86 (d, J=8.24 Hz, 1H), 7.08 (t, J=7.93 Hz, 1H), 7.35 (s, 1H), 7.38 (dt, J=7.63, 2.14 Hz, 2H), 7.54 (d, J=7.93 Hz, 1H), 7.61 (t, J=2.14 Hz, 1H), 7.66 (d, J=8.54 Hz, 1H), 8.26 (d, J=7.02 Hz, 1H), 8.82 (d, J=8.85 Hz, 1H); MS (ESI+) m/z 523 (M+TFA+H)+; (ESI−) m/z 521 (M+TFA−H)−.

Example 201

Thiophene-2-carboxylic acid {3-[4-methyl-2-(7-propyl-[1,8]naphthyridin-4-ylamino)-phenylsulfanyl]-phenyl}-amide The title compound was prepared using thiophene-2-carboxylic acid (26 mg, 0.16 mmol) as the acid in the procedure for Example 74 providing the title compound (3 mg, 5%). $^1$H NMR (500 MHz, DMSO-D$_2$O) δ ppm: 0.90 (t, J=7.32 Hz, 3H), 1.67-1.75 (m, 2H), 2.40 (s, 3H), 2.76-2.82 (m, 2H), 6.27 (d, J=7.32 Hz, 1H), 6.88 (d, J=7.93 Hz, 1H), 7.10 (t, J=7.93 Hz, 1H), 7.22-7.26 (m, 1H), 7.36 (s, 1H), 7.38-7.42 (m, 2H), 7.57-7.60 (m, 2H), 7.65 (d, J=8.54 Hz, 1H), 7.86 (dd, J=5.03, 1.07 Hz, 1H), 7.90 (dd, J=3.81, 1.07 Hz, 1H), 8.25 (d, J=7.02 Hz, 1H), 8.81 (d, J=8.54 Hz, 1H)
MS (ESI+) m/z 511 (M+TFA+H)+.

Example 202

6-Hydroxy-N-{3-[4-methyl-2-(7-propyl-[1,8]naphthyridin-4-ylamino)-phenylsulfanyl]-phenyl}-nicotinamide The title compound was prepared using 6-Hydroxy-nicotinic acid (26 mg, 0.16 mmol) as the acid in the procedure for Example 74 providing the title compound (3 mg, 5%). $^1$H NMR (500 MHz, DMSO-D$_2$O) δ ppm: 0.92 (t, J=7.32 Hz, 3H), 1.69-1.77 (m, 2H), 2.37-2.42 (m, 3H), 2.82-2.88 (m, 2H), 6.24 (d, J=7.02 Hz, 1H), 6.46 (d, J=9.46 Hz, 1H), 6.87 (d, J=8.54 Hz, 1H), 7.09 (t, J=8.09 Hz, 1H), 7.32-7.37 (m, 2H), 7.39 (d, J=7.93 Hz, 1H), 7.55-7.60 (m, 2H), 7.67 (d, J=8.85 Hz, 1H), 7.91 (dd, J=9.76, 2.75 Hz, 1H), 8.09 (d, J=2.44 Hz, 1H), 8.24 (d, J=7.02 Hz, 1H), 8.82 (d, J=8.54 Hz, 1H); MS (ESI+) m/z 522 (M+TFA+H)+; (ESI−) m/z 520 (M+TFA−H).

Example 203

2-Hydroxy-6-methyl-N-{3-[4-methyl-2-(7-propyl-[1,8]naphthyridin-4-ylamino)-phenylsulfanyl]-phenyl}-nicotinamide The title compound was prepared using 2-Hydroxy-6-methyl-nicotinic acid (26 mg, 0.16 mmol) as the acid in the procedure for Example 74 providing the title compound (3 mg, 5%). $^1$H NMR (500 MHz, DMSO-D$_2$O) δ ppm: 0.89 (t, J=7.48 Hz, 3H), 1.64-1.71 (m, J=7.48, 7.48, 7.48, 7.48 Hz, 2H), 2.36 (s, 3H), 2.40 (s, 3H), 2.76-2.81 (m, 3H), 6.22 (d, J=7.02 Hz, 1H), 6.46 (d, J=7.32 Hz, 1H), 6.86 (d, J=8.24 Hz, 1H), 7.10 (t, J=7.93 Hz, 1H), 7.14-7.18 (m, 1H), 7.35 (s, 1H), 7.39 (d, J=8.24 Hz, 1H), 7.57-7.59 (m, 1H), 7.62 (d, J=8.54 Hz, 2H), 8.21 (d, J=7.32 Hz, 1H), 8.27 (d, J=7.32 Hz, 1H), 8.82 (d, J=8.85 Hz, 1H); MS (ESI+) m/z 536 (M+TFA+H)+.

Example 204

Pyrazine-2-carboxylic acid {3-[4-methyl-2-(7-propyl-[1,8]naphthyridin-4-ylamino)-phenylsulfanyl]-phenyl}-amide The title compound was prepared using Pyrazine-2-carboxylic acid (26 mg, 0.16 mmol) as the acid in the procedure for Example 74 providing the title compound (3 mg, 5%). $^1$H NMR (500 MHz, DMSO-D$_2$O) δ ppm: 0.87 (t, J=7.48 Hz, 3H), 1.63-1.70 (m, 2H), 2.40 (s, 3H), 2.74-2.78 (m, 2H), 6.28 (d, J=7.02 Hz, 1H), 6.94 (d, J=8.54 Hz, 1H), 7.13 (t, J=7.93 Hz, 1H), 7.36 (d, J=1.22 Hz, 1H), 7.40 (d, J=7.93 Hz, 1H), 7.53 (dd, J=7.63, 1.53 Hz, 1H), 7.61 (d, J=7.93 Hz, 1H), 7.65 (d, J=8.54 Hz, 1H), 7.76 (t, J=1.83 Hz, 1H), 8.25 (d, J=7.02 Hz, 1H), 8.78-8.84 (m, 2H), 8.94 (d, J=2.44 Hz, 1H); MS (ESI+) m/z 507 (M+TFA+H)+.

Example 205

Furan-2-carboxylic acid ({3-[4-methyl-2-(7-propyl-[1,8]naphthyridin-4-ylamino)-phenylsulfanyl]-phenylcarbamoyl}-methyl)-amide The title compound was prepared using [(Furan-2-carbonyl)-amino]-acetic acid (26 mg, 0.16 mmol) as the acid in the procedure for Example 74 providing the title compound (3 mg, 5%). $^1$H NMR (500 MHz, DMSO-D$_2$O) δ ppm: 0.96 (t, J=7.32 Hz, 3H), 1.78-1.86 (m, 2H), 2.39 (s, 3H), 2.94-3.01 (m, 2H), 6.34 (d, J=7.02 Hz, 1H), 6.62-6.68 (m, 1H), 6.87 (d, J=7.63 Hz, 1H), 7.02-7.12 (m, 2H), 7.14-7.22 (m, 2H), 7.37 (d, J=5.49 Hz, 2H), 7.48 (d, J=8.54 Hz, 1H), 7.51 (s, 1H), 7.72 (d, J=8.85 Hz, 1H), 7.81-7.87 (m, 2H), 8.33 (d, J=7.02 Hz, 1H), 8.86 (d, J=8.54 Hz, 1H); MS (ESI+) m/z 552 (M+TFA+H)+.

Example 206

N-{3-[4-Methyl-2-(7-propyl-[1,8]naphthyridin-4-ylamino)-phenylsulfanyl]-phenyl}-4-thiophen-2-yl-butyramide The title compound was prepared using 4-Thiophen-2-yl-butyric (26 mg, 0.16 mmol) as the acid in the procedure for Example 74 providing the title compound (3 mg, 5%). $^1$H NMR (500 MHz, DMSO-D$_2$O) δ ppm: 0.96 (t, J=7.32 Hz, 3H), 1.79-1.84 (m, 2H), 1.85-1.89 (m, 2H), 2.28 (t, J=7.48 Hz, 2H), 2.39 (s, 3H), 2.79-2.84 (m, 2H), 2.92-2.98 (m, 2H), 6.29 (d, J=7.02 Hz, 1H), 6.82-6.88 (m, 2H), 6.96 (dd, J=4.88, 3.36 Hz, 1H), 7.05 (t, J=7.93 Hz, 1H), 7.22 (dd, J=8.24, 1.22 Hz, 1H), 7.31 (dd, J=5.03, 1.07 Hz, 1H), 7.35-7.38 (m, 2H), 7.45-7.51 (m, 2H), 7.70 (d, J=8.54 Hz, 1H), 8.27 (d, J=7.32 Hz, 1H), 8.84 (d, J=8.54 Hz, 1H); MS (ESI+) m/z 553 (M+TFA+H)+.

Example 207

N-{3-[4-Methyl-2-(7-propyl-[1,8]naphthyridin-4-ylamino)-phenylsulfanyl]-phenyl}-2-(3-phenoxy-phenyl)-acetamide The title compound was prepared using (3-Phenoxy-phenyl)-acetic acid (26 mg, 0.16 mmol) as the acid in the procedure for Example 74 providing the tile compound (3 mg, 5%). $^1$H NMR (500 MHz, DMSO-D$_2$O) δ ppm: 0.96 (t, J=7.32 Hz, 3H), 1.77-1.85 (m, 2H), 2.39 (s, 3H), 2.92-2.99 (m, 2H), 3.55 (s, 2H), 6.32 (d, J=7.32 Hz, 1H), 6.84-6.90 (m, 2H), 6.96 (s, 1H), 7.00 (d, J=7.63 Hz, 2H), 7.07 (ddd, J=7.78, 4.12, 3.97 Hz, 2H), 7.16 (t, J=7.48 Hz, 1H), 7.23 (d, J=9.15 Hz, 1H), 7.33-7.42 (m, 5H), 7.44-7.47 (m, 1H), 7.49 (s, 1H), 7.69 (d, J=8.85 Hz, 1H), 8.27 (d, J=7.02 Hz, 1H), 8.85 (d, J=8.54 Hz, 1H); MS (ESI+) m/z 611 (M+TFA+H)+.

Example 208

N-Allyl-3-[4-chloro-2-(7-methyl-[1,8]naphthyridin-4-ylamino)-phenoxy]-benzamide

Example 208a 3-(4-Chloro-2-nitro-phenoxy)-benzoic acid methyl ester

1-Bromo-4-chloro-2-nitro-benzene (7.00 g, 29.60 mmol) was dissolved in DMF to which K$_2$CO$_3$ (5.11 g, 37.01 mmol) and 3-Hydroxy-benzoic acid methyl ester (4.95 g, 32.57 mmol) were added. The reaction mixture was then heated to 100° C. for 2 h the reaction mixture was cooled to room temperature and diluted with water and extracted with ethyl acetate. Solvent dried over Na$_2$SO$_4$, filtered and concentrated under vacuum giving the title compound. (7.2 g, 79%)

Example 208b 3-(2-Amino-4-chloro-phenoxy)-benzoic acid methyl ester

The product from Example 208a (7.20 g, 23.40 mmol) was reduced with SnCl$_2$ (13.310 g, 70.20 mmol) following the procedure from Example 1f to give the title compound (6.2 g, 95%).

Example 208c

3-[4-Chloro-2-(7-methyl-[1,8]naphthyridin-4-ylamino)-phenoxy]-benzoic acid methyl ester The product from Example 1d (175 mg, 0.979 mmol) and the product from Example 208b (272 mg, 0.979 mmol) were dissolved in 2 mL of abs EtOH and heated to 80° C. for 16 hrs. At this time the reaction mixture was cooled and solvent removed yielding the title compound as a brown foam that was taken forward without purification (410 mg, 93%).

Example 208d

3-[4-Chloro-2-(7-methyl-[1,8]naphthyridin-4-ylamino)-phenoxy]-benzoic acid

The product from Example 208c (447 mg, 1.065 mmol) was dissolved in 5 ml of a 1:1 (THF:water) solution. To this was added LiOH (51 mg, 2.129 mmol) and the reaction mixture was heated to 60° C. for 2 h the reaction mixture was then allowed to cool to room temperature and brought to neutral with HOAc. The product was extracted with ethyl acetate. Dried over $Na_2SO_4$, filtered and concentrated under vacuum giving the title compound (180 mg, 42%).

Example 208e

N-Allyl-3-[4-chloro-2-(7-methyl-[1,8]naphthyridin-4-ylamino)-phenoxy]-benzamide

The product from Example 208d (60 mg, 0.147 mmol) was dissolved in THF to which was added N-methyl morpholine (49 mg, 0.162 mmol), and isopropenyl chloroformate (36 mg, 0.295 mmol). This was stirred at room temperature for 1 hr at which time the allylamine (42 mg, 0.739 mmol) was added and the reaction mixture stirred at room temperature for another 1 hr. THF was then removed under a stream of N2 and then crude oil was purified by HPLC with TFA providing the product as a trifluoroacetic acid. (8.0 mg, 9.5%). $^1$H NMR (300 MHz, DMSO-$d_6$) δ ppm: 1.92 (s, 3H), 2.74 (s, 2H), 3.86 (d, J=5.15 Hz, 2H), 5.04-5.16 (m, 2H), 5.73-5.98 (m, 1H), 6.73 (d, J=6.99 Hz, 1H), 7.10 (dd, J=7.72, 2.21 Hz, 1H), 7.27-7.43 (m, 3H), 7.51-7.65 (m, 2H), 7.69-7.82 (m, 2H), 8.54 (d, J=7.35 Hz, 1H), 8.82 (d, J=8.46 Hz, 1H); MS (ESI+) m/z 445 (M+TFA+H)+; (ESI-) m/z 443 (M+TFA-H)-.

Example 211

(5-Chloro-2-phenoxy-phenyl)-(7-phenyl-[1,8]naphthyridin-4-yl)-amine

Example 211a 2-(2,5-Dimethyl-pyrrol-1-yl)-6-phenyl-pyridine

2-Chloro-6-(2,5-dimethyl-pyrrol-1-yl)-pyridine (0.097 g, 0.47 mmol) prepared as described in Example 8a was reacted for 24 h with tributyl-phenyl-stannane (0.185 mL, 0.564 mmol) under nitrogen in toluene at 75° C. in the presence of 2 mole % tetrakis(triphenylphosphine) palladium(0). The volatiles were subsequently removed under reduced pressure to yield the crude product, which was purified by flash chromatography on silica gel to give the title compound (0.103 g, 88%).

Example 211b

6-Phenyl-pyridin-2-ylamine

The substituted pyridine described in Example 211a (0.289 g, 1.7 mmol) was reacted as described in Example 2c to give the title compound in quantitative yield.

Example 211c

5-Chloro-2-phenyl-[1,8]naphthyridine

The product from Example 211b was reacted following the procedures from Examples 2d, 2e, 2f and 2g to give the title compound.

Example 211d (5-Chloro-2-phenoxy-phenyl)-(7-phenyl-[1,8]naphthyridin-4-yl)-amine The product from Example 211f (0.108 g, 0.45 mmol) was reacted with the product from Example 42b (0.100 g, 0.46 mmol) for 28 h following the procedure from Example 1g giving the crude title compound which was purified by HPLC with TFA providing the product as the trifluoroacetic acid salt (0.144 g, 57%). $^1$H NMR (300 MHz, DMSO-$d_6$) δ ppm: 6.75 (d, J=6.99 Hz, 1H) 6.99 (d, J=7.72 Hz, 2H) 7.11 (t, J=7.35 Hz, 1H) 7.18 (d, J=8.82 Hz, 1H) 7.32 (t, J=7.91 Hz, 2H) 7.59 (dd, J=8.82, 2.57 Hz, 1H) 7.64 (m, 3H) 7.75 (d, J=2.57 Hz, 1H) 8.36 (dd, J=6.62, 2.94 Hz, 2H) 8.51 (d, J=9.19 Hz, 1H) 8.61 (d, J=6.99 Hz, 1H) 9.10 (d, J=8.82 Hz, 1H); MS (ESI+) m/z 423.9 (M+H)+; (ESI-)- m/z 422.0 (M-H)-.

Example 212

2-(7-Methyl-[1,8]naphthyridin-4-ylamino)-biphenyl-4-carboxylic acid methyl ester

Example 212a

4-Bromo-3-nitro-benzoic acid methyl ester

Commercially available 4-bromo-3-nitro-benzoic acid (1.17 g, 4.76 mmol) was dissolved in methanol (5 mL) containing five drops of concentrated sulfuric acid. The mixture was heated in air at 90° C. for six hours and more MeOH (7 mL) followed by concentrated sulfuric acid (0.6 mL) was added. Heating was continued another 24 hours. Extractive work up (ethyl acetate-water) followed by drying over $MgSO_4$, filtered and concentrated under vacuum giving the title compound in quantitative yield.

Example 212b

2-Nitro-biphenyl-4-carboxylic acid methyl ester

The product from Example 212a (0.100 g, 0.384 mmol) was combined with iodobenzene (0.375 mL, 3.35 mmol) and copper powder (0.188 g, 2.96 mmol) and the mixture heated in a sealed tube to 218° C. for 90 minutes. The reaction mixture was subsequently diluted with dichloromethane and filtered through celite. The crude product, obtained by concentration under vacuum, was purified by flash chromatography on silica gel (ethyl acetate-hexanes) to give the title compound (0.0847 g, 86

Example 212c

2-Amino-biphenyl-4-carboxylic acid methyl ester

The product from Example 212b (0.0795 g, 0.309 mmol) was dissolved in ethanol (2 mL) and to this solution was added Pt(IV) oxide (5.2 mg). The reaction mixture was vacuum degassed then exposed to one atmosphere of hydrogen for 3 h at room temperature. The catalyst was removed by filtration through celite and the filtrate concentrated under vacuum to give the title compound in quantitative yield.

Example 212d 2-(7-Methyl-[1,8]naphthyridin-4-ylamino)-biphenyl-4-carboxylic acid methyl ester The product from Example 1d (0.0552 g, 0.309 mmol) was reacted with the product from Example 212c (0.070 g, 0.309 mmol) for 92 h following the procedure of Example 1g giving the crude title compound, which was purified by HPLC with AA. The resulting solid was triturated with 4N HCl in dioxane to generate the hydrochloride salt which was collected by vacuum filtration (0.0747 g, 55%). $^1$H NMR (300 MHz, DMSO-d$_6$) δ ppm: 2.72 (s, 3H) 3.91 (s, 3H) 6.27 (d, J=6.99 Hz, 1H) 7.30 (m, J=6.99 Hz, 3H) 7.52 (m, 2H) 7.74 (d, J=8.82 Hz, 1H) 7.79 (d, J=8.09 Hz, 1H) 8.09 (d, J=1.47 Hz, 1H) 8.16 (dd, J=7.91, 1.65 Hz, 1H) 8.30 (d, J=6.99 Hz, 1H) 9.15 (d, J=8.82 Hz, 1H) 11.54 (s, 1H); MS (ESI+) m/z 369.9 (M+H)+.

Example 213

(4-Methyl-biphenyl-2-yl)-(7-propyl-[1,8]naphthyridin-4-yl)-amine

Example 213a

4-Methyl-2-nitro-biphenyl

To a solution of commercially available 1-bromo-4-methyl-2-nitro-benzene (0.107 g, 0.49 mmol) in anhydrous toluene (3 mL) was added CsCO$_3$ (0.305 g, 0.94 mmol) followed by phenylboronic acid (0.062 g, 0.49 mmol) and 2,8,9-tri-isobutyl-2,5,8,9-tetraaza-1-phosphabicyclo[3.3.3.]undecane as a 0.1M solution in toluene (0.200 mL, 4 mole %). Nitrogen was bubbled through the resulting suspension for three minutes then palladium acetate (0.0043 g, 4 mole %) was added, the reaction vessel sealed and immersed in an 80° C. oil bath and heated for 22 hours. Subsequent filtration through celite and removal of volatiles under vacuum gave the crude product (0.105 g, 100%), which was sufficiently pure for use as isolated.

Example 213b

4-Methyl-biphenyl-2-ylamine

The product from Example 213a was reacted as described in Example 212c to give the title amine (0.088 g, 100%).

Example 213c (4-Methyl-biphenyl-2-yl)-(7-propyl-[1,8]naphthyridin-4-yl)-amine

The product from Example 2g (0.106 g, 0.49 mmol) was reacted with the product from Example 213b (0.088 g, 0.49 mmol) for 65 h following the procedure of Example 1g giving the crude title compound which was purified by HPLC with TFA providing the product as a trifluoroacetic acid salt (0.122 g, 52%). $^1$H NMR (300 MHz, DMSO-d$_6$) δ ppm: 0.96 (t, J=7.35 Hz, 3H) 1.81 (d, J=7.72 Hz, 2H) 2.43 (s, 3H) 2.89-3.02 (m, 2H) 6.31 (d, J=6.99 Hz, 1H) 7.14-7.58 (m, 8H) 7.77 (d, J=8.46 Hz, 1H) 8.32 (d, J=7.35 Hz, 1H) 8.91 (d, J=8.46 Hz, 1H) 10.91-11.08 (m, 1H); MS (ESI+) m/z 354.0 (M+H)+; (ESI-) m/z 351.9 (M-H)-.

Example 214

(4-Methyl-biphenyl-2-yl)-(7-propyl-[1,8]naphthyridin-4-yl)-amine

Example 214a

4'-Methoxy-4-methyl-2-nitro-biphenyl

1-Bromo-4-methyl-2-nitro-benzene (0.107 g, 0.49 mmol) was reacted as described in Example 213a substituting 4-methoxyphenylboronic acid (0.074 g, 0.49 mmol) for boronic acid to give the title biphenyl in quantitative yield and sufficient purity to use as isolated in the next step.

Example 214b

4'-Methoxy-4-methyl-biphenyl-2-ylamine

The product from Example 214a was reacted as described in 212c to give the title amine (0.107 g, 100%).

Example 214

(4'-Methoxy-4-methyl-biphenyl-2-yl)-(7-methyl-[1,8]naphthyridin-4-yl)-amine

The product from Example 1d (0.088 g, 0.49 mmol) was reacted with the product from Example 214b (107 mg, 0.49 mmol) for 65 h following the procedure from Example 1g giving the crude title compound which was purified by HPLC with TFA providing the product as a trifluoroacetic acid salt (0.106 g, 45%). $^1$H NMR (300 MHz, DMSO-d$_6$) δ ppm: 2.41 (s, 3H) 2.72 (s, 3H) 3.66 (s, 3H) 6.29 (d, J=6.99 Hz, 1H) 6.84 (d, J=8.82 Hz, 2H) 7.27-7.53 (m, 5H) 7.75 (d, J=8.46 Hz, 1H) 8.32 (d, J=6.99 Hz, 1H) 8.90 (d, J=8.46 Hz, 1H) 10.88-11.05 (m, 1H); MS (ESI+) m/z 356.0 (M+H)+; (ESI-) m/z 354.1 (M-H)-.

Example 215

N-[4'-Methyl-2'-(7-methyl-[1,8]naphthyridin-4-ylamino)-biphenyl-4-yl]-acetamide

Example 215a

N-(4'-Methyl-2'-nitro-biphenyl-4-yl)-acetamide

1-Bromo-4-methyl-2-nitro-benzene (0.102 g, 0.49 mmol) was reacted as described in Example 213a substituting N-[4-(4,4,5,5-Tetramethyl-[1,3,2]dioxaborolan-2-yl)-phenyl]-acetamide (0.130 g, 0.49 mmol) for phenylboronic acid and heating for 18 h at 100° C. The reaction mixture was filtered through celite and the volatiles removed under vacuum and the crude product purified by flash chromatography on silica gel eluting with EtOAc-hexanes to give the title biphenyl (0.051 mg, 38%).

Example 215b

N-(2'-Amino-4'-methyl-biphenyl-4-yl)-acetamide

The product from Example 215a (0.062 g, 0.23 mmol) was reacted as described in Example 212c to give the title amine in quantitative yield.

Example 215

N-[4'-Methyl-2'-(7-methyl-[1,8]naphthyridin-4-ylamino)-biphenyl-4-yl]-acetamide

The product from Example 1d (0.041 g, 0.23 mmol) was reacted with the product from Example 215b (0.062 g, 0.23 mmol) for 46 h at 100° C. following the procedure from Example 1g giving the crude title compound which was purified by HPLC with TFA providing the product as a trifluoroacetic acid salt (0.073 g, 60%). $^1$H NMR (300 MHz, DMSO-d$_6$) δ ppm: 1.98 (s, 3H) 2.42 (s, 3H) 2.72 (s, 3H) 6.28 (d, J=6.99 Hz, 1H) 7.27-7.56 (m, 7H) 7.74 (d, J=8.46 Hz, 1H)

8.33 (d, J=7.35 Hz, 1H) 8.94 (d, J=8.82 Hz, 1H) 9.95 (s, 1H) 11.06 (s, 1H); MS (ESI+) m/z 383.1 (M+H)+, (ESI−) m/z 381.1 (M−H)−.

Example 216

N-[4'-Methyl-2'-(7-methyl-[1,8]naphthyridin-4-ylamino)-biphenyl-3-yl]-acetamide

Example 216a

N-(4'-Methyl-2'-nitro-biphenyl-3-yl)-acetamide

1-Bromo-4-methyl-2-nitro-benzene (0.107 g, 0.49 mmol) was reacted as described in Example 215a substituting 3-acetamidophenylboronic acid (0.086 g, 0.49 mmol) for phenylboronic acid, dicyclohexylamine (4 mole %) for 2,8,9-triisobutyl-2,5,8,9-tetraaza-1-phosphabicyclo[3.3.3.]undecane and substituting dioxane for toluene to give the title biphenyl (0.0552 g, 42%).

Example 216b

N-(2'-Amino-4'-methyl-biphenyl-3-yl)-acetamide

The product from Example 216a (0.070 g, 0.26 mmol) was reacted as described n 212c to give the title amine in quantitative yield.

Example 216

N-[4'-Methyl-2'-(7-methyl-[1,8]naphthyridin-4-ylamino)-biphenyl-3-yl]-acetamide

The product from Example 1g (0.046 g, 0.26 mmol) was reacted with the product from Example 216b (0.063 g, 0.26 mmol) for 47 hours at 100° C. following the procedure from Example 1g giving the crude title compound which was purified by HPLC with TFA providing the product as a trifluoroacetic acid salt (0.085 g, 64%). $^1$H NMR (300 MHz, DMSO-$d_6$) δ ppm: 1.93 (s, 3H) 2.43 (s, 3H) 2.71 (s, 3H) 6.34 (d, J=6.99 Hz, 1H) 7.04 (d, J=7.35 Hz, 1H) 7.17 (t, J=7.72 Hz, 1H) 7.22-7.31 (m, 1H) 7.36 (s, 1H) 7.40-7.54 (m, 2H) 7.72 (d, J=8.46 Hz, 1H) 7.77 (s, 1H) 8.36 (s, 1H) 8.88 (d, J=8.82 Hz, 1H) 9.88 (s, 1H) 10.99 (s, 1H); MS (ESI+) m/z 383.0 (M+H)+; (ESI−) m/z 381.1 (M−H)−.

Example 217

(3'-Methoxy-4-methyl-biphenyl-2-yl)-(7-methyl-[1,8]naphthyridin-4-yl)-amine

Example 217a

3'-Methoxy-4-methyl-2-nitro-biphenyl

1-Bromo-4-methyl-2-nitro-benzene (0.107 g, 0.49 mmol) was reacted as described in Example 216a substituting 3-methoxyphenylboronic acid (0.074 g, 0.45 mmol) for 3-acetamidophenylboronic acid to give the title biphenyl (0.083 g, 76%).

Example 217b

3'-Methoxy-4-methyl-biphenyl-2-ylamine

The product from Example 217b (0.083 g, 0.34 mmol) was reacted as described in Example 212c to give the title amine in quantitative yield.

Example 217c (3'-Methoxy-4-methyl-biphenyl-2-yl)-(7-methyl-[1,8]naphthyridin-4-yl)-amine The product from Example 1d (0.065 g, 0.36 mmol) was reacted with the product from Example 217b (0.072 g, 0.34 mmol) for 96 h at 100° C. following the procedure from Example 1g giving the crude title compound which was purified by HPLC with TFA providing a trifluoroacetic acid salt (0.102 gm, 64%). $^1$H NMR (300 MHz, DMSO-$d_6$) δ ppm: 2.43 (s, 3H) 2.72 (s, 3H) 3.62 (s, 3H) 6.29 (d, J=7.35 Hz, 1H) 6.77 (dd, J=7.91, 2.02 Hz, 1H) 6.87-7.00 (m, 2H) 7.17 (t, J=7.91 Hz, 1H) 7.36 (s, 1H) 7.41-7.46 (m, 1H) 7.51-7.56 (m, 1H) 7.75 (d, J=8.46 Hz, 1H) 8.32 (d, J=7.35 Hz, 1H) 8.91 (d, J=8.82 Hz, 1H) 11.99-12.22 (s, 1H); MS (ESI+) m/z 356.0 (M+H)+; (ESI−) m/z 354.0 (M−H)−.

Example 218

(7-Propyl-[1,8]naphthyridin-4-yl)-(4-trifluoromethyl-biphenyl-2-yl)-amine

Example 218a

2-Nitro-4-trifluoromethyl-biphenyl

Commercially available 1-bromo-2-nitro-4-trifluoromethyl-benzene (0.130 g, 0.48 mmol) was reacted with phenylboronic acid (0.072 g, 0.59 mmol) as described in Example 213a substituting dioxane for toluene, bis(triphenylphosphine)-palladium (II) chloride for palladium acetate and omitting the 2,8,9-triisobutyl-2,5,8,9-tetraaza-1-phosphabicyclo[3.3.3.]undecane. The reaction was complete after three hours and the title biphenyl recovered in quantitative yield, sufficiently pure for use as isolated.

Example 218b

4-Trifluoromethyl-biphenyl-2-ylamine

The product from Example 218a was reacted as described in Example 212c substituting 3:1 THF/EtOH (4 mL) for ethanol to give the title amine in quantitative yield.

Example 218c (7-Propyl-[1,8]naphthyridin-4-yl)-(4-trifluoromethyl-biphenyl-2-yl)-amine The product from Example 2g as a 3.15M solution in ethanol (0.078 mL, 0.24 mmol) was reacted with the product from Example 218b (0.057 g, 0.24 mmol) for 64 h at 100° C. following the procedure from Example 1g. Consumption of starting material required periodic addition of the product from Example 2g (0.103 mL, 0.32 mmol) in all, and continued heating at 100° C. (70 hrs.). The crude title compound was purified by HPLC with TFA providing the product as a trifluoroacetic acid salt (0.0058 g, 5%). $^1$H NMR (300 MHz, DMSO-d$_6$) δ ppm: 0.96 (t, J=7.35 Hz, 3H) 1.73-1.92 (m, 2H) 2.90-3.02 (m, 2H) 6.37 (d, J=6.99 Hz, 1H) 7.32 (d, J=7.72 Hz, 3H) 7.48 (dd, J=7.91, 1.65 Hz, 2H) 7.80 (d, J=8.82 Hz, 1H) 7.86 (d, J=8.09 Hz, 1H) 7.94-8.03 (m, 2H) 8.35 (d, J=6.99 Hz, 1H) 8.91 (d, J=8.82 Hz, 1H); MS (ESI+) m/z 408.1 (M+H)+; (ESI-) m/z 406.2 (M-H)-.

Example 219

(5-Methyl-biphenyl-2-yl)-(7-propyl-[1,8]naphthyridin-4-yl)-amine

Example 219a

2-Bromo-4-methyl-1-nitro-benzene

Into a flask containing 90% t-butyl nitrite (1.47 mL, 11.2 mmol) and copper (II) bromide (2.0 g, 8.95 mmol) in CH$_3$CN (40 mL) at 70° C. under nitrogen was added dropwise a solution of commercially available 5-Methyl-2-nitro-phenylamine (1.13 g, 7.46 mmol) in CH$_3$CN (8 mL). After twenty minutes the reaction was quenched by pouring into dilute HCl and the crude product isolated by extraction with ether, drying with MgSO4 and concentration under vacuum. Flash chromatography on silica gel gave the title compound (0.811 g, 50%).

Example 219b

5-Methyl-2-nitro-biphenyl

The product from Example 219a (0.20 g, 0.93 mmol) was reacted with phenylboronic acid (0.135 g, 1.11 mmol) for 19.5 h at 80° C. as described in Example 218a. The reaction mixture was cooled and filtered through celite, the filtrate concentrated under vacuum to give the crude product which was purified by flash chromatography on silica gel to give the title biphenyl (0.187 g, 94%) as a yellow oil.

Example 219c

5-Methyl-biphenyl-2-ylamine

The product from Example 219b (0.0885 g, 0.41 mmol) was reacted following the procedure described in Example 212c to give the title amine (0.0724 g, 96%).

Example 219c (5-Methyl-biphenyl-2-yl)-(7-propyl-[1,8]naphthyridin-4-yl)-amine

The product from Example 2g as a 4.1M solution in ethanol (0.10 mL, 0.40 mmol) was reacted with the product from Example 219c (0.0724 g, 0.40 mmol) for 66 h at 100° C. following the procedure from Example 1g. Consumption of starting material required a second addition of the product from Example 2g (0.03 mL, 0.12 mmol) and continued heating at 100° C. (19 h). The crude title compound was purified by HPLC with TFA providing the product as a trifluoroacetic acid salt (0.060 g, 32%). $^1$H NMR (300 MHz, DMSO-d$_6$) δ ppm: 0.95 (t, J=7.35 Hz, 3H) 1.70-1.89 (m, 2H) 2.46 (s, 3H) 2.88-3.00 (m, 2H) 6.28 (d, J=6.99 Hz, 1H) 7.11-7.53 (m, 8H) 7.76 (d, J=8.82 Hz, 1H) 8.30 (d, J=6.99 Hz, 1H) 8.91 (d, J=8.82 Hz, 1H) 10.98 (s, 1H); MS (ESI+) m/z 354.2 (M+H)+.

Example 220

[2-(4-Amino-phenylsulfanyl)-5-methyl-phenyl]-(7-propyl-[1,8]naphthyridin-4-yl)-amine The product from Example 20 (0.197 g, 0.445 mmol) was reacted as described in Example 83 giving the crude title compound that was purified by HPLC with TFA providing the product as a trifluoroacetic acid salt. $^1$H NMR (500 MHz, DMSO-d$_6$) δ ppm: 0.98 (t, J=7.25 Hz, 3H) 1.80-1.91 (m, 2H) 2.31 (s, 3H) 2.96-3.04 (m, 2H) 6.31 (d, J=6.96 Hz, 1H) 6.57 (d, J=8.69 Hz, 2H) 6.91 (d, J=8.11 Hz, 1H) 7.07 (d, J=8.69 Hz, 2H) 7.18-7.29 (m, 2H) 7.83 (d, J=8.69 Hz, 1H) 8.45 (d, J=6.96 Hz, 1H) 9.06 (d, J=8.69 Hz, 1H) 11.03 (s, 1H); MS (ESI+) m/z 401.1 (M+H)+; (ESI-) m/z 399.1 (M-H)-

Example 221

4-[4-Phenoxymethyl-2-(7-propyl-[1,8]naphthyridin-4-ylamino)-phenylsulfanyl]-phenol Example 221a (4-Bromo-3-nitro-phenyl)-methanol Commercially available 4-bromo-3-nitro-benzoic acid (5.95 g, 0.024 mole) was reacted as described in Example 115a to give the title compound in quantitative crude yield sufficiently pure for use as isolated.

Example 221b

1-Bromo-2-nitro-4-phenoxymethyl-benzene

The product from Example 221a (0.5 g, 2.15 mmol) was combined with phenol (0.203 g, 2.15 mmol) and triphenylphosphine (0.735 g, 2.80 mmol) in anhydrous THF (7 mL) under nitrogen and the resulting solution cooled in an ice bath. To the cold solution was added dropwise diisopropylazodicarboxylate (0.467 mL, 2.37 mmol). Stirring at 0° C. was continued for 15 min then the cold bath was removed and the reaction mixture allowed to warm to room temperature and 90 min before quench and workup by pouring into dilute HCl and extraction with ether. The combined extracts were dried MgSO$_4$, filtered and concentrated under vacuum giving the crude title compound that was purified by flash chromatography on silica gel eluting with EtOAc-hexanes to give the title compound (0.162 g, 25%).

Example 221c 4-(2-Nitro-4-phenoxymethyl-phenylsulfanyl)-phenol

The product from Example 221b (0.16 g, 0.52 mmol) was reacted with 90% 4-mercapto-phenol (0.073 g, 0.52 mmol) in DMF at 80° C. under nitrogen in the presence of potassium carbonate (0.126 g, 0.91 mmol). The reaction was quenched after 18 h by pouring into dilute HCl and extraction with ether. The combined extracts were dried over MgSO4, filtered and concentrated under vacuum giving the crude title compound. The crude product was purified by flash chromatography on silica gel eluting with EtOAc-hexanes to give the title compound (0.155 g, 84%).

Example 221d 4-(2-Amino-4-phenoxymethyl-phenylsulfanyl)-phenol

The product from Example 221c (0.154 g, 0.43 mmol) was reacted with stannous chloride (0.41 g, 2.17 mmol) as described in Example 1f to give the title compound (0.132 g, 100%).

Example 221

4-[4-Phenoxymethyl-2-(7-propyl-[1,8]naphthyridin-4-ylamino)-phenylsulfanyl]-phenol The product from Example 2g as a 4.1 M solution in ethanol (0.050 mL, 0.205 mmol) was reacted with the product from Example 221d (0.066 g, 0.205 mmol) for 16.5 h following the procedure from Example 1g. Consumption of starting material required a second addition of the product from Example 2g (0.025 mL, 0.102 mmol) and continued heating at 80° C. (12 h). The crude title compound was purified by HPLC with TFA providing the product as a trifluoroacetic acid salt (0.0269 g, 21.5%). $^1$H NMR (300 MHz, DMSO-$d_6$) δ ppm: 0.98 (t, J=7.54 Hz, 3H) 1.76-1.99 (m, 2H) 3.00 (t, J=7.35 Hz, 2H) 5.12 (s, 2H) 6.31 (d, J=6.99 Hz, 1H) 6.79 (d, J=8.82 Hz, 2H) 6.91-7.07 (m, 4H) 7.17-7.37 (m, 4H) 7.43-7.55 (m, 2H) 7.84 (d, J=8.82 Hz, 1H) 8.47 (d, J=7.35 Hz, 1H) 9.04 (d, J=8.46 Hz, 1H) 9.97 (s, 1H); MS (ESI+) m/z 494.2 (M+H)+; (ESI−) m/z 492.2 (M−H)−.

Example 222

4-[2-(7-Methyl-[1,8]naphthyridin-4-ylamino)-4-phenoxymethyl-phenylsulfanyl]-phenol The product from Example 1d (0.037 g, 0.205 mmol) was reacted with the product from Example 221d (0.066 g, 0.205 mmol) for 16.5 hours following the procedure from Example 1g giving the crude title compound which was purified by HPLC with TFA providing the product as a trifluoroacetic acid salt (0.041 g, 34%). $^1$H NMR (300 MHz, DMSO-$d_6$) δ ppm: 2.77 (s, 3H) 5.13 (s, 2H) 6.31 (d, J=6.99 Hz, 1H) 6.79 (d, J=8.46 Hz, 2H) 6.88-7.12 (m, 4H) 7.20-7.36 (m, 4H) 7.46-7.56 (m, 2H) 7.81 (d, J=8.82 Hz, 1H) 8.48 (d, J=6.99 Hz, 1H) 9.02 (d, J=8.46 Hz, 1H) 10.01 (s, 1H); MS (ESI+) m/z 466.3 (M+H)+; (ESI−) m/z 464.2 (M−H)−.

Example 223

4-[4-(4-Bromo-benzyloxy)-2-(7-methyl-[1,8]naphthyridin-4-ylamino)-phenylsulfanyl]-phenol

Example 223a

1-Bromo-4-(4-bromo-phenoxymethyl)-2-nitro-benzene

The product from Example 221a (0.5 g, 2.15 mmol) was reacted as described in Example 221b substituting 4-bromo-phenol (0.372 g, 2.15 mmol) for phenol to give the title compound as a white solid (0.238 g, 29%).

Example 223b

4-[4-(4-Bromo-phenoxymethyl)-2-nitro-phenylsulfanyl]-phenol

The product from Example 223a (0.236 g, 0.61 mmol) was reacted as described in Example 221c to give the title compound (0.188 g, 71%).

Example 223c

4-[2-Amino-4-(4-bromo-phenoxymethyl)-phenylsulfanyl]-phenol

The product from Example 223b (0.186 g, 0.43 mmol) was reacted as described in Example 221d to give the title compound (0.121 g, 70%).

Example 223

4-[4-(4-Bromo-phenoxymethyl)-2-(7-methyl-[1,8]naphthyridin-4-ylamino)-phenylsulfanyl]-phenol The product from Example 1d (0.03 g, 0.167 mmol) was reacted with the product from Example 223c (0.060 g, 0.15 mmol) for 17.5 h following the procedure from Example 1g. Consumption of starting material required a second addition of the product from Example 1d (0.016 g, 0.09 mmol) and continued heating at 80° C. (18 h). The crude title compound was purified by HPLC with TFA providing the product as a trifluoroacetic acid salt (0.056 g, 55%). $^1$H NMR (300 MHz, DMSO-$d_6$) δ ppm: 2.77 (s, 3H) 5.12 (s, 2H) 6.30 (d, J=6.99 Hz, 1H) 6.79 (d, J=8.82 Hz, 2H) 6.92-7.08 (m, 3H) 7.25 (d, J=8.82 Hz, 2H) 7.42-7.54 (m, 4H) 7.81 (d, J=8.82 Hz, 1H) 8.47 (d, J=6.99 Hz, 1H) 9.01 (d, J=8.46 Hz, 1H) 9.98 (s, 1H); MS (ESI+) m/z 546.0 (M+H)+.

Example 224

4-[4-(4-Bromo-benzyloxy)-2-(7-propyl-[1,8]naphthyridin-4-ylamino)-phenylsulfanyl]-phenol The product from Example 2g as a 4.1 M solution in ethanol (0.055 mL, 0.225 mmol) was reacted with the product from Example 223c (0.060 g, 0.15 mmol) for 17.5 h following the procedure from Example 1g. Consumption of starting material required a second addition of the product from Example 2g (0.028 mL, 0.114 mmol) and continued heating at 80° C. (18 h). The crude title compound was purified by HPLC with TFA providing the product as a trifluoroacetic acid salt (0.044 g, 41%). $^1$H NMR (300 MHz, DMSO-$d_6$) δ ppm: 0.98 (t, J=7.35 Hz, 3H) 1.77-1.96 (m, 2H) 3.00 (t, J=7.54 Hz, 2H) 5.13 (s, 2H) 6.31 (d, J=6.99 Hz, 1H) 6.79 (d, J=8.82 Hz, 2H) 6.91-7.07 (m, 3H) 7.26 (d, J=8.46 Hz, 2H) 7.40-7.56 (m, 4H) 7.84 (d, J=8.82 Hz, 1H) 8.47 (d, J=6.99 Hz, 1H) 9.04 (d, J=8.82 Hz, 1H) 9.98 (s, 1H); MS (ESI+) m/z 573.9 (M+H)+; (ESI−) m/z 572.1 (M−H)−

Example 225

4-[4-(3-Bromo-benzyloxy)-2-(7-methyl-[1,8]naphthyridin-4-ylamino)-phenylsulfanyl]-phenol

Example 225a

1-Bromo-4-(3-bromo-phenoxymethyl)-2-nitro-benzene

The product from Example 221a (0.5 g, 2.15 mmol) was reacted as described in Example 221b substituting 3-bromo-phenol (0.372 g, 2.15 mmol) for phenol to give the title compound (0.832 g, 56%).

Example 225b

4-[4-(3-Bromo-phenoxymethyl)-2-nitro-phenylsulfanyl]-phenol

The product from Example 225a (0.462 g, 1.19 mmol) was reacted as described in Example 221c to give the title compound (0.412 g, 80%).

Example 225c

4-[2-Amino-4-(3-bromo-phenoxymethyl)-phenylsulfanyl]-phenol

The product from Example 225b (0.412 g, 0.95 mmol) was reacted as described in Example 221d to give the title compound (0.310 g, 81%).

Example 225

4-[4-(3-Bromo-phenoxymethyl)-2-(7-methyl-[1,8]naphthyridin-4-ylamino)-phenylsulfanyl]-phenol The product from Example 1d (0.034 g, 0.193 mmol) was reacted with the product from Example 225c (0.078 g, 0.193 mmol) for 15 h following the procedure from Example 1g. Consumption of starting material required a second addition of the product from Example 1d (0.019 g, 0.109 mmol) and continued heating at 80° C. (18 h). The crude title compound was purified by HPLC with TFA providing the product as a trifluoroacetic acid salt (0.041 g, 32%). $^1$H NMR (300 MHz, DMSO-$d_6$) δ ppm: 2.77 (s, 3H) 5.15 (s, 2H) 6.30 (d, J=7.35 Hz, 1H) 6.79 (d, J=8.46 Hz, 2H) 6.95-7.08 (m, 2H) 7.16 (d, 1H) 7.20-7.30 (m, 4H) 7.45-7.55 (m, 2H) 7.81 (d, J=8.82 Hz, 1H) 8.47 (d, J=7.35 Hz, 1H) 9.01 (d, J=8.46 Hz, 1H) 9.98 (s, 1H); Ms (ESI+) m/z 546.0 (M+H)+; (ESI−) m/z 542.0.

Example 226

4-[4-(3-Bromo-benzyloxy)-2-(7-propyl-[1,8]naphthyridin-4-ylamino)-phenylsulfanyl]-phenol The product from Example 2g as a 4.1M solution in ethanol (0.075 mL, 0.308 mmol) was reacted with the product from Example 225c (0.078 g, 0.193 mmol) for 15 h following the procedure from Example 1g. Consumption of starting material required a second addition of the product from Example 2g (0.028 mL, 0.114 mmol) and continued heating at 80° C. (18 h). The crude title compound was purified by HPLC with TFA providing the product as a trifluoroacetic acid salt (0.038 g, 28%). $^1$H NMR (300 MHz, DMSO-$d_6$) δ ppm: 0.98 (t, J=7.35 Hz, 3H) 1.85 (d, J=7.35 Hz, 2H) 3.00 (t, J=7.54 Hz, 2H) 5.16 (s, 2H) 6.31 (d, J=7.35 Hz, 1H) 6.79 (d, J=8.46 Hz, 2H) 6.95-7.09 (m, 2H) 7.16 (d, 1H) 7.18-7.34 (m, 4H) 7.42-7.58 (m, 2H) 7.84 (d, J=8.46 Hz, 1H) 8.48 (d, J=6.99 Hz, 1H) 9.04 (d, J=8.46 Hz, 1H) 9.98 (s, 1H) 10.99-11.19 (m, 1H); MS (ESI+) m/z 573.9 (M+H)+; (ESI−) m/z 572.3 (M−H)−.

Example 227

(7-Methyl-[1,8]naphthyridin-4-yl)-[5-methyl-2-(pyridin-2-ylsulfanyl)-phenyl]-amine

Example 227a 2-(4-Methyl-2-nitro-phenylsulfanyl)-pyridine

The title compound was prepared from the reaction of trifluoro-methanesulfonic acid 4-methyl-2-nitro-phenyl ester (3.50 g, 12.27 mmol) reacting with pyridine-2-thiol (2.046 g, 18.41 mmol), and $K_2CO_3$ (2.968 g, 21.48 mmol) in DMF at 100° C. for 16 h the reaction mixture was then cooled to room temperature and diluted with water, extracted with EtOAc Dried over $Na_2SO_4$, filtered and concentrated under vacuum giving the title compound (2.52 g, 78%).

Example 227b

5-Methyl-2-(pyridin-2-ylsulfanyl)-phenylamine

The product from Example 277a (2.250 g, 10.23 mmol) was reduced with $SnCl_2$ (5.820 g, 30.70 mmol) 2 hrs. 80° C. following the procedure from Example 1f providing the tile compound which was purified by silica gel column chromatography eluting with 30% EtOAc/hexanes (1.52 g, 70%).

Example 227c (7-Methyl-[1,8]naphthyridin-4-yl)-[5-methyl-2-(pyridin-2-ylsulfanyl)-phenyl]-amine The product of Example 227b (60 mg, 0.278 mmol) was reacted with the product from Example 1d (50 mg, 0.278 mmol) for 16 h following the procedure from Example 1g giving the crude title compound which was purified by HPLC with TFA providing the product as a trifluoroacetic acid (24 mg, 28%). $^1$H NMR (300 MHz, DMSO-$d_6$) δ ppm: 2.44 (s, 3H), 2.73 (s, 3H), 6.45 (d, J=6.99 Hz, 1H), 7.02-7.12 (m, J=7.72, 1.10 Hz, 2H), 7.40-7.49 (m, 2H), 7.50-7.58 (m, J=1.84 Hz, 1H), 7.72 (dd, J=8.46, 3.31 Hz, 2H), 8.21-8.27 (m, J=2.94, 0.74 Hz, 1H), 8.38 (d, J=6.99 Hz, 1H), 8.85 (d, J=8.82 Hz, 1H), 10.99 (s, 1H); MS (ESI+) m/z 359 (M+H−TFA)+; (ESI−) m/z 357 (M−H−TFA)−.

Example 228

(5-Chloro-2-phenoxy-phenyl)-[1,6]naphthyridin-5-yl-amine

Example 228a

2-Trimethylsilanylethynyl-nicotinonitrile

In a suitably sized pressure vessel, commercially available 2-chloro-nictinonitrile (1.5 g, 10.8 mmol) was combined with triphenylphosphine (0.228 g, 8 mole %) and palladium (II) acetate (0.083 g, 3.5 mol %) in triethylamine (20 mL). Nitrogen was bubbled through the resulting suspension at room temperature for five minutes then trimethylsilylacetylene (8.5 mL, 60.1 mmol) was added, the vessel sealed and immersed in an 80° C. oil bath. After 18.5 h the pressure tube was cooled to room temperature and the contents were filtered. The filtrate was concentrated under vacuum and the crude product purified by flash chromatography on silica gel eluting with EtOAc/hexanes to give the title compound (1.62 g, 75%) as a tan solid.

Example 228b 2-(2,2-Dimethoxy-ethyl)-nicotinonitrile

The product from Example 228a (1.62 g, 8.09 mmol) was reacted with sodium methoxide as a 25 wt % solution (8.74 g, 40.4 mmol) in methanol (5 mL) for two hours at 80° C. The crude product was isolated by extraction with ether, dried

Example 228c 2-(2,2-Dimethoxy-ethyl)-nicotinamide

The product from Example 228b (1.46 g, 7.6 mmol) was dissolved in methanol (20 mL) to which was added at room temperature sodium carbonate as a 3N solution (35 mL) followed by hydrogen peroxide as a 15% solution (35 mL). The reaction was allowed to stir for 4.5 hours then partitioned by the addition of ethyl acetate and solid sodium chloride. The aqueous phase was extracted several times with ethyl acetate and the combined organics stirred with solid sodium bisulfite followed by drying over $MgSO_4$, filtered and concentration under vacuum to give the title compound (1.36 g, 85%) sufficiently pure for use as isolated.

Example 228d

Naphthyridin-5-ol

The product from Example 228c (1.36 g, 6.47 mmol) was dissolved in benzene (35 ml) and to this solution was added pyridinium-para-toluenesulfonate (0.20 g, 0.8 mmol). The mixture was heated to reflux for 23 h then concentrated under vacuum to give the title compound in quantitative yield sufficiently pure for use as isolated.

Example 228e

5-Chloro-[1,6]naphthyridine

The product from Example 228d (0.250 g, 1.71 mmol) was combined with phosphorous oxychloride (4 mL) and heated under a nitrogen atmosphere at 80° C. for 18.5 h followed by vacuum distillation to remove the volatiles. The residue was slurried with ice and made basic (pH 7-8) with concentrated ammonium hydroxide. The title compound was collected by vacuum filtration, water washed and dried under vacuum to give a gray solid (0.245 g, 87%) sufficiently pure for use as isolated.

Example 228f (5-Chloro-2-phenoxy-phenyl)-[1,6]naphthyridin-5-yl-amine

The product from Example 228e (0.040 g, 0.24 mmol) was reacted with the product from Example 42b (0.048 g, 0.24 mmol) for 48 h at 100° C. following the procedure from Example 1g giving the crude title compound which was purified by HPLC with TFA providing the product as a trifluoroacetic acid salt (0.046 g, 40%). $^1$H NMR (300 MHz, DMSO-$d_6$) δ ppm: 6.96 (d, J=7.35 Hz, 2H) 7.00-7.10 (m, 2H) 7.22-7.39 (m, 4H) 7.66 (dd, J=8.46, 4.41 Hz, 1H) 7.91 (d, J=1.84 Hz, 1H) 8.07 (d, J=6.25 Hz, 1H) 8.76 (d, J=8.46 Hz, 1H) 9.07 (d, J=3.31 Hz, 1H); MS (ESI+) m/z 348.0 (M+H)+; (ESI−) m/z 346.1 (M−H)−.

Example 229

N-{4-[4-Methyl-2-([1,6]naphthyridin-5-ylamino)-phenylsulfanyl]-phenyl}-acetamide The product from Example 228e (0.040 g, 0.24 mmol) was reacted with the product from Example 18b as a 1.5M solution in ethanol (0.162 mL, 0.24 mmol) for 17.5 h at 100° C. following the procedure from Example 1g. Consumption of starting material required a second addition of the product from Example 228e (0.027 g, 0.16 mmol) and continued heating at 100° C. (24 h) giving the crude title compound which was purified by HPLC with TFA providing the product as a trifluoroacetic acid salt (0.038 g, 27%). $^1$H NMR (300 MHz, DMSO-$d_6$) δ ppm: 2.02 (s, 3H) 2.36 (s, 3H) 7.12-7.37 (m, 5H) 7.38-7.53 (m, 3H) 7.73-7.92 (m, J=8.64, 4.60 Hz, 2H) 8.94 (d, J=8.46 Hz, 1H) 9.18 (d, J=4.04 Hz, 1H) 9.99 (s, 1H); MS (ESI+) m/z 401.3 (M+H)+; (ESI−) m/z 399.0 (M−H)−.

Example 230

(5-Methyl-2-phenylsulfanyl-phenyl)-[1,8]naphthyridin-4-yl-amine

The product from Example 16c (0.051 g, 0.31 mmol) was reacted with the product from Example 1f (0.066 g, 0.31 mmol) for 22.5 h following the procedure from Example 1g. Consumption of starting material required a second addition of the product from Example 16c (0.018 g, 0.113 mmol) and continued heating at 80° C. (22 h) giving the crude title compound which was purified by HPLC with ammonium acetate providing the product as the free base which was subsequently treated with trifluoroacetic acid to produce the corresponding trifluoroacetic acid salt (0.062 g, 43%). $^1$H NMR (300 MHz, DMSO-$d_6$) δ ppm: 2.38 (s, 3H) 6.36 (d, J=6.99 Hz, 1H) 7.23 (s, 5H) 7.30-7.42 (m, 3H) 7.89 (dd, J=8.46, 4.41 Hz, 1H) 8.46 (d, J=6.99 Hz, 1H) 9.03-9.10 (m, 1H) 9.15 (dd, J=4.41, 1.47 Hz, 1H) MS (ESI+) m/z 344.0 (M+H)+; (ESI−) m/z 342.0 (M−H)−.

Example 231

N-{4-[4-Chloro-2-(7-methyl-[1,8]naphthyridin-4-ylamino)-phenylsulfanyl]-phenyl}-acetamide

Example 231a

N-[4-(5-Chloro-2-nitro-phenylsulfanyl)-phenyl]-acetamide

A mixture of 2,4-Dichloro nitro benzene (0.25 g, 1.3 mmol), 4-Acetamido thiophenol (0.26 g, 1.43 mmol) and cesium carbonate (0.466 g, 1.43 mmol) in DMF (3 mL) was heated 2.5 hr at 100° C. The mixture was cooled, diluted with ethyl acetate (100 mL) and the organic layer was washed with water and aqueous 10% sodium chloride solution, then, dried over anhydrous sodium sulfate. The drying agent was filtered and the solvent removed under vacuum. The residue is purified by silica gel column chromatography eluting with $CH_2Cl_2$/methanol leaving the title compound as a yellow solid (0.25 g, 63%).

Example 231b

N-(4-(5-chloro-2-nitrophenylthio)phenyl)acetamide

A solution of the product of Example 231A (0.25 g, 0.77 mmol), iron powder (0.29 g, 5.2 mmol) and ammonium chloride (0.084 g, 1.6 mmol) in a methanol (2 mL), tetrahydrofuran (2 mL), and water (0.7 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (0.20 g, 87

Example 231c

N-{4-[5-Chloro-2-(7-methyl-[1,8]naphthyridin-4-ylamino)-phenylsulfanyl]-phenyl}-acetamide The product from Example 1d (48 mg, 0.27 mmol) was reacted in ethanol (2 ml) with the product from Example 231b (78 mg, 0.27 mmol) for 18 h following the procedure from Example 1g giving the crude title compound which was purified by HPLC with TFA providing the product as a trifluoroacetic acid salt. (12 mg, 28%). $^1$H NMR (300 MHz, DMSO-$d_6$) δ ppm: 2.06 (s, 3H) 2.77 (s, 3H), 6.39 (d, J=7.35 Hz, 1H), 6.96 (d, J=1.84 Hz, 1H), 7.38 (d, J=8.82 Hz, 2H) 7.51 (s, 2H), 7.62 (d, J=8.82 Hz, 2H), 7.81 (d, J=8.82 Hz, 1H), 8.47 (d, J=7.35 Hz, 1H) 8.97 (d, J=8.82 Hz, 1H), 10.15 (s, 1H), 11.01 (s, 1H), 14.48 (s, 1H); MS (DCI/NH3) m/z 435 (M+H)+.

Example 232

N-{4-[4-Cyanomethoxy-2-(7-methyl-[1,8]naphthyridin-4-ylamino)-phenylsulfanyl]-phenyl}-acetamide

Example 232a

N-[4-(4-Hydroxy-2-nitro-phenylsulfanyl)-phenyl]-acetamide

A mixture of 3-nitro-4-chloro phenol (1.59 g, 8.97 mmol), 4-acetamidothiophenol (2 g, 10.76 mmol) and cesium carbonate (7.0 g, 21.53 mmol) in DMF (20 mL) was heated 2.5 h at 100° C. The mixture was cooled, poured onto ice and the resulting solid is collected by filtration and dried under vacuum the title compound leaving a yellow solid (2.7 g, 100%).

Example 232b

N-[4-(2-Amino-4-hydroxy-phenylsulfanyl)-phenyl]-acetamide

A solution of the product of Example 232A (2.7 g, 8.97 mmol), iron powder (2.0 g, 35.9 mmol) and ammonium chloride (0.58 g, 10.76 mmol) in a methanol (6 mL), THF (6 mL), and water (2 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (2.46 g, 77%).

Example 232c

N-[4-(2-Amino-4-cyanomethoxy-phenylsulfanyl)-phenyl]-acetamide

A mixture of the product from Example 232b (56 mg, 0.17 mmol), 2-Bromoacetonitrile (20 mg, 0.17 mmol) and potassium carbonate (26 mg, 0.19 mmol) in DMF (1 mL) was stirred at room temperature 15 hr. The next day, the reaction mixture was poured onto ice and the solid collected by filtration providing the title compound (53 mg, 100%).

Example 232d

N-{4-[4-Cyanomethoxy-2-(7-methyl-[1,8]naphthyridin-4-ylamino)-phenylsulfanyl]-phenyl}-acetamide The product from Example 1d (30 mg, 0.17 mmol) was reacted in ethanol (1 mL) with the product from Example 232c (53 mg, 0.17 mmol) for 18 h following the procedure from Example 1g giving the crude title compound which was purified by HPLC with TFA providing the product as a trifluoroacetic acid salt (9 mg, 19%). $^1$H NMR (300 MHz, DMSO-$d_6$) δ ppm: 2.03 (s, 3H) 2.76 (s, 3H), 5.23 (s, 2H), 6.32 (d, J=6.99 Hz, 1H), 7.18 (d, J=8.46 Hz, 2H) 7.23 (dd, J=8.82, 2.57 Hz, 1H), 7.31 (d, J=2.57 Hz, 1H), 7.38 (d, J=8.82 Hz, 1H) 7.45 (d, J=8.82 Hz, 2H), 7.80 (d, J=8.46 Hz, 1H), 8.41 (d, J=6.99 Hz, 1H) 8.96 (d, J=8.46 Hz, 1H), 10.01 (s, 1H), 11.04 (s, 1H), 14.42 (s, 1H); MS (ESI+) m/z 456 (M+H)+.

Example 233

N-{4-[4-Benzyloxy-2-(7-methyl-[1,8]naphthyridin-4-ylamino)-phenylsulfanyl]-phenyl}-acetamide

Example 233a

N-[4-(2-Amino-4-benzyloxy-phenylsulfanyl)-phenyl]-acetamide

A mixture of the product from Example 232b (56 mg, 0.17 mmol), benzyl bromide (21 mg, 0.17 mmol) and potassium carbonate (26 mg, 0.19 mmol) in DMF (1 mL) was stirred at room temperature 15 hr. The next day, the reaction mixture was poured onto ice and the solid collected by filtration providing the title compound (62 mg, 100%).

Example 233b

N-{4-[4-Benzyloxy-2-(7-methyl-[1,8]naphthyridin-4-ylamino)-phenylsulfanyl]-phenyl}-acetamide The product from Example 1d (30 mg, 0.17 mmol) was reacted in ethanol (1 mL) with the product from Example 233a (62 mg, 0.17 mmol) for 18 h following the procedure from Example 1g giving the crude title compound which was purified by HPLC with TFA providing the product as a trifluoroacetic acid salt (24 mg, 47%). $^{1H}$ NMR (300 MHz, DMSO-$d_6$) δ ppm: 2.02 (s, 3H) 2.75 (s, 3H) 5.15 (s, 2H) 6.29 (d, J=7.35 Hz, 1H) 7.12 (d, J=8.82 Hz, 2H) 7.16-7.27 (m, 2H) 7.29-7.52 (m, 8H) 7.78 (d, J=8.82 Hz, 1H) 8.36 (d, J=6.99 Hz, 1H) 8.94 (d, J=8.82 Hz, 1H) 9.97 (s, 1H) 11.00 (s, 1H) 14.34 (s, 1H); MS (ESI+) m/z 507 (M+H)+.

Example 234

N-{4-[4-(2-Methyl-allyloxy)-2-(7-methyl-[1,8]naphthyridin-4-ylamino)-phenylsulfanyl]-phenyl}-acetamide

Example 234a

N-{4-[2-Amino-4-(2-methyl-allyloxy)-phenylsulfanyl]-phenyl}-acetamide

A mixture of the product from Example 232b (56 mg, 0.17 mmol), 2-methyl-3-bromo propene (20 mg, 0.17 mmol) and potassium carbonate (26 mg, 0.19 mmol) in DMF (1 mL) was stirred at room temperature 15 hr. The next day, the reaction mixture was poured onto ice and the solid collected by filtration providing the title compound (55 mg, 100%).

Example 234b

N-{4-[4-(2-Methyl-allyloxy)-2-(7-methyl-[1,8]naphthyridin-4-ylamino)-phenylsulfanyl]-phenyl}-acetamide The product from Example 1d (30 mg, 0.17 mmol) was reacted in ethanol (1 mL) with the product from Example 234a (55 mg, 0.17 mmol) for 18 h following the procedure from Example 1g giving the crude title compound which was purified by HPLC with TFA providing the product as a trifluoroacetic acid salt (12 mg, 25%). $^1$H NMR (300 MHz, DMSO-$d_6$) δ ppm: 1.76 (s, 3H) 2.02 (s, 3H), 2.75 (s, 3H), 4.52 (s, 2H), 4.98 (s, 1H), 5.05 (s, 1H), 6.30 (d, J=7.35 Hz, 1H), 7.04-7.19 (m, 4H), 7.36 (s, 1H), 7.41 (d, J=8.46 Hz, 2H) 7.78 (d, J=8.82 Hz, 1H), 8.37 (d, J=6.99 Hz, 1H), 8.94 (d, J=8.46 Hz, 1H) 9.97 (s, 1H, ) 10.99 (s, 1H), 14.33 (s, 1H); MS (ESI+) m/z 471 (M+H)+.

Example 235

N-{4-[2-(7-Methyl-[1,8]naphthyridin-4-ylamino)-4-propoxy-phenylsulfanyl]-phenyl}-acetamide

Example 235a

N-[4-(2-Amino-4-propoxy-phenylsulfanyl)-phenyl]-acetamide

A mixture of the product from Example 232b (56 mg, 0.17 mmol), 2-methyl-3-bromo propene (20 mg, 0.17 mmol) and potassium carbonate (26 mg, 0.19 mmole) in DMF (1 mL) was stirred at room temperature 15 hr. The next day, the reaction mixture was poured onto ice and the solid collected by filtration providing the title compound (55 mg, 100%).

Example 235b

N-{4-[2-(7-Methyl-[1,8]naphthyridin-4-ylamino)-4-propoxy-phenylsulfanyl]-phenyl}-acetamide The product from Example 1d (30 mg, 0.17 mmol) was reacted in ethanol (1 mL) with the product from Example 235a (55 mg, 0.17 mmol) for 18 h following the procedure from Example 1g giving the crude title compound which was purified by HPLC with TFA providing the product as a trifluoroacetic acid salt (14 mg, 30%). $^1$H NMR (300 MHz, DMSO-$d_6$) δ ppm: 0.97 (t, J=7.35 Hz, 3H) 1.59-1.83 (m, 2H) 2.02 (s, 3H) 2.75 (s, 3H) 3.97 (t, J=6.43 Hz, 2H) 6.31 (d, J=7.35 Hz, 1H) 7.04-7.18 (m, 4H) 7.25-7.45 (m, J=8.64, 3.86 Hz, 3H) 7.77 (d, J=8.46 Hz, 1H) 8.35 (d, J=7.35 Hz, 1H) 8.94 (d, J=8.82 Hz, 1H) 9.96 (s, 1H) 10.99 (s, 1H) 14.31 (s, 1H); MS (ESI+) m/z 459 (M+H)+.

Example 236

4-[4-(4-Acetylamino-phenylsulfanyl)-3-(7-propyl-[1,8]naphthyridin-4-ylamino)-phenoxymethyl]-benzoic acid methyl ester

Example 236a

4-[4-(4-Acetylamino-phenylsulfanyl)-3-amino-phenoxymethyl]-benzoic acid methyl ester A mixture of the product from Example 232b (28 mg, 0.085 mmol), 4-carbomethoxybenzyl bromide (22 mg, 0.096 mmol) and potassium carbonate (13 mg, 0.09 mmol) in DMF (1 mL) was stirred at room temperature 15 hr. The next day, the reaction mixture was poured onto ice and the solid collected by filtration providing the title compound (35 mg, 100%).

Example 236b

4-[4-(4-Acetylamino-phenylsulfanyl)-3-(7-propyl-[1,8]naphthyridin-4-ylamino)-phenoxymethyl]-benzoic acid methyl ester The product from Example 1d (18 mg, 0.085 mmol) was reacted in ethanol (1 mL) with the product from Example 236a (35 mg, 0.085 mmol) for 18 h following the procedure from Example 1g giving the crude title compound which was purified by HPLC with TFA providing the product as a trifluoroacetic acid salt (22 mg, 37%). $^1$H NMR (300 MHz, DMSO-$d_6$) δ ppm: 0.97 (t, J=7.35 Hz, 3H) 1.75-1.93 (m, 2H), 2.02 (s, 3H), 2.99 (t, J=7.54 Hz, 2H), 3.86 (s, 3H) 5.26 (s, 2H) 6.30 (d, J=6.99 Hz, 1H) 7.14 (d, J=8.82 Hz, 2H), 7.17-7.27 (m, 2H), 7.37 (d, J=8.46 Hz, 1H), 7.42 (d, J=8.82 Hz, 2H), 7.59 (d, J=8.46 Hz, 2H), 7.80 (d, J=8.46 Hz, 1H) 7.99 (d, J=8.09 Hz, 2H), 8.36 (d, J=7.35 Hz, 1H), 8.97 (d, J=8.46 Hz, 1H) 9.98 (s, 1H), 11.01 (s, 1H), 14.38 (s, 1H); MS (ESI+) m/z 593 (M+H)+.

Example 237

4-[4-(4-Methoxy-benzyloxy)-2-(7-methyl-pyrido[2,3-d]pyrimidin-4-ylamino)-phenylsulfanyl]-phenol

Example 237a

2-Amino-6-methyl-nicotinonitrile

2-Chloro-6-methyl-nicotinonitrile (25 g, 0.164 mol) and liquid ammonia (250 mL) in 500 mL of ethanol were reacted in a sealed high-pressure vessel at 130° C. for 20 hours. The reaction mixture was concentrated under vacuum and the residue washed with water (2×50 mL) then dried in a vacuum oven for 24 hours to provide the title compound as a light yellow solid (18 g, 82%). $^1$H NMR (300 MHz, DMSO-$d_6$) δ ppm:2.30 (s, 3H), 6.52 (d, J=7.7 Hz, 1H), 6.78 (s, 2H), 7.73 (d, J=7.7 Hz, 1H).

Example 237b

N'-(3-Cyano-6-methyl-pyridin-2-yl)-N,N-dimethyl-formamidine

A solution of the product of Example 237A (10 g, 75.19 mmol) and N,N-Dimethylformamide dimethyl acetal (11 mL, 82.71 mmol) in toluene (100 mL) was heated at reflux for 6 hours. After cooling to room temperature, the solution was concentrated under vacuum to provide the title compound as a yellow solid (13.78 g, 98%). $^1$H NMR (300 MHz, DMSO-$d_6$) δ ppm: 2.41 (s, 3H), 3.06 (s, 3H), 3.14 (s, 3H), 6.87 (d, J=7.7 Hz, 1H), 7.89 (d, J=8.1 Hz, 1H), 8.59 (s, 1H).

Example 237c

1-Chloro-4-(4-methoxy-benzyloxy)-2-nitro-benzene

A solution of 4-chloro-3-nitro-phenol (0.5 g, 2.88 mmol), 1-chloromethyl-4-methoxy-benzene (0.496 g, 3.17 mmol), potassium carbonate (1.19 g, 8.64 mmol) and tetrabutylammonium iodide (0.005 g, 0.0135 mmol) in N,N-dimethylformamide (5 ml) was stirred at room temperature for 16 hours. Afterwards ice water (10 mL) was added to the solution and the resultant solid was collected by filtration and dried in a vacuum oven to provide the title compound (0.812 g, 96%).

Example 237d

4-[4-(4-Methoxy-benzyloxy)-2-nitro-phenylsulfanyl]-phenol

A solution of the product of Example 237C (0.812 g, 2.76 mmol), 4-hydroxythiophenol (0.419, 3.32 mmol) and cesium carbonate (2.16 g, 6.64 mmol) in N,N-dimethylformamide (5 mL) was heated to 100° C. for 16 hours. After cooling to room temperature the mixture was poured into ice water (20 mL) and the resultant solution acidified with 1N aqueous hydrochloric acid. The solution was then extracted with ethyl acetate (3×10 mL), the combined extracts dried over magnesium sulfate, filtered and concentrated under vacuum to provide the title compound (1.06 g, 100%).

Example 237e

4-[2-Amino-4-(4-methoxy-benzyloxy)-phenylsulfanyl]-phenol

A solution of the product of Example 237D (1.06 g, 2.76 mmol), iron powder (0.63 g, 11.04 mmol) and ammonium chloride (0.18 g, 3.31 mmol) in a methanol (18 mL), tetrahydrofuran (18 mL), and water (6 mL) solution was heated to reflux for 3 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were dried over magnesium sulfate, filtered and concentrated under vacuum to provide the title compound (0.99 g, 100%).

Example 237f

4-[4-(4-Methoxy-benzyloxy)-2-(7-methyl-pyrido[2,3-d]pyrimidin-4-ylamino)-phenylsulfanyl]-phenol A solution of the product of Example 237B (28.4 mg, 0.151 mmol), and the product of Example 237E (53.3 mg, 0.151 mmol) in acetic acid (1 mL) was stirred in an oil bath preheated to 130° C. for 20 minutes. The mixture was then cooled to room temperature, the acetic acid removed under vacuum, and the resultant residue triturated with methanol to provide the title compound as a tan solid (26.5 mg, 35%). $^1$H NMR (300 MHz, DMSO-$d_6$) δ ppm: 9.92 (s, 1H), 9.63 (s, 1H), 8.70 (d, J=8.09 Hz, 1H), 8.55 (s, 1H), 7.52 (d, J=8.46 Hz, 1H), 7.38 (d, J=8.82 Hz, 2H), 7.27 (s, 1H), 7.06-7.18 (m, 3H), 6.94 (d, J=8.46 Hz, 3H), 6.61-6.72 (m, 2H), 5.02 (s, 2H), 3.75 (s, 3H), 2.66 (s, 3H); MS (ESI+) m/z 497.2 (M+H)+, (ESI−) m/z 495.3 (M−H)−.

Biological Evaluation

Representative compounds of the invention were analyzed according to the assays described below.

The following acronyms are used herein:

| | |
|---|---|
| $IC_{50}$ | 50% inhibitory concentration |
| $TC_{50}$ | 50% toxicity concentration |
| DMEM | Dulbecco's Modified Essential Medium ™ |
| RNA | ribonucleic acid |
| RT-PCR | reverse transcriptase polymerase chain reaction |
| SEAP | secreted alkaline phosphatase |

The hepatitis C virus genome encodes a large polyprotein, which after processing produces the necessary functional components to synthesize progeny RNA. Selectable cell lines that produce high and sustained levels of subgenomic HCV RNA (replicons) have been derived from human hepatoma cells (Huh7) as described in Ikeda et al., J. VIROLOGY, 76(6): 2997-3006 (2002), and Blight et al., SCIENCE, 290:1972-1974 (2000). The mechanism of RNA replication in these cell lines is considered to be identical to the replication of full length HCV RNA in infected hepatocytes. The compounds of this invention are inhibitors of HCV RNA replication in the replicon assay systems described below.

Evaluation of the HCV Inhibitors in HCV Replicon

Representative compounds of the invention were evaluated for their inhibitory effect on HCV genotype 1a and 1b replicons. They were also evaluated by MTT assay for cytotoxicity to the host cells. The cell lines were maintained according to the methods described by Yi et al., VIROLOGY, 304(2):197-210 (2002).

A. RNA Assay and SEAP Assay

The purpose of these assays was to evaluate the efficacy of the compounds in inhibiting the replication of HCV genotype 1a and 1b replicons in vitro.

Genotype 1a and/or 1b replicon cells were plated at 3-5× $10^3$ cells per well in 96-well plate in DMEM medium containing 5% fetal calf serum. The next day, the culture medium was removed and replaced with fresh medium containing eight serial dilutions of compound. The untreated control culture was treated in an identical manner except no inhibitor was added to the medium. Plates were incubated in a $CO_2$ incubator at 37° C. On day 4, 100 μl lysis buffer (RTL) (Qiagen) was added to each well after removal of culture medium. RNA was purified according to manufacturer's recommendations (Qiagen RNAeasy) and eluted in 200 μl of water. The HCV RNA level was quantified from a portion (5 μl out of 200 μl) of the purified RNA by real-time RT-PCR method. The primers and probe were derived from specific sequence in the 5'-Untranslated Region (5'UTR). RT-PCR reaction was performed at 48° C. for 30 min, followed by 40 cycles set to 95° C., 15 s; 54° C., 30 s; and 72° C., 40 s. Alternatively, the activity of SEAP was measured in each culture supernatant after four days incubation with compound according to the manufacturer's instructions. The percentage reduction of HCV RNA or SEAP in the presence of compound was calculated and the 50% inhibitory concentration ($IC_{50}$) was calculated by non-linear regression analysis using the Prism program (version 4.0, GraphPad software, San Diego, Calif.).

When tested using the above method, representative compounds of the present invention inhibited HCV replicon replication with $IC_{50}$ values in the range of from about 30 nM to about 100 μM.

B. Cytotoxicity assay

The purpose of this assay was to determine the toxicity of the compounds on viral host cells in vitro.

Cytotoxicity of the compounds was measured using a mitochondrial enzyme-based cell proliferation/viability assay in replicon cells. Briefly, HCV replicon cells were plated at 3-5×$10^3$ cells per well in 96-well plate in DMEM medium containing 5% FCS. At day 1, culture medium was removed and replaced with fresh medium containing eight serial dilutions of compound. The untreated control culture was treated in an identical manner except no inhibitor was added to the medium. Plates were incubated in a $CO_2$ incubator at 37° C. On day 4, stock solution of the tetrazolium salt, MTT (4 mg/ml in PBS, Sigma cat. # M 2128) was added to each well at 25 μl per well. Plates were further incubated for 4 hours, treated with 20% SDS plus 0.02 N HCl at 50 μl per well to lyse the cells. After an overnight incubation, optical density was measured by reading the plates at 570/650 nm wavelengths. The percent reduction of formazan blue color formed relative to control was calculated and the 50% toxicity concentration ($TC_{50}$) was calculated by non-linear regression analysis using the Prism program (version 4.0, GraphPad software, San Diego, Calif.).

When tested using the above method, the $TC_{50}$ values of representative compounds of the present invention were greater than the corresponding $IC_{50}$ values of these compounds.

Pharmaceutical Compositions and Uses

The present invention features pharmaceutical compositions comprising the compounds of the invention. As a non-limiting example, a pharmaceutical composition of the present invention comprises one or more compounds of this invention, wherein each compound is independently selected from Formulae I(a), I(b), II(a) or II(b). Preferably, each compound is independently selected from Examples 1-237.

The present invention also features pharmaceutical compositions comprising pharmaceutically acceptable salts, solvates, or prodrugs of the compounds of this invention. Pharmaceutically acceptable salts can be zwitterions or derived from pharmaceutically acceptable inorganic or organic acids or bases. Preferably, a pharmaceutically acceptable salt of a compound of the invention retains the biological effectiveness of the free acid or base of the compound without undue toxicity, irritation, or allergic response, has a reasonable benefit/risk ratio, and is effective for their intended use and not biologically or otherwise undesirable. Non-limiting examples of pharmaceutically acceptable salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. The basic nitrogen-containing groups can also be quaternized with such agents as loweralkyl halides (e.g., methyl, ethyl, propyl or butyl chlorides, bromides or iodides), dialkyl sulfates (e.g., dimethyl, diethyl, dibutyl or diamyl sulfates), long chain halides (e.g., decyl, lauryl, myristyl or stearyl chlorides, bromides or iodides), aralkyl halides (e.g., benzyl or phenethyl bromides). Other salts that can be used in the present invention include salts with alkali or alkaline earth metals, such as sodium, potassium, calcium or magnesium, or with organic bases. Examples of acids which can be used to form pharmaceutically acceptable acid addition salts include, but are not limited to, hydrochloric acid, sulphuric acid, phosphoric acid, oxalic acid, maleic acid, succinic acid, citric acid, or other suitable inorganic or organic acids.

The present invention further features pharmaceutical compositions comprising a compound of the invention (or a salt, solvate or prodrug thereof) and another therapeutic agent. In a non-limiting example, a pharmaceutical composition of the present invention includes 1, 2, 3 or more compounds of the invention (or salts, solvates or prodrugs thereof), and 1, 2, 3 or more other therapeutic agents. By way of illustration not limitation, these other therapeutic agents can be selected from antiviral agents (e.g., anti-HIV agents or other anti-HCV agents), immunomodulators, anti-cancer or chemotherapeutic agents, or anti-inflammation agents. Specific examples of these other therapeutic agents include, but are not limited to, ribavirin; interferons (e.g., IFN alpha 2a or 2b); protease inhibitors; immunosuppressants; antibodies (e.g., therapeutic monoclonal or chimeric antibodies); antisense or siRNA; HIV inhibitors; hepatitis B (HBV) inhibitors; agents for treating cirrhosis and inflammation of the liver; Omega IFN (BioMedicines Inc., Emeryville, Calif.); BILN-2061 serine protease inhibitor (Boehringer Ingelheim Pharma KG, Ingelheim, Germany); Summetrel antiviral (Endo Pharmaceuticals Holdings Inc., Chadds Ford, Pa.); Roferon A IFN-alpha 2a (F. Hoffmann-La Roche LTD, Base1, Switzerland); Pegasys PEGylated IFN-alpha 2a (F. Hoffmann-La Roche LTD, Base1, Switzerland); Pegasys and Ribavirin PEGylated IFN-alpha 2a/ribavirin (F. Hoffmann-La Roche LTD, Base1, Switzerland); CellCept HCV IgG immunosuppressant (F. Hoffmann-La Roche LTD, Base1, Switzerland); Wellferon lymphoblastoid IFN-alpha n1 (GlaxoSmithKline plc, Uxbridge, UK); Albuferon-alpha albumin IFN-alpha 2b (Human Genome Sciences Inc., Rockville, Md.); Levovirin ribavirin (ICN Pharmaceuticals, Costa Mesa, Calif.); IDN-6556 caspase inhibitor (Idun Pharmaceuticals Inc., San Diego, Calif.); IP-501 antifibrotic (Indevus Pharmaceuticals Inc., Lexington, Mass.); Actimmune INF-gamma (InterMune Inc., Brisbane, Calif.); Infergen A IFN alfacon-1 (InterMune Pharmaceuticals Inc., Brisbane, Calif.); ISIS 14803 antisense (ISIS Pharmaceuticals Inc., Carlsbad, Calif./Elan Pharmaceuticals Inc., New York, N.Y.); JTK-003 RdRp inhibitor (Japan Tobacco Inc., Tokyo, Japan); Pegasys and Ceplene PEGylated IFN-alpha 2a/immune modulator (Maxim Pharmaceuticals inc., San Diego, Calif.); Ceplene immune modulator (Maxim Pharmaceuticals Inc., San Diego, Calif.); Civacir HCV IgG immunosuppressant (Nabi Biopharmaceuticals Inc., Boca Raton, Fla.); Intron A and Zadaxin IFN-alpha 2b/alpha 1-thymosin (RegeneRx Biopharmiceuticals Inc., Bethesda, Md./SciClone Pharmaceuticals Inc., San Mateo, Calif.); Levovirin IMPDH inhibitor (Ribapharm Inc., Costa Mesa, Calif.); Viramidine IMPDH inhibitor (Ribapharm Inc., Costa Mesa, Calif.); Heptazyme ribozyme (Ribozyme Pharmaceuticals Inc., Boulder, Colo.); Intron A IFN-alpha 2b (Schering-Plough Corporation, Kenilworth, N.J.); PEG-Intron PEGylated IFN-alpha 2b (Schering-Plough Corporation, Kenilworth, N.J.); Rebetron IFN-alpha 2b/ribavirin (Schering-Plough Corporation, Kenilworth, N.J.); Ribavirin (Schering-Plough Corporation, Kenilworth, N.J.); PEG-Intron/Ribavirin PEGylated IFN-alpha 2b/ribavirin (Schering-Plough Corporation, Kenilworth, N.J.); Zadazim immune modulator (SciClone Pharmaceuticals Inc., San Mateo, Calif.); Rebif IFN-beta 1a (Serono, Geneva, Switzerland); IFN-beta and EMZ701 IFN-beta and EMZ701 (Transition Therapeutics Inc., Ontario, Canada); T67 beta-tubulin inhibitor (Tularik Inc., South San Francisco, Calif.); VX-497 IMPDH inhibitor (Vertex Pharmaceuticals Inc., Cambridge, Mass.); VX-950/LY-570310 serine protease inhibitor (Vertex Pharmaceuticals Inc., Cambridge, Mass./Eli Lilly and Co., Inc., Indianapolis, Ind.); Omniferon natural IFN-alpha (Viragen Inc., Plantation, Fla.); XTL-002 monoclonal antibody (XTL Biopharmaceuticals);

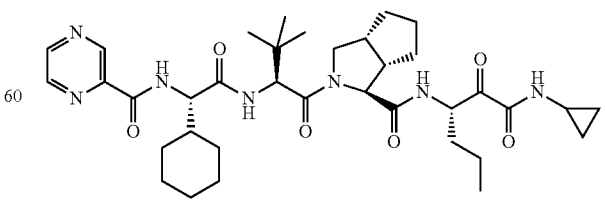

(hereinafter compound VX-950, Vertex Pharmaceuticals Inc.);

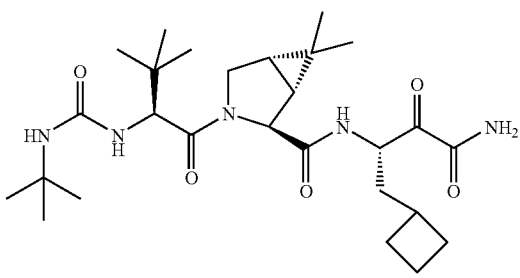

(hereinafter compound SCH503034, Schering-Plough Co.); and

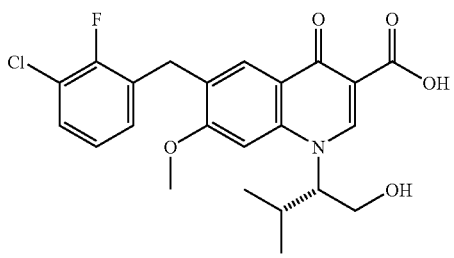

(hereinafter compound GS9137, Gilead Sciences, Inc., Foster City, Calif.). Any other desirable therapeutic agent(s) can also be included in a pharmaceutical composition of the present invention.

In one embodiment, a pharmaceutical composition of the present invention comprises one or more compounds of the present invention (or salts, solvates or prodrugs thereof), and one or more other antiviral agents.

In another embodiment, a pharmaceutical composition of the present invention comprises one or more compounds of the present invention (or salts, solvates or prodrugs thereof), and one or more other anti-HCV agents. In one example, each of the compounds of the present invention is independently selected from Formulae I(a), I(b), II(a) or II(b), or Examples 1-237, and each of the other anti-HCV agents is independently selected from HCV RNA dependent RNA polymerase inhibitors (e.g., nucleoside or non-nucleoside type polymerase inhibitors), HCV protease inhibitors, or HCV helicase inhibitors.

In a further embodiment, a pharmaceutical composition of the present invention comprises one or more compounds of the present invention (or salts, solvates or prodrugs thereof), and two or more other anti-HCV inhibitors. Preferably, each compound of the present invention is independently selected from Formulae I(a), I(b), II(a) or II(b), or from Examples 1-237. The other anti-HCV inhibitors can be selected from the same inhibitor class (e.g., all of them are selected from HCV RNA dependent RNA polymerase inhibitors, or from HCV protease inhibitors), or selected from different inhibitor classes (e.g., one or more are selected from HCV RNA dependent RNA polymerase inhibitor and the other or others are selected from HCV protease inhibitors).

In still another embodiment, a pharmaceutical composition of the present invention comprises at least one compound of the present invention (or a salt, solvate or prodrug thereof), and at least one HCV RNA dependent RNA polymerase inhibitor. Preferably, each compound of the present invention is independently selected from Formulae I(a), I(b), II(a) or II(b), or Examples 1-237.

In another embodiment, a pharmaceutical composition of the present invention comprises at least one compound of the present invention (or a salt, solvate or prodrug thereof), and at least one HCV protease inhibitor. Preferably, the compound of the present invention is selected from Formulae I(a), I(b), II(a) or II(b), or Examples 1-237.

In yet another embodiment, a pharmaceutical composition of the present invention comprises at least one compound of the present invention (or a salt, solvate or prodrug thereof), at least one HCV RNA dependent RNA polymerase inhibitor, and at least one HCV protease inhibitor. Preferably, the compound of the present invention is selected from Formulae I(a), I(b), II(a) or II(b), or Examples 1-237.

In still yet another embodiment, a pharmaceutical composition of the present invention comprises at least one compound of the present invention (or a salt, solvate or prodrug thereof), and two or more anti-HCV agents each of which is independently selected from HCV RNA dependent RNA polymerase inhibitors or HCV protease inhibitors. Preferably, the compound of the present invention is selected from Formulae I(a), I(b), II(a) or II(b), or Examples 1-237.

In still another embodiment, a pharmaceutical composition of the present invention comprises at least one compound of the present invention (or a salt, solvate or prodrug thereof), and three or more other anti-HCV agents each of which is independently selected from HCV RNA dependent RNA polymerase inhibitors or HCV protease inhibitors. Preferably, the compound of the present invention is selected from Formulae I(a), I(b), II(a) or II(b), or Examples 1-237.

Non-limiting examples of HCV RNA dependent RNA polymerase inhibitors include those described in WO0190121(A2), U.S. Pat. No. 6,348,587B1, WO0160315, WO0132153, EP1162196A1 and WO0204425. Non-limiting examples of HCV protease inhibitors include BILN-2061, VX-950, and SCH503034.

In another embodiment, a pharmaceutical composition of the present invention comprises at least one compound of the present invention (or a salt, solvate or prodrug thereof), and one or more other antiviral agents, such as anti-HBV or anti-HIV agents. Non-limiting examples of anti-HBV agents include adefovir, lamivudine, and tenofovir. Non-limiting examples of anti-HIV drugs include ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, and other HIV protease, reverse transcriptase, integrase or fusion inhibitors. Other desirable antiviral agents can also be included in a pharmaceutical composition of the present invention, as appreciated by those skilled in the art.

In one embodiment, a pharmaceutical composition of the present invention comprises at least one compound of the present invention selected from Formulae I(a), I(b), II(a) or II(b), or from Examples 1-237, or a salt, solvate or prodrug thereof, and at least one anti-HBV agent. In another embodiment, a pharmaceutical composition of the present invention comprises at least one compound of the present invention selected from Formulae I(a), I(b), II(a) or II(b), or from Examples 1-237, or a salt, solvate or prodrug thereof, and at least one anti-HIV agent. In yet another embodiment, a pharmaceutical composition of the present invention comprises at least one compound of the present invention selected from Formulae I(a), I(b), II(a) or II(b), or from Examples 1-237, or a salt, solvate or prodrug thereof, and at least one anti-hepatitis A, anti-hepatitis D, anti-hepatitis E or anti-hepatitis G agent.

In still yet another embodiment, a pharmaceutical composition of the present invention comprises at least one compound of the present invention selected from Formulae I(a), I(b), II(a) or II(b), or from Examples 1-237, or a salt, solvate or prodrug thereof, and at least one agent suitable for treating liver inflammation.

A pharmaceutical composition of the present invention typically includes a pharmaceutically acceptable carrier or excipient. Non-limiting examples of suitable pharmaceutically acceptable carriers/excipients include sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, or phosphate buffer solutions. Lubricants, coloring agents, releasing agents, coating agents, sweetening, flavoring or perfuming agents, preservatives, or antioxidants can also be included in a pharmaceutical composition of the present invention, as appreciated by those of ordinary skill in the art.

A pharmaceutical composition of the present invention can be administered to a patient in need thereof via a variety of routes, such as orally, parenterally, sublingually, rectally, topically or by inhalation spray. Topical administration may involve the use of transdermal administration such as transdermal patches or iontophoresis devices. Parenteral administration includes, but is not limited to, subcutaneous, intravenous, intramuscular or intrasternal injections, and infusion techniques.

The pharmaceutical compositions of the present invention can be formulated based on their routes of administration using methods well known in the art. For example, a sterile injectable preparation can be prepared as a sterile injectable aqueous or oleagenous suspension using suitable dispersing or wetting agents and suspending agents. Suppositories for rectal administration can be prepared by mixing drugs with a suitable nonirritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHARMACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

The present invention further features methods of using the compounds of the present invention (or salts, solvates or prodrugs thereof) to inhibit HCV replication. In one embodiment, the methods comprise contacting HCV virus with an effective amount of a compound of the present invention (or a salt, solvate or prodrug thereof), thereby inhibiting the replication of the HCV virus. In another embodiment, the methods comprise contacting cells infected with HCV virus with an effective amount of a compound of the present invention (or a salt, solvate or prodrug thereof), thereby inhibiting the replication of the HCV virus in the cells. In still another embodiment, the methods comprise contacting HCV virus or infected cells with an effective amount of two or more compounds of the present invention (or salts, solvates or prodrugs thereof), thereby inhibiting the replication of the HCV virus. As used herein, "inhibiting" means significantly reducing, or abolishing, the activity being inhibited (e.g., viral replication). In many cases, representative compounds of the present invention can reduce the replication of HCV virus (e.g., in HCV replicon assays as described above) by at least 10%, 20%, 30%, 40%, 50%, 60%, 70%, 80%, 90%, 95% or more.

The compounds of the present invention may inhibit all HCV subtypes. Examples of HCV subtypes that are amenable to the present invention include, but are not be limited to, HCV genotypes 1, 2, 3, 4, 5 and 6, including HCV genotypes 1a, 1b, 2a, 2b, 2c or 3a. In one embodiment, a compound or compounds of the present invention (or salts, solvates or prodrugs thereof) are used to inhibit the replication of HCV genotype 1a. In another embodiment, a compound or compounds of the present invention (or salts, solvates or prodrugs thereof) are used to inhibit the replication of HCV genotype 1b. In still another embodiment, a compound or compounds of the present invention (or salts, solvates or prodrugs thereof) are used to inhibit the replication of both HCV genotypes 1a and 1b.

The present invention also features methods of using the compounds of the present invention (or salts, solvates or prodrugs thereof) to treat HCV infection. These methods typically comprise administering a therapeutic effective amount of a compound of the present invention (or a salt, solvate or prodrug thereof) to an HCV patient, thereby reducing the HCV viral level in the blood or liver of the patient. As used herein, the term "treating" refers to reversing, alleviating, inhibiting the progress of, or preventing the disorder or condition, or one or more symptoms of such disorder or condition to which such term applies. The term "treatment" refers to the act of treating. In one embodiment, the methods comprise administering a therapeutic effective amount of two or more compounds of the present invention (or salts, solvates or prodrugs thereof) to an HCV patient, thereby reducing the HCV viral level in the blood or liver of the patient. Preferably, the compound(s) employed in these methods has Formulae I(a), I(b), II(a) or II(b), or is selected from Examples 1-237, or is a salt, solvate or prodrug thereof.

In another aspect, the present invention features methods of using a pharmaceutical composition of the present invention to treat HCV infection. Any pharmaceutical composition described herein can be used for this purpose. These methods typically comprise administering a therapeutic effective amount of a pharmaceutical composition of the present invention to an HCV patient, thereby reducing the HCV viral level in the blood or liver of the patient. Where the pharmaceutical composition includes other therapeutic agent(s), it may also treat other diseases, disorders or conditions in the patient.

In one embodiment, the pharmaceutical composition being administered comprises at least one compound of the present invention selected from Formulae I(a), I(b), II(a) or II(b), or from Examples 1-237, or a salt, solvate or prodrug thereof, and at least another anti-HCV agent selected from HCV RNA dependent RNA polymerase inhibitors, HCV protease inhibitors or HCV helicase inhibitors. In another embodiment, the pharmaceutical composition being administered comprises at least one compound of the present invention selected from Formulae I(a), I(b), II(a) or II(b), or from Examples 1-237, or a salt, solvate or prodrug thereof, and at least two other anti-HCV agents each of which is independently selected from HCV RNA dependent RNA polymerase inhibitors, HCV protease inhibitors or HCV helicase inhibitors. In still another embodiment, the pharmaceutical composition being administered comprises at least one compound of the present invention selected from Formulae I(a), I(b), II(a) or II(b), or from Examples 1-237, or a salt, solvate or prodrug thereof, and 1, 2 or more HCV RNA dependent RNA polymerase inhibitors (e.g., those described in WO0190121(A2), U.S. Pat. No. 6,348,587B1, WO0160315, WO0132153, EP1162196A1 and WO0204425). In yet another embodiment, the pharmaceutical composition being administered comprises at least one compound of the present invention selected from Formulae I(a), I(b), II(a) or II(b), or from Examples 1-237, or a salt, solvate or prodrug thereof, and 1, 2 or more HCV protease inhibitors (e.g., BILN-2061, VX-950, and SCH503034).

In a further embodiment, the pharmaceutical composition being administered comprises at least one compound of the present invention selected from Formulae I(a), I(b), II(a) or II(b), or from Examples 1-237, or a salt, solvate or prodrug thereof, and at least one antiviral agent selected from anti-HIV agents, anti-HBV agents, anti-hepatitis A agents, anti-hepatitis D agents, anti-hepatitis E agents, or anti-hepatitis G agents.

In yet another aspect, the present invention provides methods of using a compound(s) of the present invention and another therapeutic agent(s) to treat HCV infection. The methods comprise administering a therapeutic effective amount of a compound(s) of the present invention and another therapeutic agent(s) to an HCV patient, thereby reducing the HCV viral level in the blood or liver of the patient. Each compound of the present invention (or a salt, solvate or prodrug thereof) and the other therapeutic agent(s) can be combined in a single formulation and administered simultaneously to the patient. They can also be administered simultaneously but in different formulations. In addition, they can be administered sequentially.

In one embodiment, the compound(s) of the present invention being administered includes one or more compounds selected from Formulae I(a), I(b), II(a) or II(b), or from Examples 1-237, or salts, solvates or prodrugs thereof, and the other therapeutic agent(s) being administered includes one or more agents selected from HCV RNA dependent RNA polymerase inhibitors, HCV protease inhibitors or HCV helicase inhibitors. In another embodiment, the compound(s) of the present invention being administered includes one or more compounds selected from Formulae I(a), I(b), II(a) or II(b), or from Examples 1-237, or salts, solvates or prodrugs thereof, and the other therapeutic agent(s) being administered includes two or more agents selected from HCV RNA dependent RNA polymerase inhibitors, HCV protease inhibitors or HCV helicase inhibitors. In yet another embodiment, the compound(s) of the present invention being administered includes one or more compounds selected from Formulae I(a), I(b), II(a) or II(b), or from Examples 1-237, or salts, solvates or prodrugs thereof, and the other therapeutic agent(s) being administered includes one, two or more HCV RNA dependent RNA polymerase inhibitors (e.g., those described in WO0190121(A2), U.S. Pat. No. 6,348,587B1, WO0160315, WO0132153, EP1162196A1 and WO0204425). In still yet another embodiment, the compound(s) of the present invention being administered includes one or more compounds selected from Formulae I(a), I(b), II(a) or II(b), or from Examples 1-237, or salts, solvates or prodrugs thereof, and the other therapeutic agent(s) being administered includes one, two or more HCV protease inhibitors (e.g., BILN-2061, VX-950, and SCH503034).

A compound of the present invention (or a salt, solvate or prodrug thereof) can also be coadministered with other desired drugs, such as anti-HIV agents, anti-HBV agents, anti-hepatitis A agents, anti-hepatitis D agents, anti-hepatitis E agents, anti-hepatitis G agents, or other antiviral drugs.

A compound of the present invention (or a salt, solvent or prodrug thereof) can be administered to a patient in a single dose or divided doses. A typical daily dosage can range, without limitation, from 0.1 to 200 mg/kg body weight, such as from 0.25 to 100 mg/kg body weight. Single dose compositions can contain these amounts or submultiples thereof to make up the daily dose. Preferably, each dosage contains a sufficient amount of a compound of the present invention that is effective in reducing the HCV viral load in the blood or liver of the patient. The amount of the active ingredient, or the active ingredients that are combined, to produce a single dosage form may vary depending upon the host treated and the particular mode of administration. It will be understood that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

In still another aspect, the compounds of Formulae I(a), I(b), II(a) or II(b) or their pharmaceutically acceptable salts, stereoisomers or tautomers, can be administered as the sole active pharmaceutical agent, or used in combination with one or more other agents, to treat infections or symptoms associated with other RNA-containing viruses.

Treatment or prevention of infection caused by RNA-containing viruses can be provided by a combination therapy comprising a therapeutically effective amount of a first antiviral agent provided by one or more compounds, or salts thereof, of Formulae I(a), I(b), II(a) or II(b), along with a therapeutically-effective amount of a second agent provided by one or more compounds selected from the group consisting of another anti-viral agent; a host immune modulator; interferon derivative, such as interferon-alpha, pegylated-interferon-alpha, interferon-beta, and interferon-gamma; a cytokine; a vaccine; a nucleoside analog; inhibitors of key enzymes which result in HCV dysfunction, examples of such enzymes being HCV metalloprotease, HCV serine protease, inosine monophosphate dehydrogenase (IMPDH), and HCV helicase; inhibitors of viral particle proteins such as HCV NS4B protein, and HCV NS5a protein; and agents which inhibit HCV function, such as HCV entry, HCV assembly, and HCV egress. Also included are vaccines comprising HCV antigens or antigen adjuvant combinations directed against HCV. Further included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7.

In one embodiment, the present invention is directed to a method of treating or preventing infection caused by an RNA-containing virus comprising administering to a patient in need of such treatment a therapeutically effective amount of a compound of Formulae I(a), I(b), II(a) or II(b), or a pharmaceutically acceptable salt thereof.

In another embodiment, the present invention is directed to a method of treating or preventing infection caused by an RNA-containing virus comprising co-administering to a patient in need of such treatment one or more agents selected from the group consisting of a host immune modulator and a second antiviral agent, or a combination thereof, with a therapeutically effective amount of a compound of Formulae I(a), I(b), II(a) or II(b), or a pharmaceutically acceptable salt thereof.

In yet another embodiment, the present invention is directed to a method of treating or preventing infection caused by an RNA-containing virus comprising co-administering to a patient in need of such treatment one or more agents selected from the group consisting of interferon-alpha, pegylated-interferon-alpha, interferon-beta, interferon-gamma, a cytokine, a vaccine, and a vaccine comprising an antigen and an adjuvant, and a second antiviral agent, or a combination thereof, with a therapeutically effective amount of a compound of Formulae I(a), I(b), II(a) or II(b), or a pharmaceutically acceptable salt thereof.

In still another embodiment, the present invention provides a method of treating or preventing infection caused by an RNA-containing virus comprising co-administering to a patient in need of such treatment one or more agents selected from the group consisting of a host immune modulator and a second antiviral agent which inhibits replication of HCV by inhibiting host cellular functions associated with viral replication, or a combination thereof, with a therapeutically effective amount of a compound of Formulae I(a), I(b), II(a) or II(b), or a pharmaceutically acceptable salt thereof.

In a further embodiment, the present invention provides a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound of Formulae I(a), I(b), II(a) or II(b), or a pharmaceutically acceptable salt thereof.

In another embodiment, the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound of Formulae I(a), I(b), II(a) or II(b), or a pharmaceutically acceptable salt thereof.

In yet another embodiment, the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound of Formulae I(a), I(b), II(a) or II(b), or a pharmaceutically acceptable salt thereof.

The phrase "combination therapy" (or "co-therapy"), is intended to embrace administration of each agent in a sequential manner in a regimen that will provide beneficial effects of the drug combination, and is intended as well to embrace co-administration of these agents in a substantially simultaneous manner, such as by oral ingestion or a single capsule having a fixed ratio of these active agents or ingestion of multiple, separate capsules for each agent. "Combination therapy" will also include simultaneous or sequential administration by oral, intravenous, intramuscular or other parenteral routes into the body, including direct absorption through mucous membrane tissues, as found in the sinus passages. Sequential administration also includes drug combinations where the individual agents may be administered at different times and/or by different routes but which act in combination to provide a beneficial effect, for example, by co-action of pharmacokinetic or pharmacodynamic effects of each agent.

The present invention also features use of the compounds of the invention, or pharmaceutically acceptable salts, solvates or prodrugs thereof, for the manufacture of medicaments for the treatment of HCV or other viral infections. In one embodiment, the present invention features the use of a compound of the present invention selected from Formulae I(a), I(b), II(a) or II(b), or a salt, solvate or prodrug thereof, for the manufacture of a medicament for the treatment of HCV infection. In another embodiment, the present invention features the use of two or more compounds of the present invention (or salts, solvates or prodrugs thereof) for the manufacture of a medicament for the treatment of HCV infection, wherein each of the two or more compounds is independently selected from Formulae I(a), I(b), II(a) or II(b).

In still another embodiment, the present invention features the use of at least one compound of the present invention (or a salt, solvate or prodrug thereof) and at least one additional therapeutic agent for the manufacture of a medicament for the treatment of HCV infection. Preferably, the compound(s) of the present invention is selected from Formulae I(a), I(b), II(a) or II(b), and the additional therapeutic agent(s) can be selected, by way of illustration not limitation, from antiviral agents (e.g., anti-HIV agents or other anti-HCV agents), immunomodulators, anti-cancer or chemotherapeutic agents, and anti-inflammation agents. Specific examples of additional therapeutic agents include, but are not limited to, ribavirin; interferons (e.g., IFN alpha 2a or 2b); protease inhibitors; immunosuppressants; antibodies (e.g., therapeutic monoclonal or chimeric antibodies); antisense or siRNA; HIV inhibitors; hepatitis B (HBV) inhibitors; agents for treating cirrhosis and inflammation of the liver; Omega IFN (BioMedicines Inc., Emeryville, Calif.); BILN-2061 serine protease inhibitor (Boehringer Ingelheim Pharma KG, Ingelheim, Germany); Summetrel antiviral (Endo Pharmaceuticals Holdings Inc., Chadds Ford, Pa.); Roferon A IFN-alpha 2a (F. Hoffmann-La Roche LTD, Basel, Switzerland); Pegasys PEGylated IFN-alpha 2a (F. Hoffmann-La Roche LTD, Basel, Switzerland); Pegasys and Ribavirin PEGylated IFN-alpha 2a/ribavirin (F. Hoffmann-La Roche LTD, Basel, Switzerland); CellCept HCV IgG immunosuppressant (F. Hoffmann-La Roche LTD, Basel, Switzerland); Wellferon lymphoblastoid IFN-alpha nl (GlaxoSmithKline plc, Uxbridge, UK); Albuferon-alpha albumin IFN-alpha 2b (Human Genome Sciences Inc., Rockville, Md.); Levovirin ribavirin (ICN Pharmaceuticals, Costa Mesa, Calif.); IDN-6556 caspase inhibitor (Idun Pharmaceuticals Inc., San Diego, Calif.); IP-501 antifibrotic (Indevus Pharmaceuticals Inc., Lexington, Mass.); Actimmune INF-gamma (InterMune Inc., Brisbane, Calif.); Infergen A IFN alfacon-1 (InterMune Pharmaceuticals Inc., Brisbane, Calif.); ISIS 14803 antisense (ISIS Pharmaceuticals Inc., Carlsbad, Calif./Elan Pharmaceuticals Inc., New York, N.Y.); JTK-003 RdRp inhibitor (Japan Tobacco Inc., Tokyo, Japan); Pegasys and Ceplene PEGylated IFN-alpha 2a/immune modulator (Maxim Pharmaceuticals inc., San Diego, Calif.); Ceplene immune modulator (Maxim Pharmaceuticals Inc., San Diego, Calif.); Civacir HCV IgG immunosuppressant (Nabi Biopharmaceuticals Inc., Boca Raton, Fla.); Intron A and Zadaxin IFN-alpha 2b/alpha 1-thymosin (RegeneRx Biopharmiceuticals Inc., Bethesda, Md./SciClone Pharmaceuticals Inc., San Mateo, Calif.); Levovirin IMPDH inhibitor (Ribapharm Inc., Costa Mesa, Calif.); Viramidine IMPDH inhibitor (Ribapharm Inc., Costa Mesa, Calif.); Heptazyme ribozyme (Ribozyme Pharmaceuticals Inc., Boulder, Colo.); Intron A IFN-alpha 2b (Schering-Plough Corporation, Kenilworth, N.J.); PEG-Intron PEGylated IFN-alpha 2b (Schering-Plough Corporation, Kenilworth, N.J.); Rebetron IFN-alpha 2b/ribavirin (Schering-Plough Corporation, Kenilworth, N.J.); Ribavirin (Schering-Plough Corporation, Kenilworth, N.J.); PEG-Intron/Ribavirin PEGylated IFN-alpha 2b/ribavirin (Schering-Plough Corporation, Kenilworth, N.J.); Zadazim immune modulator (SciClone Pharmaceuticals Inc., San Mateo, Calif.); Rebif IFN-beta 1a (Serono, Geneva, Switzerland); IFN-beta and EMZ701 IFN-beta and EMZ701 (Transition Therapeutics Inc., Ontario, Canada); T67 beta-tubulin inhibitor (Tularik Inc., South San Francisco, Calif.); VX-497 IMPDH inhibitor (Vertex Pharmaceuticals Inc., Cambridge, Mass.); VX-950/LY-570310 serine protease inhibitor (Vertex Pharmaceuticals Inc., Cambridge, Mass./Eli Lilly and Co., Inc., Indianapolis, Ind.); Omniferon natural IFN-alpha (Viragen Inc., Plantation, Fla.); XTL-002 monoclonal antibody (XTL Biopharmaceuticals); compound VX-950 (Vertex Pharmaceuticals Inc.); compound SCH503034 (Schering-Plough Co.); and compound GS9137 (Gilead Sciences, Inc., Foster City, Calif.).

In yet another embodiment, the present invention features the use of at least one compound of the present invention (or a salt, solvate or prodrug thereof) and at least one additional anti-viral agent for the manufacture of a medicament for the treatment of viral infection. Preferably, the compound(s) of the present invention is selected from Formulae I(a), I(b), II(a) or II(b), and the additional anti-viral agent(s) can be selected, without limitation, from anti-HCV or anti-HIV agents. In one example, the present invention features the use of at least one compound of the present invention selected from Formulae I(a), I(b), II(a) or II(b) (or a salt, solvate or prodrug thereof), and at least one additional anti-HCV agent for the manufacture of a medicament for the treatment of HCV infection. Non-limiting examples of anti-HCV agents include HCV RNA dependent RNA polymerase inhibitors (e.g., nucleoside or non-nucleoside type polymerase inhibitors) or HCV protease inhibitors. In another example, the present invention features the use of at least one compound of the present invention selected from Formulae I(a), I(b), II(a) or II(b) (or a salt, solvate or prodrug thereof), and at least two or more additional anti-HCV agents for the manufacture of a medicament for the treatment of HCV infection. Each of the additional anti-HCV agents can be independently selected from HCV RNA dependent RNA polymerase inhibitors or HCV protease inhibitors.

In still another embodiment, the present invention features the use of at least one compound of the present invention selected from Formulae I(a), I(b), II(a) or II(b) (or a salt, solvate or prodrug thereof), and at least one anti-HIV agent for the manufacture of a medicament for the treatment of HIV or HCV infection. In still yet another embodiment, the present invention features the use of at least one compound of the present invention selected from Formulae I(a), I(b), II(a) or II(b) (or a salt, solvate or prodrug thereof), and at least one anti-hepatitis A, anti-hepatitis B, anti-hepatitis D, anti-hepatitis E or anti-hepatitis G agent for the manufacture of a medicament for the treatment of viral hepatitis. In a further embodiment, the present invention features the use of at least one compound of the present invention selected from Formulae I(a), I(b), II(a) or II(b) (or a salt, solvate or prodrug thereof), and at least one agent for treating liver inflammation, for the manufacture of a medicament for the treatment of Hepatitis C.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A compound, a tautomer of the compound, or a pharmaceutically acceptable salt of the compound or tautomer, wherein the compound has Formula I(b),

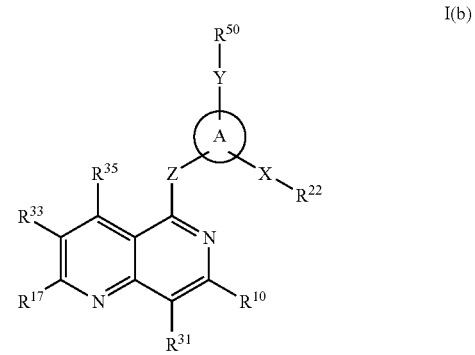

wherein:
Z is —NR$^{41}$—;
A is C$_6$carbocyclyl;
R$^{10}$, R$^{17}$, R$^{31}$, R$^{33}$, R$^{35}$ and R$^{41}$ are each hydrogen;
X is selected from the group consisting of —O—, and —S— and is ortho to Z;
R$^{22}$ is carbocyclyl, heterocyclyl, carbocyclylalkyl or heterocyclylalkyl, and is optionally substituted with one or more R$^{26}$, wherein R$^{26}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -L$_S$-O—R$_S$, -L$_S$-S—R$_S$, -L$_S$-C(O)R$_S$, -L$_S$-OC(O)R$_S$, -L$_S$-C(O)OR$_S$, -L$_S$-N(R$_S$R$_{S'}$), -L$_S$-C(=NR$_S$)R$_{S'}$, -L$_S$-S(O)R$_S$, -L$_S$-SO$_2$R$_S$, -L$_S$-OS(O)R$_S$, -L$_S$-OSO$_2$R$_S$, -L$_S$-C(O)N(R$_S$R$_{S'}$), -L$_S$-N(R$_S$)C(O)R$_{S'}$, -L$_S$-C(=NR$_S$)N(R$_S$R$_{S''}$), -L$_S$-N(R$_{S'}$)C(=NR$_S$)R$_{S''}$, -L$_S$-N(R$_S$)C(O)N(R$_S$R$_{S'}$), -L$_S$-N=C(NR$_S$R$_{S'}$)(NR$_S$R$_{S'}$), -L$_S$-N(R$_S$)SO$_2$R$_{S'}$, -L$_S$-SO$_2$N(R$_S$R$_{S'}$), -L$_S$-N(R$_S$)SO$_2$N(R$_S$R$_{S'}$), -L$_E$-Q-L$_{E'}$-(C$_3$-C$_{18}$-carbocyclyl) and -L$_E$-Q-L$_{E'}$-(M$_3$-M$_{18}$heterocyclyl); or R$^{22}$ is alkyl, alkenyl or alkynyl, and is optionally substituted with one or more R$^{26}$; or R$^{22}$ is hydrogen;
Y is selected from the group consisting of a bond, -L$_S$-O—, -L$_S$-C(O)—, -L$_S$-S(O)$_2$—, -L$_S$-S(O)—, -L$_S$-OS(O)$_2$—, -L$_S$-OS(O)—, -L$_S$-C(O)O—, -L$_S$-OC(O)—, -L$_S$-OC(O)O—, -L$_S$-C(O)N(R$^{15}$)—, -L$_S$-N(R$^{15}$)C(O)—, -L$_S$-C(O)N(R$^{15}$)O—, -L$_S$-N(R$^{15}$)C(O)O—, -L$_S$-C(O)N(R$^{15}$)N(R$^{15'}$)—, -L$_S$-S—, -L$_S$-C(S)—, -L$_S$-C(S)O—, -L$_S$-OC(S)—, -L$_S$-C(S)N(R$^{15}$)—, -L$_S$-N(R$^{15}$)—, -L$_S$-N(R$^{15}$)C(S)—, -L$_S$-N(R$^{15}$)S(O)—, -L$_S$-N(R$^{15}$)S(O)$_2$—, -L$_S$-S(O)$_2$N(R$^{15}$)—, -L$_S$-S(O)N(R$^{15}$)—, -L$_S$-C(S)N(R$^{15}$)O—, and -L$_S$-C(S)N(R$^{15}$)N(R$^{15'}$)—, wherein R$^{15}$ and R$^{15'}$ are each independently selected at each occurrence from the group consisting of hydrogen, alkyl, alkenyl and alkynyl;

$R^{50}$ is -$L^1$-$A^1$, wherein $A^1$ is selected from the group consisting of carbocyclyl, heterocyclyl, alkyl, alkenyl and alkynyl, and $L^1$ is selected from the group consisting of a bond, alkylene, alkenylene and alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_{S'}$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-(C$_3$-C$_{18}$-carbocyclyl) and -$L_E$-Q-$L_{E'}$-(M$_3$-M$_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, alkoxy, thioalkoxy, alkylcarbonyl, alkoxycarbonyl, alkylcarbonyloxy, alkylamino, alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S'}$), -$L_S$-N($R_S$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), carbocyclyl, heterocyclyl, carbocyclylalkyl, heterocyclylalkyl, -$L_E$-Q-$L_{E'}$-(C$_3$-C$_{18}$-carbocyclyl) and -$L_E$-Q-$L_{E'}$-(M$_3$-M$_{18}$heterocyclyl);

$L_S$ is independently selected at each occurrence from the group consisting of a bond, alkylene, alkenylene and alkynylene;

$R_S$, $R_{S'}$ and $R_{S''}$ are each independently selected at each occurrence from the group consisting of hydrogen, alkyl, alkenyl, alkynyl, alkoxy, thioalkoxy, alkoxyalkyl, alkoxyalkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl;

$L_E$ and $L_{E'}$ are each independently selected at each occurrence from the group consisting of a bond, alkylene, alkenylene, alkynylene, -alkylene-O-alkylene-, -alkylene-S-alkylene-, -alkylene-NC(O)-alkylene-, and -alkylene-C(O)N-alkylene-;

Q is independently selected at each occurrence from the group consisting of a bond, alkylene, alkenylene, alkynylene, —S—, —O—, C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$—O—, —S(O)—, —S(O)—O—, —C(O)O— and —C(O)—;

$R^{15}$, $R^{15'}$, $R^{26}$, $R^{30}$ and $R^{38}$ are each independently optionally substituted at each occurrence with at least one substituent selected from the group consisting of halogen, oxo, thioxo, hydroxy, mercapto, nitro, cyano, amino, carboxy, formyl, phosphate, alkoxy, alkylamino, alkoxycarbonyl, and azido; and each C$_3$-C$_{18}$carbocyclyl and M$_3$-M$_{18}$heterocyclyl moiety in -$L_E$-Q-$L_{E'}$-(C$_3$-C$_{18}$carbocyclyl) and -$L_E$-Q-$L_{E'}$-(M$_3$-M$_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, alkyl, alkenyl, alkynyl, alkoxy, thioalkoxy, alkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, carbocyclyloxy, heterocyclyloxy, carbocycloalkoxy, heterocycloalkoxy, carbocycloalkoxycarbonyl, heterocycloalkoxycarbonyl, and alkoxycarbonylaminoalkyl.

2. The compound, tautomer, or salt of claim 1, wherein:

$R^{22}$ is carbocyclyl, heterocyclyl, carbocyclylC$_1$-C$_6$alkyl or heterocyclylC$_1$-C$_6$alkyl, and is optionally substituted with one or more $R^{29}$, wherein $R^{26}$ is independently selected at each occurrence from the group consisting of halogen, oxo, thioxo, hydroxy, mercapto, nitro, cyano, amino, carboxy, formyl, phosphate, azido, C$_1$-C$_6$alkyl, C$_2$-C$_6$alkenyl, C$_2$-C$_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-OS(O)$R_S$, -$L_S$-OSO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N=C(N$R_S R_{S'}$)(N$R_S R_{S'}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-(C$_3$-C$_{18}$carbocyclyl) and -$L_E$-Q-$L_{E'}$-(M$_3$-M$_{18}$heterocyclyl); or $R^{22}$ is C$_1$-C$_6$alkyl, C$_2$-C$_6$alkenyl or C$_2$-C$_6$alkynyl, and is optionally substituted with one or more $R^{26}$; or $R^{22}$ is hydrogen;

Y is selected from the group consisting of a bond, -$L_S$-O—, -$L_S$-C(O)—, -$L_S$-S(O)$_2$—, -$L_S$-S(O)—, -$L_S$-OS(O)$_2$—, -$L_S$-OS(O)—, -$L_S$-C(O)O—, -$L_S$-OC(O)—, -$L_S$-OC(O)O—, -$L_S$-C(O)N($R^{15}$)—, -$L_S$-N($R^{15}$)C(O)—, -$L_S$-C(O)N($R^{15}$)O—, -$L_S$-N($R^{15}$)C(O)O—, -$L_S$-C(O)N($R^{15}$)N($R^{15'}$)—, -$L_S$-S—, -$L_S$-C(S)—, -$L_S$-C(S)O—, -$L_S$-OC(S)—, -$L_S$-C(S)N($R^{15}$)—, -$L_S$-N($R^{15}$)—, -$L_S$-N($R^{15}$)C(S)—, -$L_S$-N($R^{15}$)S(O)—, -$L_S$-N($R^{15}$)S(O)$_2$—, -$L_S$-S(O)$_2$N($R^{15}$)—, -$L_S$-S(O)N($R^{15}$)—, -$L_S$-C(S)N($R^{15}$)O—, and -$L_S$-C(S)N($R^{15}$)N($R^{15'}$)—, wherein $R^{15}$ and $R^{15'}$ are each independently selected at each occurrence from the group consisting of hydrogenC$_1$-C$_6$alkyl, C$_2$-C$_6$alkenyl and C$_2$-C$_6$alkynyl;

$R^{50}$ is -$L^1$-$A^1$, wherein $A^1$ is selected from the group consisting of carbocyclyl, heterocyclyl, C$_1$-C$_6$alkyl, C$_2$-C$_6$alkenyl and C$_2$-C$_6$alkynyl, and $L^1$ is selected from the group consisting of a bond, C$_1$-C$_6$alkylene, C$_2$-C$_6$alkenylene and C$_2$-C$_6$alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, C$_1$-C$_6$alkyl, C$_2$-C$_6$alkenyl, C$_2$-C$_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-(C$_3$-C$_{18}$carbocyclyl) and -$L_E$-Q-$L_{E'}$-(M$_3$-M$_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, C$_1$-C$_6$alkoxy, C$_1$-C$_6$thioalkoxy, C$_1$-C$_6$alkylcarbonyl, C$_1$-C$_6$alkoxycarbonyl, C$_1$-C$_6$alkylcarbonyloxy, C$_1$-C$_6$alkylamino, C$_1$-C$_6$alkoxycarbonylamino, -$L_S$-O—$R_S$, -$L_S$-S—$R_S$, -$L_S$-C(O)$R_S$, -$L_S$-OC(O)$R_S$, -$L_S$-C (O)OR$_S$, -L$_S$-N(R$_S$R$_{S'}$), -L$_S$-C(=NR$_S$)R$_{S'}$, -L$_S$-S(O)R$_S$, -L$_S$-SO$_2$R$_S$, -L$_S$-C(O)N(R$_S$R$_{S'}$), -L$_S$-N(R$_S$)C(O)R$_{S'}$, -L$_S$-C(=NR$_S$)N(R$_S$R$_{S'}$), -L$_S$-N(R$_{S'}$)C(=NR$_S$)R$_{S''}$, -L$_S$-N(R$_S$)C(O)N(R$_S$R$_{S''}$), -L$_S$-N(R$_S$)SO$_2$R$_{S'}$, -L$_S$-SO$_2$N(R$_S$R$_{S'}$), -L$_S$-N(R$_S$)SO$_2$N(R$_S$R$_{S''}$), carbocyclyl, heterocyclyl, carbocyclylC$_1$-C$_6$alkyl, heterocyclylC$_1$-C$_6$alkyl, -L$_E$-Q-L$_{E'}$-(C$_3$-C$_{18}$carbocyclyl) and -L$_E$-Q-L$_{E'}$-(M$_3$-M$_{18}$heterocyclyl);

L$_S$ is independently selected at each occurrence from the group consisting of a bond, C$_1$-C$_6$alkylene, C$_2$-C$_6$alkenylene and C$_2$-C$_6$alkynylene;

R$_S$, R$_{S'}$ and R$_{S''}$ are each independently selected at each occurrence from the group consisting of hydrogen, C$_1$-C$_6$alkyl, C$_2$-C$_6$alkenyl, C$_2$-C$_6$alkynyl, C$_1$-C$_6$alkoxy, C$_1$-C$_6$thioalkoxy, C$_1$-C$_6$alkoxyC$_1$-C$_6$alkyl, C$_1$-C$_6$alkoxyC$_1$-C$_6$alkoxyC$_1$-C$_6$alkyl, C$_1$-C$_6$thioalkoxyC$_1$-C$_6$alkyl, C$_1$-C$_6$alkylcarbonyl, C$_1$-C$_6$alkylcarbonylC$_1$-C$_6$alkyl, C$_1$-C$_6$alkoxycarbonyl, C$_1$-C$_6$alkoxycarbonylC$_1$-C$_6$alkyl, C$_1$-C$_6$alkylcarbonyloxy, C$_1$-C$_6$alkylcarbonyloxyC$_1$-C$_6$alkyl, C$_1$-C$_6$alkylamino, C$_1$-C$_6$alkylaminoC$_1$-C$_6$alkyl, C$_1$-C$_6$alkoxycarbonylamino, and C$_1$-C$_6$alkoxycarbonylaminoC$_1$-C$_6$alkyl;

L$_E$ and L$_{E'}$ are each independently selected at each occurrence from the group consisting of a bond, C$_1$-C$_6$alkylene, C$_2$-C$_6$alkenylene and C$_2$-C$_6$alkynylene, —C$_1$-C$_6$alkylene-O—C$_1$-C$_6$alkylene-, —C$_1$-C$_6$alkylene-S—C$_1$-C$_6$alkylene-, —C$_1$-C$_6$alkylene-NC(O)—C$_1$-C$_6$alkylene-, and —C$_1$-C$_6$alkylene-C(O)N—C$_1$-C$_6$alkylene-;

Q is independently selected at each occurrence from the group consisting of a bond, C$_1$-C$_6$alkylene, C$_2$-C$_6$alkenylene, C$_2$-C$_6$alkynylene, —S—, —O—, C(O)—, —N(R$_S$)—, —N(R$_S$)C(O)—, —C(O)N(R$_S$)—, —N(R$_S$)C(O)O—, —OC(O)N(R$_S$)—, —N(R$_S$)C(O)N(R$_{S'}$)—, —C(=NR$_S$)N(R$_{S'}$)—, —N(R$_{S'}$)C(=NR$_S$)—, —S(O)—, —SO$_2$—, —O—SO$_2$—, —SO$_2$—O—, —O—S(O)—, —S(O)—O—, —C(O)O— and —OC(O)—;

R$^{15}$, R$^{15'}$, R$^{26}$, R$^{30}$ and R$^{38}$ are each independently optionally substituted at each occurrence with at least one substituent selected from the group consisting of halogen, oxo, thioxo, hydroxy, mercapto, nitro, cyano, amino, carboxy, formyl, phosphate, C$_1$-C$_6$alkoxy, C$_1$-C$_6$alkylamino, C$_1$-C$_6$alkoxycarbonyl, and azido; and each C$_3$-C$_{18}$-carbocyclyl and M$_3$-M$_{18}$heterocyclyl moiety in -L$_E$-Q-L$_{E'}$-(C$_3$-C$_{18}$carbocyclyl) and -L$_E$-Q-L$_{E'}$-(M$_3$-M$_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, C$_1$-C$_6$alkyl, C$_2$-C$_6$alkenyl, C$_2$-C$_6$alkynyl, C$_1$-C$_6$alkoxy, C$_1$-C$_6$thioalkoxy, C$_1$-C$_6$alkoxyC$_1$-C$_6$alkyl, C$_1$-C$_6$thioalkoxyC$_1$-C$_6$alkyl, C$_1$-C$_6$alkylcarbonyl, C$_1$-C$_6$alkylcarbonylC$_1$-C$_6$alkyl, C$_1$-C$_6$alkoxycarbonyl, C$_1$-C$_6$alkoxycarbonylC$_1$-C$_6$alkyl, C$_1$-C$_6$alkylcarbonyloxy, C$_1$-C$_6$alkylcarbonyloxyC$_1$-C$_6$alkyl, C$_1$-C$_6$alkylamino, C$_1$-C$_6$alkylaminoC$_1$-C$_6$alkyl, C$_1$-C$_6$alkoxycarbonylamino, C$_3$-C$_7$-carbocylyloxy, M$_3$-M$_7$heterocyclyloxy, C$_3$-C$_7$-carbocycloC$_1$-C$_6$alkoxy, M$_3$-M$_7$heterocycloC$_1$-C$_6$alkoxy, C$_3$-C$_7$-carbocycloC$_1$-C$_6$alkoxycarbonyl, M$_3$-M$_7$heterocycloC$_1$-C$_6$alkoxycarbonyl, and C$_1$-C$_6$alkoxycarbonylaminoC$_1$-C$_6$alkyl.

3. The compound, tautomer, or salt of claim 1, wherein Y is -L$_S$-O—, -L$_S$-S—, -L$_S$-C(O)N(R$^{15}$)— or -L$_S$-N(R$^{15}$)C(O)—, R$^{15}$ is hydrogen, C$_1$-C$_6$alkyl, C$_2$-C$_6$alkenyl or C$_2$-C$_6$alkynyl, and L$^1$ is C$_1$-C$_6$alkylene optionally substituted with one or more R$^{38}$, and wherein A$^1$ is a C$_4$-C$_6$-carbocyclyl or M$_4$-M$_6$heterocyclyl and is optionally substituted with one or more R$^{30}$.

4. The compound, tautomer, or salt of claim 1, wherein Y is -L$_S$-O—, -L$_S$-S—, -L$_S$-C(O)N(R$^{15}$)— or -L$_S$-N(R$^{15}$)C(O)—, R$^{15}$ is hydrogen, C$_1$-C$_6$alkyl, C$_2$-C$_6$alkenyl or C$_2$-C$_6$alkynyl, and L$^1$ is a bond, wherein A$^1$ is a C$_4$-C$_6$carbocyclyl or M$_4$-M$_6$heterocyclyl and is optionally substituted with one or more R$^{30}$.

5. The compound, tautomer, or salt of claim 1, wherein Y is -L$_S$-O—, -L$_S$-S—, -L$_S$-C(O)N(R$^{15}$)— or -L$_S$-N(R$^{15}$)C(O)—, R$^{15}$ is hydrogen, C$_1$-C$_6$alkyl, C$_2$-C$_6$alkenyl or C$_2$-C$_6$alkynyl, and L$^1$ is a bond or C$_1$-C$_6$alkylene optionally substituted with one or more R$^{38}$, wherein A$^1$ is a bicyclic ring (e.g., a fused bicyclic ring or a bridged bicyclic ring) which has from 6 to 14 ring atoms and is optionally substituted with one or more R$^{30}$.

6. The compound, tautomer, or salt of claim 1, wherein R$^{22}$ is C$_5$-C$_6$carbocyclyl or M$_5$-M$_6$heterocyclyl and is optionally substituted with one or more R$^{26}$.

7. The compound, tautomer, or salt of claim 1, wherein R$^{22}$ is

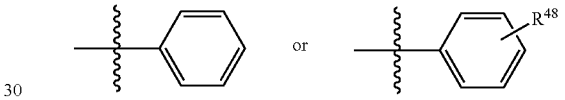

wherein R$^{48}$ is hydroxy, amino, C$_1$-C$_6$alkylamino, C$_1$-C$_6$alkoxy, C$_1$-C$_6$alkoxycarbonylamino or C$_1$-C$_6$alkylcarbonyloxy, and wherein R$^{22}$ is optionally substituted with one or more R$^{26}$.

8. A compound, a tautomer of the compound, or a pharmaceutically acceptable salt of the compound or tautomer, wherein the compound has Formula II(b),

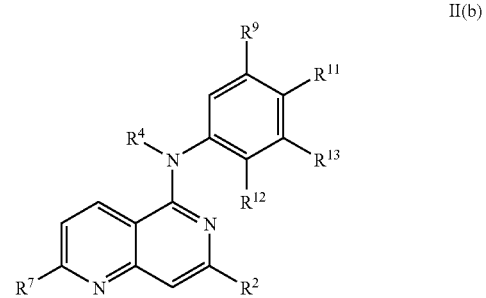

wherein:
R$^2$ is hydrogen;
R$^4$ is hydrogen;
R$^7$ is hydrogen;
R$^9$ is selected from the group consisting of hydrogen, alkyl, alkoxy, haloalkyl, arylalkylamino, hydroxy, alkoxycarbonylaminoalkyl, alkylcarbonyl, amino, halogen, N-[alkylarylamino(arylsulfanyl)arylalkyl]-N-[(alkoxycarbonyl)alkyl]amino, alkoxyarylalkoxy, haloarylalkoxy, nitroarylalkoxy, cyanoarylalkoxy, aryloxyalkyl, haloaryloxyalkyl, cyanoalkoxy, arylalkoxy, alkylarylalkoxy, haloalkylarylaminocarbonyl, alkylaminoarylaminocarbonyl, arylalkoxy, alkylallyloxy, and alkoxycarbonyl;

$R^{11}$ is hydrogen;

$R^{12}$ is selected from the group consisting of arylsulfanyl, arylsulfinyl, aryloxy, and arylalkoxy; wherein $R^{12}$ is optionally substituted with one or more substituents independently selected from $R^{16}$;

$R^{16}$ is selected from the group consisting of hydrogen, halogen, alkyl, alkoxy, hydroxy, aminocarbonyl, alkylaminocarbonyl, amino, alkylcarbonylamino, alkylheteroarylcarbonylamino, heteroarylcarbonylamino, hydroxyheteroarylcarbonylamino, hydroxyalkylheteroarylcarbonylamino, heteroarylcarbonylaminoalkylcarbonylamino, heteroarylalkylcarbonylamino, aryloxyarylalkylcarbonylamino, allylaminocarbonyl, alkoxycarbonyl, hydroxyalkyl, arylaminocarbonyl, hydroxyarylaminocarbonyl, alkoxyalkyl, alkoxyarylaminocarbonyl, azidoalkyl, alkylaminoarylsulfonyloxy, alkylsulfonyloxy, arylalkylsulfonyloxy, alkoxycarbonylalkoxy, hydroxycarbonylalkoxy, cycloalkylcarbonylamino, arylalkoxycarbonylheterocyclecarbonylamino, aryloxy, iminoalkyl, alkylthione, arylalkylcarbonylamino, alkylaryloxyalkylcarbonylamino, arylalkoxyalkylcarbonylamino, heteroarylcarbonylaminoalkylcarbonylamino, heteroarylalkylcarbonylamino, alkylcarbonylheterocyclecarbonylamino, amino, aminocarbonyl, alkylaminocarbonyl, hydroxyalkyl, aminoalkyl, alkoxyalkylaminocarbonyl, hydroxyiminoalkyl, heteroaryl substituted with alkyl, and heteroaryl; and $R^{13}$ is hydrogen.

9. The compound, tautomer, or salt of claim 8, wherein:
$R^{12}$ is selected from the group consisting of

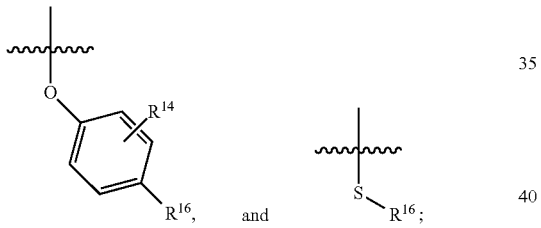

and $R^{14}$ is selected from the group consisting of hydrogen, halogen, alkyl, alkoxy, hydroxy, aminocarbonyl, alkylaminocarbonyl, amino, alkylcarbonylamino, alkylheteroarylcarbonylamino, heteroarylcarbonylamino, hydroxyheteroarylcarbonylamino, hydroxyalkylheteroarylcarbonylamino, heteroarylcarbonylaminoalkylcarbonylamino, heteroarylalkylcarbonylamino, aryloxyarylalkylcarbonylamino, allylaminocarbonyl, alkoxycarbonyl, hydroxyalkyl, arylaminocarbonyl, hydroxyarylaminocarbonyl, alkoxyalkyl, alkoxyarylaminocarbonyl, and azidoalkyl;

wherein, when $R^{12}$ is

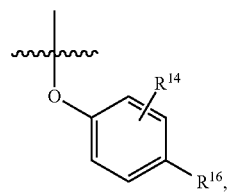

then $R^{16}$ is selected from the group consisting of hydrogen, halogen, alkyl, alkoxy, hydroxy, aminocarbonyl, alkylaminocarbonyl, amino, alkylcarbonylamino, alkylheteroarylcarbonylamino, heteroarylcarbonylamino, hydroxyheteroarylcarbonylamino, hydroxyalkylheteroarylcarbonylamino, heteroarylcarbonylaminoalkylcarbonylamino, heteroarylalkylcarbonylamino, aryloxyarylalkylcarbonylamino, allylaminocarbonyl, alkoxycarbonyl, hydroxyalkyl, arylaminocarbonyl, hydroxyarylaminocarbonyl, alkoxyalkyl, alkoxyarylaminocarbonyl, azidoalkyl, alkylaminoarylsulfonyloxy, alkylsulfonyloxy, arylalkylsulfonyloxy, alkoxycarbonylalkoxy, hydroxycarbonylalkoxy, cycloalkylcarbonylamino, arylalkoxycarbonylheterocyclecarbonylamino, aryloxy, iminoalkyl, alkylthione, arylalkylcarbonylamino, alkylaryloxyalkylcarbonylamino, arylalkoxyalkylcarbonylamino, heteroarylcarbonylaminoalkylcarbonylamino, heteroarylalkylcarbonylamino, alkylcarbonylheterocyclecarbonylamino, amino, aminocarbonyl, alkylaminocarbonyl, hydroxyalkyl, aminoalkyl, alkoxyalkylaminocarbonyl, hydroxyiminoalkyl, heteroaryl substituted with alkyl, and heteroaryl, and wherein, when $R^{12}$ is

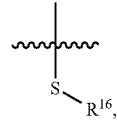

then $R^{16}$ is selected from the group consisting of aryloxyarylalkylcarbonylamino, arylaminocarbonyl, arylalkylsulfonyloxy, arylalkoxycarbonylheterocyclecarbonylamino, aryloxy, arylalkylcarbonylamino, and arylalkoxyalkylcarbonylamino.

10. The compound, tautomer, or salt of claim 8, wherein $R^9$ is selected from the group consisting of hydrogen, methyl, methoxy, phenyl, trifluoromethyl, phenylmethylamino, hydroxy, t-butoxy-carbonylaminomethyl, carbonylamino, methylcarbonyl, amino, bromo, chloro, fluoro, methyl[1,8]naphthyridin-4-ylamino-(2-phenylsulfanylphen-5-ylmethyl)amino-(N-t-butoxy-carbonyl-N-methyl), methoxyphenylmethoxy, bromophenylmethoxy, nitrophenylmethoxy, cyanophenylmethoxy, trifluoromethyl, phenoxymethyl, bromophenoxymethyl, cyanomethoxy, phenylmethoxy, methylallyloxy, propoxy, methylphenylmethoxy, methylphenylmethoxy, fluoro-3-methylphenylaminocarbonyl, trifluoromethylphenylaminocarbonyl, trifluoromethylphenylaminocarbonyl, N,N-dimethylaminophenylaminocarbonyl, fluorophenylmethoxy, and chlorophenylmethoxy; and $R^{16}$ is selected from the group consisting of hydrogen, hydroxy, methylcarbonylamino, methyl, isopropyl, fluoro, methoxy, ethoxy, propoxy, isopropoxy, N,N-dimethylamino-naphth-1-ylsulfonyloxy, ethylsulfonyloxy, isopropylsulfonyloxy, methylsulfonyloxy, benzylsulfonyloxy, ethoxycarbonylmethoxy, hydroxycarbonylmethoxy, t-butylcarbonylamino, cyclopropylcarbonylamino, benzyloxycarbonylpyrrolidinylcarbonylamino, phenoxy, methylcarbonylamino, iminoethyl, thionoethyl, (S)-1-phenylpropylcarbonylamino, methylphenoxymethylcarbonylamino, (R)-1-phenyl-1-methoxymethylcarbonylamino, (S)-1-phenyl-1-methoxymethylcarbonylamino, furanylcarbonylaminomethylcarbonylamino, thienylpropylcarbonylamino, methylcarbonylpiperidinylcarbonylamino, amino, aminocarbonyl, N-methylaminocarbonyl, ethoxycarbonylmethoxy, isopropylsulfonyloxy, methylsulfonyloxy, ethylsulfonyloxy, phenylmethylsulfonyloxy, methylcarbonylamino, N-methylaminocarbonyl, hydroxymethyl, aminoethyl, methoxyethylaminocarbonyl, propylaminocarbonyl, N-methoxy-N-methylaminocarbonyl, N,N-diethylaminocarbonyl, N-(2-methoxyethyl)aminocarbonyl, N-ethyl-N-methylaminocarbonyl, N-hydroxy-1-iminoethyl, hydroxyethyl, aminomethyl, N,N-dimethylamino-carbonyl, 2,6-dimethylfuranyl, 1H-[1,2,4]triazolyl, and pyridinyl.

11. A pharmaceutical composition comprising a compound, tautomer or salt according to claim 1.

12. A pharmaceutical composition comprising a compound, tautomer or salt according to claim 8.

13. A compound, or tautomer or salt thereof, wherein the compound is selected from the group consisting of (5-Chloro-2-phenoxy-phenyl)-[1,6]naphthyridin-5-yl-amine; and N-{4-[4-Methyl-2-([1,6]naphthyridin-5-ylamino)-phenylsulfanyl]-phenyl}-acetamide.

* * * * *